(12) United States Patent
Campbell et al.

(10) Patent No.: US 12,161,724 B2
(45) Date of Patent: Dec. 10, 2024

(54) COMPOSITIONS AND METHODS RELATED TO TUMOR ACTIVATED ANTIBODIES TARGETING EGFR AND EFFECTOR CELL ANTIGENS

(71) Applicant: JANUX THERAPEUTICS, INC., San Diego, CA (US)

(72) Inventors: David Campbell, San Diego, CA (US); Thomas R. Diraimondo, San Diego, CA (US); Ramesh Bhatt, San Diego, CA (US)

(73) Assignee: JANUX THERAPEUTICS, INC., San Diego, CA (US)

( * ) Notice: Subject to any disclaimer, the term of this patent is extended or adjusted under 35 U.S.C. 154(b) by 0 days.

(21) Appl. No.: 18/559,201

(22) PCT Filed: May 4, 2022

(86) PCT No.: PCT/US2022/027688
§ 371 (c)(1),
(2) Date: Nov. 6, 2023

(87) PCT Pub. No.: WO2022/240637
PCT Pub. Date: Nov. 17, 2022

(65) Prior Publication Data
US 2024/0252669 A1    Aug. 1, 2024

Related U.S. Application Data

(60) Provisional application No. 63/327,317, filed on Apr. 4, 2022, provisional application No. 63/187,690, filed on May 12, 2021.

(51) Int. Cl.
*A61K 47/68* (2017.01)

(52) U.S. Cl.
CPC ...... *A61K 47/6849* (2017.08); *A61K 47/6843* (2017.08); *A61K 47/6851* (2017.08); *A61K 47/6871* (2017.08); *A61K 47/6889* (2017.08)

(58) Field of Classification Search
CPC ............ A61K 39/00; A61K 39/001104; C07K 2319/00; C07K 2319/33; C07K 2319/50
See application file for complete search history.

(56) References Cited

U.S. PATENT DOCUMENTS

| | | | |
|---|---|---|---|
| 6,217,866 B1 | 4/2001 | Schlessinger et al. | |
| 7,060,808 B1 | 6/2006 | Goldstein et al. | |
| 8,557,961 B2 | 10/2013 | Silverman et al. | |
| 8,658,175 B2 | 2/2014 | Dubridge et al. | |
| 9,249,211 B2 | 2/2016 | Schellenberger et al. | |
| 9,493,563 B2 | 11/2016 | Blein et al. | |
| 9,540,440 B2 | 1/2017 | Lowman et al. | |
| 9,708,412 B2 | 7/2017 | Baeuerle et al. | |
| 9,916,166 B2 | 3/2018 | Aizawa | |
| 9,976,166 B2 | 5/2018 | Schellenberger et al. | |
| 10,118,966 B2 | 11/2018 | Qian | |
| 10,533,053 B2 | 1/2020 | Lowman et al. | |
| 10,870,874 B2 | 12/2020 | Schellenberger et al. | |
| 11,180,562 B2 | 11/2021 | Lowman et al. | |
| 11,512,113 B2 | 11/2022 | Campbell et al. | |
| 11,649,291 B2 | 5/2023 | Griswold et al. | |
| 11,773,166 B2 | 10/2023 | Ollier et al. | |
| 11,851,502 B2 | 12/2023 | Blein et al. | |
| 11,891,454 B2 | 2/2024 | Blein et al. | |
| 2004/0229310 A1 | 11/2004 | Simmons | |
| 2015/0232557 A1 | 8/2015 | Tan et al. | |
| 2016/0193332 A1 | 7/2016 | Lowman et al. | |
| 2016/0289341 A1 | 10/2016 | Wu | |
| 2017/0145115 A1 | 5/2017 | Blein et al. | |
| 2018/0112011 A1 | 4/2018 | Ollier | |
| 2018/0193477 A1 | 7/2018 | Ng et al. | |
| 2018/0333507 A1 | 11/2018 | Lowman et al. | |
| 2020/0102403 A1 | 4/2020 | Ollier | |
| 2020/0354452 A1 | 11/2020 | Qin et al. | |
| 2021/0047406 A1 | 2/2021 | Irving et al. | |
| 2021/0164011 A1 | 6/2021 | Schellenberger et al. | |
| 2022/0213227 A1 | 7/2022 | Ollier | |
| 2022/0289853 A1 | 9/2022 | Lowman et al. | |
| 2023/0061715 A1 | 3/2023 | Schellenberger et al. | |
| 2023/0062624 A1 | 3/2023 | Ollier et al. | |

(Continued)

FOREIGN PATENT DOCUMENTS

| | | | |
|---|---|---|---|
| EP | 0359282 A2 | 3/1990 | |
| WO | WO-2012025525 A1 * | 3/2012 | ........... A61K 39/395 |
| WO | WO-2020247871 A2 | 12/2020 | |

(Continued)

OTHER PUBLICATIONS

Moradi-Kalbolandi et al, Journal of Pharmacy and Pharmacology, 2018, vol. 70, pp. 841-854 (Year: 2018).*
Williams et al, Chemical Biology and Drug Design, 2018, vol. 91, pp. 605-619 (Year: 2018).*
Hossein-Nejad-Ariani et al, Scientific Reports, 2019, vol. 9, No. 2723, 8 pages (Year: 2019).*
Desnoyers et al (Science Translational Medicine, 2013, vol. 5, No. 4, 207ra144, 10 pages) (Year: 2013).*

(Continued)

*Primary Examiner* — Karen A. Canella

(74) *Attorney, Agent, or Firm* — WILSON SONSINI GOODRICH & ROSATI

(57) ABSTRACT

Provided herein are multispecific antibodies for redirecting T cells to cancers, that rely on binding of one antigen interacting portion of the antibody to a tumor-associated antigen or marker, such as epidermal growth factor receptor (EGFR), while a second antigen interacting portion can bind to an effector cell antigen on a T cell, such as CD3, pharmaceutical compositions thereof, as well as nucleic acids, and methods for making and discovering the same.

21 Claims, 46 Drawing Sheets

Specification includes a Sequence Listing.

(56) References Cited

U.S. PATENT DOCUMENTS

2023/0220109 A1     7/2023     Campbell et al.

FOREIGN PATENT DOCUMENTS

| WO | WO-2022094299 A2 | 5/2022 |
|---|---|---|
| WO | WO-2022125562 A1 | 6/2022 |
| WO | WO-2022240637 A2 | 11/2022 |
| WO | WO-2022240865 A1 | 11/2022 |
| WO | WO-2024100451 A2 | 5/2024 |
| WO | WO-2024102723 A2 | 5/2024 |

OTHER PUBLICATIONS

Melo-Braga, Marcella Nunes, et al. New insights of glycosylation role on variable domain of antibody structures. bioRxiv https://www.biorxiv.org/content/10.1101/2021.04.11.439351v1.full.pdf (37 pgs) (2021).

PCT/US2023/078935 International Search Report and Written Opinion dated May 1, 2024.

PCT/US2023/78935 Invitation to Pay Additional Fees dated Feb. 23, 2024.

Al-Lazikani et al. Standard conformations for the canonical structures of immunoglobulins. J Mol Biol. 273(4):927-48 (1997).

Altschul et al.: Basic Local Alignment Search Tool. J Mol Biol 215(3):403-410 (1990).

Altschul et al., Gapped BLAST and PSI-BLAST: A New Generation Of Protein Database Search Programs. Nucleic Acids Research 25(17):3389-3402 (Sep. 1, 1997).

Bird et al., Single-Chain Antigen-Binding Proteins, with Erratum, Science 242:423-426 (Oct. 21, 1988), 242:1494 (Dec. 16, 1988), 244:409 (Apr. 28, 1989).

Clackson et al. Making antibody fragments using phage display libraries. Nature 352(6336):624-628 (1991).

Colberre-Garapin et al. A new dominant hybrid selective marker for higher eukaryotic cells. J Mol Biol 150:1-14 (1981).

Cole et al. The EBV-hybridoma technique and its application to human lung cancer. In, Monoclonal Antibodies and Cancer Therapy (vol. 27, UCLA Symposia on Molecular and Cellular Biology, New Series) (eds. R.A. Reisfeld and S.Sell), New York: Alan R. Liss, Inc. pp. 77-96 (1985).

Courtenay-Luck. Chapter 8: Genetic manipulation of monoclonal antibodies. Monoclonal Antibodies: Production, Engineering and Clinical Application pp. 166-179 (1995).

Crouse et al. Expression and amplification of engineered mouse dihydrofolate reductase minigenes. Mol Cell Biol 3(2):257-266 (1983).

Goldspiel et al. Human gene therapy. Clin Pharm 12:488-505 (1993).

Hanes et al. In vitro selection and evolution of functional proteins by using ribosome display. PNAS USA 94:4937-4942 (1997).

Honegger et al. Yet another numbering scheme for immunoglobulin variable domains: an automatic modeling and analysis tool. J Mol Biol 309(3):657-70 (2001).

Huse et al. Generation of a large combinatorial library of the immunoglobulin repertoire in phage lambda. Science 246(4935):1275-1281 (1989).

Huston et al., Protein Engineering Of Antibody Binding Sites: Recovery Of Specific Activity In An Anti-digoxin Single-Chain Fv Analogue Produced In Escherichia coli. PNAS USA 85(16):5879-5883 (1988).

Huston et al., Protein engineering of single-chain Fv analogs and fusion proteins. Methods Enzymol. 203:46-96 (1991).

Kabat et al. Sequences of proteins of immunological interest. NIH Publ. No. 91-3242 1:647-669 (1991).

Karlin et al., Applications And Statistics For Multiple High-Scoring Segments In Molecular Sequences. PNAS USA 90(12):5873-5877 (Jun. 15, 1993).

Karlin et al., Methods For Assessing The Statistical Significance Of Molecular Sequence Features By Using General Scoring Schemes. PNAS USA 87:2264-2268 (Mar. 1990).

Kohler et al. Continuous cultures of fused cells secreting antibody of predefined specificity. Nature 256:495-497 (1975).

Kozbor et al. The production of monoclonal antibodies from human lymphocytes. Immunology Today 4:72-79 (1983).

Kutmeier et al. Assembly of humanized antibody genes from synthetic oligonucleotides using a single-round PCR. BioTechniques 17:242 (1994).

Larrick et al. PCR amplification of antibody genes. Methods 2:106-110 (1991).

Lefranc et al. IMGT unique numbering for immunoglobulin and T cell receptor variable domains and Ig superfamily V-like domains. Dev Comp Immunol 27(1):55-77 (2003).

Lowy et al., Isolation of transforming DNA: Cloning the hamster aprt gene. Cell 22:817-823 (1980).

Maccallum et al.: Antibody-Antigen Interactions: Contact Analysis and Binding Site Topography. J Mol Biol 262:732-745 (1996).

Morgan et al. Human gene therapy. Ann Rev Biochem 62:191-217 (1993).

Morrison et al. Chimeric human antibody molecules: mouse antigen-binding domains with human constant region domains. PNAS USA 81(21):6851-6855 (1984).

Mulligan et al. Selection for animal cells that express the Escherichia coli gene coding for xanthine-guanine phosphoribosyltransferase. PNAS USA 78(4):2072-2076 (1981).

Mulligan. The basic science of gene therapy. Science 260(5110):926-932 (1993).

Neuberger et al. Recombinant antibodies possessing novel effector functions. Nature 312(5995):604-608 (1984).

O'Hare et al. Transformation of mouse fibroblasts to methotrexate resistance by a recombinant plasmid expressing a prokaryotic dihydrofolate reductase. PNAS USA 78:1527-1531 (1981).

PCT/US2022/027688 International Invitation to Pay Additional Fees dated Aug. 15, 2022.

PCT/US2022/027688 International Search Report and Written Opinion dated Oct. 13, 2022.

PCT/US2022/028579 International Invitation to Pay Additional Fees dated Aug. 1, 2022.

PCT/US2022/028579 International Search Report and Written Opinion dated Oct. 6, 2022.

Santerre et al. Expression of prokaryotic genes for hygromycin B and G418 resistance as dominant-selection markers in mouse L cells. Gene 30(1-3):147-156 (1984).

Skerra et al. Assembly of a functional Immunoglobulin Fv fragment in Escherichia coli. Science 240(4855):1038-1041 (1988).

Szybalska et al. Genetics of human cell line. IV. DNA-mediated heritable transformation of a biochemical trait. PNAS USA 48:2026-2034 (1962).

Takeda et al. Construction of chimaeric processed immunoglobulin genes containing mouse variable and human constant region sequences. Nature 314(6010):452-454 (1985).

Tolstoshev. Gene Therapy, Concepts, Current Trials and Future Directions. Ann. Rev. Pharmacol. Toxicol. 32:573-596 (1993).

Ward et al., Binding Activities of a Repertoire of Single Immunoglobulin Variable Domains Secreted from Escherichia coli. Nature 341(6242):544-546 (Oct. 12, 1989).

Ward et al. Genetic Manipulation and Expression of Antibodies. Monoclonal Antibodies: Principles and Applications, Wiley-Liss Inc., pp. 137-185 (1995).

Whitelegg et al. WAM: an improved algorithm for modelling antibodies on the WEB. Protein Eng. 13:819-24 (2000).

Wigler et al. Transfer of purified herpes virus thymidine kinase gene to cultured mouse cells. Cell 11:223-232 (1977).

Wigler et al. Transformation of mammalian cells with an amplifiable dominant-acting gene. PNAS USA 77:3567-3570 (1980).

Wootton et al. Statistics of local complexity in amino acid sequences and sequence databases. Computers & Chemistry 17(2):149-163 (Jun. 1993).

Wu et al. Delivery systems for gene therapy. Biotherapy 3:87-95 (1991).

Co-pending U.S. Appl. No. 18/559,179, inventors Campbell; David et al., filed Nov. 6, 2023.

\* cited by examiner

COMPOSITIONS AND METHODS RELATED TO TUMOR ACTIVATED ANTIBODIES TARGETING EGFR AND EFFECTOR CELL ANTIGENS

CROSS-REFERENCE

The present application is a national stage entry of International Application No. PCT/US2022/027688, filed May 4, 2022, which claims the benefit of U.S. Provisional Application No. 63/187,690, filed May 12, 2021, and U.S. Provisional Application No. 63/327,317, filed Apr. 4, 2022, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Apr. 29, 2022, is named 52426-738_601_SL.txt and is 542,564 bytes in size.

SUMMARY

Described herein, in certain embodiments, are polypeptides or polypeptide complexes according to Formula I:

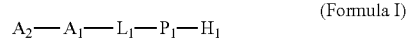

$$A_2\text{---}A_1\text{---}L_1\text{---}P_1\text{---}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR). In some embodiments, the first antigen recognizing molecule comprises an antibody or antibody fragment. In some embodiments, first antigen recognizing molecule comprises an antibody or antibody fragment that is human or humanized. In some embodiments, $L_1$ is bound to N-terminus of the first antigen recognizing molecule. In some embodiments, $A_2$ is bound to C-terminus of the first antigen recognizing molecule. In some embodiments, $L_1$ is bound to C-terminus of the first antigen recognizing molecule. In some embodiments, $A_2$ is bound to N-terminus of the first antigen recognizing molecule. In some embodiments, the antibody or antibody fragment comprises a single chain variable fragment, a single domain antibody, or a Fab fragment. In some embodiments, $A_1$ is the single chain variable fragment (scFv). In some embodiments, the scFv comprises a scFv heavy chain polypeptide and a scFv light chain polypeptide. In some embodiments, $A_1$ is the single domain antibody. In some embodiments, the antibody or antibody fragment comprises a single chain variable fragment (scFv), a heavy chain variable domain (VH domain), a light chain variable domain (VL domain), or a variable domain (VHH) of a camelid derived single domain antibody. In some embodiments, $A_1$ comprises an anti-CD3ε single chain variable fragment. In some embodiments, $A_1$ comprises an anti-CD3ε single chain variable fragment that has a $K_D$ binding of 1 μM or less to CD3 on CD3 expressing cells. In some embodiments, the effector cell antigen comprises CD3. In some embodiments, $A_1$ comprises a variable light chain and variable heavy chain each of which is capable of specifically binding to human CD3. In some embodiments, $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19. In some embodiments, the isolated polypeptide or polypeptide complex of Formula I binds to an effector cell when $L_1$ is cleaved by the tumor specific protease. In some embodiments, the isolated polypeptide or polypeptide complex of Formula I binds to an effector cell when $L_1$ is cleaved by the tumor specific protease and $A_1$ binds to the effector cell. In some embodiments, the effector cell is a T cell. In some embodiments, $A_1$ binds to a polypeptide that is part of a TCR-CD3 complex on the effector cell. In some embodiments, the polypeptide that is part of the TCR-CD3 complex is human CD3. In some embodiments, the effector cell antigen comprises CD3, wherein the scFv comprises CDRs: LC-CDR1, LC-CDR2, and LC-CDR3, wherein the LC-CDR1, the LC-CDR2, and the LC-CDR3 of the scFv LC-CDR1: SEQ ID NO: 1, LC-CDR2: SEQ ID NO: 2, and LC-CDR3: SEQ ID NO: 3; and the scFv comprises complementarity determining regions (CDRs): HC-CDR1, HC-CDR2, and HC-CDR3, wherein the HC-CDR1, the HC-CDR2, and the HC-CDR3 of the scFv: HC-CDR1: SEQ ID NO: 4, HC-CDR2: SEQ ID NO: 5, and HC-CDR3: SEQ ID NO: 6. In some embodiments, the effector cell antigen comprises CD3, and the scFv comprises an amino acid sequence according to SEQ ID NO: 13. In some embodiments, the effector cell antigen comprises CD3, wherein the scFv comprises CDRs: LC-CDR1, LC-CDR2, and LC-CDR3, wherein the LC-CDR1, the LC-CDR2, and the LC-CDR3 of the scFv LC-CDR1: SEQ ID NO: 7, LC-CDR2: SEQ ID NO: 8, and LC-CDR3: SEQ ID NO: 9; and the scFv comprises complementarity determining regions (CDRs): HC-CDR1, HC-CDR2, and HC-CDR3, wherein the HC-CDR1, the HC-CDR2, and the HC-CDR3 of the scFv: HC-CDR1: SEQ ID NO: 10, HC-CDR2: SEQ ID NO: 11, and HC-CDR3: SEQ ID NO: 12. In some embodiments, the effector cell antigen comprises CD3, and the scFv comprises an amino acid sequence according to SEQ ID NO: 14. In some embodiments, second antigen recognizing molecule comprises an antibody or antibody fragment. In some embodiments, the antibody or antibody fragment thereof comprises a single chain variable fragment, a single domain antibody, or a Fab. In some embodiments, the antibody or antibody fragment thereof comprises a single chain variable fragment (scFv), a heavy chain variable domain (VH domain), a light chain variable domain (VL domain), a variable domain (VHH) of a camelid derived single domain antibody. In some embodiments, the antibody or antibody fragment thereof is humanized or human. In some embodiments, $A_2$ is the Fab. In some embodiments, the Fab comprises (a) a Fab light chain polypeptide and (b) a Fab heavy chain polypeptide. In some embodiments, the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 15, LC-CDR2: SEQ ID NO:16, and LC-CDR3: SEQ ID NO: 17; and the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 18, HC-CDR2: SEQ ID NO: 19, and HC-CDR3: SEQ ID NO: 20. In some embodiments, the Fab light chain polypeptide comprises an amino acid sequence according to SEQ ID NO: 21. In some embodiments, the Fab light chain polypeptide comprises an amino acid sequence according to SEQ ID NO: 22. In some embodiments, Fab heavy chain polypeptide comprises an amino acid sequence according to SEQ ID NO: 23. In some embodiments, Fab heavy chain polypeptide comprises an amino acid sequence according to SEQ ID NO: 24. In some embodiments, the Fab light chain polypeptide of $A_2$ is bound to a C-terminus of the single chain variable fragment (scFv) of $A_1$. In some embodiments, the Fab heavy chain polypeptide of $A_2$ is bound to a C-terminus of the single chain variable fragment (scFv) $A_1$. In some embodiments, the Fab light chain polypeptide of $A_2$ is bound to a N-terminus of the single chain variable fragment (scFv) of $A_1$. In some embodiments, the Fab heavy chain polypeptide of $A_2$ is bound to a N-terminus of the single chain variable fragment (scFv) $A_1$. In some embodiments, the Fab heavy chain polypeptide of $A_2$ is bound to the scFv heavy chain polypeptide of $A_1$. In some embodiments, the Fab light chain polypeptide of $A_2$ is bound to the scFv heavy chain polypeptide of $A_1$. In some embodiments, the Fab heavy chain polypeptide of $A_2$ is bound to the scFv light chain polypeptide of $A_1$. In some embodiments, the Fab light chain polypeptide of $A_2$ is bound to the scFv light chain polypeptide of $A_1$. In some embodiments, $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease. In some embodiments, the isolated polypeptide or polypeptide complex is according to Formula Ia:

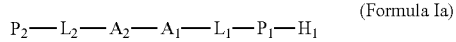

$$P_2—L_2—A_2—A_1—L_1—P_1—H_1 \quad \text{(Formula Ia)}$$

In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$. In some embodiments, $P_1$ impairs binding of $A_1$ to the effector cell antigen. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ has less than 70% sequence homology to the effector cell antigen. In some embodiments, $P_2$ impairs binding of $A_2$ to EGFR. In some embodiments, $P_2$ is bound to $A_2$ through ionic interactions, electrostatic interactions, hydrophobic interactions, Pi-stacking interactions, and H-bonding interactions, or a combination thereof. In some embodiments, $P_2$ is bound to $A_2$ at or near an antigen binding site. In some embodiments, $P_2$ has less than 70% sequence homology to EGFR. In some embodiments, $P_1$ or $P_2$ comprises a peptide sequence of at least 10 amino acids in length. In some embodiments, $P_1$ or $P_2$ comprises a peptide sequence of at least 10 amino acids in length and no more than 20 amino acids in length. In some embodiments, $P_1$ or $P_2$ comprises a peptide sequence of at least 16 amino acids in length. In some embodiments, $P_1$ or $P_2$ comprises a peptide sequence of no more than 40 amino acids in length. In some embodiments, $P_1$ or $P_2$ comprises at least two cysteine amino acid residues. In some embodiments, $P_1$ or $P_2$ comprises a cyclic peptide or a linear peptide. In some embodiments, $P_1$ or $P_2$ comprises a cyclic peptide. In some embodiments, $P_1$ or $P_2$ comprises a linear peptide. In some embodiments, $P_1$ comprises at least two cysteine amino acid residues. In some embodiments, $P_1$ comprises an amino acid sequence according to SEQ ID NO: 25. In some embodiments, $P_2$ comprises an amino acid sequence according to SEQ ID NO: 26. In some embodiments, $P_2$ comprises an amino acid sequence according to SEQ ID NO: 115. In some embodiments, $P_2$ comprises an amino acid sequence according to SEQ ID NO: 116. In some embodiments, $P_1$ comprises an amino acid sequence according to SEQ ID NO: 70. In some embodiments, $L_1$ is bound to N-terminus of $A_1$. In some embodiments, $L_1$ is bound to C-terminus of $A_1$. In some embodiments, $L_2$ is bound to N-terminus of $A_2$. In some embodiments, $L_2$ is bound to C-terminus of $A_2$. In some embodiments, $L_1$ or $L_2$ is a peptide sequence having at least 5 to no more than 50 amino acids. In some embodiments, $L_1$ or $L_2$ is a peptide sequence having at least 10 to no more than 30 amino acids. In some embodiments, $L_1$ or $L_2$ is a peptide sequence having at least 10 amino acids. In some embodiments, $L_1$ or $L_2$ is a peptide sequence having at least 18 amino acids. In some embodiments, $L_1$ or $L_2$ is a peptide sequence having at least 26 amino acids. In some embodiments, $L_1$ or $L_2$ has a formula comprising $(G_2S)_n$, wherein n is an integer from 1 to 3 (SEQ ID NO: 840). In some embodiments, $L_1$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1. In some embodiments, $P_1$ becomes unbound from $A_1$ when $L_1$ is cleaved by the tumor specific protease thereby exposing $A_1$ to the effector cell antigen. In some embodiments, $P_2$ becomes unbound from $A_2$ when $L_2$ is cleaved by the tumor specific protease thereby exposing $A_2$ to EGFR. In some embodiments, the tumor specific protease is selected from the group consisting of a matrix metalloprotease (MMP), serine protease, cysteine protease, threonine protease, and aspartic protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $L_1$ or $L_2$ comprises a urokinase cleavable amino acid sequence, a matriptase cleavable amino acid sequence, matrix metalloprotease cleavable amino acid sequence, or a legumain cleavable amino acid sequence. In some embodiments, $L_1$ or $L_2$ comprises an amino acid sequence according to SEQ ID NO: 30 or 31. In some embodiments, $L_1$ or $L_2$ comprises an amino acid sequence according to any one of SEQ ID NOs: 27-35. In some embodiments, $L_1$ or $L_2$ comprises an amino acid sequence of Linker 4 (ISSGLLSGRSDAG) (SEQ ID NO: 66), Linker 5 (AAGLLAPPGGLSGRSDAG) (SEQ ID NO: 67), Linker 6 (SPLGLSGRSDAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7. In some embodiments, $H_1$ comprises a polymer. In some embodiments, the polymer is polyethylene glycol (PEG). In some embodiments, $H_1$ comprises albumin. In some embodiments, $H_1$ comprises an Fc domain. In some embodiments, the albumin is serum albumin. In some embodiments, the albumin is human serum albumin. In some embodiments, H₁ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment, or a Fab. In some embodiments, the single domain antibody comprises a single domain antibody that binds to albumin. In some embodiments, the single domain antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A 10m3 or a fragment thereof. In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10E. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 39, HC-CDR2: SEQ ID NO: 40, and HC-CDR3: SEQ ID NO: 41. In some embodiments, the single domain antibody is SA21. In some embodiments, the isolated polypeptide or polypeptide complex comprises a modified amino acid, a non-natural amino acid, a modified non-natural amino acid, or a combination thereof. In some embodiments, the modified amino acid or modified non-natural amino acid comprises a post-translational modification. In some embodiments, H₁ comprises a linking moiety ($L_3$) that connects H₁ to P₁. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ has a formula selected from the group consisting of $(G_2S)_n$, $(GS)_n$, $(GSGGS)_n$ (SEQ ID NO: 836), $(GGGS)_n$ (SEQ ID NO: 837) $(GGGGS)_n$ (SEQ ID NO: 838), and $(GSSGGS)_n$ (SEQ ID NO: 839), wherein n is an integer of at least 1. In some embodiments, $L_3$ comprises an amino acid sequence according to SEQ ID NO: 29. In some embodiments, the isolated polypeptide or polypeptide complex comprises an amino acid sequence with at least 95% sequence identity to any one of SEQ ID NOs: 44-61. In some embodiments, the isolated polypeptide or polypeptide complex comprises an amino acid sequence with at least 95% sequence identity to SEQ ID NO: 50. In some embodiments, the isolated polypeptide or polypeptide complex comprises an amino acid sequence with at least 95% sequence identity to SEQ ID NO: 51. In some embodiments, the isolated polypeptide or polypeptide complex comprises an amino acid sequence with at least 95% sequence identity to SEQ ID NO: 44 and SEQ ID NO: 45. In some embodiments, the isolated polypeptide or polypeptide complex comprises an amino acid sequence with at least 95% sequence identity to SEQ ID NO: 46 and SEQ ID NO: 47. In some embodiments, the isolated polypeptide or polypeptide complex comprises an amino acid sequence with at least 95% sequence identity to SEQ ID NO: 48 and SEQ ID NO: 49. In some embodiments, the isolated polypeptide or polypeptide complex comprises an amino acid sequence with at least 95% sequence identity to SEQ ID NO: 50 and SEQ ID NO: 51. In some embodiments, the isolated polypeptide or polypeptide complex comprises an amino acid sequence with at least 95% sequence identity to SEQ ID NO: 52 and SEQ ID NO: 53. In some embodiments, the isolated polypeptide or polypeptide complex comprises an amino acid sequence with at least 95% sequence identity to SEQ ID NO: 54 and SEQ ID NO: 55. In some embodiments, the isolated polypeptide or polypeptide complex comprises an amino acid sequence with at least 95% sequence identity to SEQ ID NO: 56 and SEQ ID NO: 57. In some embodiments, the isolated polypeptide or polypeptide complex comprises an amino acid sequence with at least 95% sequence identity to SEQ ID NO: 58 and SEQ ID NO: 59. In some embodiments, the isolated polypeptide or polypeptide complex comprises an amino acid sequence with at least 95% sequence identity to SEQ ID NO: 60 and SEQ ID NO: 61. In some embodiments, the isolated polypeptide or polypeptide complex comprises an amino acid sequence with at least 95% sequence identity to SEQ ID NO: 62 and SEQ ID NO: 63. In some embodiments, the isolated polypeptide or polypeptide complex comprises an amino acid sequence with at least 95% sequence identity to SEQ ID NO: 64 and SEQ ID NO: 65.

Described herein, in certain embodiments, are pharmaceutical compositions comprising: (a) the isolated polypeptide or polypeptide complex described herein; and (b) a pharmaceutically acceptable excipient.

Described herein, in certain embodiments, are isolated recombinant nucleic acid molecules encoding the isolated polypeptide or polypeptide complex described herein.

Described herein, in certain embodiments, are polypeptide or polypeptide complexes according to Formula II

(Formula II)

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to EGFR; $P_{1a}$ comprises a peptide that binds to the first antigen recognizing molecule when $L_{1a}$ is uncleaved; and $H_{1a}$ comprises a half-life extending molecule. In some embodiments, Pa when $L_{1a}$ is uncleaved impairs binding of the first antigen recognizing molecule to the effector cell antigen. In some embodiments, the first antigen recognizing molecule comprises an antibody or antibody fragment. In some embodiments, the effector cell antigen is an anti-CD3 effector cell antigen. In some embodiments, $P_{1a}$ has less than 70% sequence homology to the effector cell antigen. In some embodiments, $P_{1a}$ comprises a peptide sequence of at least 10 amino acids in length. In some embodiments, $P_{1a}$ comprises a peptide sequence of at least 10 amino acids in length and no more than 20 amino acids in length. In some embodiments, $P_{1a}$ comprises a peptide sequence of at least 16 amino acids in length. In some embodiments, $P_{1a}$ comprises a peptide sequence of no more than 40 amino acids in length. In some embodiments, $P_{1a}$ comprises at least two cysteine amino acid residues. In some embodiments, $P_{1a}$ comprises a cyclic peptide or a linear peptide. In some embodiments, $P_{1a}$ comprises a cyclic peptide. In some embodiments, $P_{1a}$ comprises a linear peptide. In some embodiments, $P_{1a}$ comprises an amino acid sequence selected from the group consisting of SEQ ID NO: 25. In some embodiments, $P_1$ comprises an amino acid sequence according to SEQ ID NO: 70. In some embodiments, $H_{1a}$ comprises a polymer. In some embodiments, the polymer is polyethylene glycol (PEG). In some embodiments, $H_{1a}$ comprises albumin. In some embodiments, $H_{1a}$ comprises an Fc domain. In some embodiments, the albumin is serum albumin. In some embodiments, the albumin is human serum albumin. In some embodiments, $H_{1a}$ comprises a polypeptide, a ligand, or a small molecule. In some embodiments, the polypeptide, the ligand or the small molecule binds a serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, slgA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the antibody comprises a single domain antibody that binds to albumin. In some embodiments, the antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A10m3 or a fragment thereof. In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10G. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 39, HC-CDR2: SEQ ID NO: 40, and HC-CDR3: SEQ ID NO: 41. In some embodiments, the single domain antibody is SA21. In some embodiments, $H_{1a}$ comprises a linking moiety ($L_{1a}$) that connects $H_{1a}$ to $P_{1a}$. In some embodiments, $L_{1a}$ is a peptide sequence having at least 5 to no more than 50 amino acids. In some embodiments, $L_{1a}$ is a peptide sequence having at least 10 to no more than 30 amino acids. In some embodiments, $L_{1a}$ is a peptide sequence having at least 10 amino acids. In some embodiments, $L_{1a}$ is a peptide sequence having at least 18 amino acids. In some embodiments, $L_{1a}$ is a peptide sequence having at least 26 amino acids. In some embodiments, $L_{1a}$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1. In some embodiments, $L_{1a}$ comprises an amino acid sequence according to SEQ ID NO: 30 or 31. In some embodiments, $L_1$ or $L_2$ comprises an amino acid sequence according to any one of SEQ ID NOs: 27-35. In some embodiments, $L_1$ or L2 comprises an amino acid sequence of Linker 4 (ISSGLLS-GRSDAG) (SEQ ID NO: 66), Linker 5 (AAGLLAPPG-GLSGRSDAG) (SEQ ID NO: 67), Linker 6 (SPLGLSGRS-DAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7.

Described herein, in certain embodiments, are polypeptide complexes comprising a structural arrangement according to Configuration 1 (FIG. 1A), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab heavy chain polypeptide to $P_2$ and is a substrate for a tumor specific protease.

Described herein, in certain embodiments, are polypeptide complexes comprising a structural arrangement according to Configuration 2 (FIG. 1B), wherein the isolated polypeptide or polypeptide complex comprises a single chain variable fragment (scFv) comprising a light chain variable domain and a heavy chain variable domain, wherein the scFv is linked to a peptide (Pt) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab light chain polypeptide to $P_2$ and is a substrate for a tumor specific protease.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of which:

DETAILED DESCRIPTION

Figure 1A:
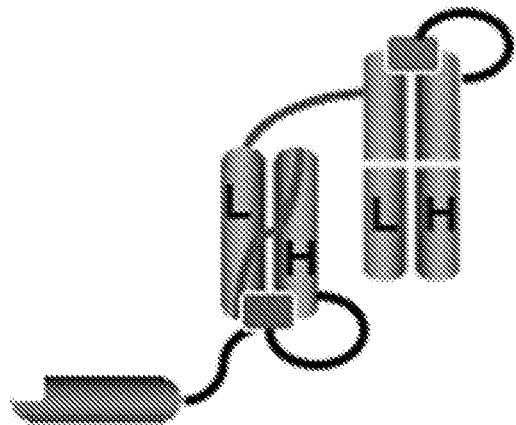
FIGS. 1A-1B illustrate polypeptide complexes of this disclosure.

Multispecific antibodies combine the benefits of different binding specificities derived from two or more antibodies into a single composition. Multispecific antibodies for redirecting T cells to cancers have shown promise in both pre-clinical and clinical studies. This approach relies on binding of one antigen interacting portion of the antibody to a tumor-associated antigen or marker, while a second antigen interacting portion can bind to an effector cell antigen on a T cell, such as CD3, which then triggers cytotoxic activity. One such tumor-associated antigen is epidermal growth factor receptor (EGFR). EGFR is a transmembrane protein that is a receptor for members of the epidermal growth factor family of extracellular protein ligands. EGFR is the most commonly overexpressed membrane protein in cancer. However, EGFR expression is not limited to tumors and is widely expressed throughout the body, resulting in systemic toxicities with EGFR-directed therapies.

T cell engagers (TCEs) therapeutics have several benefits including they are not cell therapies and thus can be offered as off-the-shelf therapies as opposed to chimeric antigen receptor T cell (CAR T cell) therapies. While TCE therapeutics have displayed potent anti-tumor activity in hematological cancers, developing TCEs to treat solid tumors has faced challenges due to the limitations of prior TCE technologies, namely (i) overactivation of the immune system leading to cytokine release syndrome (CRS), (ii) on-target, healthy tissue toxicities and (iii) poor pharmacokinetics (PK) leading to short half-life. CRS arises from the systemic activation of T cells and can result in life-threatening elevations in inflammatory cytokines such as interleukin-6 (IL-6). Severe and acute CRS leading to dose limited toxicities and deaths have been observed upon the dosing of T cell engagers develop using other platforms to treat cancer patients in poor clinical studies. This toxicity restricts the maximum blood levels of T cell engagers that can be safely dosed. T cell engager effectiveness has also been limited because of on-target, healthy tissue toxicity. T cell engagers developed using a platform not designed for tumor-specification activation have resulted in clinicals holds and dose-limiting toxicities resulting from target expression in healthy tissues. T cell engagers have also been limited by short half-lives. T cell engagers quickly reach sub-therapeutic levels after being administered as they are quickly eliminated from the body due to their short exposure half-lives. For this reason, T cell engagers such as blinatumomab are typically administered by a low-dose, continuous infusion pump over a period of weeks to overcome the challenge of a short half-life and to maintain therapeutic levels of drug in the body. A continuous dosing regimen represents a significant burden for patients.

To overcome these challenges associated with the effectiveness of T cell engagers, described herein, are polypeptide or polypeptide complexes that comprise binding domains that selectively bind to an effector cell antigen and EGFR, in which one or more of the binding domains is selectively activated in the tumor microenvironment and the isolated polypeptide or polypeptide complex comprises a half-life extending molecule. Such modifications reduce CRS and on-target healthy tissue toxicity risk, improves stability in the bloodstream and serum half-life prior to activation. The polypeptide or polypeptide complexes described herein have activity at low levels of target expression, and are easily manufactured.

In some embodiments, the polypeptides or polypeptide complexes described herein are used in a method of treating cancer. In some embodiments, the cancer has cells that express EGFR. In some embodiments, the polypeptides or polypeptide complexes described herein are used in a method of treating colorectal cancer (CRC), squamous cell carcinoma of the head and Neck (SCCHN), non-small cell lung cancer (NSCLC), prostate cancer, breast cancer, colon/rectum cancer, head and neck cancer, esophagogastric cancer, liver cancer, glioblastoma, cervical cancer, ovarian cancer, bladder cancer, kidney cancer, or pancreatic cancer. In some embodiments, the polypeptides or polypeptide complexes described herein are used in a method of treating subjects who are resistant to EGFR inhibitor treatment. In some embodiments, the polypeptides or polypeptide complexes described herein are used in a method of treating subjects who harbor KRAS mutations. In some embodiments, the polypeptides or polypeptide complexes described herein are used in a method of treating subjects who are resistant to EGFR inhibitor treatment and harbor KRAS mutations. In some embodiments, are methods of treating cancer comprising administering to a subject in need thereof an isolated polypeptide or polypeptide complex according to Formula I:

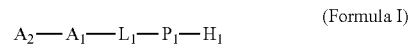
(Formula I)

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR).

Disclosed herein, in some embodiments, are polypeptides or polypeptide complexes according to Formula I:

$$A_2\text{—}A_1\text{—}L_1\text{—}P_1\text{—}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR).

Disclosed herein, in some embodiments, are polypeptides or polypeptide complexes according to Formula I:

$$A_2\text{—}A_1\text{—}L_1\text{—}P_1\text{—}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to epidermal growth factor receptor (EGFR).

Disclosed herein, in some embodiments, are polypeptides or polypeptide complexes comprising Formula I:

$$A_2\text{—}A_1\text{—}L_1\text{—}P_1\text{—}H_1 \quad \text{(Formula I)}$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR).

Disclosed herein, in some embodiments, are polypeptides or polypeptide complexes comprising Formula I:

$$A_2\text{—}A_1\text{—}L_1\text{—}P_1\text{—}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to epidermal growth factor receptor (EGFR).

Disclosed herein, in some embodiments, are polypeptides or polypeptide complexes according to Formula I:

$$A_2\text{—}A_1\text{—}L_1\text{—}P_1\text{—}H_1 \quad \text{(Formula I)}$$

wherein: $A_1$ comprises a first antigen recognizing molecule that binds to epidermal growth factor receptor (EGFR); $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to an effector cell antigen.

Disclosed herein, in some embodiments, are polypeptides or polypeptide complexes according to Formula I:

$$A_2\text{—}A_1\text{—}L_1\text{—}P_1\text{—}H_1 \quad \text{(Formula I)}$$

wherein: $A_1$ is a first antigen recognizing molecule that binds to epidermal growth factor receptor (EGFR); $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to effector cell antigen.

Disclosed herein, in some embodiments, are polypeptides or polypeptide complexes comprising Formula I:

$$A_2\text{—}A_1\text{—}L_1\text{—}P_1\text{—}H_1 \quad \text{(Formula I)}$$

wherein: $A_1$ comprises a first antigen recognizing molecule that binds to epidermal growth factor receptor (EGFR); $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to an effector cell antigen.

Disclosed herein, in some embodiments, are polypeptides or polypeptide complexes comprising Formula I:

$$A_2\text{—}A_1\text{—}L_1\text{—}P_1\text{—}H_1 \quad \text{(Formula I)}$$

wherein: $A_1$ is a first antigen recognizing molecule that binds epidermal growth factor receptor (EGFR); $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to an effector cell antigen.

Disclosed herein, in some embodiments, are polypeptides or polypeptide complexes according to Formula Ia:

$$P_2\text{—}L_2\text{—}A_2\text{—}A_1\text{—}L_1\text{—}P_1\text{—}H_1 \quad \text{(Formula Ia)}$$

wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Disclosed herein, in some embodiments, are polypeptides or polypeptide complexes according to Formula Ia:

$$P_2\text{—}L_2\text{—}A_2\text{—}A_1\text{—}L_1\text{—}P_1\text{—}H_1 \quad \text{(Formula Ia)}$$

wherein $A_2$ further comprises $P_2$ and $L_2$, wherein $P_2$ is a peptide that binds to $A_2$; and $L_2$ is a linking moiety that connects $A_2$ to $P_2$ and is a substrate for a tumor specific protease.

Disclosed herein, in some embodiments, are polypeptides or polypeptide complexes comprising Formula Ia:

$$P_2-L_2-A_2-A_1-L_1-P_1-H_1 \quad \text{(Formula Ia)}$$

wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Disclosed herein, in some embodiments, are polypeptides or polypeptide complexes comprising Formula Ia:

$$P_2-L_2-A_2-A_1-L_1-P_1-H_1 \quad \text{(Formula Ia)}$$

wherein $A_2$ further comprises $P_2$ and $L_2$, wherein $P_2$ is a peptide that binds to $A_2$; and $L_2$ is a linking moiety that connects $A_2$ to $P_2$ and is a substrate for a tumor specific protease.

Disclosed herein, in some embodiments, are polypeptides or polypeptide complexes according to Formula II:

$$L_{1a}-P_{1a}-H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are polypeptides or polypeptide complexes comprising Formula II:

$$L_{1a}-P_{1a}-H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are polypeptides or polypeptide complexes according to Formula II:

$$L_{1a}-P_{1a}-H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ is a peptide that binds to the first antigen recognizing molecule when $L_{1a}$ is uncleaved; and $H_{1a}$ is a half-life extending molecule.

Disclosed herein, in some embodiments, are polypeptides or polypeptide complexes comprising Formula II:

$$L_{1a}-P_{1a}-H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ is a peptide that binds to the first antigen recognizing molecule when $L_{1a}$ is uncleaved; and $H_{1a}$ is a half-life extending molecule.

First Antigen Recognizing Molecule ($A_1$)

Disclosed herein, in some embodiments, are polypeptides or polypeptide complexes, wherein the first antigen recognizing molecule binds to an effector cell antigen and the second antigen recognizing molecule binds to EGFR. In some embodiments, the effector cell antigen comprises CD3. In some embodiments, $A_1$ comprises a first antigen recognizing molecule that binds to an effector cell antigen.

In some embodiments, $A_1$ comprises an antibody or antibody fragment. In some embodiments, $A_1$ comprises an antibody or antibody fragment that is human or humanized. In some embodiments, $L_1$ is bound to N-terminus of the antibody or antibody fragment. In some embodiments, $L_1$ is bound to N-terminus of the antibody or antibody fragment and $A_2$ is bound to the other N-terminus of the antibody or antibody fragment. In some embodiments, $A_2$ is bound to C-terminus of the antibody or antibody fragment. In some embodiments, $L_1$ is bound to C-terminus of the antibody or antibody fragment and $A_2$ is bound to N-terminus of the antibody or antibody fragment. In some embodiments, the antibody or antibody fragment comprises a single chain variable fragment, a single domain antibody, or a Fab fragment. In some embodiments, $A_1$ is the single chain variable fragment (scFv). In some embodiments, the scFv comprises a scFv heavy chain polypeptide and a scFv light chain polypeptide. In some embodiments, $A_1$ is the single domain antibody. In some embodiments, $A_1$ comprises a variable light chain and variable heavy chain each of which is capable of specifically binding to human CD3. In some embodiments, the effector cell antigen comprises CD3. In some embodiments, $A_1$ comprises an anti-CD3ε single chain variable fragment. In some embodiments, $A_1$ comprises an anti-CD3ε single chain variable fragment that has a $K_D$ binding of 1 μM or less to CD3 on CD3 expressing cells. In some embodiments, $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

In some embodiments, $A_1$ comprises a first antigen recognizing molecule that binds EGFR. In some embodiments, $A_1$ comprises a variable light chain and variable heavy chain each of which is capable of specifically binding to human EGFR.

In some embodiments, the scFv that binds to CD3 comprises a scFv light chain variable domain and a scFv heavy chain variable domain. In some embodiments, the scFv heavy chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity). In some embodiments, the scFv light chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity).

In some embodiments, the scFv heavy chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity); and the scFv light chain variable domain comprises at least one, two, or three complementarity determining regions (CDR)s disclosed in Table 1 or a sequence substantially identical thereto (e.g., a sequence that has at least 90%, 95%, 96%, 97%, 98%, or 99% sequence identity).

TABLE 1 anti-CD3 amino acid sequences (CDRs as determined by IMGT numbering system)

| Construct Description | Amino Acid Sequence (N to C) | SEQ ID NO: |
|---|---|---|
| SP34.185 CD3: LC: CDR1 | TGAVTSGNY | 1 |
| SP34.185 CD3: LC: CDR2 | GTK | 2 |
| SP34.185 CD3: LC: CDR3 | VLWYSNRWV | 3 |
| SP34.185 CD3: HC: CDR1 | GFTFNKYA | 4 |
| SP34.185 CD3: HC: CDR2 | IRSKYNNYAT | 5 |
| SP34.185 CD3: HC: CDR3 | VRHGNFGNSYISYWAY | 6 |
| SP34.194 CD3: LC: CDR1 | TGAVTTSNY | 7 |
| SP34.194 CD3: LC: CDR2 | GTN | 8 |
| SP34.194 CD3: LC: CDR3 | ALWYSNLWV | 9 |
| SP34.194 CD3: HC: CDR1 | GFTFNTYA | 10 |
| SP34.194 CD3: HC: CDR2 | IRSKYNNYAT | 11 |
| SP34.194 CD3: HC: CDR3 | VRHGNFGNSYVSWFAY | 12 |
| SP34.185 scFv (VH-linker 1-VL) | EVQLVESGGGLVQPGGSLKLSCAASGFTFNKYAMNWVRQAPGKGLEWVARIRSKYNNYATYYADSVKDRFTISRDDSKNTAYLQMNNLKTEDTAVYYCVRHGNFGNSYISYWAYWGQGTLVTVSSGGGGSGGGGSGGGGSQTVVTQEPSLTVSPGGTVTLTCGSTGAVTSGNYPNWVQQKPGQAPRGLIGGTKFLAPGTPARFSGSLLGGKAALTLSGVQPEDEAEYYCVLWYSNRWVFGGGTKLTVL | 13 |
| SP34.194 scFv (VL-linker 1-VH) | QTVVTQEPSLTVSPGGTVTLTCRSSTGAVTTSNYANWVQQKPGQAPRGLIGGTNKRAPGTPARFSGSLLGGKAALTLSGVQPEDEAEYYCALWYSNLWVFGGGTKLTVLGGGGSGGGGSGGGGSEVQLVESGGGLVQPGGSLKLSCAASGFTFNTYAMNWVRQAPGKGLEWVARIRSKYNNYATYYADSVKDRFTISRDDSKNTAYLQMNNLKTEDTAVYYCVRHGNFGNSYVSWFAYWGQGTLVTVSS | 14 |

In some embodiments, the scFv light chain variable domain comprises complementarity determining regions (CDRs): LC-CDR1, LC-CDR2, and LC-CDR3, wherein the LC-CDR1, the LC-CDR2, and the LC-CDR3 of the scFv light chain variable domain comprise: LC-CDR1: SEQ ID NO: 1, LC-CDR2: SEQ ID NO: 2, and LC-CDR3: SEQ ID NO: 3, and wherein the CDRs comprise from 0-2 amino acid modifications in at least one of the LC-CDR1, LC-CDR2, or LC-CDR3. In some embodiments, the scFv light chain variable domain comprises complementarity determining regions (CDRs): LC-CDR1, LC-CDR2, and LC-CDR3, wherein the LC-CDR1, the LC-CDR2, and the LC-CDR3 of the scFv light chain variable domain comprise: LC-CDR1: SEQ ID NO: 7, LC-CDR2: SEQ ID NO: 8, and LC-CDR3: SEQ ID NO: 9, and wherein the CDRs comprise from 0-2 amino acid modifications in at least one of the LC-CDR1, LC-CDR2, or LC-CDR3. In some embodiments, the scFv heavy chain variable domain comprises complementarity determining regions (CDRs): HC-CDR1, HC-CDR2, and HC-CDR3, wherein the HC-CDR1, the HC-CDR2, and the HC-CDR3 of the scFv heavy chain variable domain comprise: HC-CDR1: SEQ ID NO: 4, HC-CDR2: SEQ ID NO: 5, and HC-CDR3: SEQ ID NO: 6, and wherein the CDRs comprise from 0-2 amino acid modifications in at least one of the HC-CDR1, HC-CDR2, or HC-CDR3. In some embodiments, the scFv heavy chain variable domain comprises complementarity determining regions (CDRs): HC-CDR1, HC-CDR2, and HC-CDR3, wherein the HC-CDR1, the HC-CDR2, and the HC-CDR3 of the scFv heavy chain variable domain comprise: HC-CDR1: SEQ ID NO: 10, HC-CDR2: SEQ ID NO: 11, and HC-CDR3: SEQ ID NO: 12, and wherein the CDRs comprise from 0-2 amino acid modifications in at least one of the HC-CDR1, HC-CDR2, or HC-CDR3.

In some embodiments, the isolated polypeptide or polypeptide complex of Formula I binds to an effector cell when $L_1$ is cleaved by the tumor specific protease. In some embodiments, the isolated polypeptide or polypeptide complex of Formula I binds to an effector cell when $L_1$ is cleaved by the tumor specific protease and $A_1$ binds to the effector cell. In some embodiments, the effector cell is a T cell. In some embodiments, $A_1$ binds to a polypeptide that is part of a TCR-CD3 complex on the effector cell. In some embodiments, the polypeptide that is part of the TCR-CD3 complex is human CD3R. In some embodiments, the effector cell antigen comprises CD3, wherein the effector cell antigen comprises CD3, wherein the scFv comprises CDRs: LC-CDR1, LC-CDR2, and LC-CDR3, wherein the LC-CDR1, the LC-CDR2, and the LC-CDR3 of the scFv LC-CDR1: SEQ ID NO: 1, LC-CDR2: SEQ ID NO: 2, and LC-CDR3: SEQ ID NO: 3; and the scFv comprises complementarity determining regions (CDRs): HC-CDR1, HC-CDR2, and HC-CDR3, wherein the HC-CDR1, the HC-CDR2, and the HC-CDR3 of the scFv: HC-CDR1: SEQ ID NO: 4, HC-CDR2: SEQ ID NO: 5, and HC-CDR3: SEQ ID NO: 6. In some embodiments, the effector cell antigen comprises CD3, and the scFv comprises an amino acid sequence according to SEQ ID NO: 13. In some embodiments, the effector cell antigen comprises CD3, wherein the effector cell antigen comprises CD3, wherein the scFv comprises CDRs: LC-CDR1, LC-CDR2, and LC-CDR3, wherein the LC-CDR1, the LC-CDR2, and the LC-CDR3 of the scFv LC-CDR1: SEQ ID NO: 7, LC-CDR2: SEQ ID NO: 8, and LC-CDR3: SEQ ID NO: 9; and the scFv comprises complementarity determining regions (CDRs): HC-CDR1, HC-CDR2, and HC-CDR3, wherein the HC-CDR1, the HC-CDR2, and the HC-CDR3 of the scFv: HC-CDR1: SEQ ID NO: 10, HC-CDR2: SEQ ID NO: 11, and HC-CDR3: SEQ ID NO: 12. In some embodiments, the effector cell antigen comprises CD3, and the scFv comprises an amino acid sequence according to SEQ ID NO: 14.

In some embodiments, the effector cell antigen comprises CD3, and $A_1$ comprises CDRs: LC-CDR1, LC-CDR2, and LC-CDR3, wherein the LC-CDR1, the LC-CDR2, and the LC-CDR3 of $A_1$ comprise LC-CDR1: SEQ ID NO: 1, LC-CDR2: SEQ ID NO: 2, and LC-CDR3: SEQ ID NO: 3; and $A_1$ comprises complementarity determining regions (CDRs): HC-CDR1, HC-CDR2, and HC-CDR3, wherein the HC-CDR1, the HC-CDR2, and the HC-CDR3 of $A_1$ comprise: HC-CDR1: SEQ ID NO: 4, HC-CDR2: SEQ ID NO: 5, and HC-CDR3: SEQ ID NO: 6.

In some embodiments, the effector cell antigen comprises CD3, and $A_1$ comprises CDRs: LC-CDR1, LC-CDR2, and LC-CDR3, wherein the LC-CDR1, the LC-CDR2, and the LC-CDR3 of $A_1$ comprise: LC-CDR1: SEQ ID NO: 7, LC-CDR2: SEQ ID NO: 8, and LC-CDR3: SEQ ID NO: 9; and $A_1$ comprises complementarity determining regions (CDRs): HC-CDR1, HC-CDR2, and HC-CDR3, wherein the HC-CDR1, the HC-CDR2, and the HC-CDR3 of $A_1$ comprise: HC-CDR1: SEQ ID NO: 10, HC-CDR2: SEQ ID NO: 11, and HC-CDR3: SEQ ID NO: 12.

In some embodiments, $A_1$ comprises an amino acid sequence according to SEQ ID NO: 13. In some embodiments, $A_1$ comprises an amino acid sequence that has at least 80% sequence identity to SEQ ID NO: 13. In some embodiments, $A_1$ comprises an amino acid sequence that has at least 85% sequence identity to SEQ ID NO: 13. In some embodiments, $A_1$ comprises an amino acid sequence that has at least 90% sequence identity to SEQ ID NO: 13. In some embodiments, $A_1$ comprises an amino acid sequence that has at least 95% sequence identity to SEQ ID NO: 13. In some embodiments, $A_1$ comprises an amino acid sequence that has at least 99% sequence identity to SEQ ID NO: 13.

In some embodiments, $A_1$ comprises an amino acid sequence according to SEQ ID NO: 14. In some embodiments, $A_1$ comprises an amino acid sequence that has at least 80% sequence identity to SEQ ID NO: 14. In some embodiments, $A_1$ comprises an amino acid sequence that has at least 85% sequence identity to SEQ ID NO: 14. In some embodiments, $A_1$ comprises an amino acid sequence that has at least 90% sequence identity to SEQ ID NO: 14. In some embodiments, $A_1$ comprises an amino acid sequence that has at least 95% sequence identity to SEQ ID NO: 14. In some embodiments, $A_1$ comprises an amino acid sequence that has at least 99% sequence identity to SEQ ID NO: 14.

In some embodiments, the isolated polypeptide or polypeptide complex has weaker binding affinity for the tumor cell antigen as compared to the binding affinity for the tumor cell antigen of an isolated polypeptide or polypeptide complex that does not have $P_1$ or $L_1$. In some embodiments, the isolated polypeptide or polypeptide complex has weaker binding affinity for the tumor cell antigen that is at least 5× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 8× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 10× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 15× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 20× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 25× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 30× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 35× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 40× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 45× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 50× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 55× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 60× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 65× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 70× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 75× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 80× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 85× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 90× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 95× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 100× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 120× higher than the binding affinity for the tumor cell antigen of a form of the isolated polypeptide or polypeptide complex that does not have $P_1$ or $L_1$. In some embodiments, the isolated polypeptide or polypeptide complex has weaker binding affinity for the tumor cell antigen that is at least 1000× higher than the binding affinity for the tumor cell antigen of a form of the isolated polypeptide or polypeptide complex that does not have $P_1$ or $L_1$.

In some embodiments, the isolated polypeptide or polypeptide complex has weaker binding affinity for the tumor cell antigen as compared to the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 5× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 8× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 10× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 15× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 20× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 25× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 30× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 35× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 40× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 45× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 50× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 55× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 60× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 65× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 70× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 75× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 80× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 85× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 90× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 95× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 100× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 120× higher than the binding affinity for the tumor cell antigen of the isolated polypeptide or polypeptide complex in which $L_1$ has been cleaved by the tumor specific protease. In some embodiments, the isolated polypeptide or polypeptide complex has weaker binding affinity for the tumor cell antigen that is at least 1000× higher than the binding affinity for the tumor cell antigen of the isolated polypeptide or polypeptide complex in which $L_1$ has been cleaved by the tumor specific protease.

In some embodiments, the isolated polypeptide or polypeptide complex has an increased $EC_{50}$ in an IFNγ release T-cell activation assay as compared to the $EC_{50}$ in an IFNγ release T-cell activation assay of an isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 10× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 20× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 30× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 40× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 50× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 60× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 70× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 80× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 90× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 100× higher than the $EC_{50}$ in an IFNγ release T-cell activation assay of a form of the isolated polypeptide or polypeptide complex that does not have $P_1$ or $L_1$. In some embodiments, the isolated polypeptide or polypeptide complex has an increased $EC_{50}$ in an IFNγ release T-cell activation assay that is at least 1000× higher than the $EC_{50}$ in an IFNγ release T-cell activation assay of a form of the isolated polypeptide or polypeptide complex that does not have $P_1$ or $L_1$.

In some embodiments, the isolated polypeptide or polypeptide complex has an increased $EC_{50}$ in an IFNγ release T-cell activation assay as compared to the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 10× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 20× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 30× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 40× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 50× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 60× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 70× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 80× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 90× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 100× higher than the $EC_{50}$ in an IFNγ release T-cell activation assay of the isolated polypeptide or polypeptide complex in which $L_1$ has been cleaved by the tumor specific protease. In some embodiments, the isolated polypeptide or polypeptide complex has an increased $EC_{50}$ in an IFNγ release T-cell activation assay that is at least 1000× higher than the $EC_{50}$ in an IFNγ release T-cell activation assay of the isolated polypeptide or polypeptide complex in which $L_1$ has been cleaved by the tumor specific protease.

In some embodiments, the isolated polypeptide or polypeptide complex has an increased $EC_{50}$ in a T-cell cytolysis assay as compared to the $EC_{50}$ in a T-cell cytolysis assay of an isolated polypeptide or polypeptide complex that does not have $P_1$ or $L_1$. In some embodiments, the isolated polypeptide or polypeptide complex has an increased $EC_{50}$ in a T-cell cytolysis assay that is at least 10× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 20× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 30× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 40× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 50× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 60× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 70× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 80× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 90× higher than the $EC_{50}$ in a T-cell cytolysis assay of a form of the isolated polypeptide or polypeptide complex that does not have $P_1$ or $L_1$. In some embodiments, the isolated polypeptide or polypeptide complex has an increased $EC_{50}$ in a T-cell cytolysis assay that is at least 100× higher than the $EC_{50}$ in a T-cell cytolysis assay of an isolated polypeptide or polypeptide complex that does not have $P_1$ or $L_1$. In some embodiments, the isolated polypeptide or polypeptide complex has an increased $EC_{50}$ in a T-cell cytolysis assay that is at least 1000× higher than the $EC_{50}$ in a T-cell cytolysis assay of an isolated polypeptide or polypeptide complex that does not have $P_1$ or $L_1$.

In some embodiments, the isolated polypeptide or polypeptide complex has an increased $EC_{50}$ in a T-cell cytolysis assay as compared to the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 10× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 20× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 30× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 40× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 50× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 60× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 70× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 80× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 90× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 100× higher than the $EC_{50}$ in a T-cell cytolysis assay of the isolated polypeptide or polypeptide complex in which $L_1$ has been cleaved by the tumor specific protease. In some embodiments, the isolated polypeptide or polypeptide complex has an increased $EC_{50}$ in a T-cell cytolysis assay that is at least 1,000× higher than the $EC_{50}$ in a T-cell cytolysis assay of the isolated polypeptide or polypeptide complex in which $L_1$ has been cleaved by the tumor specific protease.

In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen as compared to the binding affinity for the tumor cell antigen of an isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 10× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 50× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ta) has weaker binding affinity for the tumor cell antigen that is at least 75× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 100× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 120× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 200× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 300× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 400× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 500× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 600× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 700× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 800× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 900× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 1000× higher than the binding affinity for the tumor cell antigen of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ta) has weaker binding affinity for the tumor cell antigen that is at least 10,000× higher than the binding affinity for the tumor cell antigen of a form of the isolated polypeptide or polypeptide complex of Formula Ia that does not have $P_1$, $L_1$, $P_2$, or $L_2$.

In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen as compared to the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$(Formula Ia) has weaker binding affinity for the tumor cell antigen that is at least 10× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 50× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 75× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 100× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 120× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 200× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 300× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 400× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 500× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 600× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 700× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 800× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 900× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 1000× higher than the binding affinity for the tumor cell antigen of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has weaker binding affinity for the tumor cell antigen that is at least 10,000× higher than the binding affinity for the tumor cell antigen of the isolated polypeptide or polypeptide complex of Formula Ia in which $L_1$ and $L_2$ have been cleaved by the tumor specific proteases.

In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay as compared to the $EC_{50}$ in an IFNγ release T-cell activation assay of an isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$(Formula Ia) has an increased $EC_{50}$ in an IFNγ release T-cell activation assay that is at least 10× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 50× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 75× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$(Formula Ia) has an increased $EC_{50}$ in an IFNγ release T-cell activation assay that is at least 100× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$(Formula Ia) has an increased $EC_{50}$ in an IFNγ release T-cell activation assay that is at least 200× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 300× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 400× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 500× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 600× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 700× higher than the $EC_{50}$ in an IFNγ release T-cell activation assay of a form of the isolated polypeptide or polypeptide complex of Formula Ia that does not $P_1$, $L_1$, $P_2$, or $L_2$. In some embodiments, the isolated polypeptide or polypeptide complex $P_2$-$L_2$-$A_2$-$A_1$-$L_1$-$P_1$—$H_j$(Formula Ia) has an increased $EC_{50}$ in an IFNγ release T-cell activation assay that is at least 800× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 900× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 1000× higher than the $EC_{50}$ in an IFNγ release T-cell activation assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in an IFNγ release T-cell activation assay that is at least 10,000× higher than the $EC_{50}$ in an IFNγ release T-cell activation assay of a form of the isolated polypeptide or polypeptide complex of Formula Ia that does not have $P_1$, $L_1$, $P_2$, or $L_2$.

In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay as compared to the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10× higher than the $EC_{50}$ in a T-cell cytolysis assay of the isolated polypeptide or polypeptide complex of Formula Ia in which $L_1$ and $L_2$ have been cleaved by the tumor specific proteases, some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 50× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 75× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 100× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 200× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 300× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 400× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—H1 (Formula Ia) has an increased $EC_{50}$ in a T-cell cytolysis assay that is at least 500× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 600× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ta) has an increased $EC_{50}$ in a T-cell cytolysis assay that is at least 700× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 800× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 900× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 1000× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10,000× higher than the $EC_{50}$ in a T-cell cytolysis assay of the isolated polypeptide or polypeptide complex of Formula Ia in which $L_1$ and $L_2$ have been cleaved by the tumor specific proteases.

In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay as compared to the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10× higher than the $EC_{50}$ in a T-cell cytolysis assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 50× higher than the $EC_{50}$ in a T-cell cytolysis assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 75× higher than the $EC_{50}$ in a T-cell cytolysis assay of a form of the isolated polypeptide or polypeptide complex of Formula Ia that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 100× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 200× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 300× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 400× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 500× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ta) has an increased $EC_0$ in a T-cell cytolysis assay that is at least 600× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_0$ in a T-cell cytolysis assay that is at least 700× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 800× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 900× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 1000× higher than the $EC_{50}$ in a T-cell cytolysis assay of an isolated polypeptide or polypeptide complex that does not have $P_1$, $L_1$, $P_2$, or $L_2$. In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay that is at least 10,000× higher than the $EC_{50}$ in a T-cell cytolysis assay of an isolated polypeptide or polypeptide complex that does not have $P_1$, $L_1$, $P_2$, or $L_2$.

In some embodiments, the isolated polypeptide or polypeptide complex $P_2$-$L_2$-$A_2$-$A_1$-$L_1$-$P_1$—$H_1$ (Formula Ia) has an increased $EC_{50}$ in a T-cell cytolysis assay as compared to the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 10× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 50× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 75× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 100× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 200× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 300× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 400× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 500× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 600× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 700× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 800× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 900× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 1000× higher than the $EC_{50}$ in a T-cell cytolysis assay of the isolated polypeptide or polypeptide complex of Formula Ia in which $L_1$ and $L_2$ have been cleaved by the tumor specific proteases. In some embodiments, the isolated polypeptide or polypeptide complex $P_2\text{-}L_2\text{-}A_2\text{-}A_1\text{-}L_1\text{-}P_1\text{—}H_1$ (Formula Ia) has an increased $EC_{50}$ in a T-cell cytolysis assay that is at least 10,000× higher than the $EC_{50}$ in a T-cell cytolysis assay of the isolated polypeptide or polypeptide complex of Formula Ia in which $L_1$ and $L_2$ have been cleaved by the tumor specific proteases.

Second Antigen Recognizing Molecule ($A_2$)

In some embodiments, $A_2$ comprises an antibody or antibody fragment. In some embodiments, the antibody or antibody fragment thereof comprises a single chain variable fragment, a single domain antibody, a Fab, or a Fab'. In some embodiments, the antibody or antibody fragment thereof comprises a single chain variable fragment (scFv), a heavy chain variable domain (VH domain), a light chain variable domain (VL domain), a variable domain (VHH) of a camelid derived single domain antibody. In some embodiments, the antibody or antibody fragment thereof is humanized or human. In some embodiments, $A_2$ is the Fab or Fab'. In some embodiments, the Fab or Fab' comprises (a) a Fab light chain polypeptide and (b) a Fab heavy chain polypeptide. In some embodiments, the antibody or antibody fragment thereof comprises a EGFR binding domain.

In some embodiments, the antigen binding fragment (Fab) or Fab' that binds to EGFR comprises a Fab light chain polypeptide chain and a Fab heavy chain polypeptide. In some embodiments, the Fab light chain polypeptide comprises a Fab light chain variable domain. In some embodiments, the Fab heavy chain polypeptide comprises a Fab heavy chain variable domain. In some embodiments, the Fab heavy chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity). In some embodiments, the Fab light chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity).

In some embodiments, the Fab heavy chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity); and the Fab light chain variable domain comprises at least one, two, or three complementarity determining regions (CDR)s disclosed in Table 2 or a sequence substantially identical thereto (e.g., a sequence that has at least 90%, 95%, 96%, 97%, 98%, or 99% sequence identity).

TABLE 2 anti-EGFR amino acid sequences (as determined by IMGT numbering system)

| Construct Description | Amino Acid Sequence (N to C) | SEQ ID NO: |
|---|---|---|
| EGFR: LC: CDR1 | QSIGTN | 15 |
| EGFR: LC: CDR2 | YAS | 16 |
| EGFR: LC: CDR3 | QQNNNWPTT | 17 |
| EGFR: HC: CDR1 | GFSLTNYG | 18 |
| EGFR: HC: CDR2 | IWSGGNT | 19 |
| EGFR: HC: CDR3 | ARALTYYDYEFAY | 20 |
| EGFR Fab LC v1 | QILLTQSPVILSVSPGERVSFSCRASQSIGTNIHW YQQRTNGSPRLLIKYASESISGIPSRFSGSGSGTD FTLSINSVESEDIADYYCQQNNNWPTTFGAGTK LELKRTVAAPSVFIFPPSDEQLKSGTASVVCLLN NFYPREAKVQWKVDNALQSGNSQESVTEQDSK DSTYSLSSTLTLSKADYEKHKVYACEVTHQGLS SPVTKSFNRGEC | 21 |
| EGFR Fab LC v2 | DILLTQSPVILSVSPGERVSFSCRASQSIGTNIHW YQQRTNGSPRLLIKYASESISGIPSRFSGSGSGTD FTLSINSVESEDIADYYCQQNNNWPTTFGAGTK LELKRTVAAPSVFIFPPSDEQLKSGTASVVCLLN NFYPREAKVQWKVDNALQSGNSQESVTEQDSK DSTYSLSSTLTLSKADYEKHKVYACEVTHQGLS SPVTKSFNRGEC | 22 |
| EGFR Fab HC | QVQLKQSGPGLVQPSQSLSITCTVSGFSLTNYG VHWVRQSPGKGLEWLGVIWSGGNTDYNTPFT SRLSINKDNSKSQVFFKMNSLQSNDTAIYYCAR ALTYYDYEFAYWGQGTLVTVSAASTKGPSVFP LAPSSKSTSGGTAALGCLVKDYFPEPVTVSWNS GALTSGVHTFPAVLQSSGLYSLSSVVTVPSSSLG TQTYICNVNHKPSNTKVDKKVEPKSC | 23 |
| EGFR Fab HC (N88Q) | QVQLKQSGPGLVQPSQSLSITCTVSGFSLTNYG VHWVRQSPGKGLEWLGVIWSGGNTDYNTPFT SRLSINKDNSKSQVFFKMNSLQSQDTAIYYCAR ALTYYDYEFAYWGQGTLVTVSAASTKGPSVFP LAPSSKSTSGGTAALGCLVKDYFPEPVTVSWNS GALTSGVHTFPAVLQSSGLYSLSSVVTVPSSSLG TQTYICNVNHKPSNTKVDKKVEPKSC | 24 |

In some embodiments, the Fab comprises complementarity determining regions (CDRs): LC-CDR1, LC-CDR2, and LC-CDR3, wherein the LC-CDR1, the LC-CDR2, and the LC-CDR3 of the Fab comprise LC-CDR1: SEQ ID NO: 15, LC-CDR2: SEQ ID NO:16, and LC-CDR3: SEQ ID NO: 17; and the Fab comprises CDRs: HC-CDR1, HC-CDR2, and HC-CDR3, wherein the HC-CDR1, the HC-CDR2, and the HC-CDR3 of the Fab comprise: HC-CDR1: SEQ ID NO: 18, HC-CDR2: SEQ ID NO: 19, and HC-CDR3: SEQ ID NO: 20. In some embodiments, the Fab comprises complementarity determining regions (CDRs): LC-CDR1, LC-CDR2, and LC-CDR3, wherein the LC-CDR1, the LC-CDR2, and the LC-CDR3 of the Fab comprise LC-CDR1: SEQ ID NO: 15, LC-CDR2: SEQ ID NO:16, and LC-CDR3: SEQ ID NO: 17 and wherein the CDRs comprise from 0-2 amino acid modifications in at least one of the HC-CDR1, HC-CDR2, or HC-CDR3; and the Fab comprises CDRs: HC-CDR1, HC-CDR2, and HC-CDR3, wherein the HC-CDR1, the HC-CDR2, and the HC-CDR3 of the Fab comprise: HC-CDR1: SEQ ID NO: 18, HC-CDR2: SEQ ID NO: 19, and HC-CDR3: SEQ ID NO: 20 and wherein the CDRs comprise from 0-2 amino acid modifications in at least one of the LC-CDR1, LC-CDR2, or LC-CDR3.

In some embodiments, $A_2$ comprises CDRs: LC-CDR1, LC-CDR2, and LC-CDR3, wherein the LC-CDR1, the LC-CDR2, and the LC-CDR3 of $A_2$ comprise LC-CDR1: SEQ ID NO: 15, LC-CDR2: SEQ ID NO: 16, and LC-CDR3: SEQ ID NO: 17; and $A_2$ comprises complementarity determining regions (CDRs): HC-CDR1, HC-CDR2, and HC-CDR3, wherein the HC-CDR1, the HC-CDR2, and the HC-CDR3 of $A_2$ comprise: HC-CDR1: SEQ ID NO: 18, HC-CDR2: SEQ ID NO: 19, and HC-CDR3: SEQ ID NO: 20.

In some embodiments, the Fab light chain polypeptide comprises the amino acid sequence according to SEQ ID NO: 21. In some embodiments, the Fab light chain polypeptide comprises an amino acid sequence that has at least 80% sequence identity according to SEQ ID NO: 21. In some embodiments, the Fab light chain polypeptide comprises an amino acid sequence that has at least 85% sequence identity according to SEQ ID NO: 21. In some embodiments, the Fab light chain polypeptide comprises an amino acid sequence that has at least 90% sequence identity according to SEQ ID NO: 21. In some embodiments, the Fab light chain polypeptide comprises an amino acid sequence that has at least 95% sequence identity according to SEQ ID NO: 21. In some embodiments, the Fab light chain polypeptide comprises an amino acid sequence that has at least 99% sequence identity according to SEQ ID NO: 21.

In some embodiments, the Fab light chain polypeptide comprises the amino acid sequence according to SEQ ID NO: 22. In some embodiments, the Fab light chain polypeptide comprises an amino acid sequence that has at least 80% sequence identity according to SEQ ID NO: 22. In some embodiments, the Fab light chain polypeptide comprises an amino acid sequence that has at least 85% sequence identity according to SEQ ID NO: 22. In some embodiments, the Fab light chain polypeptide comprises an amino acid sequence that has at least 90% sequence identity according to SEQ ID NO: 22. In some embodiments, the Fab light chain polypeptide comprises an amino acid sequence that has at least 95% sequence identity according to SEQ ID NO: 22. In some embodiments, the Fab light chain polypeptide comprises an amino acid sequence that has at least 99% sequence identity according to SEQ ID NO: 22.

In some embodiments, the Fab heavy chain polypeptide comprises the amino acid sequence according to SEQ ID NO: 23. In some embodiments, the Fab light chain polypeptide comprises an amino acid sequence that has at least 80% sequence identity according to SEQ ID NO: 23. In some embodiments, the Fab light chain polypeptide comprises an amino acid sequence that has at least 85% sequence identity according to SEQ ID NO: 23. In some embodiments, the Fab light chain polypeptide comprises an amino acid sequence that has at least 90% sequence identity according to SEQ ID NO: 23. In some embodiments, the Fab light chain polypeptide comprises an amino acid sequence that has at least 95% sequence identity according to SEQ ID NO: 23. In some embodiments, the Fab light chain polypeptide comprises an amino acid sequence that has at least 99% sequence identity according to SEQ ID NO: 23.

In some embodiments, the Fab heavy chain polypeptide comprises the amino acid sequence according to SEQ ID NO: 24. In some embodiments, the Fab light chain polypeptide comprises an amino acid sequence that has at least 80% sequence identity according to SEQ ID NO: 24. In some embodiments, the Fab light chain polypeptide comprises an amino acid sequence that has at least 85% sequence identity according to SEQ ID NO: 24. In some embodiments, the Fab light chain polypeptide comprises an amino acid sequence that has at least 90% sequence identity according to SEQ ID NO: 24. In some embodiments, the Fab light chain polypeptide comprises an amino acid sequence that has at least 95% sequence identity according to SEQ ID NO: 24. In some embodiments, the Fab light chain polypeptide comprises an amino acid sequence that has at least 99% sequence identity according to SEQ ID NO: 24.

In some embodiments, the Fab light chain polypeptide of $A_2$ is bound to a C-terminus of the single chain variable fragment (scFv) of $A_1$. In some embodiments, the Fab heavy chain polypeptide of $A_2$ is bound to a C-terminus of the single chain variable fragment (scFv) $A_1$. In some embodiments, the Fab light chain polypeptide of $A_2$ is bound to a N-terminus of the single chain variable fragment (scFv) of $A_1$. In some embodiments, the Fab heavy chain polypeptide of $A_2$ is bound to a N-terminus of the single chain variable fragment (scFv) $A_1$. In some embodiments, the Fab heavy chain polypeptide of $A_2$ is bound to the scFv heavy chain polypeptide of $A_1$. In some embodiments, Fab light chain polypeptide of $A_2$ is bound to the scFv heavy chain polypeptide of $A_1$. In some embodiments, the Fab heavy chain polypeptide of $A_2$ is bound to the scFv light chain polypeptide of $A_1$. In some embodiments, the Fab light chain polypeptide of $A_2$ is bound to the scFv light chain polypeptide of $A_1$.

In some embodiments, $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease. In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$.

In some embodiments, the Fab heavy chain polypeptide of $A_2$ is bound to the scFv heavy chain polypeptide of $A_1$ and $L_2$ is bound to the Fab light chain polypeptide of $A_2$. In some embodiments, the Fab light chain polypeptide of $A_2$ is bound to the scFv heavy chain polypeptide of $A_1$ and $L_2$ is bound to the Fab heavy chain polypeptide of $A_2$. In some embodiments, the Fab heavy chain polypeptide of $A_2$ is bound to the scFv light chain polypeptide of $A_1$ and $L_2$ is bound to the Fab light chain polypeptide of $A_2$. In some embodiments, the Fab light chain polypeptide of $A_2$ is bound to the scFv light chain polypeptide of $A_1$ and $L_2$ is bound to the Fab heavy chain polypeptide of $A_2$.

Peptide ($P_1$ and $P_2$ and $P_{1a}$)

In some embodiments, $P_1$, $P_2$, or $P_{1a}$ comprises a sequence as disclosed in Table 3 or a sequence substantially identical thereto (e.g., a sequence that has 0, 1, or 2 amino acid modifications).

TABLE 3

$P_1$ and $P_2$ and $P_{1a}$ Sequences

| Peptide | Amino Acid Sequence (N to C) | SEQ ID NO: |
|---|---|---|
| SP34.185 scFv mask | VYCGPEFDESVGCM | 25 |
| EGFR Fab mask | PCRSHIDVAKPICV | 26 |
| SP34.194 scFv mask | GYLWGCEWNCAGITT | 70 |

In some embodiments, $P_1$ impairs binding of $A_1$ to a first target antigen. In some embodiments, $P_1$ impairs binding of $A_1$ to the effector cell antigen. In some embodiments, $P_1$ is bound to $A_1$ through ionic interactions, electrostatic interactions, hydrophobic interactions, Pi-stacking interactions, and H-bonding interactions, or a combination thereof. In some embodiments, $P_1$ is bound to $A_1$ at or near an antigen binding site. In some embodiments, $P_1$ becomes unbound from $A_1$ when $L_1$ is cleaved by the tumor specific protease thereby exposing $A_1$ to the effector cell antigen. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $P_1$ has less than 70% sequence identity to the effector cell antigen. In some embodiments, $P_1$ has less than 75% sequence identity to the effector cell antigen. In some embodiments, $P_1$ has less than 80% sequence identity to the effector cell antigen. In some embodiments, $P_1$ has less than 85% sequence identity to the effector cell antigen. In some embodiments, $P_1$ has less than 90% sequence identity to the effector cell antigen. In some embodiments, $P_1$ has less than 95% sequence identity to the effector cell antigen. In some embodiments, $P_1$ has less than 98% sequence identity to the effector cell antigen. In some embodiments, $P_1$ has less than 99% sequence identity to the effector cell antigen. In some embodiments, $P_1$ comprises a de novo amino acid sequence that shares less than 10% sequence identity to the effector cell antigen. In some embodiments, $P_1$ comprises an amino acid sequence according to SEQ ID NO: 25.

In some embodiments, $A_1$ comprises a first antigen recognizing molecule that comprises an antibody or antibody binding fragment that binds to CD3. In some embodiments, $P_1$ comprises an amino acid sequence according to any one of SEQ ID NOs: 25, 797-835, or 843-1690 or an amino acid sequence that has 1, 2, or 3 amino acid mutations, substitutions, or deletions relative to any one of SEQ ID NOs: 25, 797-835, or 843-1690.

In some embodiments, $P_1$ comprises an amino acid sequence according to $Z_1$—$Z_2$—C—$Z_4$—P—$Z_6$—$Z_7$—$Z_8$—$Z_9$—$Z_{10}$—$Z_{11}$—$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S. In some embodiments, $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_8$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; and $Z_{14}$ is selected from D, Y, N, F, I, and P. In some embodiments, $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N. In some embodiments, $P_1$ comprises an amino acid sequence according to $U_1$—$U_2$—C—$U_4$—P—$U_6$—$U_7$—$U_8$—$U_9$—$U_{10}$—$U_{11}$—$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S. In some embodiments, $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P. In some embodiments, $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

In some embodiments, $P_1$ comprises the amino acid sequences according to any one of SEQ ID NOs: 797-823.

In some embodiments, $P_1$ comprises an amino acid sequences according to any one of SEQ ID NOs: 25, 824-835 and 843-1690.

In some embodiments, $P_1$ comprises the amino acid sequences according to any of SEQ ID NOs: 824-835.

In some embodiments, $P_1$ comprises the amino acid sequence according to SEQ ID NO: 810 or an amino acid sequence that has 1, 2, or 3, amino acid substitutions, additions, or deletions relative to the amino acid sequence of SEQ ID NO: 810.

In some embodiments, $P_1$ comprises the amino acid sequence according to SEQ ID NO: 811 or an amino acid sequence that has 1, 2, or 3, amino acid substitutions, additions, or deletions relative to the amino acid sequence of SEQ ID NO: 811.

In some embodiments, $P_1$ comprises the amino acid sequence according to SEQ ID NO: 834 or an amino acid sequence that has 1, 2, or 3, amino acid substitutions, additions, or deletions relative to the amino acid sequence of SEQ ID NO: 834.

In some embodiments, $P_1$ comprises the amino acid sequence according to SEQ ID NO: 810.

In some embodiments, $P_1$ comprises the amino acid sequence according to SEQ ID NO: 811.

In some embodiments, $P_1$ comprises the amino acid sequence according to SEQ ID NO: 834.

In some embodiments, $P_2$ impairs binding of $A_2$ to the second target antigen. In some embodiments, wherein $P_2$ impairs binding of $A_2$ to EGFR. In some embodiments, $P_2$ is bound to $A_2$ through ionic interactions, electrostatic interactions, hydrophobic interactions, Pi-stacking interactions, and H-bonding interactions, or a combination thereof. In some embodiments, $P_2$ is bound to $A_2$ at or near an antigen binding site. In some embodiments, $P_2$ becomes unbound from $A_2$ when $L_2$ is cleaved by the tumor specific protease thereby exposing $A_2$ to the EGFR. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $P_2$ has less than 70% sequence identity to the EGFR. In some embodiments, $P_2$ has less than 75% sequence identity to the EGFR. In some embodiments, $P_2$ has less than 80% sequence identity to the EGFR. In some embodiments, $P_2$ has less than 85% sequence identity to the EGFR. In some embodiments, $P_2$ has less than 90% sequence identity to the EGFR. In some embodiments, $P_2$ has less than 95% sequence identity to the EGFR. In some embodiments, $P_2$ has less than 98% sequence identity to the EGFR. In some embodiments, $P_2$ has less than 99% sequence identity to the EGFR. In some embodiments, $P_2$ comprises a de novo amino acid sequence that shares less than 10% sequence identity to the EGFR. In some embodiments, $P_2$ comprises an amino acid sequence according to SEQ ID NO: 26. In some embodiments, $P_2$ comprises an amino acid sequence according to SEQ ID NO: 115. In some embodiments, $P_2$ comprises an amino acid sequence according to SEQ ID NO: 116.

In some embodiments, $P_2$ comprises an amino acid sequence according to any one of SEQ ID NOs: 26, 71-96, 98-776, or an amino acid sequence that has 1, 2, or 3 amino acid mutations, substitutions, or deletions relative to any one of SEQ ID NOs: 26, 71-96, 98-776. In some embodiments, $P_2$ comprises an an amino acid sequence according to $X_1$—C—$X_2$—$X_3$—$X_4$—$X_5$-D-$X_6$-A-$X_7$—P—$X_8$—C—$X_9$ wherein $X_1$ is selected from P and L; $X_2$ is selected from R, L, T, A, N, I, V, S, H, and P; $X_3$ is selected from S, P, F, and Y; $X_4$ is selected from H, L, Q, P, R, F, N; $X_5$ is selected from I, F, Y, H, N, T, S, D, A, L, and V; $X_6$ is selected from T, P, N, L, I, V, S, D, H, A, and Y; $X_7$ is selected from K and Y; $X_8$ is selected from I, P, L, and M; and $X_9$ is selected from A, V, I, T, L, S, D, F, V, and H (SEQ ID NO: 841). In some embodiments, $X_1$ is selected from P and L; $X_2$ is selected from R, L, T, A, and N; $X_3$ is selected from S, P, and F; $X_4$ is selected from H, L, Q, and P; $X_5$ is selected from I, F, Y, H, N, and T; $X_6$ is selected from T, P, N, L, I, and V; $X_7$ is K; $X_8$ is I; and $X_9$ is selected from A, V, I, T, L, and S. In some embodiments, $X_1$ is P; $X_2$ is selected from R, L, and T; $X_3$ is S; $X_4$ is selected from H, L, Q, and P; $X_5$ is selected from I, F, Y, and T; $X_6$ is selected from T, P, N, and V; $X_7$ is K; $X_8$ is I; and $X_9$ is selected from A, V, and I.

In some embodiments, $P_2$ comprises an amino acid sequence according to any one of SEQ ID NOs: 26, 86-96, or an amino acid sequence that has 1, 2, or 3 amino acid mutations, substitutions, or deletions relative to any one of 26, 86-96. In some embodiments, $P_2$ comprises an amino acid sequence according to any one of SEQ ID NOs: 26, 86-96.

In some embodiments, $P_2$ comprises an amino acid sequence according to any one of SEQ ID NOs: 98-776 or an amino acid sequence that has 1, 2, or 3 amino acid mutations, substitutions, or deletions relative to any one of SEQ ID NOs: 98-776. In some embodiments, $P_2$ comprises an amino acid sequence according to any one of SEQ ID NOs: SEQ ID NOs: 98-776.

In some embodiments, $P_2$ comprises an amino acid sequence according to any one of SEQ ID NOs: 99-118 or an amino acid sequence that has 1, 2, or 3 amino acid mutations, substitutions, or deletions relative to any one of 99-118. In some embodiments, $P_2$ comprises an amino acid sequence according to any one of SEQ ID NOs: 99-118.

In some embodiments, $P_2$ comprises an amino acid sequence according to SEQ ID NO: 26 or an amino acid sequence that has 1, 2, or 3 amino acid mutations, substitutions, or deletions relative to SEQ ID NO: 26. In some embodiments, $P_2$ comprises the amino acid sequence according to SEQ ID NO: 26.

In some embodiments, $P_2$ comprises an amino acid sequence according to SEQ ID NO: 115 or an amino acid sequence that has 1, 2, or 3 amino acid mutations, substitutions, or deletions relative to SEQ ID NO: 115. In some embodiments, $P_2$ comprises the amino acid sequence according to SEQ ID NO: 115.

In some embodiments, $P_2$ comprises an amino acid sequence according to SEQ ID NO: 115 or an amino acid sequence that has 1, 2, or 3 amino acid mutations, substitutions, or deletions relative to SEQ ID NO: 116. In some embodiments, $P_2$ comprises the amino acid sequence according to SEQ ID NO: 116.

In some embodiments, $P_{1a}$ when $L_{1a}$ is uncleaved impairs binding of the antigen recognizing molecule to the target antigen. In some embodiments, the antigen recognizing molecule comprises an antibody or antibody fragment. In some embodiments, the target antigen is an anti-CD3 effector cell antigen. In some embodiments, the target antigen is epidermal growth factor receptor (EGFR). In some embodiments, $P_{1a}$ has less than 70% sequence identity to the target antigen. In some embodiments, $P_{1a}$ has less than 75% sequence identity to the target antigen. In some embodiments, $P_{1a}$ has less than 80% sequence identity to the target antigen. In some embodiments, $P_{1a}$ has less than 85% sequence identity to the target antigen. In some embodiments, $P_{1a}$ has less than 90% sequence identity to the target antigen. In some embodiments, $P_{1a}$ has less than 95% sequence identity to the target antigen. In some embodiments, $P_{1a}$ has less than 98% sequence identity to the target antigen. In some embodiments, $P_{1a}$ has less than 99% sequence identity to the target antigen. In some embodiments, $P_{1a}$ comprises a de novo amino acid sequence that shares less than 10% sequence identity to the second target antigen.

In some embodiments, $P_{1a}$ comprises an amino acid sequence according to any one of SEQ ID NOs: 25, 797-835, or 843-1690 or an amino acid sequence that has 1, 2, or 3 amino acid mutations, substitutions, or deletions relative to any one of SEQ ID NOs: 25, 797-835, or 843-1690.

In some embodiments, $P_{1a}$ comprises an amino acid sequence according to $Z_1$—$Z_2$—C—$Z_4$—P—$Z_6$-$Z_7$—$Z_8$—$Z_9$-$Z_{10}$—$Z_{11}$—$Z_{12}$—C—$Z_{14}$ and Z1 is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S. In some embodiments, Z, is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_8$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; and $Z_{14}$ is selected from D, Y, N, F, I, and P. In some embodiments, $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N. In some embodiments, $P_1$ comprises an amino acid sequence according to $U_1$—$U_2$—C—$U_4$—P—$U_6$—$U_7$—$U_8$—$U_9$—$U_{10}$—$U_1$n-$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S. In some embodiments, $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P. In some embodiments, $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

In some embodiments, $P_{1a}$ comprises the amino acid sequences according to any one of SEQ ID NOs: 797-823.

In some embodiments, $P_{1a}$ comprises an amino acid sequences according to any one of SEQ ID NOs: 25, 824-835 or 843-1690.

In some embodiments, $P_{1a}$ comprises the amino acid sequences according to any of SEQ ID NOs: 824-835.

In some embodiments, $P_{1a}$ comprises the amino acid sequence according to SEQ ID NO: 810 or an amino acid sequence that has 1, 2, or 3, amino acid substitutions, additions, or deletions relative to the amino acid sequence of SEQ ID NO: 810.

In some embodiments, $P_{1a}$ comprises the amino acid sequence according to SEQ ID NO: 811 or an amino acid sequence that has 1, 2, or 3, amino acid substitutions, additions, or deletions relative to the amino acid sequence of SEQ ID NO: 811.

In some embodiments, $P_{1a}$ comprises the amino acid sequence according to SEQ ID NO: 834 or an amino acid sequence that has 1, 2, or 3, amino acid substitutions, additions, or deletions relative to the amino acid sequence of SEQ ID NO: 834.

In some embodiments, $P_{1a}$ comprises the amino acid sequence according to SEQ ID NO: 810.

In some embodiments, $P_{1a}$ comprises the amino acid sequence according to SEQ ID NO: 811.

In some embodiments, $P_{1a}$ comprises the amino acid sequence according to SEQ ID NO: 834.

In some embodiments, $P_1$, $P_2$, or $P_{1a}$ comprises a peptide sequence of at least 5 amino acids in length. In some embodiments, $P_1$, $P_2$, or $P_{1a}$ comprises a peptide sequence of at least 6 amino acids in length. In some embodiments, $P_1$, $P_2$, or $P_{1a}$ comprises a peptide sequence of at least 10 amino acids in length. In some embodiments, $P_1$, $P_2$, or $P_{1a}$ comprises a peptide sequence of at least 10 amino acids in length and no more than 20 amino acids in length. In some embodiments, $P_1$, $P_2$, or $P_{1a}$ comprises a peptide sequence of at least 16 amino acids in length. In some embodiments, $P_1$, $P_2$, or $P_{1a}$ comprises a peptide sequence of no more than 40 amino acids in length. In some embodiments, $P_1$, $P_2$, or $P_{1a}$ comprises at least two cysteine amino acid residues. In some embodiments, $P_1$, $P_2$, or $P_{1a}$ comprises a cyclic peptide or a linear peptide. In some embodiments, $P_1$, $P_2$, or $P_{1a}$ comprises a cyclic peptide. In some embodiments, $P_1$, $P_2$, or $P_{1a}$ comprises a linear peptide.

In some embodiments, $P_1$, $P_2$, or $P_{1a}$ or $P_1$, $P_2$, and $P_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments $P_1$, $P_2$, or $P_{1a}$ or $P_1$, $P_2$, and $P_{1a}$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $P_1$, $P_2$, or $P_{1a}$ or $P_1$, $P_2$, and $P_{1a}$ including the peptide backbone, the amino acid side chains, and the terminus.

In some embodiments, $P_1$, $P_2$, or $P_{1a}$ does not comprise albumin or an albumin fragment. In some embodiments, $P_1$, $P_2$, or $P_{1a}$ does not comprise an albumin binding domain.

Linking Moiety ($L_1$, $L_2$, $L_3$, and $L_{1a}$)

In some embodiments, $L_1$, $L_2$, $L_3$, or $L_{1a}$ is a peptide sequence having at least 5 to no more than 50 amino acids. In some embodiments $L_1$, $L_2$, $L_3$, or $L_{1a}$ is a peptide sequence having at least 10 to no more than 30 amino acids. In some embodiments, $L_1$, $L_2$, $L_3$, or $L_{1a}$ is a peptide sequence having at least 10 amino acids. In some embodiments, $L_1$, $L_2$, $L_3$, or $L_{1a}$ is a peptide sequence having at least 18 amino acids. In some embodiments, $L_1$, $L_2$, $L_3$, or $L_{1a}$ is a peptide sequence having at least 26 amino acids. In some embodiments, $L_1$, $L_2$, $L_3$, or $L_{1a}$ has a formula comprising $(G_2S)_n$, wherein n is an integer from 1 to 3 (SEQ ID NO: 840). In some embodiments, $L_1$, $L_2$, $L_3$, or $L_{1a}$ has a formula comprising $(G_2S)_n$, wherein n is an integer of at least 1. In some embodiments, $L_1$, $L_2$, $L_3$, or $L_{1a}$ has a formula selected from the group consisting of $(G_2S)_n$, $(GS)_3$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1. In some embodiments, the tumor specific protease is selected from the group consisting of metalloprotease, serine protease, cysteine protease, threonine protease, and aspartic protease. In some embodiments $L_1$, $L_2$, $L_3$, or $L_{1a}$ comprises a urokinase cleavable amino acid sequence, a matriptase (MTSP1) cleavable amino acid sequence, a legumain cleavable amino acid sequence, or a matrix metalloprotease cleavable amino acid sequence. In some instances, the matrix metalloprotease comprises MMP2, MMP7, MMP9, MMP13, or MMP14. In some instances, the serine protease comprises matriptase (MTSP1), urokinase, or hepsin.

In some embodiments, $L_1$, $L_2$, $L_3$, or $L_{1a}$ comprises a sequence as disclosed in Table 4 or a sequence substantially identical thereto (e.g., a sequence that has 0, 1, or 2 amino acid modifications).

In some embodiments, $L_1$ comprises an amino acid sequence of Linker 4 (ISSGLLSGRSDAG) (SEQ ID NO: 66), Linker 5 (AAGLLAPPGGLSGRSDAG) (SEQ ID NO: 67), Linker 6 (SPLGLSGRSDAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7. In some embodiments, $L_1$ comprises an amino acid sequence of Linker 4 (ISSGLLSGRSDAG) (SEQ ID NO: 66). In some embodiments, $L_1$ comprises an amino acid sequence of Linker 5 (AAGLLAPPGGLSGRSDAG) (SEQ ID NO: 67). In some embodiments, $L_1$ comprises an amino acid sequence of Linker 6 (SPLGLSGRSDAG) (SEQ ID NO: 68). In some embodiments, $L_1$ comprises an amino acid sequence of Linker 7 (LSGRSDAGSPLGLAG) (SEQ ID NO: 69).

In some embodiments, $L_2$ comprises an amino acid sequence of Linker 4 (ISSGLLSGRSDAG) (SEQ ID NO: 66), Linker 5 (AAGLLAPPGGLSGRSDAG) (SEQ ID NO: 67), Linker 6 (SPLGLSGRSDAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7. In some embodiments, $L_2$ comprises an amino acid sequence of Linker 4 (ISSGLLSGRSDAG) (SEQ ID NO: 66). In some embodiments, $L_1$ comprises an amino acid sequence of Linker 5 (AAGLLAPPGGLSGRSDAG) (SEQ ID NO: 67). In some embodiments, $L_2$ comprises an amino acid sequence of Linker 6 (SPLGLSGRSDAG) (SEQ ID NO: 68). In some embodiments, $L_2$ comprises an amino acid sequence of Linker 7 (LSGRSDAGSPLGLAG) (SEQ ID NO: 69).

ment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $L_1$, $L_2$, $L_3$, or $L_{1a}$ including the peptide backbone, or the amino acid side chains.

In some embodiments, the cleavable linker is cleavable by a protease. In some embodiments, the protease is present in higher levels in a disease-state microenvironment relative to levels in healthy tissue or a microenvironment that is not the

TABLE 4

$L_1$, $L_2$, $L_3$, and $L_{1a}$ Sequences

| Construct Description | Amino Acid Sequence (N to C) | SEQ ID NO: |
|---|---|---|
| Linker 1 | GGGGSGGGGSGGGGS | 27 |
| Linker 2 | GGGGS | 28 |
| Linker 3 | GGGGSGGGS | 29 |
| Cleavable linker 1 | GGGGSGGGLSGRSDAGSPLGLAGSGGGS | 30 |
| Cleavable linker 2 | GGGGSGGLSGRSDAGSPLGLAGSGGS | 31 |
| Cleavable linker 3 | GGGGSSGGSAAGLLAPPGGLSGRSDAGGGGS | 32 |
| Cleavable linker 4 | GSSGGSAAGLLAPPGGLSGRSDAGGGGS | 33 |
| Non-cleavable linker 1 | GGGGSGGGGSGGGGSGGASSGAGGS | 34 |
| Non-cleavable linker 2 | GGGGSGGGSGGGGSGGASSGAGGSGGGS | 35 |
| Linker 4 | ISSGLLSGRSDAG | 66 |
| Linker 5 | AAGLLAPPGGLSGRSDAG | 67 |
| Linker 6 | SPLGLSGRSDAG | 68 |
| Linker 7 | LSGRSDAGSPLGLAG | 69 |

In some embodiments, $L_1$ is bound to N-terminus of $A_1$. In some embodiments, $L_1$ is bound to C-terminus of $A_1$. In some embodiments, $L_2$ is bound to N-terminus of $A_2$. In some embodiments, $L_2$ is bound to C-terminus of $A_2$. In some embodiments, $P_1$ becomes unbound from $A_1$ when $L_1$ is cleaved by the tumor specific protease thereby exposing $A_1$ to the effector cell antigen. In some embodiments, $P_2$ becomes unbound from $A_2$ when $L_2$ is cleaved by the tumor specific protease thereby exposing $A_2$ to EGFR.

In some embodiments, $L_1$, $L_2$, $L_3$, or $L_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments, $L_1$, $L_2$, $L_3$, or $L_{1a}$ comprise a modification including, but not limited to, acetylation, acylation, ADP-ribosylation, amidation, covalent attachdisease-state microenvironment. In some embodiments, the protease comprises a tumor specific protease. In some embodiments, the protease comprises a matrix metalloprotease (MMP) or a serine protease. In some embodiments, the matrix metalloprotease comprises MMP2, MMP7, MMP9, MMP13, or MMP14. In some embodiments, the matrix metalloprotease is selected from the group consisting of MMP2, MMP7, MMP9, MMP13, and MMP14. In some embodiments, the matrix metalloprotease comprises MMP2. In some embodiments, the matrix metalloprotease comprises MMP7. In some embodiments, the matrix metalloprotease comprises MMP9. In some embodiments, the matrix metalloprotease comprises MMP13. In some embodiments, the matrix metalloprotease comprises MMP14. In some embodiments, the serine protease comprises matriptase (MTSP1), urokinase, or hepsin. In some embodiments, the serine protease is selected from the group consisting of matriptase (MTSP1), urokinase, and hepsin. In some embodiments, the serine protease comprises matriptase (MTSP1). In some embodiments, the serine protease comprises urokinase. In some embodiments, the serine protease comprises hepsin. In some embodiments, the cleavable linker is cleaved by a variety of proteases. In some embodiments, the cleavable linker is cleaved by at least 1, 2, 3, 4, 5, 6, 7, 8, 9, 10, 15, 20, or more than 20 different proteases.

Half-Life Extending Molecule ($H_1$ and $H_{1a}$)

In some embodiments, $H_1$ does not block A, binding to the effector cell antigen. In some embodiments, $H_1$ comprises a linking moiety ($L_3$) that connects $H_1$ to $P_1$. In some embodiments, $H_{1a}$ does not block the first antigen recognizing molecule binding to the effector cell antigen. In some embodiments, $H_{1a}$ comprises a linking moiety ($L_3$) that connects $H_{1a}$ to $P_{1a}$. In some embodiments, half-life extending molecule ($H_1$ or $H_{1a}$) does not have binding affinity to antigen recognizing molecule. In some embodiments, half-life extending molecule ($H_1$ or $H_{1a}$) does not have binding affinity to the effector cell antigen. In some embodiments, half-life extending molecule ($H_1$ or $H_{1a}$) does not shield antigen recognizing molecule from the effector cell antigen. In some embodiments, half-life extending molecule ($H_1$ or $H_{1a}$) is not directly linked to antigen recognizing molecule.

In some embodiments, $H_1$ or $H_{1a}$ comprises a sequence as disclosed in Table 5 or a sequence substantially identical thereto (e.g., a sequence that has at least 90%, 95%, 96%, 97%, 98%, or 99% sequence identity).

structure, as measured or determined by means, including, but not limited to, spectrophotometry (e.g. by circular dichroism spectroscopy in the "far-UV" spectral region (190-250 nm), and computer programs or algorithms, such as the Chou-Fasman algorithm and the Garnier-Osguthorpe-Robson ("GOR") algorithm.

In some embodiments, $H_1$ or $H_{1a}$ comprises a polymer. In some embodiments, the polymer is polyethylene glycol (PEG). In some embodiments, $H_1$ or $H_{1a}$ comprises albumin. In some embodiments, $H_1$ or $H_{1a}$ comprises an Fc domain. In some embodiments, the albumin is serum albumin. In some embodiments, the albumin is human serum albumin. In some embodiments, $H_1$ or $H_{1a}$ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, s1gA, IgM or IgD. In some embodiments, the serum protein is albumin. In some embodiments, the polypeptide is an antibody. In some embodiments, the antibody comprises a single domain antibody, a single chain variable fragment or a Fab. In some embodiments, the single domain antibody comprises a single domain antibody that binds to albumin.

TABLE 5

$H_1$ and $H_{1a}$ Sequences

| Construct Description | Amino Acid Sequence (N to C) | SEQ ID NO: |
|---|---|---|
| Anti-Albumin: CDR-H1 | GSTFYTAV | 36 |
| Anti-Albumin: CDR-H2 | IRWTALTT | 37 |
| Anti-Albumin: CDR-H3 | AARGTLGLFTTADSYDY | 38 |
| 10G Anti-Albumin: CDR-H1 | GFTFSKFG | 39 |
| 10G Anti-Albumin: CDR-H2 | ISGSGRDT | 40 |
| 10G Anti-Albumin: CDR-H3 | TIGGSLSV | 41 |
| Anti-albumin | EVQLVESGGGLVQPGGSLRLS CAASGSTFYTAVMGWVRQAP GKGLEWVAAIRWTALTTSYA DSVKGRFTISRDGAKTTLYLQ MNSLRPEDTAVYYCAARGTL GLFTTADSYDYWGQGTLVTV SS | 42 |
| 10G anti-albumin | EVQLVESGGGLVQPGNSLRLS CAASGFTFSKFGMSWVRQAP GKGLEWVSSISGSGRDTLYAD SVKGRFTISRDNAKTTLYLQM NSLRPEDTAVYYCTIGGSLSV SSQGTLVTVSS | 43 |

In some embodiments, $H_1$ or $H_{1a}$ comprise an amino acid sequence that has repetitive sequence motifs. In some embodiments, $H_1$ or $H_{1a}$ comprises an amino acid sequence that has highly ordered secondary structure. "Highly ordered secondary structure," as used in this context, means that at least about 50%, or about 70%, or about 80%, or about 90%, of amino acid residues of $H_1$ or $H_{1a}$ contribute to secondary In some embodiments, the single domain antibody is a human or humanized antibody. In some embodiments, the single domain antibody is selected from the group consisting of 645gH1gL1, 645dsgH5gL4, 23-13-A01-sc02, A10m3 or a fragment thereof, DOM7r-31, DOM7h-11-15, Alb-1, Alb-8, Alb-23, 10G, 10E and SA21. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38; and wherein the CDRs comprise from 0-2 amino acid modifications in at least one of the HC-CDR1, HC-CDR2, or HC-CDR3. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 39, HC-CDR2: SEQ ID NO: 40, and HC-CDR3: SEQ ID NO: 41. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 39, HC-CDR2: SEQ ID NO: 40, and HC-CDR3: SEQ ID NO: 41; and wherein the CDRs comprise from 0-2 amino acid modifications in at least one of the HC-CDR1, HC-CDR2, or HC-CDR3.

In some embodiments, $H_1$ comprises an amino acid sequence according to SEQ ID NO: 42. In some embodiments, $H_1$ comprises an amino acid sequence that has at least 80% sequence identity to SEQ ID NO: 42. In some embodiments, $H_1$ comprises an amino acid sequence that has at least 85% sequence identity to SEQ ID NO: 42. In some embodiments, $H_1$ comprises an amino acid sequence that has at least 90% sequence identity to SEQ ID NO: 42. In some embodiments, $H_1$ comprises an amino acid sequence that has at least 95% sequence identity to SEQ ID NO: 42. In some embodiments, $H_1$ comprises an amino acid sequence that has at least 99% sequence identity to SEQ ID NO: 42.

In some embodiments, $H_{1a}$ comprises an amino acid sequence according to SEQ ID NO: 42. In some embodiments, $H_{1a}$ comprises an amino acid sequence that has at least 80% sequence identity to SEQ ID NO: 42. In some embodiments, $H_{1a}$ comprises an amino acid sequence that has at least 85% sequence identity to SEQ ID NO: 42. In some embodiments, $H_{1a}$ comprises an amino acid sequence that has at least 90% sequence identity to SEQ ID NO: 42. In some embodiments, $H_{1a}$ comprises an amino acid sequence that has at least 95% sequence identity to SEQ ID NO: 42. In some embodiments, $H_{1a}$ comprises an amino acid sequence that has at least 99% sequence identity to SEQ ID NO: 42.

In some embodiments, $H_1$ comprises an amino acid sequence according to SEQ ID NO: 43. In some embodiments, $H_1$ comprises an amino acid sequence that has at least 80% sequence identity to SEQ ID NO: 43. In some embodiments, $H_1$ comprises an amino acid sequence that has at least 85% sequence identity to SEQ ID NO: 43. In some embodiments, $H_1$ comprises an amino acid sequence that has at least 90% sequence identity to SEQ ID NO: 43. In some embodiments, $H_1$ comprises an amino acid sequence that has at least 95% sequence identity to SEQ ID NO: 43. In some embodiments, $H_1$ comprises an amino acid sequence that has at least 99% sequence identity to SEQ ID NO: 43.

In some embodiments, $H_{1a}$ comprises an amino acid sequence according to SEQ ID NO: 43. In some embodiments, $H_{1a}$ comprises an amino acid sequence that has at least 80% sequence identity to SEQ ID NO: 43. In some embodiments, $H_{1a}$ comprises an amino acid sequence that has at least 85% sequence identity to SEQ ID NO: 43. In some embodiments, $H_{1a}$ comprises an amino acid sequence that has at least 90% sequence identity to SEQ ID NO: 43. In some embodiments, $H_{1a}$ comprises an amino acid sequence that has at least 95% sequence identity to SEQ ID NO: 43. In some embodiments, $H_{1a}$ comprises an amino acid sequence that has at least 99% sequence identity to SEQ ID NO: 43.

In some embodiments, $H_1$ or $H_{1a}$ or $H_1$ and $H_{1a}$ comprise a modified amino acid or non-natural amino acid, or a modified non-natural amino acid, or a combination thereof. In some embodiments, the modified amino acid or a modified non-natural amino acid comprises a post-translational modification. In some embodiments $H_1$ or $H_{1a}$ or $H_1$ and $H_a$ comprise a modification including, but not limited to acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination. Modifications are made anywhere to $H_1$ or $H_{1a}$ or $H_1$ and $H_{1a}$ including the peptide backbone, the amino acid side chains, and the terminus.

In some embodiments, $H_1$ comprises a linking moiety ($L_3$) that connects $H_1$ to $P_1$. In some embodiments, $L_3$ is a peptide sequence having at least 5 to no more than 50 amino acids. In some embodiments, $L_3$ is a peptide sequence having at least 10 to no more than 30 amino acids. In some embodiments, $L_3$ is a peptide sequence having at least 10 amino acids. In some embodiments, $L_3$ is a peptide sequence having at least 18 amino acids. In some embodiments, $L_3$ is a peptide sequence having at least 26 amino acids. In some embodiments, $L_3$ has a formula selected from the group consisting of $(G_2S)_n$, $(GS)_n$, $(GSGGS)_n$ (SEQ ID NO: 836), $(GGGS)_n$, (SEQ ID NO: 837) $(GGGGS)_n$ (SEQ ID NO: 838), and $(GSSGGS)_n$ (SEQ ID NO: 839), wherein n is an integer of at least 1. In some embodiments, $L_3$ comprises an amino acid sequence according to SEQ ID NO: 29.

In some embodiments, $H_{1a}$ comprises a linking moiety ($L_{1a}$) that connects $H_{1a}$ to $P_{1a}$. In some embodiments, $L_{1a}$ is a peptide sequence having at least 5 to no more than 50 amino acids. In some embodiments, $L_{1a}$ is a peptide sequence having at least 10 to no more than 30 amino acids. In some embodiments, $L_{1a}$ is a peptide sequence having at least 10 amino acids. In some embodiments, $L_{1a}$ is a peptide sequence having at least 18 amino acids. In some embodiments, $L_{1a}$ is a peptide sequence having at least 26 amino acids. In some embodiments, $L_{1a}$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1. In some embodiments, $L_{1a}$ comprises an amino acid sequence according to SEQ ID NO: 30 or 31.

Antibodies that Bind to EGFR and CD3

In some embodiments, the isolated polypeptide or polypeptide complex comprises an amino acid sequence disclosed in Table 6 or a sequence substantially identical thereto (e.g., a sequence that has at least 90%, 95%, 96%, 97%, 98%, or 99% sequence identity). In some embodiments, the isolated polypeptide or polypeptide complex comprises an amino acid sequence with at least 95% sequence identity to SEQ ID NOs: 44-61. In some embodiments, the isolated polypeptide or polypeptide complex comprises an amino acid sequence with at least 95% sequence identity to SEQ ID NO: 50. In some embodiments, the isolated polypeptide or polypeptide complex comprises an amino acid sequence with at least 95% sequence identity to SEQ ID NO: 51.

TABLE 6

Polypeptide complex sequences

| Construct Description | Amino Acid Sequence (N to C) | SEQ ID NO: |
|---|---|---|
| PC1: LC EGFR Fab LC | QILLTQSPVILSVSPGERVSFSCRASQSIGTNIHWYQQRT NGSPRLLIKYASESISGIPSRFSGSGSGTDFTLSINSVESE DIADYYCQQNNNWPTTFGAGTKLELKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC | 44 |
| PC1: HC SP34.185 scFv (VH - linker 1 - VL) + Linker 2 + EGFR Fab HC | EVQLVESGGGLVQPGGSLKLSCAASGFTFNKYAMNW VRQAPGKGLEWVARIRSKYNNYATYYADSVKDRFTIS RDDSKNTAYLQMNNLKTEDTAVYYCVRHGNFGNSYI SYWAYWGQGTLVTVSSGGGGSGGGGSGGGGSQTVVT QEPSLTVSPGGTVTLTCGSSTGAVTSGNYPNWVQQKP GQAPRGLIGGTKFLAPGTPARFSGSLLGGKAALTLSGV QPEDEAEYYCVLWYSNRWVFGGGTKLTVLGGGGSQV QLKQSGPGLVQPSQSLSITCTVSGFSLTNYGVHWVRQS PGKGLEWLGVIWSGGNTDYNTPFTSRLSINKDNSKSQ VFFKMNSLQSQDTAIYYCARALTYYDYEFAYWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSC | 45 |
| PC2: LC EGFR Fab LC | QILLTQSPVILSVSPGERVSFSCRASQSIGTNIHWYQQRT NGSPRLLIKYASESISGIPSRFSGSGSGTDFTLSINSVESE DIADYYCQQNNNWPTTFGAGTKLELKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC | 46 |
| PC2: HC SP34.194 scFv (VL-linker 1- VH) + Linker 2 + EGFR Fab HC | QTVVTQEPSLTVSPGGTVTLTCRSSTGAVTTSNYANW VQQKPGQAPRGLIGGTNKRAPGTPARFSGSLLGGKAAL TLSGVQPEDEAEYYCALWYSNLWVFGGGTKLTVLGG GGSGGGGSGGGGSEVQLVESGGGLVQPGGSLKLSCAA SGFTFNTYAMNWVRQAPGKGLEWVARIRSKYNNYAT YYADSVKDRFTISRDDSKNTAYLQMNNLKTEDTAVYY CVRHGNFGNSYVSWFAYWGQGTLVTVSSGGGSQV QLKQSGPGLVQPSQSLSITCTVSGFSLTNYGVHWVRQS PGKGLEWLGVIWSGGNTDYNTPFTSRLSINKDNSKSQ VFFKMNSLQSQDTAIYYCARALTYYDYEFAYWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSC | 47 |
| PC3: LC EGFR Fab LC | DILLTQSPVILSVSPGERVSFSCRASQSIGTNIHWYQQRT NGSPRLLIKYASESISGIPSRFSGSGSGTDFTLSINSVESE DIADYYCQQNNNWPTTFGAGTKLELKRTVAAPSVFIFP PSDEQLKSGTASVVCLLNNFYPREAKVQWKVDNALQS GNSQESVTEQDSKDSTYSLSSTLTLSKADYEKHKVYAC EVTHQGLSSPVTKSFNRGEC | 48 |
| PC3: HC SP34.194 scFv (VL-linker 1- VH) + Linker 2 + EGFR Fab HC | QTVVTQEPSLTVSPGGTVTLTCRSSTGAVTTSNYANW VQQKPGQAPRGLIGGTNKRAPGTPARFSGSLLGGKAAL TLSGVQPEDEAEYYCALWYSNLWVFGGGTKLTVLGG GGSGGGGGGGGSEVQLVESGGGLVQPGGSLKLSCAA SGFTFNTYAMNWVRQAPGKGLEWVARIRSKYNNYAT YYADSVKDRFTISRDDSKNTAYLQMNNLKTEDTAVYY CVRHGNFGNSYVSWFAYWGQGTLVTVSSGGGSQV QLKQSGPGLVQPSQSLSITCTVSGFSLTNYGVHWVRQS PGKGLEWLGVIWSGGNTDYNTPFTSRLSINKDNSKSQ VFFKMNSLQSNDTAIYYCARALTYYDYEFAYWGQGT LVTVSAASTKGPSVFPLAPSSKSTSGGTAALGCLVKDY FPEPVTVSWNSGALTSGVHTFPAVLQSSGLYSLSSVVT VPSSSLGTQTYICNVNHKPSNTKVDKKVEPKSC | 49 |
| PC4: LC EGFR Fab mask + cleavable linker | GGPCRSHIDVAKPICVGGGGSGGLSGRSDAGSPLGLAG SGGSDILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS | 50 |

TABLE 6-continued

Polypeptide complex sequences

| Construct Description | Amino Acid Sequence (N to C) | SEQ ID NO: |
|---|---|---|
| 2 + EGFR Fab LC | VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC | |
| PC4: HC Anti-albumin + Linker 3 + SP34.185 scFv mask + Cleavable Linker 1 + SP34.185 scFv (VH-linker 1-VL) + Linker 2 + EGFR Fab HC | EVQLVESGGGLVQPGGSLRLSCAASGSTFYTAVMGWV RQAPGKGLEWVAAIRWTALTTSYADSVKGRFTISRDG AKTTLYLQMNSLRPEDTAVYYCAARGTLGLFTTADS YDYWGQGTLVTVSSGGGGSGGGGSGGVYCGPEFDESVG CMGGGGGSGGGLSGRSDAGSPLGLAGSGGGSEVQLVES GGGLVQPGGSLKLSCAASGFTENKYAMNWVRQAPGK GLEWVARIRSKYNNYATYYADSVKDRFTISRDDSKNT AYLQMNNLKTEDTAVYYCVRHGNFGNSYISYWAYW GQGTLVTVSSGGGGSGGGGSGGGGSQTVVTQEPSLTV SPGGTVTLTCGSSTGAVTSGNYPNWVQQKPGQAPRGL IGGGTKFLAPGTPARFSGSLLGGKAALTLSGVQPEDEAE YYCVLWYSNRWVFGGGTKLTVLGGGGSQVQLKQSGP GLVQPSQSLSITCTVSGFSLTNYGVHWVRQSPGKGLE WLGVIWSGGNTDYNTPFTSRLSINKDNSKSQVFFKMN SLQSNDTAIYYCARALTYYDYEFAYWGQGTLVTVSAA STKGPSVFPLAPSSKSTSGGTAALGCLVKDYFPEPVTVS WNSGALTSGVHTFPAVLQSSGLYSLSSVVTVPSSSLGT QTYICNVNHKPSNTKVDKKVEPKSC | 51 |
| PC5: LC EGFR Fab mask + cleavable linker 2 + EGFR Fab LC v2 | GGPCRSHIDVAKPICVGGGGSGGLSGRSDAGSPLGLAG SGGSDILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC | 52 |
| PC5: HC 10G + Linker 3 + SP34.185 scFv mask + Cleavable Linker 1 + SP34.185 scFv (VH-linker 1-VL) + Linker 2 + EGFR Fab HC | EVQLVESGGGLVQPGNSLRLSCAASGFTFSKFGMSWV RQAPGKGLEWVSSISGSGRDTLYADSVKGRFTISRDNA KTTLYLQMNSLRPEDTAVYYCTIGGSLSVSSQGTLVTV SSGGGGSGGGGSGGVYCGPEFDESVGCMGGGGSGGGLS GRSDAGSPLGLAGSGGGSEVQLVESGGGLVQPGGSLKL SCAASGFTFNKYAMNWVRQAPGKGLEWVARIRSKYN NYATYYADSVKDRFTISRDDSKNTAYLQMNNLKTEDT AVYYCVRHGNFGNSYISYWAYWGQGTLVTVSSGGGG SGGGGSGGGGSQTVVTQEPSLTVSPGGTVTLTCGSSTG AVTSGNYPNWVQQKPGQAPRGLIGGGTKFLAPGTPARF SGSLLGGKAALTLSGVQPEDEAEYYCVLWYSNRWVF GGGTKLTVLGGGGSQVQLKQSGPGLVQPSQSLSITCTV SGFSLTNYGVHWVRQSPGKGLEWLGVIWSGGNTDYN TPFTSRLSINKDNSKSQVFFKMNSLQSNDTAIYYCARAL TYYDYEFAYWGQGTLVTVSAASTKGPSVFPLAPSSKST SGGTAALGCLVKDYFPEPVTVSWNSGALTSGVHTFPA VLQSSGLYSLSSVVTVPSSSLGTQTYICNVNHKPSNTKV DKKVEPKSC | 53 |
| PC6: LC EGFR Fab mask + Non-cleavable linker 1 + EGFR Fab LC v2 | GGPCRSHIDVAKPICVGGGGSGGGGSGGGGSGGASSG AGGSDILLTQSPVILSVSPGERVSFSCRASQSIGTNIHWY QQRTNGSPRLLIKYASESISGIPSRFSGSGSGTDFTLSINS VESEDIADYYCQQNNNWPTTFGAGTKLELKRTVAAPS VFIFPPSDEQLKSGTASVVCLLNNFYPREAKVQWKVDN ALQSGNSQESVTEQDSKDSTYSLSSTLTLSKADYEKHK VYACEVTHQGLSSPVTKSFNRGEC | 54 |
| PC6: HC 10G + Linker 3 + SP34.185 scFv mask + Non-cleavable linker 2 + SP34.185 scFv (VH-linker 1-VL) + Linker 2 + EGFR Fab HC (N88Q) | EVQLVESGGGLVQPGNSLRLSCAASGFTFSKFGMSWV RQAPGKGLEWVSSISGSGRDTLYADSVKGRFTISRDNA KTTLYLQMNSLRPEDTAVYYCTIGGSLSVSSQGTLVTV SSGGGGSGGGSGGVYCGPEFDESVGCMGGGGSGGGSG GGSGGASSGAGGSGGGGSEVQLVESGGGLVQPGGSLK LSCAASGFTFNKYAMNWVRQAPGKGLEWVARIRSKY NNYATYYADSVKDRFTISRDDSKNTAYLQMNNLKTED TAVYYCVRHGNFGNSYISYWAYWGQGTLVTVSSGGG GSGGGGSGGGGSQTVVTQEPSLTVSPGGTVTLTCGSST GAVTSGNYPNWVQQKPGQAPRGLIGGGTKFLAPGTPAR FSGSLLGGKAALTLSGVQPEDEAEYYCVLWYSNRWVF GGGTKLTVLGGGGSQVQLKQSGPGLVQPSQSLSITCTV SGFSLTNYGVHWVRQSPGKGLEWLGVIWSGGNTDYN TPFTSRLSINKDNSKSQVFFKMNSLQSQDTAIYYCARAL TYYDYEFAYWGQGTLVTVSAASTKGPSVFPLAPSSKST SGGTAALGCLVKDYFPEPVTVSWNSGALTSGVHTFPA | 55 |

TABLE 6-continued

Polypeptide complex sequences

| Construct Description | Amino Acid Sequence (N to C) | SEQ ID NO: |
|---|---|---|
| | VLQSSGLYSLSSVVTVPSSSLGTQTYICNVNHKPSNTKV<br>DKKVEPKSC | |
| PC7: LC<br>EGFR Fab<br>mask +<br>cleavable linker<br>3 + EGFR Fab<br>LC v2 | GGPCRSHIDVAKPICVGGGGSSGGSAAGLLAPPGGLSG<br>RSDAGGGGSDILLTQSPVILSVSPGERVSFSCRASQSIGT<br>NIHWYQQRTNGSPRLLIKYASESISGIPSRFSGSGSGTDF<br>TLSINSVESEDIADYYCQQNNNWPTTFGAGTKLELKRT<br>VAAPSVFIFPPSDEQLKSGTASVVCLLNNFYPREAKVQ<br>WKVDNALQSGNSQESVTEQDSKDSTYSLSSTLTLSKAD<br>YEKHKVYACEVTHQGLSSPVTKSFNRGEC | 56 |
| PC7: HC<br>10G + Linker 3<br>+ SP34.185<br>scFv mask +<br>Cleavable<br>Linker 4 +<br>SP34.185 scFv<br>(VH-linker 1-<br>VL) + Linker<br>2 + EGFR Fab<br>HC (N88Q) | EVQLVESGGGLVQPGNSLRLSCAASGFTFSKFGMSWV<br>RQAPGKGLEWVSSISGSGRDTLYADSVKGRFTISRDNA<br>KTTLYLQMNSLRPEDTAVYYCTIGGSLSVSSQGTLVTV<br>SSGGGGSGGGSGGVYCGPEFDESVGCMGSSGGSAAGL<br>LAPPGGLSGRSDAGGGGSEVQLVESGGGLVQPGGSLKL<br>SCAASGFTFNKYAMNWVRQAPGKGLEWVARIRSKYN<br>NYATYYADSVKDRFTISRDDSKNTAYLQMNNLKTEDT<br>AVYYCVRHGNFGNSYISYWAYWGQGTLVTVSSGGGG<br>SGGGGSGGGGSQTVVTQEPSLTVSPGGTVTLTCGSSTG<br>AVTSGNYPNWVQQKPGQAPRGLIGGTKFLAPGTPARF<br>SGSLLGGKAALTLSGVQPEDEAEYYCVLWYSNRWVF<br>GGGTKLTVLGGGSQVQLKQSGPGLVQPSQSLSITCTV<br>SGFSLTNYGVHWVRQSPGKGLEWLGVIWSGGNTDYN<br>TPFTSRLSINKDNSKSQVFFKMNSLQSQDTAIYYCARAL<br>TYYDYEFAYWGQGTLVTVSAASTKGPSVFPLAPSSKST<br>SGGTAALGCLVKDYFPEPVTVSWNSGALTSGVHTFPA<br>VLQSSGLYSLSSVVTVPSSSLGTQTYICNVNHKPSNTKV<br>DKKVEPKSC | 57 |
| PC8: LC<br>EGFR Fab<br>mask +<br>cleavable linker<br>2 + EGFR Fab<br>LC v2 | GGPCRSHIDVAKPICVGGGGSGGLSGRSDAGSPLGLAG<br>SGGSDILLTQSPVILSVSPGERVSFSCRASQSIGTNIHWY<br>QQRINGSPRLLIKYASESISGIPSRFSGSGSGTDFTLSINS<br>VESEDIADYYCQQNNNWPTTFGAGTKLELKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC | 58 |
| PC8: HC<br>Anti-albumin +<br>Linker 3 +<br>SP34.185 scFv<br>mask +<br>Cleavable<br>Linker 1 +<br>SP34.185 scFv<br>(VH-linker 1-<br>VL) + Linker<br>2 + EGFR Fab<br>HC (N88Q) | EVQLVESGGGLVQPGGSLRLSCAASGSTFYTAVMGWV<br>RQAPGKGLEWVAAIRWTALTTSYADSVKGRFTISRDG<br>AKTTLYLQMNSLRPEDTAVYYCAARGTLGLFTTADS<br>YDYWGQGTLVTVSSGGGGSGGGGSGGVYCGPEFDESVG<br>CMGGGGSGGGLSGRSDAGSPLGLAGSGGGSEVQLVES<br>GGGLVQPGGSLKLSCAASGFTFNKYAMNWVRQAPGK<br>GLEWVARIRSKYNNYATYYADSVKDRFTISRDDSKNT<br>AYLQMNNLKTEDTAVYYCVRHGNFGNSYISYWAYW<br>GQGTLVTVSSGGGGSGGGGSGGGGSQTVVTQEPSLTV<br>SPGGTVTLTCGSSTGAVTSGNYPNWVQQKPGQAPRGL<br>IGGTKFLAPGTPARFSGSLLGGKAALTLSGVQPEDEAE<br>YYCVLWYSNRWVFGGGTKLTVLGGGSQVQLKQSGP<br>GLVQPSQSLSITCTVSGFSLTNYGVHWVRQSPGKGLE<br>WLGVIWSGGNTDYNTPFTSRLSINKDNSKSQVFFKMN<br>SLQSQDTAIYYCARALTYYDYEFAYWGQGTLVTVSAA<br>STKGPSVFPLAPSSKSTSGGTAALGCLVKDYFPEPVTVS<br>WNSGALTSGVHTFPAVLQSSGLYSLSSVVTVPSSSLGT<br>QTYICNVNHKPSNTKVDKKVEPKSC | 59 |
| PC9: LC<br>EGFR Fab<br>mask +<br>cleavable linker<br>2 + EGFR Fab<br>LC v2 | GGPCRSHIDVAKPICVGGGGSGGLSGRSDAGSPLGLAG<br>SGGSDILLTQSPVILSVSPGERVSFSCRASQSIGTNIHWY<br>QQRINGSPRLLIKYASESISGIPSRFSGSGSGTDFTLSINS<br>VESEDIADYYCQQNNNWPTTFGAGTKLELKRTVAAPS<br>VFIFPPSDEQLKSGTASVVCLLNNFYPREAKVQWKVDN<br>ALQSGNSQESVTEQDSKDSTYSLSSTLTLSKADYEKHK<br>VYACEVTHQGLSSPVTKSFNRGEC | 60 |
| PC9: HC<br>10G + Linker 3<br>+ SP34.185<br>scFv mask +<br>Cleavable<br>Linker 1 +<br>SP34.185 scFv<br>(VH-linker 1-<br>VL) + Linker<br>2 + EGFR Fab | EVQLVESGGGLVQPGNSLRLSCAASGFTFSKFGMSWV<br>RQAPGKGLEWVSSISGSGRDTLYADSVKGRFTISRDNA<br>KTTLYLQMNSLRPEDTAVYYCTIGGSLSVSSQGTLVTV<br>SSGGGGSGGGSGGVYCGPEFDESVGCMGGGGSGGGLS<br>GRSDAGSPLGLAGSGGGSEVQLVESGGGLVQPGGSLKL<br>SCAASGFTFNKYAMNWVRQAPGKGLEWVARIRSKYN<br>NYATYYADSVKDRFTISRDDSKNTAYLQMNNLKTEDT<br>AVYYCVRHGNFGNSYISYWAYWGQGTLVTVSSGGGG<br>SGGGGSGGGGSQTVVTQEPSLTVSPGGTVTLTCGSSTG<br>AVTSGNYPNWVQQKPGQAPRGLIGGTKFLAPGTPARF | 61 |

TABLE 6-continued

Polypeptide complex sequences

| Construct Description | Amino Acid Sequence (N to C) | SEQ ID NO: |
|---|---|---|
| HC (N88Q) | SGSLLGGKAALTLSGVQPEDEAEYYCVLWYSNRWVF GGGTKLTVLGGGSQVQLKQSGPGLVQPSQSLSITCTV SGFSLTNYGVHWVRQSPGKGLEWLGVIWSGGNTDYN TPFTSRLSINKDNSKSQVFFKMNSLQSQDTAIYYCARAL TYYDYEFAYWGQGTLVTVSAASTKGPSVFPLAPSSKST SGGTAALGCLVKDYFPEPVTVSWNSGALTSGVHTFPA VLQSSGLYSLSSVVTVPSSSLGTQTYICNVNHKPSNTKV DKKVEPKSC | |
| PC10: LC SP34.185 scFv (VH-linker 1-VL) + Linker 2 + EGFR Fab LC | EVQLVESGGGLVQPGGSLKLSCAASGFTFNKYAMNW VRQAPGKGLEWVARIRSKYNNYATYYADSVKDRFTIS RDDSKNTAYLQMNNLKTEDTAVYYCVRHGNFGNSYI SYWAYWGQGTLVTVSSGGGGSGGGGSGGGGSQTVVT QEPSLTVSPGGTVTLTCGSSTGAVTSGNYPNWVQQKP GQAPRGLIGGTKFLAPGTPARFSGSLLGGKAALTLSGV QPEDEAEYYCVLWYSNRWVFGGGTKLTVLGGGGSQI LLTQSPVILSVSPGERVSFSCRASQSIGTNIHWYQQRTN GSPRLLIKYASESISGIPSRFSGSGSGTDFTLSINSVESEDI ADYYCQQNNNWPTTFGAGTKLELKRTVAAPSVFIFPP SDEQLKSGTASVVCLLNNFYPREAKVQWKVDNALQSG NSQESVTEQDSKDSTYSLSSTLTLSKADYEKHKVYACE VTHQGLSSPVTKSFNRGEC | 62 |
| PC10: HC EGFR Fab HC (N88Q) | QVQLKQSGPGLVQPSQSLSITCTVSGFSLTNYGVHWVR QSPGKGLEWLGVIWSGGNTDYNTPFTSRLSINKDNSKS QVFFKMNSLQSQDTAIYYCARALTYYDYEFAYWGQG TLVTVSAASTKGPSVFPLAPSSKSTSGGTAALGCLVKD YFPEPVTVSWNSGALTSGVHTFPAVLQSSGLYSLSSVV TVPSSSLGTQTYICNVNHKPSNTKVDKKVEPKSC | 63 |
| PC11: LC Anti-albumin + Linker 3 + SP34.185 scFv mask + Cleavable Linker 1 + SP34.185 scFv (VH-linker 1-VL) + Linker 2 + EGFR Fab LC | EVQLVESGGGLVQPGGSLRLSCAASGSTFYTAVMGWV RQAPGKGLEWVAAIRWTALTTSYADSVKGRFTISRDG AKTTLYLQMNSLRPEDTAVYYCAARGTLGLFTTADS YDYWGQGTLVTVSSGGGGSGGGSGGVYCGPEFDESVG CMGGGGSGGGLSGRSDAGSPLGLAGSGGGSEVQLVES GGGLVQPGGSLKLSCAASGFTFNKYAMNWVRQAPGK GLEWVARIRSKYNNYATYYADSVKDRFTISRDDSKNT AYLQMNNLKTEDTAVYYCVRHGNFGNSYISYWAYW GQGTLVTVSSGGGGSGGGGSGGGGSQTVVTQEPSLTV SPGGTVTLTCGSSTGAVTSGNYPNWVQQKPGQAPRGL IGGTKFLAPGTPARFSGSLLGGKAALTLSGVQPEDEAE YYCVLWYSNRWVFGGGTKLTVLGGGGSQILLTQSPVI LSVSPGERVSFSCRASQSIGTNIHWYQQRTNGSPRLLIK YASESISGIPSRFSGSGSGTDFTLSINSVESEDIADYYCQ QNNNWPTTFGAGTKLELKRTVAAPSVFIFPPSDEQLKS GTASVVCLLNNFYPREAKVQWKVDNALQSGNSQESVT EQDSKDSTYSLSSTLTLSKADYEKHKVYACEVTHQGLS SPVTKSFNRGEC | 64 |
| PC11: HC EGFR Fab mask + cleavable linker 2 + EGFR Fab HC (N88Q) | GGPCRSHIDVAKPICVGGGGSGGLSGRSDAGSPLGLAG SGGGSQVQLKQSGPGLVQPSQSLSITCTVSGFSLTNYGV HWVRQSPGKGLEWLGVIWSGGNTDYNTPFTSRLSINK DNSKSQVFFKMNSLQSQDTAIYYCARALTYYDYEFAY WGQGTLVTVSAASTKGPSVFPLAPSSKSTSGGTAALGC LVKDYFPEPVTVSWNSGALTSGVHTFPAVLQSSGLYSL SSVVTVPSSSLGTQTYICNVNHKPSNTKVDKKVEPKSC | 65 |

In some embodiments, the isolated polypeptide or polypeptide complex comprises amino acid sequences according to SEQ ID NO: 44 and SEQ ID NO: 45. In some embodiments, the isolated polypeptide or polypeptide complex comprises amino acid sequences with at least 90% sequence identity to SEQ ID NO: 44 and SEQ ID NO: 45. In some embodiments, the isolated polypeptide or polypeptide complex comprises amino acid sequences with at least 95% sequence identity to SEQ ID NO: 44 and SEQ ID NO: 45. In some embodiments, the isolated polypeptide or polypeptide complex comprises amino acid sequences with at least 99% sequence identity to SEQ ID NO: 44 and SEQ ID NO: 45.

In some embodiments, the isolated polypeptide or polypeptide complex comprises amino acid sequences according to SEQ ID NO: 46 and SEQ ID NO: 47. In some embodiments, the isolated polypeptide or polypeptide complex comprises amino acid sequences with at least 90% sequence identity to SEQ ID NO: 46 and SEQ ID NO: 47. In some embodiments, the isolated polypeptide or polypeptide complex comprises amino acid sequences with at least 95% sequence identity to SEQ ID NO: 46 and SEQ ID NO: 47. In some embodiments, the isolated polypeptide or polypeptide complex comprises amino acid sequences with at least 99% sequence identity to SEQ ID NO: 46 and SEQ ID NO: 47.

In some embodiments, the isolated polypeptide or polypeptide complex comprises amino acid sequences according to SEQ ID NO: 48 and SEQ ID NO: 49. In some embodiments, the isolated polypeptide or polypeptide complex comprises amino acid sequences with at least 90% sequence identity to SEQ ID NO: 48 and SEQ ID NO: 49. In some embodiments, the isolated polypeptide or polypeptide complex comprises amino acid sequences with at least 95% sequence identity to SEQ ID NO: 48 and SEQ ID NO: 49. In some embodiments, the isolated polypeptide or polypeptide complex comprises amino acid sequences with at least 99% sequence identity to SEQ ID NO: 48 and SEQ ID NO: 49.

In some embodiments, the isolated polypeptide or polypeptide complex comprises amino acid sequences according to SEQ ID NO: 50 and SEQ ID NO: 51. In some embodiments, the isolated polypeptide or polypeptide complex comprises amino acid sequences with at least 90% sequence identity to SEQ ID NO: 50 and SEQ ID NO: 51. In some embodiments, the isolated polypeptide or polypeptide complex comprises amino acid sequences with at least 95% sequence identity to SEQ ID NO: 50 and SEQ ID NO: 51. In some embodiments, the isolated polypeptide or polypeptide complex comprises amino acid sequences with at least 99% sequence identity to SEQ ID NO: 50 and SEQ ID NO: 51.

In some embodiments, the isolated polypeptide or polypeptide complex comprises amino acid sequences according to SEQ ID NO: 52 and SEQ ID NO: 53. In some embodiments, the isolated polypeptide or polypeptide complex comprises amino acid sequences with at least 90% sequence identity to SEQ ID NO: 52 and SEQ ID NO: 53. In some embodiments, the isolated polypeptide or polypeptide complex comprises amino acid sequences with at least 95% sequence identity to SEQ ID NO: 52 and SEQ ID NO: 53. In some embodiments, the isolated polypeptide or polypeptide complex comprises amino acid sequences with at least 99% sequence identity to SEQ ID NO: 52 and SEQ ID NO: 53.

In some embodiments, the isolated polypeptide or polypeptide complex comprises amino acid sequences according to SEQ ID NO: 54 and SEQ ID NO: 55. In some embodiments, the isolated polypeptide or polypeptide complex comprises amino acid sequences with at least 90% sequence identity to SEQ ID NO: 54 and SEQ ID NO: 55. In some embodiments, the isolated polypeptide or polypeptide complex comprises amino acid sequences with at least 95% sequence identity SEQ ID NO: 54 and SEQ ID NO: 55. In some embodiments, the isolated polypeptide or polypeptide complex comprises amino acid sequences with at least 99% sequence identity to SEQ ID NO: 54 and SEQ ID NO: 55.

In some embodiments, the isolated polypeptide or polypeptide complex comprises amino acid sequences according to SEQ ID NO: 56 and SEQ ID NO: 57. In some embodiments, the isolated polypeptide or polypeptide complex comprises amino acid sequences with at least 90% sequence identity to SEQ ID NO: 56 and SEQ ID NO: 57. In some embodiments, the isolated polypeptide or polypeptide complex comprises amino acid sequences with at least 95% sequence identity SEQ ID NO: 56 and SEQ ID NO: 57. In some embodiments, the isolated polypeptide or polypeptide complex comprises amino acid sequences with at least 99% sequence identity to SEQ ID NO: 56 and SEQ ID NO: 57.

In some embodiments, the isolated polypeptide or polypeptide complex comprises amino acid sequences according to SEQ ID NO: 58 and SEQ ID NO: 59. In some embodiments, the isolated polypeptide or polypeptide complex comprises amino acid sequences with at least 90% sequence identity to SEQ ID NO: 58 and SEQ ID NO: 59. In some embodiments, the isolated polypeptide or polypeptide complex comprises amino acid sequences with at least 95% sequence identity SEQ ID NO: 58 and SEQ ID NO: 59. In some embodiments, the isolated polypeptide or polypeptide complex comprises amino acid sequences with at least 99% sequence identity to SEQ ID NO: 58 and SEQ ID NO: 59.

In some embodiments, the isolated polypeptide or polypeptide complex comprises amino acid sequences according to SEQ ID NO: 60 and SEQ ID NO: 61. In some embodiments, the isolated polypeptide or polypeptide complex comprises amino acid sequences with at least 90% sequence identity to SEQ ID NO: 60 and SEQ ID NO: 61. In some embodiments, the isolated polypeptide or polypeptide complex comprises amino acid sequences with at least 95% sequence identity SEQ ID NO: 60 and SEQ ID NO: 61. In some embodiments, the isolated polypeptide or polypeptide complex comprises amino acid sequences with at least 99% sequence identity to SEQ ID NO: 60 and SEQ ID NO: 61.

In some embodiments, the isolated polypeptide or polypeptide complex comprises amino acid sequences according to SEQ ID NO: 62 and SEQ ID NO: 63. In some embodiments, the isolated polypeptide or polypeptide complex comprises amino acid sequences with at least 90% sequence identity to SEQ ID NO: 62 and SEQ ID NO: 63. In some embodiments, the isolated polypeptide or polypeptide complex comprises amino acid sequences with at least 95% sequence identity SEQ ID NO: 62 and SEQ ID NO: 63. In some embodiments, the isolated polypeptide or polypeptide complex comprises amino acid sequences with at least 99% sequence identity to SEQ ID NO: 62 and SEQ ID NO: 63.

In some embodiments, the isolated polypeptide or polypeptide complex comprises amino acid sequences according to SEQ ID NO: 64 and SEQ ID NO: 65. In some embodiments, the isolated polypeptide or polypeptide complex comprises amino acid sequences with at least 90% sequence identity to SEQ ID NO: 64 and SEQ ID NO: 65. In some embodiments, the isolated polypeptide or polypeptide complex comprises amino acid sequences with at least 95% sequence identity SEQ ID NO: 64 and SEQ ID NO: 65. In some embodiments, the isolated polypeptide or polypeptide complex comprises amino acid sequences with at least 99% sequence identity to SEQ ID NO: 64 and SEQ ID NO: 65.

Polypeptides or polypeptide complexes, in some embodiments, comprise a sequence set forth in Table 6. In some embodiments, the sequence comprises at least or about 70%, 80%, 85%, 90%, 91%, 92%, 93%, 94%, 95%, 96%, 97%, 98%, 99%, or 100% sequence identity to any one of SEQ ID NOs: 44-65. In some instances, the sequence comprises at least or about 95% homology to SEQ ID NOs: 44-65. In some instances, the sequence comprises at least or about 97% homology to SEQ ID NOs: 44-65. In some instances, the sequence comprises at least or about 99% homology to SEQ ID NOs: 44-65. In some instances, the sequence comprises at least or about 100% homology to SEQ ID NOs: 44-65. In some instances, the sequence comprises at least a portion having at least or about 10, 20, 30, 40, 50, 60, 70, 80, 90, 100, 110, 120, 130, 140, 150, 160, 170, 180, 190, 200, 210, or more than 210 amino acids of any one of SEQ ID NOs: 44, 46, 48, 50, 52, 54, 56, 58, 60, 63, or 65. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, or more than 450 amino acids of any one of SEQ ID NOs: 45, 47, 49, 51, 53, 55, 57, 59, or 62. In some instances, the sequence comprises at least a portion having at least or about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, or more than 640 amino acids of any one of SEQ ID NOs: 61 or 64.

As used herein, the term "percent (%) amino acid sequence identity" with respect to a sequence is defined as the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as EMBOSS MATCHER, EMBOSS WATER, EMBOSS STRETCHER, EMBOSS NEEDLE, EMBOSS LALIGN, BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

Disclosed herein, in some embodiments, are polypeptides or polypeptide complexes comprising a structural arrangement according to Configuration 1 (FIG. 1A), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab heavy chain polypeptide to $P_2$ and is a substrate for a tumor specific protease.

Figure 1B:
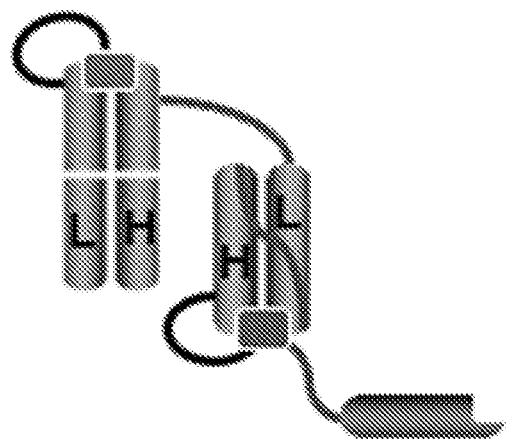

Disclosed herein, in some embodiments, are polypeptides or polypeptide complexes comprising a structural arrangement according to Configuration 2 (FIG. 1B), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab light chain polypeptide to $P_2$ and is a substrate for a tumor specific protease.

Polynucleotides Encoding Polypeptides or Polypeptide Complexes

Disclosed herein, in some embodiments, are isolated recombinant nucleic acid molecules encoding polypeptides or polypeptide complexes as disclosed herein. In some embodiments, the polypeptides or polypeptide complexes comprise an antibody or an antibody fragment. In some embodiments, the polypeptides or polypeptide complexes comprise a Fab and a single chain variable fragment (scFv).

Disclosed herein, in some embodiments, are isolated recombinant nucleic acid molecules encoding polypeptides or polypeptide complexes according to Formula I:

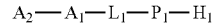

(Formula I)

$$A_2 - A_1 - L_1 - P_1 - H_1$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR).

Disclosed herein, in some embodiments, are isolated recombinant nucleic acid molecules encoding polypeptides or polypeptide complexes according to Formula I:

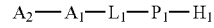

(Formula I)

$$A_2 - A_1 - L_1 - P_1 - H_1$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to epidermal growth factor receptor (EGFR).

Disclosed herein, in some embodiments, are isolated recombinant nucleic acid molecules encoding polypeptides or polypeptide complexes comprising Formula I:

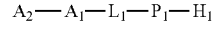

(Formula I)

$$A_2 - A_1 - L_1 - P_1 - H_1$$

wherein: $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR).

Disclosed herein, in some embodiments, are isolated recombinant nucleic acid molecules encoding polypeptides or polypeptide complexes comprising Formula I:

$$A_2\text{---}A_1\text{---}L_1\text{---}P_1\text{---}H_1 \quad \text{(Formula I)}$$

wherein: $A_1$ is a first antigen recognizing molecule that binds to an effector cell antigen; $P_1$ is a peptide that binds to $A_1$; $L_1$ is a linking moiety that connects $A_1$ to $P_1$ and is a substrate for a tumor specific protease; $H_1$ is a half-life extending molecule; and $A_2$ is a second antigen recognizing molecule that binds to epidermal growth factor receptor (EGFR).

Disclosed herein, in some embodiments, are isolated recombinant nucleic acid molecules encoding polypeptides or polypeptide complexes according to Formula Ia:

$$P_2\text{---}L_2\text{---}A_2\text{---}A_1\text{---}L_1\text{---}P_1\text{---}H_1. \quad \text{(Formula Ia)}$$

Disclosed herein, in some embodiments, are isolated recombinant nucleic acid molecules encoding polypeptides or polypeptide complexes according to Formula II:

$$L_{1a}\text{---}P_{1a}\text{---}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds epidermal growth factor receptor (EGFR); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated recombinant nucleic acid molecules encoding polypeptides or polypeptide complexes comprising Formula II:

$$L_{1a}\text{---}P_{1a}\text{---}H_{1a} \quad \text{(Formula II)}$$

wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ comprises a peptide that binds to the first antigen recognizing molecule when $L_{1a}$ is uncleaved; and $H_{1a}$ comprises a half-life extending molecule.

Disclosed herein, in some embodiments, are isolated recombinant nucleic acid molecules encoding polypeptides or polypeptide complexes according to Formula II:

$$L_{1a}\text{---}P_{1a}\text{---}H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ is a peptide that binds to the first antigen recognizing molecule when $L_{1a}$ is uncleaved; and $H_{1a}$ is a half-life extending molecule.

Disclosed herein, in some embodiments, are isolated recombinant nucleic acid molecules encoding polypeptides or polypeptide complexes comprising Formula II:

$$L_{1a}\text{---}P_{1a}\text{---}H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ is a peptide that binds to the first antigen recognizing molecule when $L_{1a}$ is uncleaved; and $H_{1a}$ is a half-life extending molecule.

Disclosed herein, in some embodiments, are isolated nucleic acid molecules encoding polypeptides or polypeptide complexes comprising a structural arrangement according to Configuration 1 (FIG. 1A), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab heavy chain polypeptide to $P_2$ and is a substrate for a tumor specific protease.

Disclosed herein, in some embodiments, are isolated nucleic acid molecules encoding polypeptides or polypeptide complexes comprising a structural arrangement according to Configuration 2 (FIG. 1B), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab light chain polypeptide to $P_2$ and is a substrate for a tumor specific protease.

Pharmaceutical Compositions

Disclosed herein, in some embodiments, are pharmaceutical compositions com the first antigen recognizing molecule when $L_{1a}$ is uncleaved; and $H_{1a}$ is a half-life extending molecule; and (b) a pharmaceutically acceptable excipient.

In some embodiments, the pharmaceutical composition comprises (a) polypeptides or polypeptide complexes comprising Formula II:

$$L_{1a} - P_{1a} - H_{1a} \quad \text{(Formula II)}$$

wherein: $L_{1a}$ is a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to epidermal growth factor receptor (EGFR); $P_{1a}$ is a peptide that binds to the first antigen recognizing molecule when $L_{1a}$ is uncleaved; and $H_{1a}$ is a half-life extending molecule; and (b) a pharmaceutically acceptable excipient.

Disclosed herein, in some embodiments, the pharmaceutical composition comprises (a) polypeptides or polypeptide complexes comprising a structural arrangement according to Configuration 1 (FIG. 1A), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab heavy chain polypeptide to $P_2$ and is a substrate for a tumor specific protease; and (b) a pharmaceutically acceptable excipient.

Disclosed herein, in some embodiments, the pharmaceutical composition comprises (a) polypeptides or polypeptide complexes comprising a structural arrangement according to Configuration 2 (FIG. 1B), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab light chain polypeptide to $P_2$ and is a substrate for a tumor specific protease; and (b) a pharmaceutically acceptable excipient.

In some embodiments, the isolated polypeptide or polypeptide complex further comprises a detectable label, a therapeutic agent, or a pharmacokinetic modifying moiety. In some embodiments, the detectable label comprises a fluorescent label, a radiolabel, an enzyme, a nucleic acid probe, or a contrast agent.

For administration to a subject, the isolated polypeptide or polypeptide complex as disclosed herein, may be provided in a pharmaceutical composition together with one or more pharmaceutically acceptable carriers or excipients. The term "pharmaceutically acceptable carrier" includes, but is not limited to, any carrier that does not interfere with the effectiveness of the biological activity of the ingredients and that is not toxic to the patient to whom it is administered. Examples of suitable pharmaceutical carriers are well known in the art and include phosphate buffered saline solutions, water, emulsions, such as oil/water emulsions, various types of wetting agents, sterile solutions etc. Such carriers can be formulated by conventional methods and can be administered to the subject at a suitable dose. Preferably, the compositions are sterile. These compositions may also contain adjuvants such as preservative, emulsifying agents and dispersing agents. Prevention of the action of microorganisms may be ensured by the inclusion of various antibacterial and antifungal agents.

The pharmaceutical composition may be in any suitable form, (depending upon the desired method of administration). It may be provided in unit dosage form, may be provided in a sealed container and may be provided as part of a kit. Such a kit may include instructions for use. It may include a plurality of said unit dosage forms.

The pharmaceutical composition may be adapted for administration by any appropriate route, including a parenteral (e.g., subcutaneous, intramuscular, or intravenous) route. Such compositions may be prepared by any method known in the art of pharmacy, for example by mixing the active ingredient with the carrier(s) or excipient(s) under sterile conditions.

Dosages of the substances of the present disclosure can vary between wide limits, depending upon the disease or disorder to be treated, the age and condition of the individual to be treated, etc. and a physician will ultimately determine appropriate dosages to be used.

Peptides that Impair Binding of Anti-EGFR Binding Domains to EGFR

Disclosed herein are polypeptide or polypeptide complex comprising an anti-EGFR binding domain that are linked to a peptide that impairs binding of the anti-EGFR binding domain to EGFR wherein the peptide comprises an amino acid sequence according to any one of SEQ ID NOs: 26, 71-96, 98-776 or an amino acid sequence that has 1, 2, or 3 amino acid mutations, substitutions, or deletions relative to any one of SEQ ID NOs: 26, 71-96, 98-776.

In some embodiments, the peptide comprises an amino acid sequence according to any one of 26, 71-96, 98-776.

In some embodiments, the peptide comprises an amino acid sequence according to any one of SEQ ID NOs: 26, 86-96 or an amino acid sequence that has 1, 2, or 3 amino acid mutations, substitutions, or deletions relative to any one of SEQ ID NOs: 26, 86-96.

In some embodiments, the peptide comprises an amino acid sequence according to any one of SEQ ID NOs: 26, 86-96.

In some embodiments, the peptide comprises an amino acid sequence according to any one of SEQ ID NOs: 98-776 or an amino acid sequence that has 1, 2, or 3 amino acid mutations, substitutions, or deletions relative to any of SEQ ID NOs: 98-776.

In some embodiments, the peptide comprises an amino acid sequence according to any one of SEQ ID NOs: 98-776.

In some embodiments, the peptide comprises an amino acid sequence according to any one of SEQ ID NOs: 99-118 or an amino acid sequence that has 1, 2, or 3 amino acid mutations, substitutions, or deletions relative to any one of SEQ ID NOs: 99-118.

In some embodiments, the peptide comprises an amino acid sequence according to any one of SEQ ID NOs: 99-118.

In some embodiments, the peptide comprises the amino acid sequence according to SEQ ID NO: 71 or an amino acid sequence that has 1, 2, or 3 amino acid mutations, substitutions, or deletions relative to SEQ ID NO: 71.

In some embodiments, the peptide comprises the amino acid sequence according to SEQ ID NO: 71.

In some embodiments, the peptide comprises the amino acid sequence according to SEQ ID NO: 26 or an amino acid sequence that has 1, 2, or 3 amino acid mutations, substitutions, or deletions relative to SEQ ID NO: 26.

In some embodiments, the peptide comprises the amino acid sequence according to SEQ ID NO: 26.

In some embodiments, the peptide comprises the amino acid sequence according to SEQ ID NO: 115 or an amino acid sequence that has 1, 2, or 3 amino acid mutations, substitutions, or deletions relative to SEQ ID NO: 115. In some embodiments, the peptide comprises the amino acid sequence according to SEQ ID NO: 115.

In some embodiments, the peptide comprises the amino acid sequence according to SEQ ID NO: 116 or an amino acid sequence that has 1, 2, or 3 amino acid mutations, substitutions, or deletions relative to SEQ ID NO: 116. In some embodiments, the peptide comprises the amino acid sequence according to SEQ ID NO: 116.

Disclosed herein are polypeptide or polypeptide complex comprising an anti-EGFR binding domain that are linked to a peptide that impairs binding of the anti-EGFR binding to EGFR wherein the peptide comprises an amino acid sequence according to $X_1$—C—$X_2$—$X_3$—$X_4$—$X_5$-D-$X_6$-A-$X_7$—P—$X_8$—C—$X_9$ wherein $X_1$ is selected from P and L; $X_2$ is selected from R, L, T, A, N, I, V, S, H, and P; $X_3$ is selected from S, P, F, and Y; $X_4$ is selected from H, L, Q, P, R, F, N; $X_5$ is selected from I, F, Y, H, N, T, S, D, A, L, and V; $X_6$ is selected from T, P, N, L, I, V, S, D, H, A, and Y; $X_7$ is selected from K and Y; $X_8$ is selected from I, P, L, and M; and $X_9$ is selected from A, V, I, T, L, S, D, F, V, and H (SEQ ID NO: 841). In some embodiments, $X_1$ is selected from P and L; $X_2$ is selected from R, L, T, A, and N; $X_3$ is selected from S, P, and F; $X_4$ is selected from H, L, Q, and P; $X_5$ is selected from I, F, Y, H, N, and T; $X_6$ is selected from T, P, N, L, I, and V, $X_7$ is K; $X_8$ is I; and $X_9$ is selected from A, V, I, T, L, and S. In some embodiments, $X_1$ is P; $X_2$ is selected from R, L, and T; $X_3$ is S; $X_4$ is selected from H, L, Q, and P; $X_5$ is selected from I, F, Y, and T; $X_6$ is selected from T, P, N, and V; $X_7$ is K; $X_8$ is I; and $X_9$ is selected from A, V, and I;

In some embodiments, the peptide comprises an amino acid sequence according to any one of SEQ ID NOs: 98-776. In some embodiments, the peptide comprises an amino acid sequence according to any one of SEQ ID NOs: 99-118. In some embodiments, the peptide comprises the amino acid sequence according to SEQ ID NO: 26. In some embodiments, the peptide comprises the amino acid sequence according to SEQ ID NO: 115. In some embodiments, the peptide comprises the amino acid sequence according to SEQ ID NO: 116.

In some embodiments, the anti-EGFR binding domain comprises an antibody or an antibody fragment. In some embodiments, the antibody or antibody fragment comprises a single chain variable fragment, a single domain antibody, Fab, or Fab'. In some embodiments, the anti-EGFR binding domain comprises heavy chain complementarity determining regions HC-CDR1, HC-CDR2, and HC-CDR3, wherein the HC-CDR1, the HC-CDR2, and the HC-CDR3 comprise: HC-CDR1: SEQ ID NO: 15, HC-CDR2: SEQ ID NO: 16, and HC-CDR3: SEQ ID NO: 17; and the anti-EGFR binding domain comprises light chain complementarity determining regions CDRs: LC-CDR1, LC-CDR2, and LC-CDR3, wherein the LC-CDR1, the LC-CDR2, and the LC-CDR3 of the Fab comprise LC-CDR1: SEQ ID NO: 18, LC-CDR2: SEQ ID NO:19, and LC-CDR3: SEQ ID NO: 20.

In some embodiments, the antibody or antibody fragment comprises the Fab. In some embodiments, the anti-EGFR binding domain comprises an amino acid sequences according to any of SEQ ID NOs: 21-24.

In some embodiments, the anti-EGFR binding domain is linked to the peptide through a linking moiety ($L_1$). In some embodiments, $L_1$ is a substrate for a tumor specific protease. In some embodiments, $L_1$ is bound to N-terminus of the anti-EGFR binding domain. In some embodiments, $L_1$ is bound to C-terminus of the anti-EGFR binding domain. In some embodiments, $L_1$ is a peptide sequence having at least 5 to no more than 50 amino acids. In some embodiments, $L_1$ is a peptide sequence having at least 10 to no more than 30 amino acids. In some embodiments, $L_1$ is a peptide sequence having at least 10 amino acids. In some embodiments, $L_1$ is a peptide sequence having at least 18 amino acids. In some embodiments, $L_1$ is a peptide sequence having at least 26 amino acids. In some embodiments, $L_1$ has a formula comprising $(G_2S)_n$, wherein n is an integer from 1 to 3 (SEQ ID NO: 840). In some embodiments, $L_1$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1. In some embodiments, the peptide becomes unbound from the anti-EGFR binding domain when $L_1$ is cleaved by the tumor specific protease thereby exposing the anti-EGFR binding domain to EGFR. In some embodiments, the tumor specific protease is selected from the group consisting of a matrix metalloprotease (MMP), serine protease, cysteine protease, threonine protease, and aspartic protease. In some embodiments, the matrix metalloprotease comprises MMP2, MMP7, MMP9, MMP13, or MMP14. In some embodiments, the serine protease comprises matriptase (MTSP1), urokinase, or hepsin. In some embodiments, $L_1$ comprises a urokinase cleavable amino acid sequence, a matriptase cleavable amino acid sequence, matrix metalloprotease cleavable amino acid sequence, or a legumain cleavable amino acid sequence. In some embodiments, $L_1$ comprises an amino acid sequence according to any of SEQ ID NO: 30 or 31. In some embodiments, $L_1$ comprises an amino acid sequence according to SEQ ID NO: 27-35. In some embodiments, $L_1$ comprises an amino acid sequence of of Linker 4 (ISSGLLSGRSDAG) (SEQ ID NO: 66), Linker 5 (AAGLLAPPGGLSGRSDAG) (SEQ ID NO: 67), Linker 6 (SPLGLSGRSDAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7.

In some embodiments, the isolated polypeptide or polypeptide complex further comprises a half-life extending molecule ($H_1$). In some embodiments, the half-life extending molecule is linked to the peptide. In some embodiments, H₁ comprises a polymer. In some embodiments, the polymer is polyethylene glycol (PEG). In some embodiments, H₁ comprises albumin. In some embodiments, H₁ comprises an Fc domain. In some embodiments, the albumin is serum albumin. In some embodiments, the albumin is human serum albumin. In some embodiments, H₁ comprises a polypeptide, a ligand, or a small molecule. In some embodiments, the polypeptide, the ligand or the small molecule binds serum protein or a fragment thereof, a circulating immunoglobulin or a fragment thereof, or CD35/CR1. In some embodiments, the serum protein comprises a thyroxine-binding protein, a transthyretin, a 1-acid glycoprotein, a transferrin, transferrin receptor or a transferrin-binding portion thereof, a fibrinogen, or an albumin. In some embodiments, the circulating immunoglobulin molecule comprises IgG1, IgG2, IgG3, IgG4, sIgA, IgM or IgD. In some embodiments, the serum protein is albumin. In some embodiments, the polypeptide is an antibody. In some embodiments, the antibody comprises a single domain antibody, a single chain variable fragment, or a Fab. In some embodiments, the single domain antibody comprises a single domain antibody that binds to albumin. In some embodiments, the single domain antibody is a human or humanized antibody. In some embodiments, the single domain antibody is 645gH1gL1. In some embodiments, the single domain antibody is 645dsgH5gL4. In some embodiments, the single domain antibody is 23-13-A01-sc02. In some embodiments, the single domain antibody is A10m3 or a fragment thereof. In some embodiments, the single domain antibody is DOM7r-31. In some embodiments, the single domain antibody is DOM7h-11-15. In some embodiments, the single domain antibody is Alb-1, Alb-8, or Alb-23. In some embodiments, the single domain antibody is 10E. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38. In some embodiments, the single domain antibody comprises an amino acid sequence according to SEQ ID NO: 69. In some embodiments, the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38. In some embodiments, the single domain antibody comprises an amino acid sequence according to SEQ ID NO: 42. In some embodiments, the single domain antibody is SA21. In some embodiments, the isolated polypeptide or polypeptide complex comprises a modified amino acid, a non-natural amino acid, a modified non-natural amino acid, or a combination thereof. In some embodiments, the modified amino acid or modified non-natural amino acid comprises a post-translational modification. In some embodiments, H₁ comprises a linking moiety (L₃) that connects H₁ to the peptide. In some embodiments, L₃ is a peptide sequence having at least 5 to no more than 50 amino acids. In some embodiments, L₃ is a peptide sequence having at least 10 to no more than 30 amino acids. In some embodiments, L₃ is a peptide sequence having at least 10 amino acids. In some embodiments, L₃ is a peptide sequence having at least 18 amino acids. In some embodiments, L₃ is a peptide sequence having at least 26 amino acids. In some embodiments, L₃ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1. In some embodiments, L₃ comprises an amino acid sequence according to SEQ ID NO: 29.

Methods of Treatment

In some embodiments, the polypeptides or polypeptide complexes described herein are used in a method of treating cancer. In some embodiments, the cancer has cells that express EGFR. In some embodiments, the polypeptides or polypeptide complexes described herein are used in a method of treating colorectal cancer (CRC), squamous cell carcinoma of the head and Neck (SCCHN), non-small cell lung cancer (NSCLC), prostate cancer, breast cancer, colon/rectum cancer, head and neck cancer, esophagogastric cancer, liver cancer, glioblastoma, cervical cancer, ovarian cancer, bladder cancer, kidney cancer, or pancreatic cancer. In some embodiments, the polypeptides or polypeptide complexes described herein are used in a method of treating subjects who are resistant to EGFR inhibitor treatment. In some embodiments, the polypeptides or polypeptide complexes described herein are used in a method of treating subjects who harbor KRAS mutations. In some embodiments, the polypeptides or polypeptide complexes described herein are used in a method of treating subjects who are resistant to EGFR inhibitor treatment and harbor KRAS mutations.

Described herein, in some embodiments, are polypeptides or polypeptide complexes, wherein the polypeptides or polypeptide complexes comprise a long half-life. In some instances, the half-life of the polypeptides or polypeptide complexes is at least or about 12 hours, 24 hours 36 hours, 48 hours, 60 hours, 72 hours, 84 hours, 96 hours, 100 hours, 108 hours, 120 hours, 140 hours, 160 hours, 180 hours, 200 hours, or more than 200 hours. In some instances, the half-life of the polypeptides or polypeptide complexes is in a range of about 12 hours to about 300 hours, about 20 hours to about 280 hours, about 40 hours to about 240 hours, about 60 hours to about 200 hours, or about 80 hours to about 140 hours.

Described herein, in some embodiments, are polypeptide or polypeptide complexes administered as once weekly. In some embodiments, the polypeptide or polypeptide complexes are administered once weekly by intravenous, intramuscular, intralesional, topical, subcutaneous, infusion, or oral. In some embodiments, the polypeptide or polypeptide complexes are administered once weekly by bolus injection. In some embodiments, the polypeptide or polypeptide complexes are administered once weekly by continuous infusion. In some embodiments, the isolated polypeptide or polypeptide complex is administered to the subject once a week as a continuous infusion over a period of no more than 60 minutes. In some embodiments, the isolated polypeptide or polypeptide complex is administered to the subject once a week as a continuous intravenous infusion over a period of no more than 30 minutes. In some embodiments, the isolated polypeptide or polypeptide complex is administered to the subject once a week as a continuous intravenous infusion over a period of at least 10 minutes.

In some embodiments, the isolated polypeptide or polypeptide complex is administered to the subject once a week and the isolated polypeptide or polypeptide complex has a half-life of at least 30 hours. In some embodiments, the isolated polypeptide or polypeptide complex is administered to the subject once a week and the isolated polypeptide or polypeptide complex has a half-life of at least 50 hours. In some embodiments, the isolated polypeptide or polypeptide complex is administered to the subject once a week and the isolated polypeptide or polypeptide complex has a half-life of at least 60 hours. In some embodiments, the isolated polypeptide or polypeptide complex is administered to the subject once a week and the isolated polypeptide or polypeptide complex has a half-life of at least 70 hours. In some embodiments, the isolated polypeptide or polypeptide complex is administered to the subject once a week and the isolated polypeptide or polypeptide complex has a half-life of at least 80 hours. In some embodiments, the isolated polypeptide or polypeptide complex is administered to the subject once a week and the isolated polypeptide or polypeptide complex has a half-life of at least 90 hours. In some embodiments, the isolated polypeptide or polypeptide complex is administered to the subject once a week and the isolated polypeptide or polypeptide complex has a half-life of at least 100 hours. In some embodiments, the isolated polypeptide or polypeptide complex is administered to the subject once a week and the isolated polypeptide or polypeptide complex has a half-life of at least 110 hours. In some embodiments, the isolated polypeptide or polypeptide complex is administered to the subject once a week and the isolated polypeptide or polypeptide complex has a half-life of at least 115 hours.

Production of Antibodies that Bind to EGFR and CD3

In some embodiments, polypeptides described herein (e.g., antibodies and its binding fragments) are produced using any method known in the art to be useful for the synthesis of polypeptides (e.g., antibodies), in particular, by chemical synthesis or by recombinant expression, and are preferably produced by recombinant expression techniques.

In some instances, an antibody or its binding fragment thereof is expressed recombinantly, and the nucleic acid encoding the antibody or its binding fragment is assembled from chemically synthesized oligonucleotides (e.g., as described in Kutmeier et al., 1994, BioTechniques 17:242), which involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody is optionally generated from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

In some instances, an antibody or its binding is optionally generated by immunizing an animal, such as a mouse, to generate polyclonal antibodies or, more preferably, by generating monoclonal antibodies, e.g., as described by Kohler and Milstein (1975, Nature 256:495-497) or, as described by Kozbor et al. (1983, Immunology Today 4:72) or Cole et al. (1985 in Monoclonal Antibodies and Cancer Therapy, Alan R. Liss, Inc., pp. 77-96). Alternatively, a clone encoding at least the Fab portion of the antibody is optionally obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

In some embodiments, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454) by splicing genes from a mouse antibody molecule of appropriate antigen specificity together with genes from a human antibody molecule of appropriate biological activity are used. A chimeric antibody is a molecule in which different portions are derived from different animal species, such as those having a variable region derived from a murine monoclonal antibody and a human immunoglobulin constant region.

In some embodiments, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334:544-54) are adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* are also optionally used (Skerra et al., 1988, Science 242:1038-1041).

In some embodiments, an expression vector comprising the nucleotide sequence of an antibody or the nucleotide sequence of an antibody is transferred to a host cell by conventional techniques (e.g., electroporation, liposomal transfection, and calcium phosphate precipitation), and the transfected cells are then cultured by conventional techniques to produce the antibody. In specific embodiments, the expression of the antibody is regulated by a constitutive, an inducible or a tissue, specific promoter.

In some embodiments, a variety of host-expression vector systems is utilized to express an antibody, or its binding fragment described herein. Such host-expression systems represent vehicles by which the coding sequences of the antibody is produced and subsequently purified, but also represent cells that are, when transformed or transfected with the appropriate nucleotide coding sequences, express an antibody or its binding fragment in situ. These include, but are not limited to, microorganisms such as bacteria (e.g., *E. coli* and *B. subtilis*) transformed with recombinant bacteriophage DNA, plasmid DNA or cosmid DNA expression vectors containing an antibody or its binding fragment coding sequences; yeast (e.g., *Saccharomyces Pichia*) transformed with recombinant yeast expression vectors containing an antibody or its binding fragment coding sequences; insect cell systems infected with recombinant virus expression vectors (e.g., baculovirus) containing an antibody or its binding fragment coding sequences; plant cell systems infected with recombinant virus expression vectors (e.g., cauliflower mosaic virus (CaMV) and tobacco mosaic virus (TMV)) or transformed with recombinant plasmid expression vectors (e.g., Ti plasmid) containing an antibody or its binding fragment coding sequences; or mammalian cell systems (e.g., COS, CHO, BH, 293, 293T, 3T3 cells) harboring recombinant expression constructs containing promoters derived from the genome of mammalian cells (e.g., metallothionein promoter) or from mammalian viruses (e.g. the adenovirus late promoter; the vaccinia virus 7.5K promoter).

For long-term, high-yield production of recombinant proteins, stable expression is preferred. In some instances, cell lines that stably express an antibody are optionally engineered. Rather than using expression vectors that contain viral origins of replication, host cells are transformed with DNA controlled by appropriate expression control elements (e.g., promoter, enhancer, sequences, transcription terminators, polyadenylation sites, etc.), and a selectable marker. Following the introduction of the foreign DNA, engineered cells are then allowed to grow for 1-2 days in an enriched media, and then are switched to a selective media. The selectable marker in the recombinant plasmid confers resistance to the selection and allows cells to stably integrate the plasmid into their chromosomes and grow to form foci that in turn are cloned and expanded into cell lines. This method can advantageously be used to engineer cell lines which express the antibody or its binding fragments.

In some instances, a number of selection systems are used, including but not limited to the herpes simplex virus thymidine kinase (Wigler et al., 1977, Cell 11:223), hypoxanthine-guanine phosphoribosyltransferase (Szybalska & Szybalski, 192, Proc. Natl. Acad. Sci. USA 48:202), and adenine phosphoribosyltransferase (Lowy et al., 1980, Cell 22:817) genes are employed in tk-, hgprt- or aprt-cells, respectively. Also, antimetabolite resistance are used as the basis of selection for the following genes: dhfr, which confers resistance to methotrexate (Wigler et al., 1980, Proc. Natl. Acad. Sci. USA 77:357; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May 1993, TIB TECH11(5):155-215) and hygro, which confers resistance to hygromycin (Santerre et al., 1984, Gene 30:147). Methods commonly known in the art of recombinant DNA technology which can be used are described in Ausubel et al. (eds., 1993, Current Protocols in Molecular Biology, John Wiley & Sons, NY; Kriegler, 1990, Gene Transfer and Expression, A Laboratory Manual, Stockton Press, NY; and in Chapters 12 and 13, Dracopoli et al. (eds), 1994, Current Protocols in Human Genetics, John Wiley & Sons, NY; Colberre-Garapin et al., 1981, J. Mol. Biol. 150:1).

In some instances, the expression levels of an antibody are increased by vector amplification (for a review, see Bebbington and Hentschel, the use of vectors based on gene amplification for the expression of cloned genes in mammalian cells in DNA cloning, Vol. 3. (Academic Press, New York, 1987)). When a marker in the vector system expressing an antibody is amplifiable, an increase in the level of inhibitor present in culture of host cell will increase the number of copies of the marker gene. Since the amplified region is associated with the nucleotide sequence of the antibody, production of the antibody will also increase (Crouse et al., 1983, Mol. Cell Biol. 3:257).

In some instances, any method known in the art for purification of an antibody is used, for example, by chromatography (e.g., ion exchange, affinity, particularly by affinity for the specific antigen after Protein A, and sizing column chromatography), centrifugation, differential solubility, or by any other standard technique for the purification of proteins.

Expression Vectors

In some embodiments, vectors include any suitable vectors derived from either a eukaryotic or prokaryotic sources. In some cases, vectors are obtained from bacteria (e.g. *E. coli*), insects, yeast (e.g. *Pichia pastoris*), algae, or mammalian sources. Exemplary bacterial vectors include pACYC177, pASK75, pBAD vector series, pBADM vector series, pET vector series, pETM vector series, pGEX vector series, pHAT, pHAT2, pMal-c2, pMal-p2, pQE vector series, pRSET A, pRSET B, pRSET C, pTrcHis2 series, pZA31-Luc, pZE21-MCS-1, pFLAG ATS, pFLAG CTS, pFLAG MAC, pFLAG Shift-12c, pTAC-MAT-1, pFLAG CTC, or pTAC-MAT-2.

Exemplary insect vectors include pFastBacl, pFastBac DUAL, pFastBac ET, pFastBac HTa, pFastBac HTb, pFastBac HTc, pFastBac M30a, pFastBact M30b, pFastBac, M30c, pVL1392, pVL1393, pVL1393 M10, pVL1393 M11, pVL1393 M12, FLAG vectors such as pPolh-FLAG1 or pPolh-MAT 2, or MAT vectors such as pPolh-MAT1, or pPolh-MAT2.

In some cases, yeast vectors include Gateway® pDEST™ 14 vector, Gateway® pDEST™ 15 vector, Gateway® pDEST™ 17 vector, Gateway® pDEST™ 24 vector, Gateway® pYES-DEST52 vector, pBAD-DEST49 Gateway® destination vector, pAO815 Pichia vector, pFLD1 *Pichia pastoris* vector, pGAPZA,B, & C *Pichia pastoris* vector, pPIC3.5K Pichia vector, pPIC6 A, B, & C Pichia vector, pPIC9K Pichia vector, pTEFl/Zeo, pYES2 yeast vector, pYES2/CT yeast vector, pYES2/NT A, B, & C yeast vector, or pYES3/CT yeast vector.

Exemplary algae vectors include pChlamy-4 vector or MCS vector.

Examples of mammalian vectors include transient expression vectors or stable expression vectors. Mammalian transient expression vectors may include pRK5, p3xFLAG-CMV 8, pFLAG-Myc-CMV 19, pFLAG-Myc-CMV 23, pFLAG-CMV 2, pFLAG-CMV 6a,b,c, pFLAG-CMV 5.1, pFLAG-CMV 5a,b,c, p3xFLAG-CMV 7.1, pFLAG-CMV 20, p3xFLAG-Myc-CMV 24, pCMV-FLAG-MAT1, pCMV-FLAG-MAT2, pBICEP-CMV 3, or pBICEP-CMV 4. Mammalian stable expression vector may include pFLAG-CMV 3, p3xFLAG-CMV 9, p3xFLAG-CMV 13, pFLAG-Myc-CMV 21, p3xFLAG-Myc-CMV 25, pFLAG-CMV 4, p3xFLAG-CMV 10, p3xFLAG-CMV 14, pFLAG-Myc-CMV 22, p3xFLAG-Myc-CMV 26, pBICEP-CMV 1, or pBICEP-CMV 2.

In some instances, a cell-free system is a mixture of cytoplasmic and/or nuclear components from a cell and is used for in vitro nucleic acid synthesis. In some cases, a cell-free system utilizes either prokaryotic cell components or eukaryotic cell components. Sometimes, a nucleic acid synthesis is obtained in a cell-free system based on for example *Drosophila* cell, *Xenopus* egg, or *HeLa* cells. Exemplary cell-free systems include, but are not limited to, *E. coli* S30 Extract system, *E. coli* T7 S30 system, or PURExpress@.

Host Cells

In some embodiments, a host cell includes any suitable cell such as a naturally derived cell or a genetically modified cell. In some instances, a host cell is a production host cell. In some instances, a host cell is a eukaryotic cell. In other instances, a host cell is a prokaryotic cell. In some cases, a eukaryotic cell includes fungi (e.g., yeast cells), animal cell or plant cell. In some cases, a prokaryotic cell is a bacterial cell. Examples of bacterial cell include gram-positive bacteria or gram-negative bacteria. Sometimes the gram-negative bacteria is anaerobic, rod-shaped, or both.

In some instances, gram-positive bacteria include Actinobacteria, Firmicutes or Tenericutes. In some cases, gram-negative bacteria include Aquificae, Deinococcus-Thermus, Fibrobacteres-Chlorobi/Bacteroidetes (FCB group), Fusobacteria, Gemmatimonadetes, Nitrospirae, Planctomycetes-Verrucomicrobia/Chlamydiae (PVC group), Proteobacteria, Spirochaetes or Synergistetes. Other bacteria can be Acidobacteria, Chloroflexi, Chrysiogenetes, Cyanobacteria, Deferribacteres, Dictyoglomi, Thermodesulfobacteria or Thermotogae. A bacterial cell can be *Escherichia coli, Clostridium botulinum*, or *Coli* bacilli.

Exemplary prokaryotic host cells include, but are not limited to, BL21, Mach1™, DH10B™, TOP10, DH5α, DH10Bac™, OmniMax™, MegaX™, DH12S™, INV110, TOP10F', INVαF, TOP10/P3, ccdB Survival, PIR1, PIR2, Stb12™, Stb13™, or Stb14™.

In some instances, animal cells include a cell from a vertebrate or from an invertebrate. In some cases, an animal cell includes a cell from a marine invertebrate, fish, insects, amphibian, reptile, or mammal. In some cases, a fungus cell includes a yeast cell, such as brewer's yeast, baker's yeast, or wine yeast.

Fungi include ascomycetes such as yeast, mold, filamentous fungi, basidiomycetes, or zygomycetes. In some instances, yeast includes Ascomycota or Basidiomycota. In some cases, Ascomycota includes Saccharomycotina (true yeasts, e.g. *Saccharomyces cerevisiae* (baker's yeast)) or Taphrinomycotina (e.g. Schizosaccharomycetes (fission yeasts)). In some cases, Basidiomycota includes Agaricomycotina (e.g. Tremellomycetes) or Pucciniomycotina (e.g. Microbotryomycetes).

Exemplary yeast or filamentous fungi include, for example, the genus: *Saccharomyces, Schizosaccharomyces, Candida, Pichia, Hansenula, Kluyveromyces, Zygosaccharomyces, Yarrowia, Trichosporon, Rhodosporidi, Aspergillus, Fusarium*, or *Trichoderma*. Exemplary yeast or filamentous fungi include, for example, the species: *Saccharomyces cerevisiae, Schizosaccharomyces pombe, Candida utilis, Candida boidini, Candida albicans, Candida tropicalis, Candida stellatoidea, Candida glabrata, Candida krusei, Candida parapsilosis, Candida guilliermondii, Candida viswanathii, Candida lusitaniae, Rhodotorula mucilaginosa, Pichia metanolica, Pichia angusta, Pichia pastoris, Pichia anomala, Hansenula polymorpha, Kluyveromyces lactis, Zygosaccharomyces rouxii, Yarrowia lipolytica, Trichosporon pullulans, Rhodosporidium toru-Aspergillus niger, Aspergillus nidulans, Aspergillus awamori, Aspergillus oryzae, Trichoderma reesei, Yarrowia lipolytica, Brettanomyces bruxellensis, Candida stellata, Schizosaccharomyces pombe, Torulaspora delbrueckii, Zygosaccharomyces bailii, Cryptococcus neoformans, Cryptococcus gattii*, or *Saccharomyces boulardii*.

Exemplary yeast host cells include, but are not limited to, *Pichia pastoris* yeast strains such as GS115, KM71H1 SMD1168, SMD1168H1 and X-33; and *Saccharomyces cerevisiae* yeast strain such as INVSc1.

In some instances, additional animal cells include cells obtained from a mollusk, arthropod, annelid or sponge. In some cases, an additional animal cell is a mammalian cell, e.g., from a primate, ape, equine, bovine, porcine, canine, feline or rodent. In some cases, a rodent includes mouse, rat, hamster, gerbil, hamster, chinchilla, fancy rat, or guinea pig.

Exemplary mammalian host cells include, but are not limited to, 293A cell line, 293FT cell line, 293F cells, 293 H cells, CHO DG44 cells, CHO-S cells, CHO-K1 cells, FUT8 KO CHOK1, Expi293F™ cells, Flp-In™ T-REx™ 293 cell line, Flp-In™-293 cell line, Flp-In™-3T3 cell line, Flp-In™—BHK cell line, Flp-In™—CHO cell line, Flp-In™—CV-1 cell line, Flp-In™-Jurkat cell line, FreeStyle™ 293-F cells, FreeStyle™ CHO—S cells, GripTite™ 293 MSR cell line, GS-CHO cell line, HepaRG™ cells, T-REx™ Jurkat cell line, Per.C6 cells, T-REx™-293 cell line, T-REx™—CHO cell line, and T-REx™-*HeLa* cell line.

In some instances, a mammalian host cell is a stable cell line, or a cell line that has incorporated a genetic material of interest into its own genome and has the capability to express the product of the genetic material after many generations of cell division. In some cases, a mammalian host cell is a transient cell line, or a cell line that has not incorporated a genetic material of interest into its own genome and does not have the capability to express the product of the genetic material after many generations of cell division.

Exemplary insect host cells include, but are not limited to, *Drosophila* S2 cells, Sf9 cells, Sf21 cells, High Five™ cells, and expresSF+® cells.

In some instances, plant cells include a cell from algae. Exemplary insect cell lines include, but are not limited to, strains from *Chlamydomonas reinhardtii* 137c, or *Synechococcus elongatus* PPC 7942.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antibody comprising a first antigen-binding site that specifically binds to CD3 and a second antigen-binding site that specifically binds to EGFR as defined herein before.

The label or package insert indicates that the composition is used for treating the condition of choice. Moreover, the article of manufacture may comprise (a) a first container with a composition contained therein, wherein the composition comprises the bispecific antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Certain Definitions

The terminology used herein is for the purpose of describing particular cases only and is not intended to be limiting. As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising."

The term "antibody" is used in the broadest sense and covers fully assembled antibodies, antibody fragments that can bind antigen, for example, Fab, F(ab')2, Fv, single chain antibodies (scFv), diabodies, antibody chimeras, hybrid antibodies, bispecific antibodies, and the like.

The term "complementarity determining region" or "CDR" is a segment of the variable region of an antibody that is complementary in structure to the epitope to which the antibody binds and is more variable than the rest of the variable region. Accordingly, a CDR is sometimes referred to as hypervariable region. A variable region comprises three CDRs. CDR peptides can be obtained by constructing genes encoding the CDR of an antibody of interest. Such genes are prepared, for example, by using the polymerase chain reaction to synthesize the variable region from RNA of antibody-producing cells. See, for example, Larrick et al., *Methods: A Companion to Methods in Enzymology* 2: 106 (1991); Courtenay-Luck, "Genetic Manipulation of Monoclonal Antibodies," in *Monoclonal Antibodies: Production, Engineering and Clinical Application*, Ritter et al. (eds.), pages 166-179 (Cambridge University Press 1995); and Ward et al., "Genetic Manipulation and Expression of Antibodies," in *Monoclonal Antibodies: Principles and Applications*, Birch et al., (eds.), pages 137-185 (Wiley-Liss, Inc. 1995).

The term "Fab" refers to a protein that contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. Fab' fragments are produced by reducing the F(ab')2 fragment's heavy chain disulfide bridge. Other chemical couplings of antibody fragments are also known.

A "single-chain variable fragment (scFv)" is a fusion protein of the variable regions of the heavy (VH) and light chains (VL) of an antibody, connected with a short linker peptide of ten to about 25 amino acids. The linker is usually rich in glycine for flexibility, as well as serine or threonine for solubility, and can either connect the N-terminus of the VH with the C-terminus of the VL, or vice versa. This protein retains the specificity of the original antibody, despite removal of the constant regions and the introduction of the linker. scFv antibodies are, e.g. described in Houston, J. S., Methods in Enzymol. 203 (1991) 46-96). In addition, antibody fragments comprise single chain polypeptides having the characteristics of a VH domain, namely being able to assemble together with a VL domain, or of a VL domain, namely being able to assemble together with a VH domain to a functional antigen binding site and thereby providing the antigen binding property of full length antibodies.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

EMBODIMENTS

Embodiment 1 comprises an isolated polypeptide or polypeptide complex according to Formula I: $A_2$-$A_1$-$L_1$-$P_1$—$H_1$ wherein $A_1$ comprises a first antigen recognizing molecule that binds to an effector cell antigen; $P_1$ comprises a peptide that binds to $A_1$; $L_1$ comprises a linking moiety that connects $A_1$ to $P_1$ and is a substrate for a tumor specific protease; $H_1$ comprises a half-life extending molecule; and $A_2$ comprises a second antigen recognizing molecule that binds to epidermal growth factor receptor (EGFR).

Embodiment 2 comprises the isolated polypeptide or polypeptide complex of embodiment 1, wherein the first antigen recognizing molecule comprises an antibody or antibody fragment.

Embodiment 3 comprises the isolated polypeptide or polypeptide complex of embodiment 1, wherein first antigen recognizing molecule comprises an antibody or antibody fragment that is human or humanized.

Embodiment 4 comprises the isolated polypeptide or polypeptide complex of any one of embodiments 1-3, wherein $L_1$ is bound to N-terminus of the first antigen recognizing molecule.

Embodiment 5 comprises the isolated polypeptide or polypeptide complex of any one of embodiments 1-3, wherein $A_2$ is bound to C-terminus of the first antigen recognizing molecule.

Embodiment 6 comprises the isolated polypeptide or polypeptide complex of any one of embodiments 1-3, wherein $L_1$ is bound to C-terminus of the first antigen recognizing molecule.

Embodiment 7 comprises the isolated polypeptide or polypeptide complex of any one of embodiments 1-3, wherein $A_2$ is bound to N-terminus of the first antigen recognizing molecule.

Embodiment 8 comprises the isolated polypeptide or polypeptide complex of any one of embodiments 2-7, wherein the antibody or antibody fragment comprises a single chain variable fragment, a single domain antibody, or a Fab fragment.

Embodiment 9 comprises the isolated polypeptide or polypeptide complex of embodiment 8, wherein $A_1$ is the single chain variable fragment (scFv).

Embodiment 10 comprises the isolated polypeptide or polypeptide complex of embodiment 9, wherein the scFv comprises a scFv heavy chain polypeptide and a scFv light chain polypeptide.

Embodiment 11 comprises the isolated polypeptide or polypeptide complex of embodiment 8, wherein $A_1$ is the single domain antibody, Embodiment 12 comprises the isolated polypeptide or polypeptide complex of embodiment 8, wherein the antibody or antibody fragment comprises a single chain variable fragment (scFv), a heavy chain variable domain (VH domain), a light chain variable domain (VL domain), or a variable domain (VHH) of a camelid derived single domain antibody.

Embodiment 13 comprises the isolated polypeptide or polypeptide complex of any one of embodiments 1-12, wherein $A_1$ comprises an anti-CD3ε single chain variable fragment.

Embodiment 14 comprises the isolated polypeptide or polypeptide complex of any one of embodiments 1-12, wherein $A_1$ comprises an anti-CD3ε single chain variable fragment that has a KD binding of 1 μM or less to CD3 on CD3 expressing cells.

Embodiment 15 comprises the isolated polypeptide or polypeptide complex of any one of embodiments 1-14, wherein the effector cell antigen comprises CD3.

Embodiment 16 comprises the isolated polypeptide or polypeptide complex of embodiment 1, wherein $A_1$ comprises a variable light chain and variable heavy chain each of which is capable of specifically binding to human CD3.

Embodiment 17 comprises the isolated polypeptide or polypeptide complex of embodiment 1, wherein $A_1$ comprises complementary determining regions (CDRs) selected from the group consisting of muromonab-CD3 (OKT3), otelixizumab (TRX4), teplizumab (MGA031), visilizumab (Nuvion), SP34, X35, VIT3, BMA030 (BW264/56), CLB-T3/3, CRIS7, YTH12.5, F111-409, CLB-T3.4.2, TR-66, WT32, SPv-T3b, 11D8, XIII-141, XIII-46, XIII-87, 12F6, T3/RW2-8C8, T3/RW2-4B6, OKT3D, M-T301, SMC2, F101.01, UCHT-1, WT-31, 15865, 15865v12, 15865v16, and 15865v19.

Embodiment 18 comprises the isolated polypeptide or polypeptide complex of embodiment 1, wherein the isolated polypeptide or polypeptide complex of Formula I binds to an effector cell when $L_1$ is cleaved by the tumor specific protease.

Embodiment 19 comprises the isolated polypeptide or polypeptide complex of embodiment 1, wherein the isolated polypeptide or polypeptide complex of Formula I binds to an effector cell when $L_1$ is cleaved by the tumor specific protease and $A_1$ binds to the effector cell.

Embodiment 20 comprises the isolated polypeptide or polypeptide complex of embodiment 19, wherein the effector cell is a T cell.

Embodiment 21 comprises the isolated polypeptide or polypeptide complex of embodiment 1, wherein $A_1$ binds to a polypeptide that is part of a TCR-CD3 complex on the effector cell.

Embodiment 22 comprises the isolated polypeptide or polypeptide complex of embodiment 21, wherein the polypeptide that is part of the TCR-CD3 complex is human CD3R.

Embodiment 23 comprises the isolated polypeptide or polypeptide complex of embodiment 1, wherein the effector cell antigen comprises CD3, wherein the scFv comprises CDRs: LC-CDR1, LC-CDR2, and LC-CDR3, wherein the LC-CDR1, the LC-CDR2, and the LC-CDR3 of the scFv LC-CDR1: SEQ ID NO: 1, LC-CDR2: SEQ ID NO: 2, and LC-CDR3: SEQ ID NO: 3; and the scFv comprises complementarity determining regions (CDRs): HC-CDR1, HC-CDR2, and HC-CDR3, wherein the HC-CDR1, the HC-CDR2, and the HC-CDR3 of the scFv: HC-CDR1: SEQ ID NO: 4, HC-CDR2: SEQ ID NO: 5, and HC-CDR3: SEQ ID NO: 6.

Embodiment 24 comprises the isolated polypeptide or polypeptide complex of embodiment 1, wherein the effector cell antigen comprises CD3, and $A_1$ comprises CDRs: LC-CDR1, LC-CDR2, and LC-CDR3, wherein the LC-CDR1, the LC-CDR2, and the LC-CDR3 of $A_1$ comprise LC-CDR1: SEQ ID NO: 1, LC-CDR2: SEQ ID NO: 2, and LC-CDR3: SEQ ID NO: 3; and $A_1$ comprises complementarity determining regions (CDRs): HC-CDR1, HC-CDR2, and HC-CDR3, wherein the HC-CDR1, the HC-CDR2, and the HC-CDR3 of $A_1$ comprise: HC-CDR1: SEQ ID NO: 4, HC-CDR2: SEQ ID NO: 5, and HC-CDR3: SEQ ID NO: 6.

Embodiment 25 comprises the isolated polypeptide or polypeptide complex of embodiment 1, wherein the effector cell antigen comprises CD3, and the scFv comprises an amino acid sequence according to SEQ ID NO: 13.

Embodiment 26 comprises the isolated polypeptide or polypeptide complex of embodiment 1, wherein the effector cell antigen comprises CD3, wherein the scFv comprises CDRs: LC-CDR1, LC-CDR2, and LC-CDR3, wherein the LC-CDR1, the LC-CDR2, and the LC-CDR3 of the scFv LC-CDR1: SEQ ID NO: 7, LC-CDR2: SEQ ID NO: 8, and LC-CDR3: SEQ ID NO: 9; and the scFv comprises complementarity determining regions (CDRs): HC-CDR1, HC-CDR2, and HC-CDR3, wherein the HC-CDR1, the HC-CDR2, and the HC-CDR3 of the scFv: HC-CDR1: SEQ ID NO: 10, HC-CDR2: SEQ ID NO: 11, and HC-CDR3: SEQ ID NO: 12.

Embodiment 27 comprises the isolated polypeptide or polypeptide complex of embodiment 1, wherein the effector cell antigen comprises CD3, and $A_1$ comprises CDRs: LC-CDR1, LC-CDR2, and LC-CDR3, wherein the LC-CDR1, the LC-CDR2, and the LC-CDR3 of $A_1$ comprise: LC-CDR1: SEQ ID NO: 7, LC-CDR2: SEQ ID NO: 8, and LC-CDR3: SEQ ID NO: 9; and $A_1$ comprises complementarity determining regions (CDRs): HC-CDR1, HC-CDR2, and HC-CDR3, wherein the HC-CDR1, the HC-CDR2, and the HC-CDR3 of $A_1$ comprise: HC-CDR1: SEQ ID NO: 10, HC-CDR2: SEQ ID NO: 11, and HC-CDR3: SEQ ID NO: 12.

Embodiment 28 comprises the isolated polypeptide or polypeptide complex of embodiment 1, wherein the effector cell antigen comprises CD3, and the scFv comprises an amino acid sequence according to SEQ ID NO: 14.

Embodiment 29 comprises the isolated polypeptide or polypeptide complex of any one of embodiments 1-28, wherein second antigen recognizing molecule comprises an antibody or antibody fragment.

Embodiment 30 comprises the isolated polypeptide or polypeptide complex of embodiment 29, wherein the antibody or antibody fragment thereof comprises a single chain variable fragment, a single domain antibody, or a Fab.

Embodiment 31 comprises the isolated polypeptide or polypeptide complex of embodiment 29, wherein the antibody or antibody fragment thereof comprises a single chain variable fragment (scFv), a heavy chain variable domain (VH domain), a light chain variable domain (VL domain), a variable domain (VHH) of a camelid derived single domain antibody.

Embodiment 32 comprises the isolated polypeptide or polypeptide complex of embodiment 29, wherein the antibody or antibody fragment thereof is humanized or human.

Embodiment 33 comprises the isolated polypeptide or polypeptide complex of embodiment 30, wherein $A_2$ is the Fab.

Embodiment 34 comprises the isolated polypeptide or polypeptide complex of embodiment 33, wherein the Fab comprises (a) a Fab light chain polypeptide and (b) a Fab heavy chain polypeptide.

Embodiment 35 comprises the isolated polypeptide or polypeptide complex of embodiment 33, wherein the Fab comprises CDRs: LC-CDR1, LC-CDR2, and LC-CDR3, wherein the LC-CDR1, the LC-CDR2, and the LC-CDR3 of the Fab comprise LC-CDR1: SEQ ID NO: 15, LC-CDR2: SEQ ID NO:16, and LC-CDR3: SEQ ID NO: 17; and the Fab comprises complementarity determining regions (CDRs): HC-CDR1, HC-CDR2, and HC-CDR3, wherein the HC-CDR1, the HC-CDR2, and the HC-CDR3 of the Fab comprise: HC-CDR1: SEQ ID NO: 18, HC-CDR2: SEQ ID NO: 19, and HC-CDR3: SEQ ID NO: 20.

Embodiment 36 comprises the isolated polypeptide or polypeptide complex of embodiment 29, wherein $A_2$ comprises CDRs: LC-CDR1, LC-CDR2, and LC-CDR3, wherein the LC-CDR1, the LC-CDR2, and the LC-CDR3 of $A_2$ comprise LC-CDR1: SEQ ID NO: 15, LC-CDR2: SEQ ID NO:16, and LC-CDR3: SEQ ID NO: 17; and $A_2$ comprises complementarity determining regions (CDRs): HC-CDR1, HC-CDR2, and HC-CDR3, wherein the HC-CDR1, the HC-CDR2, and the HC-CDR3 of $A_2$ comprise: HC-CDR1: SEQ ID NO: 18, HC-CDR2: SEQ ID NO: 19, and HC-CDR3: SEQ ID NO: 20.

Embodiment 37 comprises the isolated polypeptide or polypeptide complex of embodiment 34, wherein the Fab light chain polypeptide comprises an amino acid sequence according to SEQ ID NO: 21.

Embodiment 38 comprises the isolated polypeptide or polypeptide complex of embodiment 34, wherein the Fab light chain polypeptide comprises an amino acid sequence according to SEQ ID NO: 22.

Embodiment 39 comprises the isolated polypeptide or polypeptide complex of embodiment 34, wherein Fab heavy chain polypeptide comprises an amino acid sequence according to SEQ ID NO: 23.

Embodiment 40 comprises the isolated polypeptide or polypeptide complex of embodiment 34, wherein Fab heavy chain polypeptide comprises an amino acid sequence according to SEQ ID NO: 24.

Embodiment 41 comprises the isolated polypeptide or polypeptide complex of embodiment 34, wherein the Fab light chain polypeptide of $A_2$ is bound to a C-terminus of the single chain variable fragment (scFv) of $A_1$.

Embodiment 42 comprises the isolated polypeptide or polypeptide complex of embodiment 34, wherein the Fab heavy chain polypeptide of $A_2$ is bound to a C-terminus of the single chain variable fragment (scFv) $A_1$.

Embodiment 43 comprises the isolated polypeptide or polypeptide complex of embodiment 34, wherein the Fab light chain polypeptide of $A_2$ is bound to a N-terminus of the single chain variable fragment (scFv) of $A_1$.

Embodiment 44 comprises the isolated polypeptide or polypeptide complex of embodiment 34, wherein the Fab heavy chain polypeptide of $A_2$ is bound to a N-terminus of the single chain variable fragment (scFv) $A_1$.

Embodiment 45 comprises the isolated polypeptide or polypeptide complex of embodiment 34, wherein the Fab heavy chain polypeptide of $A_2$ is bound to the scFv heavy chain polypeptide of $A_1$.

Embodiment 46 comprises the isolated polypeptide or polypeptide complex of embodiment 34, wherein the Fab light chain polypeptide of $A_2$ is bound to the scFv heavy chain polypeptide of $A_1$.

Embodiment 47 comprises the isolated polypeptide or polypeptide complex of embodiment 34, wherein the Fab heavy chain polypeptide of $A_2$ is bound to the scFv light chain polypeptide of $A_1$.

Embodiment 48 comprises the isolated polypeptide or polypeptide complex of embodiment 34, wherein the Fab light chain polypeptide of $A_2$ is bound to the scFv light chain polypeptide of $A_1$.

Embodiment 49 comprises the isolated polypeptide or polypeptide complex of any one of embodiments 1-48, wherein $A_2$ further comprises $P_2$ and $L_2$, wherein $P_2$ comprises a peptide that binds to $A_2$; and $L_2$ comprises a linking moiety that connects $A_2$ to $P_2$ and is a substrate for a tumor specific protease.

Embodiment 50 comprises the isolated polypeptide or polypeptide complex of embodiment 49, wherein the isolated polypeptide or polypeptide complex is according to Formula Ia: $P_2\text{-}L_2\text{-}A_2\text{-}A_1\text{-}L_1\text{-}P_1\text{—}H_1$.

Embodiment 51 comprises the isolated polypeptide or polypeptide complex of embodiment 50, wherein the Fab heavy chain polypeptide of $A_2$ is bound to the scFv heavy chain polypeptide of $A_1$ and $L_2$ is bound to the Fab light chain polypeptide of $A_2$.

Embodiment 52 comprises the isolated polypeptide or polypeptide complex of embodiment 50, wherein the Fab light chain polypeptide of $A_2$ is bound to the scFv heavy chain polypeptide of $A_1$ and $L_2$ is bound to the Fab heavy chain polypeptide of $A_2$.

Embodiment 53 comprises the isolated polypeptide or polypeptide complex of embodiment 50, wherein the Fab heavy chain polypeptide of $A_2$ is bound to the scFv light chain polypeptide of $A_1$ and $L_2$ is bound to the Fab light chain polypeptide of $A_2$.

Embodiment 54 comprises the isolated polypeptide or polypeptide complex of embodiment 50, wherein the Fab light chain polypeptide of $A_2$ is bound to the scFv light chain polypeptide of $A_1$ and $L_2$ is bound to the Fab heavy chain polypeptide of $A_2$.

Embodiment 55 comprises the isolated polypeptide or polypeptide complex of any one of embodiments 1-54, wherein $P_1$ impairs binding of $A_1$ to the effector cell antigen.

Embodiment 56 comprises the isolated polypeptide or polypeptide complex of any one of embodiments 1-55, wherein $P_1$ is bound to $A_1$ through ionic interactions, electrostatic interactions, hydrophobic interactions, Pi-stacking interactions, and H-bonding interactions, or a combination thereof.

Embodiment 57 comprises the isolated polypeptide or polypeptide complex of any one of embodiments 1-56, wherein $P_1$ has less than 70% sequence homology to the effector cell antigen.

Embodiment 58 comprises the isolated polypeptide or polypeptide complex of any one of embodiments 49-57, wherein $P_2$ impairs binding of $A_2$ to EGFR.

Embodiment 59 comprises the isolated polypeptide or polypeptide complex of any one of embodiments 49-58, wherein $P_2$ is bound to $A_2$ through ionic interactions, electrostatic interactions, hydrophobic interactions, Pi-stacking interactions, and H-bonding interactions, or a combination thereof.

Embodiment 60 comprises the isolated polypeptide or polypeptide complex of any one of embodiments 49-59, wherein $P_2$ is bound to $A_2$ at or near an antigen binding site.

Embodiment 61 comprises the isolated polypeptide or polypeptide complex of any one of embodiments 49-60, wherein $P_2$ has less than 70% sequence homology to EGFR.

Embodiment 62 comprises the isolated polypeptide or polypeptide complex of any one of embodiments 1-61, wherein $P_1$ or $P_2$ comprises a peptide sequence of at least 10 amino acids in length.

Embodiment 63 comprises the isolated polypeptide or polypeptide complex of any one of embodiments 1-62, wherein $P_1$ or $P_2$ comprises a peptide sequence of at least 10 amino acids in length and no more than 20 amino acids in length.

Embodiment 64 comprises the isolated polypeptide or polypeptide complex of any one of embodiments 1-63, wherein $P_1$ or $P_2$ comprises a peptide sequence of at least 16 amino acids in length.

Embodiment 65 comprises the isolated polypeptide or polypeptide complex of any one of embodiments 1-61, wherein $P_1$ or $P_2$ comprises a peptide sequence of no more than 40 amino acids in length.

Embodiment 66 comprises the isolated polypeptide or polypeptide complex of any one of embodiments 1-61, wherein $P_1$ or $P_2$ comprises at least two cysteine amino acid residues.

Embodiment 67 comprises the isolated polypeptide or polypeptide complex of any one of embodiments 1-61, wherein $P_1$ or $P_2$ comprises a cyclic peptide or a linear peptide.

Embodiment 68 comprises the isolated polypeptide or polypeptide complex of any one of embodiments 1-61, wherein $P_1$ or $P_2$ comprises a cyclic peptide.

Embodiment 69 comprises the isolated polypeptide or polypeptide complex of any one of embodiments 1-61, wherein $P_1$ or $P_2$ comprises a linear peptide.

Embodiment 70 comprises the isolated polypeptide or polypeptide complex of any one of embodiments 1-61, wherein $P_1$ comprises at least two cysteine amino acid residues.

Embodiment 71 comprises the isolated polypeptide or polypeptide complex of any one of embodiments 1-61, wherein $P_1$ comprises an amino acid sequence according to SEQ ID NO: 25.

Embodiment 72 comprises the isolated polypeptide or polypeptide complex of any one of embodiments 1-61, wherein $P_2$ comprises an amino acid sequence according to SEQ ID NO: 26.

Embodiment 73 comprises the isolated polypeptide or polypeptide complex of any one of embodiments 1-61, wherein $P_1$ comprises an amino acid sequence according to SEQ ID NO: 70.

Embodiment 74 comprises the isolated polypeptide or polypeptide complex of any one of embodiments 1-61, wherein $P_2$ comprises an amino acid sequence according to any one of SEQ ID NOs: 26, 71-96, 98-776, or an amino acid sequence that has 1, 2, or 3 amino acid mutations, substitutions, or deletions relative to any one of SEQ ID NOs: 26, 71-96, 98-776.

Embodiment 75 comprises the isolated polypeptide or polypeptide complex of any one of embodiments 1-61, wherein $P_2$ comprises an an amino acid sequence according to $X_1$—C—$X_2$—$X_3$—$X_4$—$X_5$-D-$X_6$-A-$X_7$—P—$X_8$—C—$X_9$ wherein $X_1$ is selected from P and L; $X_2$ is selected from R, L, T, A, N, I, V, S, H, and P; $X_3$ is selected from S, P, F, and Y; $X_4$ is selected from H, L, Q, P, R, F, N; $X_5$ is selected from I, F, Y, H, N, T, S, D, A, L, and V; $X_6$ is selected from T, P, N, L, I, V, S, D, H, A, and Y; $X_7$ is selected from K and Y; $X_8$ is selected from I, P, L, and M; and $X_9$ is selected from A, V, I, T, L, S, D, F, V, and H (SEQ ID NO: 841).

Embodiment 76 comprises the isolated polypeptide or polypeptide complex of embodiment 75, wherein $X_1$ is selected from P and L; $X_2$ is selected from R, L, T, A, and N; $X_3$ is selected from S, P, and F; $X_4$ is selected from H, L, Q, and P; $X_5$ is selected from I, F, Y, H, N, and T; $X_6$ is selected from T, P, N, L, I, and V; $X_7$ is K; $X_8$ is I; and $X_9$ is selected from A, V, I, T, L, and S.

Embodiment 77 comprises the isolated polypeptide or polypeptide complex of embodiment 76, wherein $X_1$ is P; $X_2$ is selected from R, L, and T; $X_3$ is S; $X_4$ is selected from H, L, Q, and P; $X_5$ is selected from I, F, Y, and T; $X_6$ is selected from T, P, N, and V; $X_7$ is K; $X_8$ is I; and $X_9$ is selected from A, V, and I.

Embodiment 78 comprises the isolated polypeptide or polypeptide complex of any one of embodiments 1-77, wherein $P_2$ comprises an amino acid sequence according to any one of SEQ ID NOs: 26, 86-96, or an amino acid sequence that has 1, 2, or 3 amino acid mutations, substitutions, or deletions relative to any one of SEQ ID NOs: 26, 86-96.

Embodiment 79 comprises the isolated polypeptide or polypeptide complex of embodiment 78, wherein $P_2$ comprises an amino acid sequence according to any one of SEQ ID NOs: 26, 86-96.

Embodiment 80 comprises the isolated polypeptide or polypeptide complex of any one of embodiments 1-77, wherein $P_2$ comprises an amino acid sequence according to any one of SEQ ID NOs: 98-776 or an amino acid sequence that has 1, 2, or 3 amino acid mutations, substitutions, or deletions relative to any one of SEQ ID NOs: 98-776.

Embodiment 81 comprises the isolated polypeptide or polypeptide complex of embodiment 80, wherein $P_2$ comprises an amino acid sequence according to any one of SEQ ID NOs: 98-776.

Embodiment 82 comprises the isolated polypeptide or polypeptide complex of any one of embodiments 1-77, wherein $P_2$ comprises an amino acid sequence according to any one of SEQ ID NOs: 99-118 or an amino acid sequence that has 1, 2, or 3 amino acid mutations, substitutions, or deletions relative to any one of SEQ ID NOs: 99-118.

Embodiment 83 comprises the isolated polypeptide or polypeptide complex of embodiment 82, wherein $P_2$ comprises an amino acid sequence according to any one of SEQ ID NOs: 99-118.

Embodiment 84 comprises the isolated polypeptide or polypeptide complex of any one of embodiments 1-77, wherein $P_2$ comprises an amino acid sequence according to SEQ ID NO: 26 or an amino acid sequence that has 1, 2, or 3 amino acid mutations, substitutions, or deletions relative to SEQ ID NO: 26.

Embodiment 85 comprises the isolated polypeptide or polypeptide complex of embodiment 84, wherein $P_2$ comprises the amino acid sequence according to SEQ ID NO: 26.

Embodiment 86 comprises the isolated polypeptide or polypeptide complex of any one of embodiments 1-85, wherein $P_1$ comprises an amino acid sequence according to any one of SEQ ID NOs: 25, 797-835, or 843-1690 or an amino acid sequence that has 1, 2, or 3 amino acid mutations, substitutions, or deletions relative to any one of SEQ ID NOs: 25, 797-835, or 843-1690.

Embodiment 87 comprises the isolated polypeptide or polypeptide complex of any one of embodiments 1-85, wherein $P_1$ comprises an amino acid sequence according to $Z_1$—$Z_2$—C—$Z_4$—P—$Z_6$-$Z_7$—$Z_8$—$Z_9$-$Z_{10}$—$Z_{11}$—$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S.

Embodiment 88 comprises the isolated polypeptide or polypeptide complex of embodiment 87, wherein $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_8$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; and $Z_{14}$ is selected from D, Y, N, F, I, and P.

Embodiment 89 comprises the isolated polypeptide or polypeptide complex of embodiment 88, wherein $Z_1$ is selected from D, Y, and F; $Z_2$ is selected from D, Y, L, and F; $Z_4$ is selected from G and W; $Z_6$ is selected from E and D; $Z_7$, is selected from W, L, and F; $Z_8$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N.

Embodiment 90 comprises the isolated polypeptide or polypeptide complex of any one of embodiments 1-85, wherein $P_1$ comprises an amino acid sequence according to $U_1$—$U_2$—C—$U_4$—P—$U_6$—$U_7$—$U_8$—$U_9$—$U_{10}$—$U_{11}$—$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S.

Embodiment 91 comprises the isolated polypeptide or polypeptide complex of embodiment 90, wherein $U_1$ is selected from D, Y, F, I, V, and N; $U_2$ is selected from D, Y, L, F, I, and N; $U_4$ is selected from G and W; $U_6$ is selected from E and D; $U_7$ is selected from W, L, F, G, and Y; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P.

Embodiment 92 comprises the isolated polypeptide or polypeptide complex of embodiment 91, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; $U_9$ is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

Embodiment 93 comprises the isolated polypeptide or polypeptide complex of any one of embodiments 1-92, wherein $P_1$ comprises the amino acid sequences according to any one of SEQ ID NOs: 797-823.

Embodiment 94 comprises the isolated polypeptide or polypeptide complex of any one of embodiments 1-92, wherein $P_1$ comprises an amino acid sequences according to any one of SEQ ID NOs: 25, 824-835, or 843-1690.

Embodiment 95 comprises the isolated polypeptide or polypeptide complex of any one of embodiments 1-92, wherein $P_1$ comprises the amino acid sequences according to any of SEQ ID NOs: 824-835.

Embodiment 96 comprises the isolated polypeptide or polypeptide complex of any one of embodiments 1-92, wherein $P_1$ comprises the amino acid sequence according to SEQ ID NO: 810 or an amino acid sequence that has 1, 2, or 3, amino acid substitutions, additions, or deletions relative to the amino acid sequence of SEQ ID NO: 810.

Embodiment 97 comprises the isolated polypeptide or polypeptide complex of any one of embodiments 1-92, wherein $P_1$ comprises the amino acid sequence according to SEQ ID NO: 811 or an amino acid sequence that has 1, 2, or 3, amino acid substitutions, additions, or deletions relative to the amino acid sequence of SEQ ID NO: 811.

Embodiment 98 comprises the isolated polypeptide or polypeptide complex of any one of embodiments 1-92, wherein $P_1$ comprises the amino acid sequence according to SEQ ID NO: 834 or an amino acid sequence that has 1, 2, or 3, amino acid substitutions, additions, or deletions relative to the amino acid sequence of SEQ ID NO: 834.

Embodiment 99 comprises the isolated polypeptide or polypeptide complex of any one of embodiments 1-92, wherein $P_1$ comprises the amino acid sequence according to SEQ ID NO: 810.

Embodiment 100 comprises the isolated polypeptide or polypeptide complex of any one of embodiments 1-92, wherein $P_1$ comprises the amino acid sequence according to SEQ ID NO: 811.

Embodiment 101 comprises the isolated polypeptide or polypeptide complex of any one of embodiments 1-92, wherein $P_1$ comprises the amino acid sequence according to SEQ ID NO: 834.

Embodiment 102 comprises the isolated polypeptide or polypeptide complex of any one of embodiments 1-101, wherein $L_1$ is bound to N-terminus of $A_1$.

Embodiment 103 comprises the isolated polypeptide or polypeptide complex of any one of embodiments 1-101, wherein $L_1$ is bound to C-terminus of $A_1$.

Embodiment 104 comprises the isolated polypeptide or polypeptide complex of any one of embodiments 49-101, wherein $L_2$ is bound to N-terminus of $A_2$.

Embodiment 105 comprises the isolated polypeptide or polypeptide complex of any one of embodiments 49-101, wherein $L_2$ is bound to C-terminus of $A_2$.

Embodiment 106 comprises the isolated polypeptide or polypeptide complex of any one of embodiments 1-105, wherein $L_1$ or $L_2$ is a peptide sequence having at least 5 to no more than 50 amino acids.

Embodiment 107 comprises the isolated polypeptide or polypeptide complex of any one of embodiments 1-105, wherein $L_1$ or $L_2$ is a peptide sequence having at least 10 to no more than 30 amino acids.

Embodiment 108 comprises the isolated polypeptide or polypeptide complex of any one of embodiments 1-105, wherein $L_1$ or $L_2$ is a peptide sequence having at least 10 amino acids.

Embodiment 109 comprises the isolated polypeptide or polypeptide complex of any one of embodiments 1-105, wherein $L_1$ or $L_2$ is a peptide sequence having at least 18 amino acids.

Embodiment 110 comprises the isolated polypeptide or polypeptide complex of any one of embodiments 1-105, wherein $L_1$ or $L_2$ is a peptide sequence having at least 26 amino acids.

Embodiment 111 comprises the isolated polypeptide or polypeptide complex of any one of embodiments 1-105, wherein $L_1$ or $L_2$ has a formula comprising $(G_2S)_n$, wherein n is an integer from 1 to 3 (SEQ ID NO: 840).

Embodiment 112 comprises the isolated polypeptide or polypeptide complex of any one of embodiments 1-105, wherein $L_1$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1.

Embodiment 113 comprises the isolated polypeptide or polypeptide complex of any one of embodiments 1-105, wherein $P_1$ becomes unbound from $A_1$ when $L_1$ is cleaved by the tumor specific protease thereby exposing $A_1$ to the effector cell antigen.

Embodiment 114 comprises the isolated polypeptide or polypeptide complex of any one of embodiments 1-105, wherein $P_2$ becomes unbound from $A_2$ when $L_2$ is cleaved by the tumor specific protease thereby exposing $A_2$ to EGFR.

Embodiment 115 comprises the isolated polypeptide or polypeptide complex of any one of embodiments 1-105, wherein the tumor specific protease is selected from the group consisting of a matrix metalloprotease (MMP), serine protease, cysteine protease, threonine protease, and aspartic protease.

Embodiment 116 comprises the isolated polypeptide or polypeptide complex of embodiment 115, wherein the matrix metalloprotease comprises MMP2, MMP7, MMP9, MMP13, or MMP14.

Embodiment 117 comprises the isolated polypeptide or polypeptide complex of embodiment 115, wherein the serine protease comprises matriptase (MTSP1), urokinase, or hepsin.

Embodiment 118 comprises the isolated polypeptide or polypeptide complex of any one of embodiments 1-105, wherein $L_1$ or $L_2$ comprises a urokinase cleavable amino acid sequence, a matriptase cleavable amino acid sequence, matrix metalloprotease cleavable amino acid sequence, or a legumain cleavable amino acid sequence.

Embodiment 119 comprises the isolated polypeptide or polypeptide complex of any one of embodiments 1-105, wherein $L_1$ or $L_2$ comprises an amino acid sequence according to SEQ ID NO: 30 or 31.

Embodiment 120 comprises the isolated polypeptide or polypeptide complex of any one of embodiments 1-105, wherein $L_1$ or $L_2$ comprises an amino acid sequence according to any one of SEQ ID NOs: 27-35.

Embodiment 121 comprises the isolated polypeptide or polypeptide complex of any one of embodiments 1-105, wherein $L_1$ or $L_2$ comprises an amino acid sequence of Linker 4 (ISSGLLSGRSDAG) (SEQ ID NO: 66), Linker 5 (AAGLLAPPGGLSGRSDAG) (SEQ ID NO: 67), Linker 6 (SPLGLSGRSDAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7.

Embodiment 122 comprises the isolated polypeptide or polypeptide complex of any one of embodiments 1-121, wherein $H_1$ comprises a polymer.

Embodiment 123 comprises the isolated polypeptide or polypeptide complex of any one of embodiments 1-121, wherein the polymer is polyethylene glycol (PEG).

Embodiment 124 comprises the isolated polypeptide or polypeptide complex of any one of embodiments 1-121, wherein $H_1$ comprises albumin.

Embodiment 125 comprises the isolated polypeptide or polypeptide complex of any one of embodiments 1-121, wherein $H_1$ comprises an Fc domain.

Embodiment 126 comprises the isolated polypeptide or polypeptide complex of embodiment 124, wherein the albumin is serum albumin.

Embodiment 127 comprises the isolated polypeptide or polypeptide complex of embodiment 124, wherein the albumin is human serum albumin.

Embodiment 128 comprises the isolated polypeptide or polypeptide complex of any one of embodiments 1-121, wherein $H_1$ comprises a polypeptide, a ligand, or a small molecule.

Embodiment 129 comprises the isolated polypeptide or polypeptide complex of embodiment 128, wherein the polypeptide, the ligand or the small molecule binds serum protein or a fragment thereof, a circulating immunoglobulin or a fragment thereof, or CD35/CR1.

Embodiment 130 comprises the isolated polypeptide or polypeptide complex of embodiment 129, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 131 comprises the isolated polypeptide or polypeptide complex of embodiment 129, wherein the circulating immunoglobulin molecule comprises IgG1, IgG2, IgG3, IgG4, sIgA, IgM or IgD.

Embodiment 132 comprises the isolated polypeptide or polypeptide complex of embodiment 129, wherein the serum protein is albumin.

Embodiment 133 comprises the isolated polypeptide or polypeptide complex of embodiment 128, wherein the polypeptide is an antibody.

Embodiment 134 comprises the isolated polypeptide or polypeptide complex of embodiment 133, wherein the antibody comprises a single domain antibody, a single chain variable fragment, or a Fab.

Embodiment 135 comprises the isolated polypeptide or polypeptide complex of embodiment 134, wherein the single domain antibody comprises a single domain antibody that binds to albumin.

Embodiment 136 comprises the isolated polypeptide or polypeptide complex of embodiment 134, wherein the single domain antibody is a human or humanized antibody.

Embodiment 137 comprises the isolated polypeptide or polypeptide complex of embodiment 134, wherein the single domain antibody is 645gH1 gL1.

Embodiment 138 comprises the isolated polypeptide or polypeptide complex of embodiment 134, wherein the single domain antibody is 645dsgH5gL4.

Embodiment 139 comprises the isolated polypeptide or polypeptide complex of embodiment 134, wherein the single domain antibody is 23-13-A01-sc02.

Embodiment 140 comprises the isolated polypeptide or polypeptide complex of embodiment 134, wherein the single domain antibody is A10m3 or a fragment thereof.

Embodiment 141 comprises the isolated polypeptide or polypeptide complex of embodiment 134, wherein the single domain antibody is DOM7r-31.

Embodiment 142 comprises the isolated polypeptide or polypeptide complex of embodiment 134, wherein the single domain antibody is DOM7h-11-15.

Embodiment 143 comprises the isolated polypeptide or polypeptide complex of embodiment 134, wherein the single domain antibody is Alb-1, Alb-8, or Alb-23.

Embodiment 144 comprises the isolated polypeptide or polypeptide complex of embodiment 134, wherein the single domain antibody is 10E.

Embodiment 145 comprises the isolated polypeptide or polypeptide complex of embodiment 134, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38.

Embodiment 146 comprises the isolated polypeptide or polypeptide complex of embodiment 134, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 39, HC-CDR2: SEQ ID NO: 40, and HC-CDR3: SEQ ID NO: 41.

Embodiment 147 comprises the isolated polypeptide or polypeptide complex of embodiment 134, wherein the single domain antibody is SA21.

Embodiment 148 comprises the isolated polypeptide or polypeptide complex of any one of embodiments 1-147, wherein the isolated polypeptide or polypeptide complex comprises a modified amino acid, a non-natural amino acid, a modified non-natural amino acid, or a combination thereof.

Embodiment 149 comprises the isolated polypeptide or polypeptide complex of embodiment 148, wherein the modified amino acid or modified non-natural amino acid comprises a post-translational modification.

Embodiment 150 comprises the isolated polypeptide or polypeptide complex of any one of embodiments 1-149, wherein $H_1$ comprises a linking moiety ($L_3$) that connects $H_1$ to $P_1$.

Embodiment 151 comprises the isolated polypeptide or polypeptide complex of embodiment 150, wherein $L_3$ is a peptide sequence having at least 5 to no more than 50 amino acids.

Embodiment 152 comprises the isolated polypeptide or polypeptide complex of embodiment 150, wherein $L_3$ is a peptide sequence having at least 10 to no more than 30 amino acids.

Embodiment 153 comprises the isolated polypeptide or polypeptide complex of embodiment 150, wherein $L_3$ is a peptide sequence having at least 10 amino acids.

Embodiment 154 comprises the isolated polypeptide or polypeptide complex of embodiment 150, wherein $L_3$ is a peptide sequence having at least 18 amino acids.

Embodiment 155 comprises the isolated polypeptide or polypeptide complex of embodiment 150, wherein $L_3$ is a peptide sequence having at least 26 amino acids.

Embodiment 156 comprises the isolated polypeptide or polypeptide complex of embodiment 150, wherein $L_3$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1.

Embodiment 157 comprises the isolated polypeptide or polypeptide complex of embodiment 150, wherein $L_3$ comprises an amino acid sequence according to SEQ ID NO: 29.

Embodiment 158 comprises the isolated polypeptide or polypeptide complex of embodiment 1, wherein the isolated polypeptide or polypeptide complex comprises an amino acid sequence with at least 95% sequence identity to any one of SEQ ID NOs: 44-61.

Embodiment 159 comprises the isolated polypeptide or polypeptide complex of embodiment 1, wherein the isolated polypeptide or polypeptide complex comprises an amino acid sequence with at least 95% sequence identity to SEQ ID NO: 50.

Embodiment 160 comprises the isolated polypeptide or polypeptide complex of embodiment 1, wherein the isolated polypeptide or polypeptide complex comprises an amino acid sequence with at least 95% sequence identity to SEQ ID NO: 51.

Embodiment 161 comprises the isolated polypeptide or polypeptide complex of embodiment 1, wherein the isolated polypeptide or polypeptide complex comprises an amino acid sequence with at least 95% sequence identity to SEQ ID NO: 44 and SEQ ID NO: 45.

Embodiment 162 comprises the isolated polypeptide or polypeptide complex of embodiment 1, wherein the isolated polypeptide or polypeptide complex comprises an amino acid sequence with at least 95% sequence identity to SEQ ID NO: 46 and SEQ ID NO: 47.

Embodiment 163 comprises the isolated polypeptide or polypeptide complex of embodiment 1, wherein the isolated polypeptide or polypeptide complex comprises an amino acid sequence with at least 95% sequence identity to SEQ ID NO: 48 and SEQ ID NO: 49.

Embodiment 164 comprises the isolated polypeptide or polypeptide complex of embodiment 1, wherein the isolated polypeptide or polypeptide complex comprises an amino acid sequence with at least 95% sequence identity to SEQ ID NO: 50 and SEQ ID NO: 51.

Embodiment 165 comprises the isolated polypeptide or polypeptide complex of embodiment 1, wherein the isolated polypeptide or polypeptide complex comprises an amino acid sequence with at least 95% sequence identity to SEQ ID NO: 52 and SEQ ID NO: 53.

Embodiment 166 comprises the isolated polypeptide or polypeptide complex of embodiment 1, wherein the isolated polypeptide or polypeptide complex comprises an amino acid sequence with at least 95% sequence identity to SEQ ID NO: 54 and SEQ ID NO: 55.

Embodiment 167 comprises the isolated polypeptide or polypeptide complex of embodiment 1, wherein the isolated polypeptide or polypeptide complex comprises an amino acid sequence with at least 95% sequence identity to SEQ ID NO: 56 and SEQ ID NO: 57.

Embodiment 168 comprises the isolated polypeptide or polypeptide complex of embodiment 1, wherein the isolated polypeptide or polypeptide complex comprises an amino acid sequence with at least 95% sequence identity to SEQ ID NO: 58 and SEQ ID NO: 59.

Embodiment 169 comprises the isolated polypeptide or polypeptide complex of embodiment 1, wherein the isolated polypeptide or polypeptide complex comprises an amino acid sequence with at least 95% sequence identity to SEQ ID NO: 60 and SEQ ID NO: 61.

Embodiment 170 comprises the isolated polypeptide or polypeptide complex of embodiment 1, wherein the isolated polypeptide or polypeptide complex comprises an amino acid sequence with at least 95% sequence identity to SEQ ID NO: 62 and SEQ ID NO: 63.

Embodiment 171 comprises the isolated polypeptide or polypeptide complex of embodiment 1, wherein the isolated polypeptide or polypeptide complex comprises an amino acid sequence with at least 95% sequence identity to SEQ ID NO: 64 and SEQ ID NO: 65.

Embodiment 172 comprises a pharmaceutical composition comprising: (a) the isolated polypeptide or polypeptide complex of any one of embodiments 1-171; and (b) a pharmaceutically acceptable excipient.

Embodiment 173 comprises an isolated recombinant nucleic acid molecule encoding the isolated polypeptide or polypeptide complex of any one of embodiments 1-171.

Embodiment 174 an isolated polypeptide or polypeptide complex according to Formula II: $L_{1a}$-$P_{1a}$ $H_{1a}$ wherein: $L_{1a}$ comprises a tumor specific protease-cleaved linking moiety that when uncleaved connects $P_{1a}$ to a first antigen recognizing molecule that binds to an effector cell antigen and the first antigen recognizing molecule is connected to a second antigen recognizing molecule that binds to EGFR; $P_{1a}$ comprises a peptide that binds to the first antigen recognizing molecule when $L_{1a}$ is uncleaved; and $H_{1a}$ comprises a half-life extending molecule.

Embodiment 175 comprises the isolated polypeptide or polypeptide complex of embodiment 174, wherein $P_{1a}$ when $L_{1a}$ is uncleaved impairs binding of the first antigen recognizing molecule to the effector cell antigen.

Embodiment 176 comprises the isolated polypeptide or polypeptide complex of embodiment 174, wherein the first antigen recognizing molecule comprises an antibody or antibody fragment.

Embodiment 177 comprises the isolated polypeptide or polypeptide complex of embodiment 174, wherein the effector cell antigen is an anti-CD3 effector cell antigen.

Embodiment 178 comprises the isolated polypeptide or polypeptide complex of embodiment 174, wherein $P_{1a}$ has less than 70% sequence homology to the effector cell antigen.

Embodiment 179 comprises the isolated polypeptide or polypeptide complex of embodiment 174, wherein $P_{1a}$ comprises a peptide sequence of at least 10 amino acids in length.

Embodiment 180 comprises the isolated polypeptide or polypeptide complex of embodiment 174, wherein $P_{1a}$ comprises a peptide sequence of at least 10 amino acids in length and no more than 20 amino acids in length.

Embodiment 181 comprises the isolated polypeptide or polypeptide complex of embodiment 174, wherein $P_{1a}$ comprises a peptide sequence of at least 16 amino acids in length.

Embodiment 182 comprises the isolated polypeptide or polypeptide complex of embodiment 174, wherein $P_{1a}$ comprises a peptide sequence of no more than 40 amino acids in length.

Embodiment 183 comprises the isolated polypeptide or polypeptide complex of embodiment 174, wherein $P_{1a}$ comprises at least two cysteine amino acid residues.

Embodiment 184 comprises the isolated polypeptide or polypeptide complex of embodiment 174, wherein $P_{1a}$ comprises a cyclic peptide or a linear peptide.

Embodiment 185 comprises the isolated polypeptide or polypeptide complex of embodiment 174, wherein $P_{1a}$ comprises a cyclic peptide.

Embodiment 186 comprises the isolated polypeptide or polypeptide complex of embodiment 174, wherein $P_{1a}$ comprises a linear peptide.

Embodiment 187 comprises the isolated polypeptide or polypeptide complex of embodiment 174, wherein $P_{1a}$ comprises an amino acid sequence selected from the group consisting of SEQ ID NO: 25.

Embodiment 188 comprises the isolated polypeptide or polypeptide complex of embodiment 174, wherein $P_{1a}$ comprises an amino acid sequence according to SEQ ID NO: 70.

Embodiment 189 comprises the isolated polypeptide or polypeptide complex of any one of embodiments 174-187, wherein $H_{1a}$ comprises a polymer.

Embodiment 190 comprises the isolated polypeptide or polypeptide complex of embodiment 189, wherein the polymer is polyethylene glycol (PEG).

Embodiment 191 comprises the isolated polypeptide or polypeptide complex of any one of embodiments 174-190, wherein $P_{1a}$ comprises an amino acid sequence according to any one of SEQ ID NOs: 25, 797-835, or 843-1690, or an amino acid sequence that has 1, 2, or 3 amino acid mutations, substitutions, or deletions relative to any one of SEQ ID NOS: 25, 797-835, or 843-1690.

Embodiment 192 comprises the isolated polypeptide or polypeptide complex of any one of embodiments 174-190, wherein $P_{1a}$ comprises an amino acid sequence according to $Z_1$—$Z_2$—C—$Z_4$—P—$Z_6$-$Z_7$—$Z_8$—$Z_9$-$Z_{10}$—$Z_{11}$—$Z_{12}$—C—$Z_{14}$ and $Z_1$ is selected from D, Y, F, I, N, V, H, L, A, T, S, and P; $Z_2$ is selected from D, Y, L, F, I, N, A, V, H, T, and S; $Z_4$ is selected from G and W; $Z_6$ is selected from E, D, V, and P; $Z_7$ is selected from W, L, F, V, G, M, I, and Y; $Z_8$ is selected from E, D, P, and Q; $Z_9$ is selected from E, D, Y, V, F, W, P, L, and Q; $Z_{10}$ is selected from S, D, Y, T, I, F, V, N, A, P, L, and H; $Z_{11}$ is selected from I, Y, F, V, L, T, N, S, D, A, and H; $Z_{12}$ is selected from F, D, Y, L, I, V, A, N, T, P, S, and H; and $Z_{14}$ is selected from D, Y, N, F, I, P, V, A, T, H, L and S.

Embodiment 193 comprises the isolated polypeptide or polypeptide complex of embodiment 192, wherein $Z_1$ is selected from D, Y, F, I, and N; $Z_2$ is selected from D, Y, L, F, I, and N; $Z_4$ is selected from G and W; $Z_6$ is selected from E and D; $Z_7$ is selected from W, L, F, and V; $Z_8$ is selected from E and D; $Z_9$ is selected from E, D, Y, and V; $Z_{10}$ is selected from S, D, Y, T, and I; $Z_{11}$ is selected from I, Y, F, V, L, and T; $Z_{12}$ is selected from F, D, Y, L, I, V, A, and N; and $Z_{14}$ is selected from D, Y, N, F, I, and P.

Embodiment 194 comprises the isolated polypeptide or polypeptide complex of embodiment 193, wherein $Z_1$ is selected from D, Y, and F; $Z_2$ is selected from D, Y, L, and F; $Z_4$ is selected from G and W; $Z_6$ is selected from E and D; $Z_7$ is selected from W, L, and F; $Z_8$ is selected from E and D; $Z_9$ is selected from E and D; $Z_{10}$ is selected from S, D, and Y; $Z_{11}$ is selected from I, Y, and F; $Z_{12}$ is selected from F, D, Y, and L; and $Z_{14}$ is selected from D, Y, and N.

Embodiment 195 comprises the isolated polypeptide or polypeptide complex of any one of embodiments 174-190, wherein $P_{1a}$ comprises an amino acid sequence according to $U_1$—$U_2$—C—$U_4$—P—$U_6$—$U_7$—$U_8$—$U_9$—$U_{10}$—$U_{11}$—$U_{12}$—C—$U_{14}$ and $U_1$ is selected from D, Y, F, I, N, V, H, L, A, T, S, and P; $U_2$ is selected from D, Y, L, F, I, N, A, V, H, T, and S; $U_4$ is selected from G and W; $U_6$ is selected from E, D, V, and P; $U_7$ is selected from W, L, F, V, G, M, I, and Y; $U_8$ is selected from E, D, P, and Q; $U_9$ is selected from E, D, Y, V, F, W, P, L, and Q; $U_{10}$ is selected from S, D, Y, T, I, F, V, N, A, P, L, and H; $U_{11}$ is selected from I, Y, F, V, L, T, N, S, D, A, and H; $U_{12}$ is selected from F, D, Y, L, I, V, A, N, T, P, S, G, and H; and $U_{14}$ is selected from D, Y, N, F, I, P, V, A, T, H, L, M, and S.

Embodiment 196 comprises the isolated polypeptide or polypeptide complex of embodiment 195, wherein $U_1$ is selected from D, Y, F, 1, V, and N; $U_2$ is selected from D, Y, L, F, I, and N; $U_4$ is selected from G and W; $U_6$ is selected from E and D; $U_7$ is selected from W, L, F, G, and V; $U_8$ is selected from E and D; $U_9$ is selected from E, D, Y, and V; $U_{10}$ is selected from S, D, Y, T, and I; $U_{11}$ is selected from I, Y, F, V, L, and T; $U_{12}$ is selected from F, D, Y, L, I, V, A, G, and N; and $U_{14}$ is selected from D, Y, N, F, I, M, and P.

Embodiment 197 comprises the isolated polypeptide or polypeptide complex of embodiment 196, wherein $U_1$ is selected from D, Y, V, and F; $U_2$ is selected from D, Y, L, and F; $U_4$ is selected from G and W; $U_6$ is selected from E and D; $U_7$ is selected from W, L, G, and F; $U_8$ is selected from E and D; U9 is selected from E and D; $U_{10}$ is selected from S, D, T, and Y; $U_{11}$ is selected from I, Y, V, L, and F; $U_{12}$ is selected from F, D, Y, G, A, and L; and $U_{14}$ is selected from D, Y, M, and N.

Embodiment 198 comprises the isolated polypeptide or polypeptide complex of any one of embodiments 174-197, wherein $P_{1a}$ comprises an amino acid sequence according to any one of SEQ ID NOs: 797-823.

Embodiment 199 comprises the isolated polypeptide or polypeptide complex of any one of embodiments 174-197, wherein $P_{1a}$ comprises an amino acid sequence according to any one of SEQ ID NOs: 25, 824-835 or 843-1690.

Embodiment 200 comprises the isolated polypeptide or polypeptide complex of any one of embodiments 174-197, wherein $P_{1a}$ comprises an amino acid sequence according to any one of SEQ ID NOs: 824-835.

Embodiment 201 comprises the isolated polypeptide or polypeptide complex of any one of embodiments 174-197, wherein $P_{1a}$ comprises the amino acid sequence according to SEQ ID NO: 810 or an amino acid sequence that has 1, 2, or 3, amino acid substitutions, additions, or deletions relative to the amino acid sequence of SEQ ID NO: 810.

Embodiment 202 comprises the isolated polypeptide or polypeptide complex of any one of embodiments 174-197, wherein $P_{1a}$ comprises the amino acid sequence according to SEQ ID NO: 811 or an amino acid sequence that has 1, 2, or 3, amino acid substitutions, additions, or deletions relative to the amino acid sequence of SEQ ID NO: 811.

Embodiment 203 comprises the isolated polypeptide or polypeptide complex of any one of embodiments 174-197, wherein $P_{1a}$ comprises the amino acid sequence according to SEQ ID NO: 834 or an amino acid sequence that has 1, 2, or 3, amino acid substitutions, additions, or deletions relative to the amino acid sequence of SEQ ID NO: 834.

Embodiment 204 comprises the isolated polypeptide or polypeptide complex of any one of embodiments 174-197, wherein $P_{1a}$ comprises the amino acid sequence according to SEQ ID NO: 810.

Embodiment 205 comprises the isolated polypeptide or polypeptide complex of any one of embodiments 174-197, wherein $P_{1a}$ comprises the amino acid sequence according to SEQ ID NO: 811.

Embodiment 206 comprises the isolated polypeptide or polypeptide complex of any one of embodiments 174-197, wherein $P_{1a}$ comprises the amino acid sequence according to SEQ ID NO: 834.

Embodiment 207 comprises the isolated polypeptide or polypeptide complex of any one of embodiments 174-206, wherein $H_{1a}$ comprises albumin.

Embodiment 208 comprises the isolated polypeptide or polypeptide complex of any one of embodiments 174-206, wherein $H_{1a}$ comprises an Fc domain.

Embodiment 209 comprises the isolated polypeptide or polypeptide complex of embodiment 207, wherein the albumin is serum albumin.

Embodiment 210 comprises the isolated polypeptide or polypeptide complex of embodiment 209, wherein the albumin is human serum albumin.

Embodiment 211 comprises the isolated polypeptide or polypeptide complex of any one of embodiments 174-206, wherein $H_{1a}$ comprises a polypeptide, a ligand, or a small molecule.

Embodiment 212 comprises the isolated polypeptide or polypeptide complex of embodiment 211, wherein the polypeptide, the ligand or the small molecule binds a serum protein or a fragment thereof, a circulating immunoglobulin or a fragment thereof, or CD35/CR1.

Embodiment 213 comprises the isolated polypeptide or polypeptide complex of embodiment 212, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 214 comprises the isolated polypeptide or polypeptide complex of embodiment 212, wherein the circulating immunoglobulin molecule comprises IgG1, IgG2, IgG3, IgG4, sIgA, IgM or IgD.

Embodiment 215 comprises the isolated polypeptide or polypeptide complex of embodiment 212, wherein the serum protein is albumin.

Embodiment 216 comprises the isolated polypeptide or polypeptide complex of embodiment 211, wherein the polypeptide is an antibody.

Embodiment 217 comprises the isolated polypeptide or polypeptide complex of embodiment 216, wherein the antibody comprises a single domain antibody, a single chain variable fragment or a Fab.

Embodiment 218 comprises the isolated polypeptide or polypeptide complex of embodiment 216, wherein the antibody comprises a single domain antibody that binds to albumin.

Embodiment 219 comprises the isolated polypeptide or polypeptide complex of embodiment 216, wherein the antibody is a human or humanized antibody.

Embodiment 220 comprises the isolated polypeptide or polypeptide complex of embodiment 217, wherein the single domain antibody is 645gH1gL1.

Embodiment 221 comprises the isolated polypeptide or polypeptide complex of embodiment 217, wherein the single domain antibody is 645dsgH5gL4.

Embodiment 222 comprises the isolated polypeptide or polypeptide complex of embodiment 217, wherein the single domain antibody is 23-13-A01-sc02.

Embodiment 223 comprises the isolated polypeptide or polypeptide complex of embodiment 217, wherein the single domain antibody is A 10m3 or a fragment thereof.

Embodiment 224 comprises the isolated polypeptide or polypeptide complex of embodiment 217, wherein the single domain antibody is DOM7r-31.

Embodiment 225 comprises the isolated polypeptide or polypeptide complex of embodiment 217, wherein the single domain antibody is DOM7h-11-15.

Embodiment 226 comprises the isolated polypeptide or polypeptide complex of embodiment 217, wherein the single domain antibody is Alb-1, Alb-8, or Alb-23.

Embodiment 227 comprises the isolated polypeptide or polypeptide complex of embodiment 217, wherein the single domain antibody is 10G.

Embodiment 228 comprises the isolated polypeptide or polypeptide complex of embodiment 217, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38.

Embodiment 229 comprises the isolated polypeptide or polypeptide complex of embodiment 217, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 39, HC-CDR2: SEQ ID NO: 40, and HC-CDR3: SEQ ID NO: 41.

Embodiment 230 comprises the isolated polypeptide or polypeptide complex of embodiment 217, wherein the single domain antibody is SA21.

Embodiment 231 comprises the isolated polypeptide or polypeptide complex of any one of embodiments 174-230, wherein $H_{1a}$ comprises a linking moiety ($L_{1a}$) that connects $H_{1a}$ to $P_{1a}$.

Embodiment 232 comprises the isolated polypeptide or polypeptide complex of embodiment 231, wherein $L_{1a}$ is a peptide sequence having at least 5 to no more than 50 amino acids.

Embodiment 233 comprises the isolated polypeptide or polypeptide complex of embodiment 231, wherein $L_{1a}$ is a peptide sequence having at least 10 to no more than 30 amino acids.

Embodiment 234 comprises the isolated polypeptide or polypeptide complex of embodiment 231, wherein $L_{1a}$ is a peptide sequence having at least 10 amino acids.

Embodiment 235 comprises the isolated polypeptide or polypeptide complex of embodiment 231, wherein $L_{1a}$ is a peptide sequence having at least 18 amino acids.

Embodiment 236 comprises the isolated polypeptide or polypeptide complex of embodiment 231, wherein $L_{1a}$ is a peptide sequence having at least 26 amino acids.

Embodiment 237 comprises the isolated polypeptide or polypeptide complex of embodiment 231, wherein $L_{1a}$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1.

Embodiment 238 comprises the isolated polypeptide or polypeptide complex of embodiment 231, wherein $L_{1a}$ comprises an amino acid sequence according to SEQ ID NO: 30 or 31.

Embodiment 239 comprises the isolated polypeptide or polypeptide complex of embodiment 231, wherein $L_1$ or $L_2$ comprises an amino acid sequence according to any one of SEQ ID NOs: 27-35.

Embodiment 240 comprises the isolated polypeptide or polypeptide complex of embodiment 231, wherein $L_1$ or $L_2$ comprises an amino acid sequence of Linker 4 (ISSGLLS-GRSDAG) (SEQ ID NO: 66), Linker 5 (AAGLLAPPG-GLSGRSDAG) (SEQ ID NO: 67), Linker 6 (SPLGLSGRS-DAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7.

Embodiment 241 comprises an isolated polypeptide complex comprising a structural arrangement according to Configuration 1 (FIG. 1A), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab light chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab heavy chain polypeptide to $P_2$ and is a substrate for a tumor specific protease.

Embodiment 242 comprises an isolated polypeptide complex comprising a structural arrangement according to Configuration 2 (FIG. 1B), wherein the isolated polypeptide or polypeptide complex comprises a single chain variable fragment (scFv) comprising a light chain variable domain and a heavy chain variable domain, wherein the scFv is linked to a peptide ($P_1$) that impairs binding of the scFv to an effector cell antigen and $P_1$ is linked to a N-terminus of the heavy chain variable domain of the scFv with a linking moiety ($L_1$) that is a substrate for a tumor specific protease, and $P_1$ is further linked to a half-life extending molecule; and a Fab that binds to epidermal growth factor receptor (EGFR), wherein the Fab comprises a Fab light chain polypeptide and a Fab heavy chain polypeptide, wherein the Fab heavy chain polypeptide is linked to a C terminus of the light chain variable domain of the scFv, and wherein the Fab is linked to $P_2$ and $L_2$, wherein $P_2$ comprises a peptide that impairs binding to EGFR; and $L_2$ comprises a linking moiety that connects the Fab light chain polypeptide to $P_2$ and is a substrate for a tumor specific protease.

Embodiment 243 comprises an isolated polypeptide or polypeptide complex comprising an anti-EGFR binding domain that is linked to a peptide that impairs binding of the anti-EGFR binding domain to EGFR wherein the peptide comprises an amino acid sequence according to any one of SEQ ID NOs: 26, 71-96, 98-776 or an amino acid sequence that has 1, 2, or 3 amino acid mutations, substitutions, or deletions relative to any one of SEQ ID NOs: 26, 71-96, 98-776.

Embodiment 244 comprises the isolated polypeptide or polypeptide complex of embodiment 243, wherein the peptide comprises an amino acid sequence according to any one of SEQ ID NOs: 26, 71-96, 98-776.

Embodiment 245 comprises the isolated polypeptide or polypeptide complex of embodiment 243, wherein the peptide comprises an amino acid sequence according to any one of SEQ ID NOs: 26, 86-96 or an amino acid sequence that has 1, 2, or 3 amino acid mutations, substitutions, or deletions relative to any one of SEQ ID NOs: 26, 86-96.

Embodiment 246 comprises the isolated polypeptide or polypeptide complex of embodiment 245, wherein the peptide comprises an amino acid sequence according to any one of SEQ ID NOs: 26, 86-96.

Embodiment 247 comprises the isolated polypeptide or polypeptide complex of embodiment 243, wherein the peptide comprises an amino acid sequence according to any one of SEQ ID NOs: 98-776 or an amino acid sequence that has 1, 2, or 3 amino acid mutations, substitutions, or deletions relative to any of SEQ ID NOs: 98-776.

Embodiment 248 comprises the isolated polypeptide or polypeptide complex of embodiment 247, wherein the peptide comprises an amino acid sequence according to any one of SEQ ID NOs: 98-776.

Embodiment 249 comprises the isolated polypeptide or polypeptide complex of embodiment 243, wherein the peptide comprises an amino acid sequence according to any one of SEQ ID NOs: 99-118 or an amino acid sequence that has 1, 2, or 3 amino acid mutations, substitutions, or deletions relative to any one of SEQ ID NOs: 99-118.

Embodiment 250 comprises the isolated polypeptide or polypeptide complex of embodiment 249, wherein the peptide comprises an amino acid sequence according to any one of SEQ ID NOs: 99-118.

Embodiment 251 comprises the isolated polypeptide or polypeptide complex of embodiment 243, wherein the peptide comprises the amino acid sequence according to SEQ ID NO: 71 or an amino acid sequence that has 1, 2, or 3 amino acid mutations, substitutions, or deletions relative to SEQ ID NO: 71.

Embodiment 252 comprises the isolated polypeptide or polypeptide complex of embodiment 251, wherein the peptide comprises the amino acid sequence according to SEQ ID NO: 71.

Embodiment 253 comprises the isolated polypeptide or polypeptide complex of embodiment 243, wherein the peptide comprises the amino acid sequence according to SEQ ID NO: 26 or an amino acid sequence that has 1, 2, or 3 amino acid mutations, substitutions, or deletions relative to SEQ ID NO: 26.

Embodiment 254 comprises the isolated polypeptide or polypeptide complex of embodiment 253, wherein the peptide comprises the amino acid sequence according to SEQ ID NO: 26.

Embodiment 255 comprises an isolated polypeptide or polypeptide complex comprising an anti-EGFR binding domain that is linked to a peptide that impairs binding of the anti-EGFR binding to EGFR wherein the peptide comprises an amino acid sequence according to $X_1$—C—$X_2$—$X_3$—$X_4$—$X_5$-D-$X_6$-A-$X_7$—P—$X_8$—C—$X_9$ wherein $X_1$ is selected from P and L; $X_2$ is selected from R, L, T, A, N, I, V, S, H, and P; $X_3$ is selected from S, P, F, and Y; $X_4$ is selected from H, L, Q, P, R, F, N; $X_5$ is selected from I, F, Y, H, N, T, S, D, A, L, and V; $X_6$ is selected from T, P, N, L, I, V, S, D, H, A, and Y; $X_7$ is selected from K and Y; $X_8$ is selected from I, P, L, and M; and $X_9$ is selected from A, V, I, T, L, S, D, F, V, and H (SEQ ID NO: 841).

Embodiment 256 comprises the isolated polypeptide or polypeptide complex of embodiment 255, wherein $X_1$ is selected from P and L; $X_2$ is selected from R, L, T, A, and N; $X_3$ is selected from S, P, and F; $X_4$ is selected from H, L, Q, and P; $X_5$ is selected from I, F, Y, H, N, and T; $X_6$ is selected from T, P, N, L, I, and V; $X_7$ is K; $X_8$ is I; and $X_9$ is selected from A, V, I, T, L, and S.

Embodiment 257 comprises the isolated polypeptide or polypeptide complex of embodiment 256, wherein $X_1$ is P; $X_2$ is selected from R, L, and T; $X_3$ is S; $X_4$ is selected from H, L, Q, and P; $X_5$ is selected from I, F, Y, and T; $X_6$ is selected from T, P, N, and V; $X_7$ is K; $X_8$ is I; and $X_9$ is selected from A, V, and I.

Embodiment 258 comprises the isolated polypeptide or polypeptide complex of any one of embodiments 255-257, wherein the peptide comprises an amino acid sequence according to any one of SEQ ID NOs: 98-776.

Embodiment 259 comprises the isolated polypeptide or polypeptide complex of any one of embodiments 255-258, wherein the peptide comprises an amino acid sequence according to any one of SEQ ID NOs: 99-118.

Embodiment 260 comprises the isolated polypeptide or polypeptide complex of any one of embodiments 255-257, wherein the peptide comprises the amino acid sequence according to SEQ ID NO: 26.

Embodiment 261 comprises the isolated polypeptide or polypeptide complex of any one of embodiments 243-260, wherein the anti-EGFR binding domain comprises an antibody or an antibody fragment.

Embodiment 262 comprises the isolated polypeptide or polypeptide complex of embodiment 261, wherein the antibody or antibody fragment comprises a single chain variable fragment, a single domain antibody, Fab, or Fab'.

Embodiment 263 comprises the isolated polypeptide or polypeptide complex of any one of embodiments 243-262, wherein the anti-EGFR binding domain comprises heavy chain complementarity determining regions HC-CDR1, HC-CDR2, and HC-CDR3, wherein the HC-CDR1, the HC-CDR2, and the HC-CDR3 comprise: HC-CDR1: SEQ ID NO: 15, HC-CDR2: SEQ ID NO: 16, and HC-CDR3: SEQ ID NO: 17; and the anti-EGFR binding domain comprises light chain complementarity determining regions CDRs: LC-CDR1, LC-CDR2, and LC-CDR3, wherein the LC-CDR1, the LC-CDR2, and the LC-CDR3 of the Fab comprise LC-CDR1: SEQ ID NO: 18, LC-CDR2: SEQ ID NO:19, and LC-CDR3: SEQ ID NO: 20.

Embodiment 264 comprises the isolated polypeptide or polypeptide complex of embodiment 261, wherein the antibody or antibody fragment comprises the Fab.

Embodiment 265 comprises the isolated polypeptide or polypeptide complex of any one of embodiments 243-264, wherein the anti-EGFR binding domain comprises an amino acid sequence according to any of SEQ ID NOs: 21-24.

Embodiment 266 comprises the isolated polypeptide or polypeptide complex of any one of embodiments 243-265, wherein the anti-EGFR binding domain is linked to the peptide through a linking moiety ($L_1$).

Embodiment 267 comprises the isolated polypeptide or polypeptide complex of any one of embodiments 243-266, wherein $L_1$ is a substrate for a tumor specific protease.

Embodiment 268 comprises the isolated polypeptide or polypeptide complex of any one of embodiments 243-267, wherein $L_1$ is bound to N-terminus of the anti-EGFR binding domain.

Embodiment 269 comprises the isolated polypeptide or polypeptide complex of any one of embodiments 243-267, wherein $L_1$ is bound to C-terminus of the anti-EGFR binding domain.

Embodiment 270 comprises the isolated polypeptide or polypeptide complex of any one of embodiments 243-267, wherein $L_1$ is a peptide sequence having at least 5 to no more than 50 amino acids.

Embodiment 271 comprises the isolated polypeptide or polypeptide complex of any one of embodiments 243-267, wherein $L_1$ is a peptide sequence having at least 10 to no more than 30 amino acids.

Embodiment 272 comprises the isolated polypeptide or polypeptide complex of any one of embodiments 243-267, wherein $L_1$ is a peptide sequence having at least 10 amino acids.

Embodiment 273 comprises the isolated polypeptide or polypeptide complex of any one of embodiments 243-267, wherein $L_1$ is a peptide sequence having at least 18 amino acids.

Embodiment 274 comprises the isolated polypeptide or polypeptide complex of any one of embodiments 243-267, wherein $L_1$ is a peptide sequence having at least 26 amino acids.

Embodiment 275 comprises the isolated polypeptide or polypeptide complex of any one of embodiments 243-267, wherein $L_1$ has a formula comprising $(G_2S)_n$, wherein n is an integer from 1 to 3 (SEQ ID NO: 840).

Embodiment 276 comprises the isolated polypeptide or polypeptide complex of any one of embodiments 243-267, wherein $L_1$ has a formula selected from the group consisting of $(G2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1.

Embodiment 277 comprises the isolated polypeptide or polypeptide complex of any one of embodiments 243-276, wherein the peptide becomes unbound from the anti-EGFR binding domain when $L_1$ is cleaved by the tumor specific protease thereby exposing the anti-EGFR binding domain to EGFR.

Embodiment 278 comprises the isolated polypeptide or polypeptide complex of any one of embodiments 267-277, wherein the tumor specific protease is selected from the group consisting of a matrix metalloprotease (MMP), serine protease, cysteine protease, threonine protease, and aspartic protease.

Embodiment 279 comprises the isolated polypeptide or polypeptide complex of embodiment 278, wherein the matrix metalloprotease comprises MMP2, MMP7, MMP9, MMP13, or MMP14.

Embodiment 280 comprises the isolated polypeptide or polypeptide complex of embodiment 278, wherein the serine protease comprises matriptase (MTSP1), urokinase, or hepsin.

Embodiment 281 comprises the isolated polypeptide or polypeptide complex of any one of embodiments 267-277, wherein $L_1$ comprises a urokinase cleavable amino acid sequence, a matriptase cleavable amino acid sequence, matrix metalloprotease cleavable amino acid sequence, or a legumain cleavable amino acid sequence.

Embodiment 282 comprises the isolated polypeptide or polypeptide complex of embodiment 266, wherein $L_1$ comprises an amino acid sequence according to any of SEQ ID NO: 30 or 31.

Embodiment 283 comprises the isolated polypeptide or polypeptide complex of embodiment 266, wherein $L_1$ comprises an amino acid sequence according to SEQ ID NO: 27-35.

Embodiment 284 comprises the isolated polypeptide or polypeptide complex of embodiment 266, wherein $L_1$ comprises an amino acid sequence of Linker 4 (ISSGLLSGRSDAG) (SEQ ID NO: 66), Linker 5 (AAGLLAPPGGLSGRSDAG) (SEQ ID NO: 67), Linker 6 (SPLGLSGRSDAG) (SEQ ID NO: 68), or Linker 7 (LSGRSDAGSPLGLAG) (SEQ ID NO: 69), or an amino acid sequence that has 1, 2, or 3 amino acid substitutions, additions, or deletions relative to the amino acid sequence of Linker 4, Linker 5, Linker 6, or Linker 7.

Embodiment 285 comprises the isolated polypeptide or polypeptide complex of any one of embodiments 243-284, wherein the isolated polypeptide or polypeptide complex further comprises a half-life extending molecule ($H_1$)

Embodiment 286 comprises the isolated polypeptide or polypeptide complex of embodiment 285, wherein the half-life extending molecule is linked to the peptide.

Embodiment 287 comprises the isolated polypeptide or polypeptide complex of embodiment 285, wherein $H_1$ comprises a polymer.

Embodiment 288 comprises the isolated polypeptide or polypeptide complex of embodiment 287, wherein the polymer is polyethylene glycol (PEG).

Embodiment 289 comprises the isolated polypeptide or polypeptide complex of embodiment 285, wherein $H_1$ comprises albumin.

Embodiment 290 comprises the isolated polypeptide or polypeptide complex of embodiment 285, wherein $H_1$ comprises an Fc domain.

Embodiment 291 comprises the isolated polypeptide or polypeptide complex of embodiment 289, wherein the albumin is serum albumin.

Embodiment 292 comprises the isolated polypeptide or polypeptide complex of embodiment 289, wherein the albumin is human serum albumin.

Embodiment 293 comprises the isolated polypeptide or polypeptide complex of embodiment 285, wherein $H_1$ comprises a polypeptide, a ligand, or a small molecule.

Embodiment 294 comprises the isolated polypeptide or polypeptide complex of embodiment 293, wherein the polypeptide, the ligand or the small molecule binds serum protein or a fragment thereof, a circulating immunoglobulin or a fragment thereof, or CD35/CR1.

Embodiment 295 comprises the isolated polypeptide or polypeptide complex of embodiment 294, wherein the serum protein comprises a thyroxine-binding protein, a transthyretin, a 1-acid glycoprotein, a transferrin, transferrin receptor or a transferrin-binding portion thereof, a fibrinogen, or an albumin.

Embodiment 296 comprises the isolated polypeptide or polypeptide complex of embodiment 294, wherein the circulating immunoglobulin molecule comprises IgG1, IgG2, IgG3, IgG4, sIgA, IgM or IgD.

Embodiment 297 comprises the isolated polypeptide or polypeptide complex of embodiment 294, wherein the serum protein is albumin.

Embodiment 298 comprises the isolated polypeptide or polypeptide complex of embodiment 294, wherein the polypeptide is an antibody.

Embodiment 299 comprises the isolated polypeptide or polypeptide complex of embodiment 298, wherein the antibody comprises a single domain antibody, a single chain variable fragment, or a Fab.

Embodiment 300 comprises the isolated polypeptide or polypeptide complex of embodiment 299, wherein the single domain antibody comprises a single domain antibody that binds to albumin.

Embodiment 301 comprises the isolated polypeptide or polypeptide complex of embodiment 300, wherein the single domain antibody is a human or humanized antibody.

Embodiment 302 comprises the isolated polypeptide or polypeptide complex of embodiment 299, wherein the single domain antibody is 645gH1gL1.

Embodiment 303 comprises the isolated polypeptide or polypeptide complex of embodiment 299, wherein the single domain antibody is 645dsgH5gL4.

Embodiment 304 comprises the isolated polypeptide or polypeptide complex of embodiment 299, wherein the single domain antibody is 23-13-A01-sc02.

Embodiment 305 comprises the isolated polypeptide or polypeptide complex of embodiment 299, wherein the single domain antibody is A10m3 or a fragment thereof.

Embodiment 306 comprises the isolated polypeptide or polypeptide complex of embodiment 299, wherein the single domain antibody is DOM7r-31.

Embodiment 307 comprises the isolated polypeptide or polypeptide complex of embodiment 299, wherein the single domain antibody is DOM7h-11-15.

Embodiment 308 comprises the isolated polypeptide or polypeptide complex of embodiment 299, wherein the single domain antibody is Alb-1, Alb-8, or Alb-23.

Embodiment 309 comprises the isolated polypeptide or polypeptide complex of embodiment 299, wherein the single domain antibody is I0E.

Embodiment 310 comprises the isolated polypeptide or polypeptide complex of embodiment 299, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38.

Embodiment 311 comprises the isolated polypeptide or polypeptide complex of embodiment 299, wherein the single domain antibody comprises an amino acid sequence according to SEQ ID NO: 69.

Embodiment 312 comprises the isolated polypeptide or polypeptide complex of embodiment 299, wherein the single domain antibody comprises complementarity determining regions (CDRs): HC-CDR1, HC-CDR2, and HC-CDR3, wherein the HC-CDR1, the HC-CDR2, and the HC-CDR3 of the single domain antibody comprise: HC-CDR1: SEQ ID NO: 36, HC-CDR2: SEQ ID NO: 37, and HC-CDR3: SEQ ID NO: 38.

Embodiment 313 comprises the isolated polypeptide or polypeptide complex of embodiment 299, wherein the single domain antibody comprises an amino acid sequence according to SEQ ID NO: 42.

Embodiment 314 comprises the isolated polypeptide or polypeptide complex of embodiment 299, wherein the single domain antibody is SA21.

Embodiment 315 comprises the isolated polypeptide or polypeptide complex of any one of embodiments 1-314, wherein the isolated polypeptide or polypeptide complex comprises a modified amino acid, a non-natural amino acid, a modified non-natural amino acid, or a combination thereof.

Embodiment 316 comprises the isolated polypeptide or polypeptide complex of embodiment 315, wherein the modified amino acid or modified non-natural amino acid comprises a post-translational modification.

Embodiment 317 comprises the isolated polypeptide or polypeptide complex of any one of embodiments 285-316, wherein $H_1$ comprises a linking moiety ($L_3$) that connects $H_1$ to $P_1$.

Embodiment 318 comprises the isolated polypeptide or polypeptide complex of embodiment 317, wherein $L_3$ is a peptide sequence having at least 5 to no more than 50 amino acids.

Embodiment 319 comprises the isolated polypeptide or polypeptide complex of embodiment 317, wherein $L_3$ is a peptide sequence having at least 10 to no more than 30 amino acids.

Embodiment 320 comprises the isolated polypeptide or polypeptide complex of embodiment 317, wherein $L_3$ is a peptide sequence having at least 10 amino acids.

Embodiment 321 comprises the isolated polypeptide or polypeptide complex of embodiment 317, wherein $L_3$ is a peptide sequence having at least 18 amino acids.

Embodiment 322 comprises the isolated polypeptide or polypeptide complex of embodiment 317, wherein $L_3$ is a peptide sequence having at least 26 amino acids.

Embodiment 323 comprises the isolated polypeptide or polypeptide complex of embodiment 317, wherein $L_3$ has a formula selected from the group consisting of $(G_2S)_n$, $(GS)_n$, $(GSGGS)_n$ (SEQ ID NO: 836), $(GGGS)_n$ (SEQ ID NO: 837), $(GGGGS)_n$ (SEQ ID NO: 838), and $(GSSGGS)_n$ (SEQ ID NO: 839), wherein n is an integer of at least 1.

Embodiment 324 comprises the isolated polypeptide or polypeptide complex of embodiment 317, wherein $L_3$ comprises an amino acid sequence according to SEQ ID NO: 29.

Embodiment 325 comprises a method of treating cancer comprising administering the polypeptides or polypeptide complexes of any of the above embodiments to a subject in need thereof.

Embodiment 326 comprises the method of embodiment 325, wherein the cancer has cells that express EGFR.

Embodiment 327 comprises a method of treating colorectal cancer (CRC), squamous cell carcinoma of the head and Neck (SCCHN), non-small cell lung cancer (NSCLC), prostate cancer, breast cancer, colon/rectum cancer, head and neck cancer, esophagogastric cancer, liver cancer, glioblastoma, cervical cancer, ovarian cancer, bladder cancer, kidney cancer, or pancreatic cancer comprising administering the polypeptides or polypeptide complexes of any of the above embodiments to a subject in need thereof.

Embodiment 328 comprises the method of embodiment 327, wherein the subject in need thereof is resistant to EGFR inhibitor treatment.

Embodiment 329 comprises the method of embodiment 327, wherein the subject in need thereof harbors KRAS mutations.

Embodiment 330 comprises the method of embodiment 327, wherein the subject in need thereof is resistant to EGFR inhibitor treatment and harbors KRAS mutations.

Embodiment 331 comprises the isolated polypeptide or polypeptide complex of any one of embodiments 1-77, wherein $P_2$ comprises the amino acid sequence according to SEQ ID NO: 115 or an amino acid sequence that has 1, 2, or 3 amino acid mutations, substitutions, or deletions relative to SEQ ID NO: 115.

Embodiment 332 comprises the isolated polypeptide or polypeptide complex of embodiment 331, wherein $P_2$ comprises the amino acid sequence according to SEQ ID NOs: 115.

Embodiment 333 comprises the isolated polypeptide or polypeptide complex of any one of embodiments 1-77, wherein $P_2$ comprises the amino acid sequence according to SEQ ID NO: 116 or an amino acid sequence that has 1, 2, or 3 amino acid mutations, substitutions, or deletions relative to SEQ ID NO: 116.

Embodiment 334 comprises the isolated polypeptide or polypeptide complex of embodiment 333, wherein $P_2$ comprises the amino acid sequence according to SEQ ID NOs: 116.

Embodiment 335 comprises the isolated polypeptide or polypeptide complex of any one of embodiments 255-257, wherein the peptide comprises the amino acid sequence according to SEQ ID NO: 115.

Embodiment 336 comprises the isolated polypeptide or polypeptide complex of any one of embodiments 255-257, wherein the peptide comprises the amino acid sequence according to SEQ ID NO: 116.

EXAMPLES

Example 1: EGFR Polypeptide Complex Binding

The EGFR-CD3 polypeptide complexes were evaluated for EGFR and CD3s binding.

Briefly, the polypeptide complex molecules were evaluated for their ability to bind EGFR as well as CD3 in a standard enzyme linked immunosorbent assay (ELISA) format. Polypeptide complex binding of EGFR or CD3 were measured before and after protease treatment. Briefly, biotinylated antigen was captured on neutravidin coated plates. Polypeptide complex molecules were treated with active matriptase (MTSP1) where indicated. Polypeptide complex molecules diluted in buffer were then added to the antigen coated plates. Bound polypeptide complex was detected using a standard horse radish peroxidase conjugate secondary antibody. The concentration of polypeptide complex required to achieve 50% maximal signal (EC50) was calculated using Graphpad Prism software.

Figure 2:
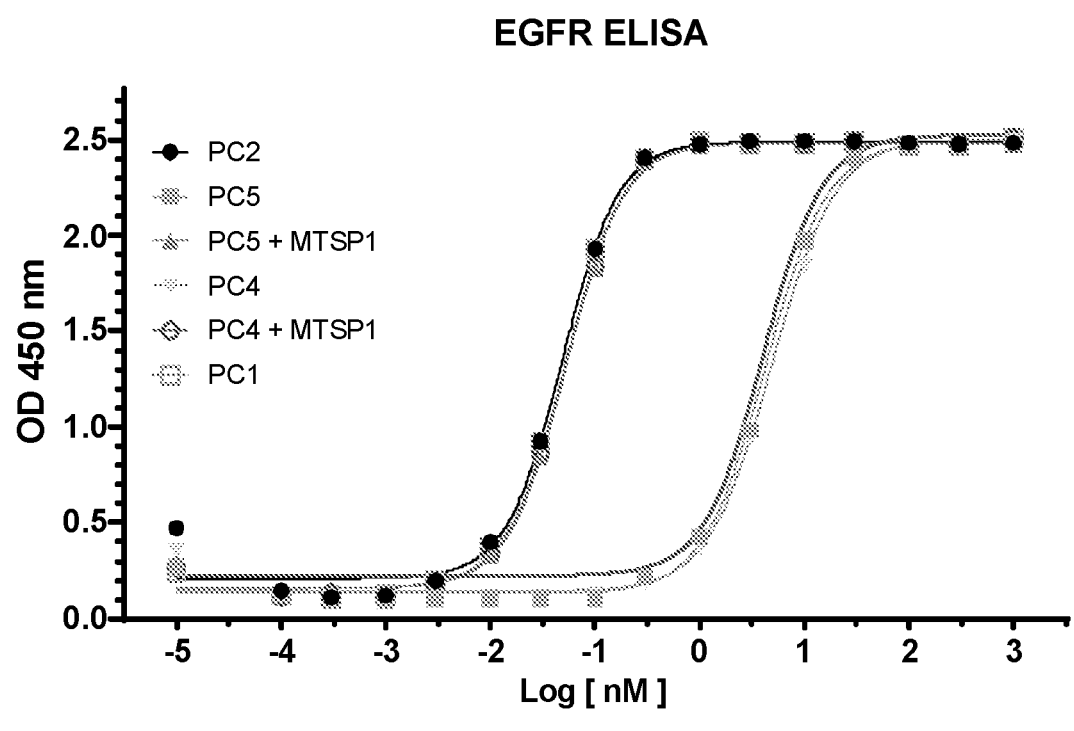
FIG. 2 illustrates binding to EGFR for several polypeptide complexes of this disclosure measured by ELISA.
Figure 3:
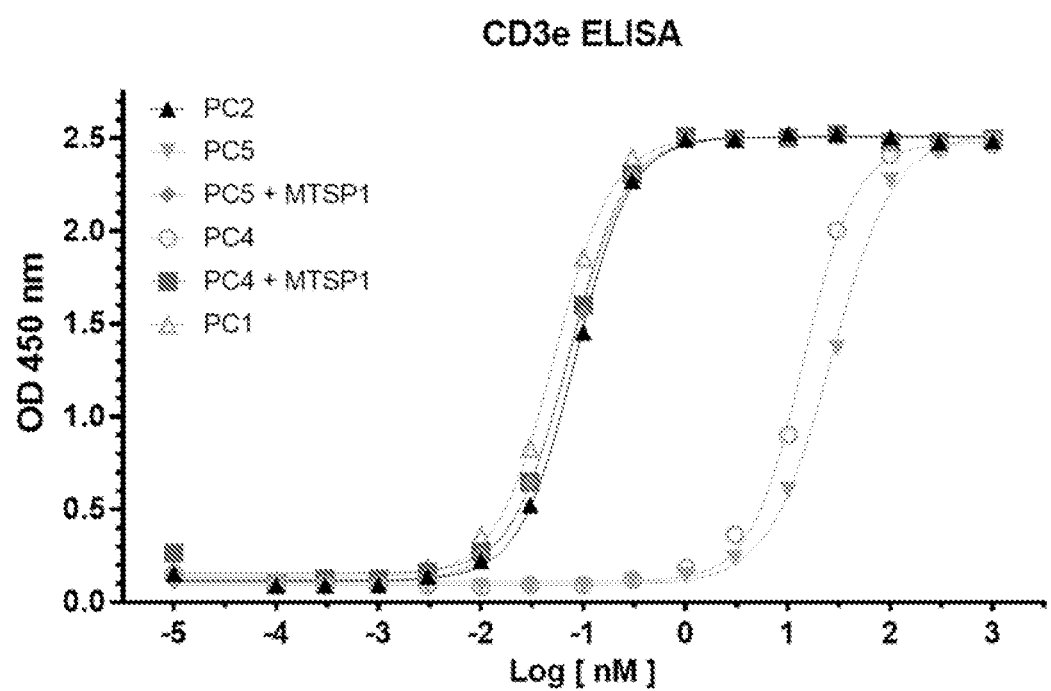
FIG. 3 illustrates binding to CD3 for several polypeptide complexes of this disclosure measured by ELISA.

FIG. 2 shows representative polypeptide molecule binding to EGFR measured by ELISA. FIG. 3 shows representative polypeptide binding to CD3 measured by ELISA.

Example 2: Polypeptide Complex Mediated Tumor Cytotoxicity and T Cell Activation Polypeptide complexes were evaluated in a functional in vitro tumor cell killing assay using the EGFR positive tumor cell lines HCT116 and $A_{431}$. Tumor cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. 10,000 tumor cells were added per well and allowed to adhere overnight on a 96 well E-Plate. The following day polypeptide complexes titrated in human serum supplemented medium along with 30,000 CD8+ T cells were added to the wells. Cell index measurements were taken every 10 minutes for an additional 72 hours. The cell index times number of hours (tumor cell growth kinetics) was then plotted versus concentration of polypeptide complex where the concentration required to reduce the tumor growth 50% (IC50) was calculated using Graphpad Prism software.

Figure 4:
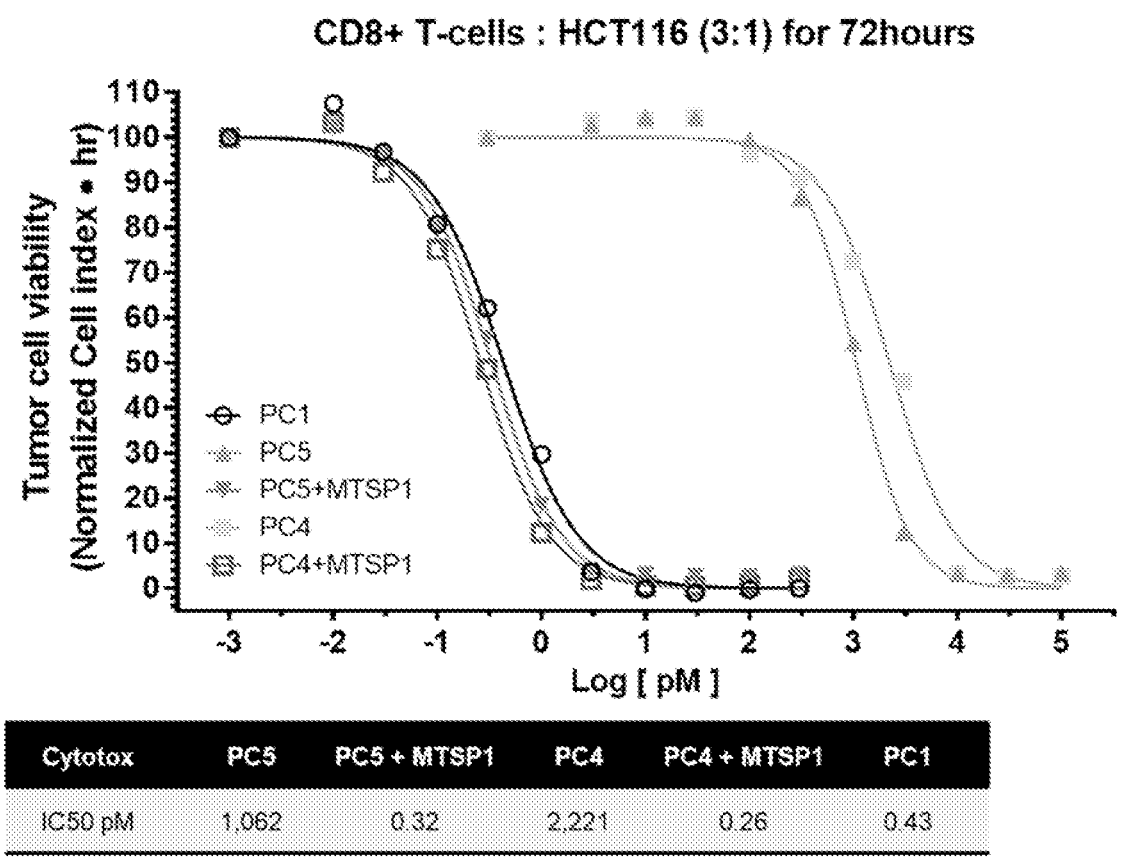
FIG. 4 illustrates polypeptide complexes of this disclosure mediated HCT116 tumor cell killing in the presence of CD8+ T cells.
Figure 5:
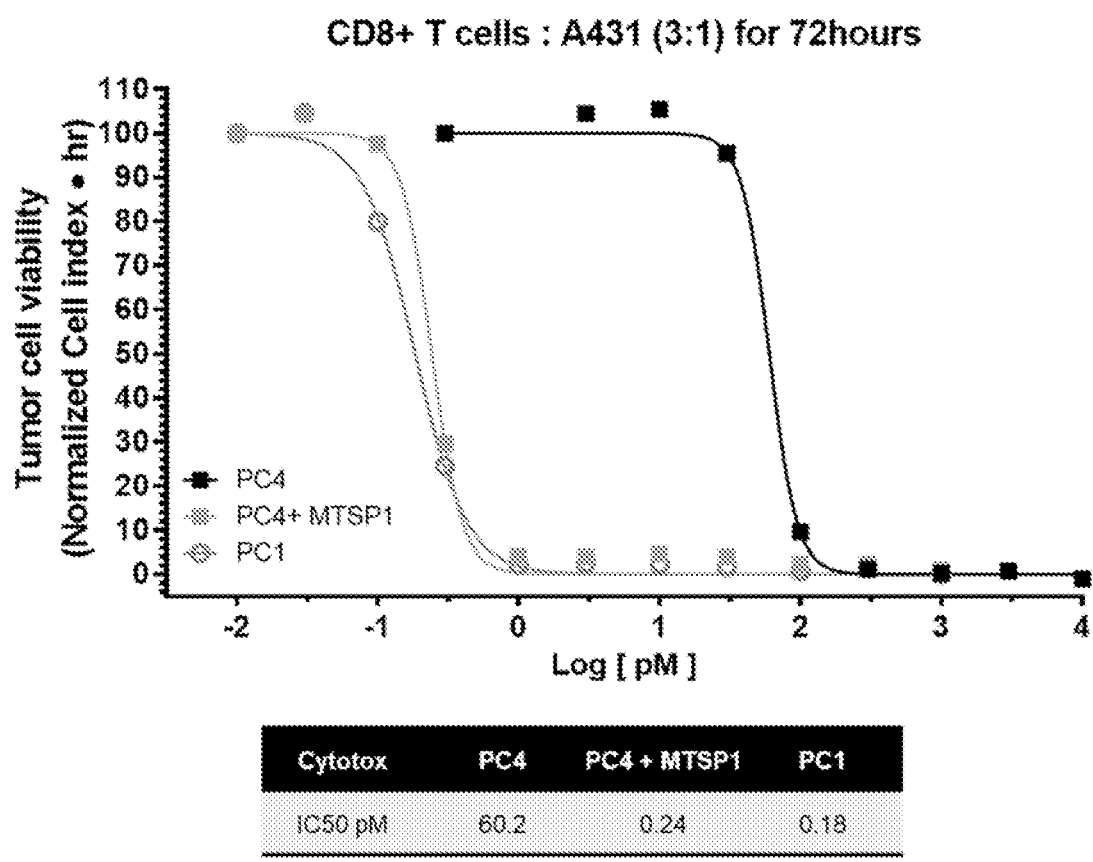
FIG. 5 illustrates polypeptide complexes of this disclosure mediated A431 tumor cell killing in the presence of CD8+ T cells.

FIG. 4 shows a graph of polypeptide complex mediated HCT116 tumor cell killing in the presence of CD8+ T cells. FIG. 5 shows a graph of polypeptide complex mediated $A_{431}$ tumor cell killing in the presence of CD8+ T cells.

Example 3: Polypeptide Complex Binding

Polypeptide complexes were evaluated in binding studies to EGFR and CD3R.

Figure 6:
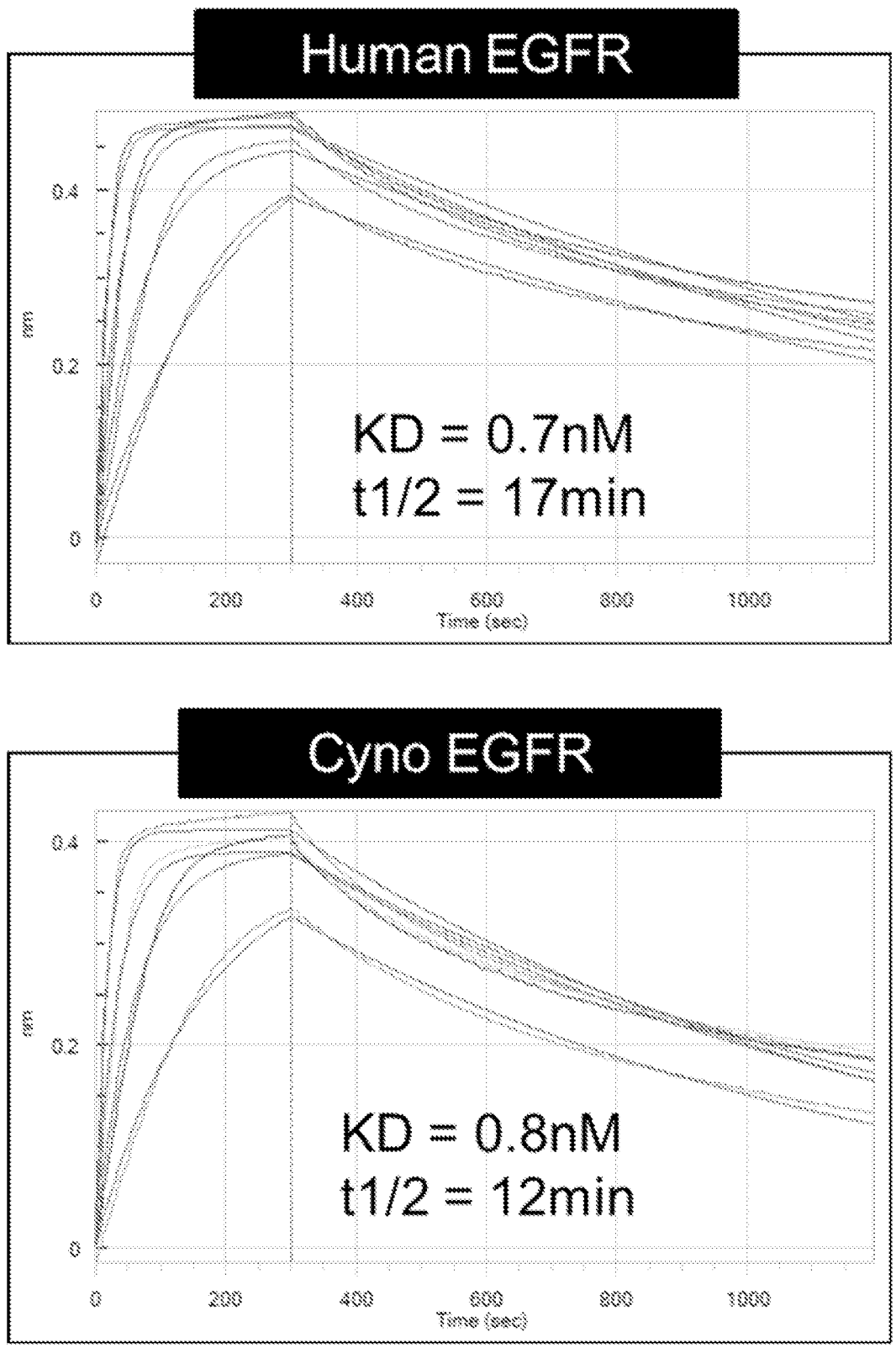
FIG. 6 illustrates kinetic binding and cross reactivity against human and cynomolgus monkey EGFR for polypeptide complexes of this disclosure.

Kinetic binding of polypeptide molecules to human and cynomolgus monkey EGFR was evaluated by bio-layer interferometry using an Octet RED96 instrument. Briefly, biosensors were loaded with antigen and baselined in buffer. Polypeptide molecules were titrated in solution at 50 nM, 25 nM, 12.5 nM, and 6.25 nM then associated onto the antigen loaded sensors. After a short association period, sensors were transferred into buffer and the dissociation of bound polypeptide molecules was measured. The timing and steps of the experiment are shown in Table 7. Association and dissociation signals were recorded in real time and analyzed using a 1:1 binding model within the instrument software. Analysis using a 1:1 binding model enabled the calculation of the on and off rate constants as well as affinity, KD. Off rate constants were converted to half-life shown in the accompanying figures. Data is seen in FIG. 6.

TABLE 7

| Step | Time | pH |
| --- | --- | --- |
| Baseline: Octet buffer | 60 sec | pH 7.4 |
| Load: | 300 sec | pH 7.4 |
| 15 nM human EGFR | | |
| 15 nM cyno EGFR | | |
| Baseline: Octet buffer | 300 sec | pH 7.4 |
| Association in octet buffer | 300 sec | pH 7.4 |
| 50 nM PC1 | | |
| 25 nM PC1 | | |
| 12.5 nM PC1 | | |
| 6.25 nM PC1 | | |
| Dissociation: Octet Buffer | 900 sec | pH 7.4 |

Figure 7:
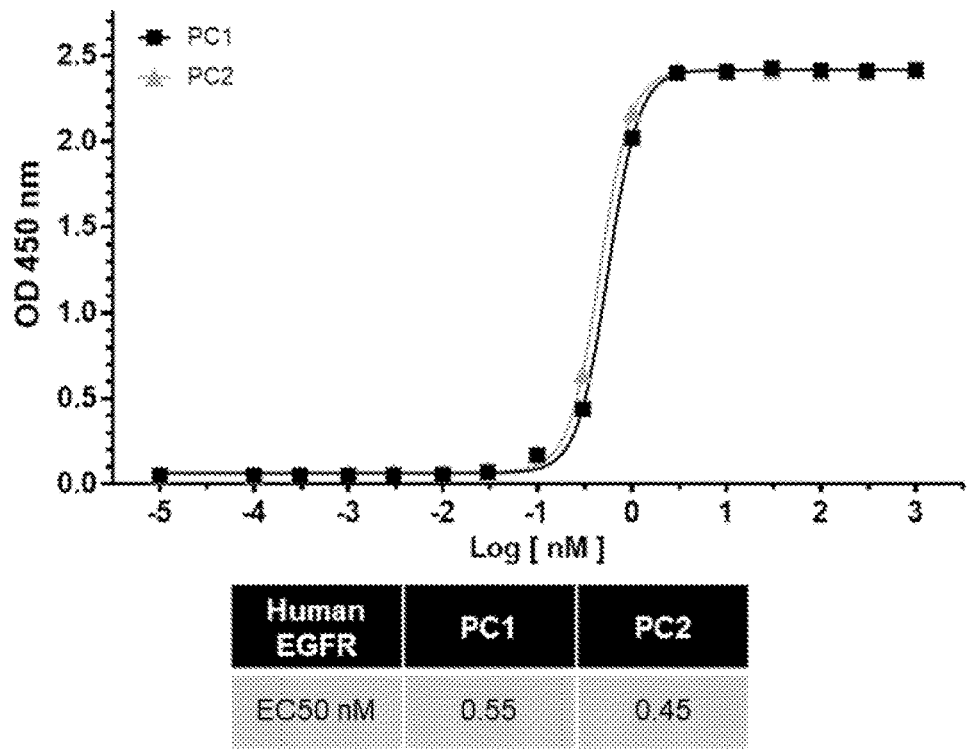
FIG. 7 illustrates binding and cross reactivity against human and cynomolgus EGFR for polypeptide complexes of this disclosure equilibrium.
Figure 7:
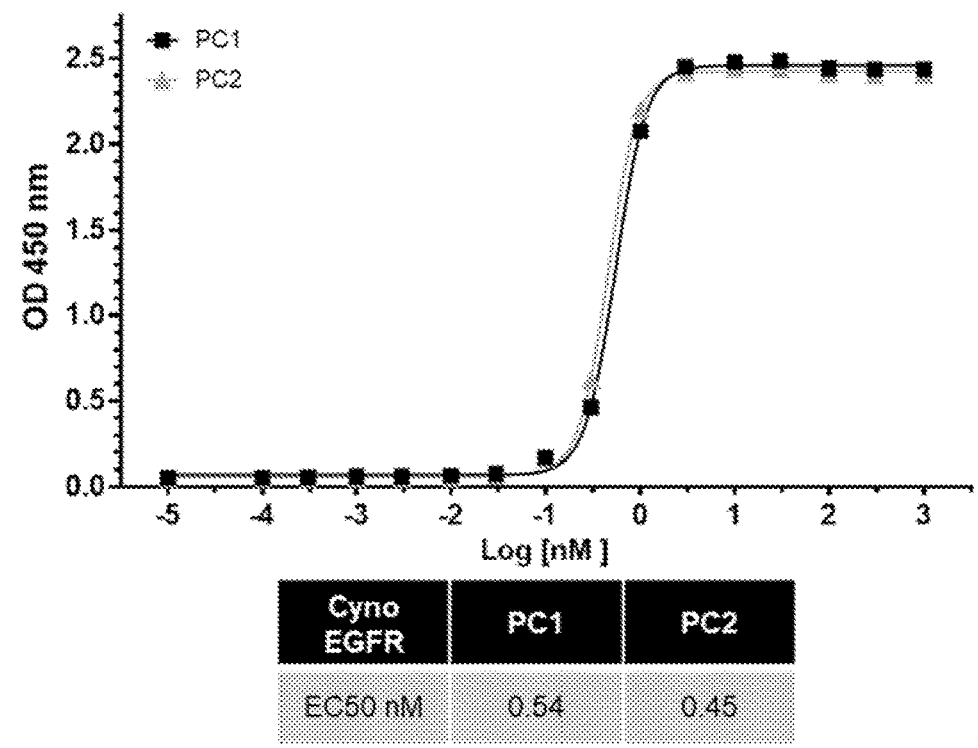

The polypeptide complex molecules were also evaluated for their ability to bind human and cynomolgus monkey antigen EGFR in a standard enzyme linked immunosorbent assay (ELISA) format. Briefly, antigens fused to a human Fc domain were directly coated on high binding ELISA plates. Polypeptide complex molecules diluted in buffer were then added to the antigen coated plates. Bound polypeptide complex was detected using a standard horse radish peroxidase conjugate secondary antibody. The concentration of polypeptide complex required to achieve 50% maximal signal (EC50) was calculated using Graphpad Prism software. Data is seen in FIG. 7.

Figure 8:
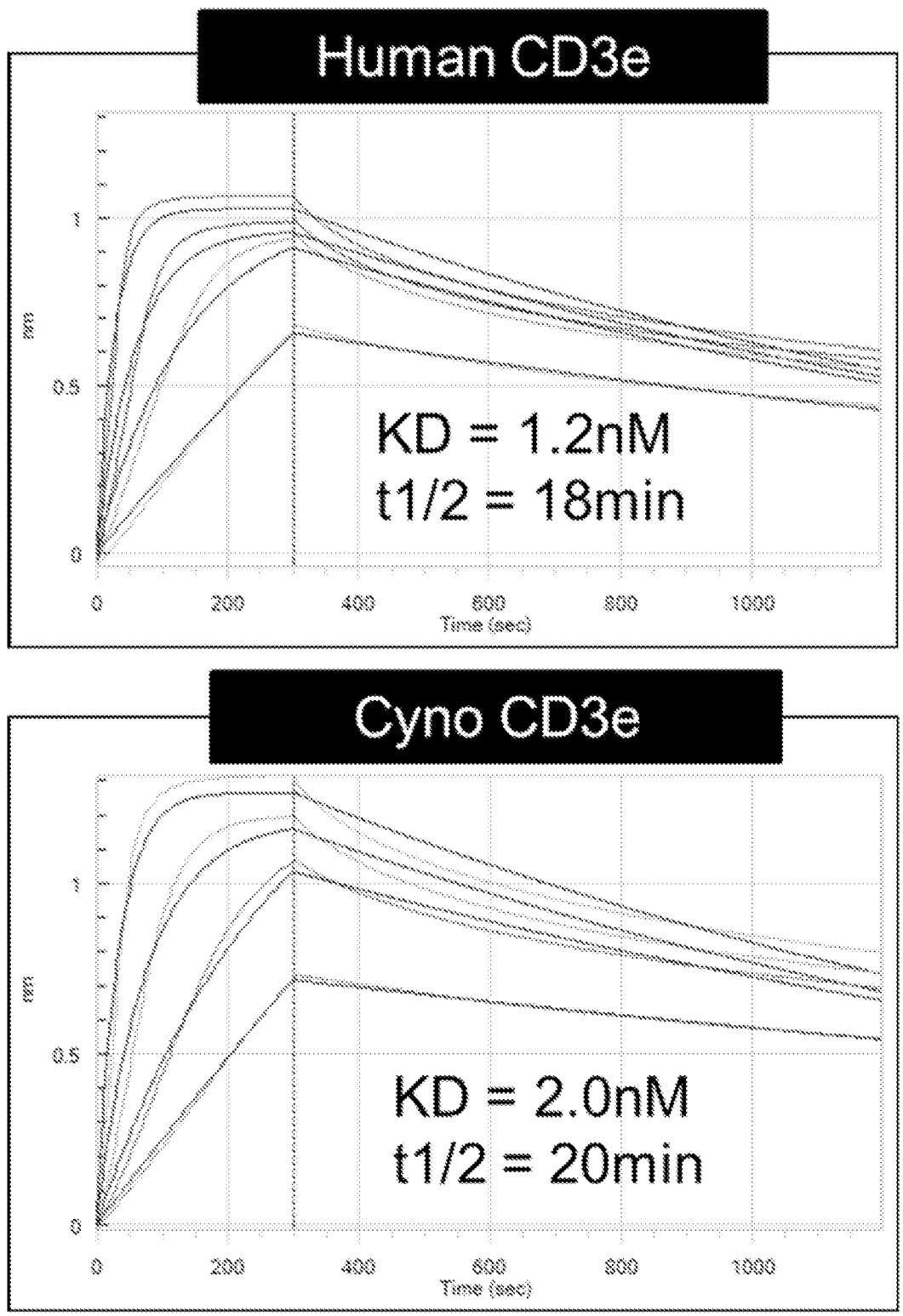
FIG. 8 illustrates kinetic binding and cross reactivity against human and cynomolgus CD3ε for several polypeptide complexes.

Kinetic binding of polypeptide molecules to human and cyno CD3 was evaluated by bio-layer interferometry using an Octet RED96 instrument. Briefly, biosensors were loaded with antigen and baselined in buffer. Polypeptide molecules were titrated in solution at 50 nM, 25 nM, 12.5 nM, and 6.25 nM then associated onto the antigen loaded sensors. After a short association period, sensors were transferred into buffer and the dissociation of bound polypeptide molecules was measured. The timing and steps of the experiment are shown in Table 8. Association and dissociation signals were recorded in real time and analyzed using a 1:1 binding model within the instrument software. Analysis using a 1:1 binding model enabled the calculation of the on and off rate constants as well as affinity, KD. Off rate constants were converted to half-life shown in the accompanying figures. Data is seen in FIG. 8.

TABLE 8

| Step | Time | pH |
| --- | --- | --- |
| Baseline: Octet buffer | 60 sec | pH 7.4 |
| Load: | 300 sec | pH 7.4 |
| 15 nM human CD3e | | |
| 15 nM cyno CD3e | | |
| Baseline: Octet buffer | 300 sec | pH 7.4 |
| Association in octet buffer | 300 sec | pH 7.4 |
| 50 nM PC1 | | |
| 25 nM PC1 | | |
| 12.5 nM PC1 | | |
| 6.25 nM PC1 | | |
| Dissociation: Octet Buffer | 900 sec | pH 7.4 |

Figure 9:
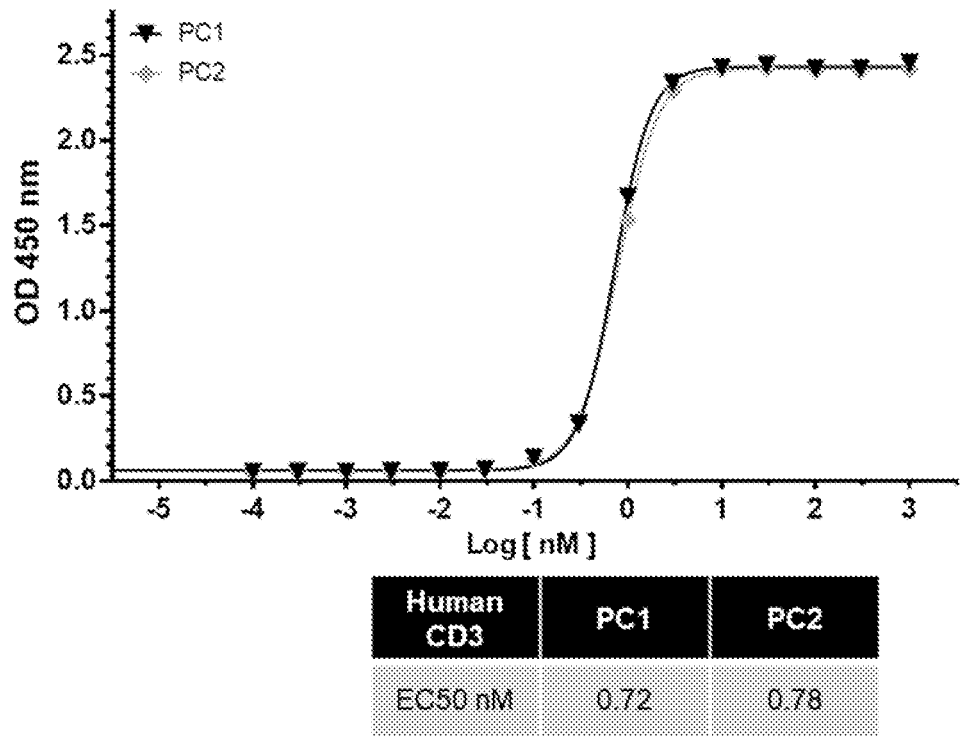
FIG. 9 illustrates equilibrium binding and cross reactivity against human and cynomolgus CD3ε for polypeptide complexes of this disclosure.
Figure 9:
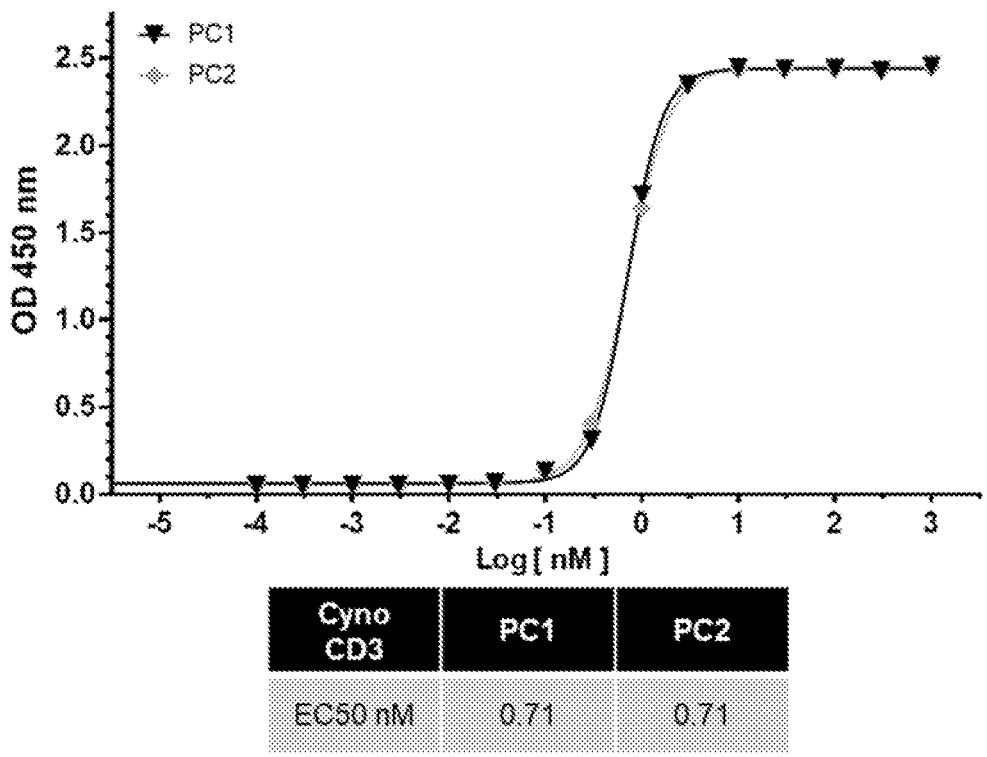

The polypeptide complex molecules were evaluated for their ability to bind human and cynomolgus monkey antigen CD3 in a standard enzyme linked immunosorbent assay (ELISA) format. Briefly, antigens fused to a human Fc domain were directly coated on high binding ELISA plates. Polypeptide complex molecules diluted in buffer were then added to the antigen coated plates. Bound polypeptide complex was detected using a standard horse radish peroxidase conjugate secondary antibody. The concentration of polypeptide complex required to achieve 50% maximal signal (EC50) was calculated using Graphpad Prism software. Data is seen in FIG. 9.

Example 4: Polypeptide Complex Pharmacokinetics in Cynomolgus Monkey

Figure 10A:
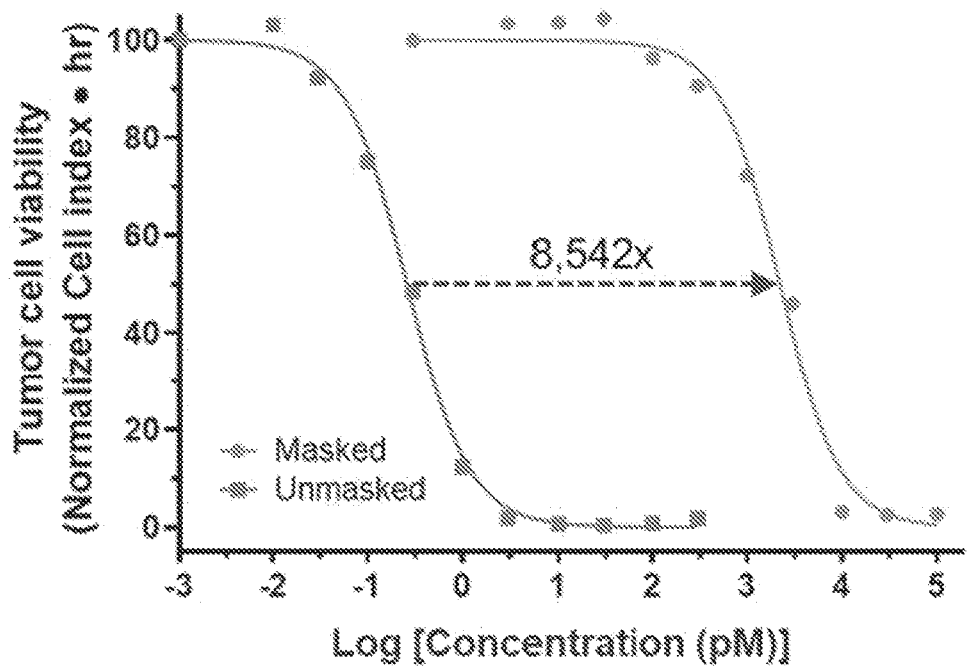
FIGS. 10A-10B illustrate pharmacokinetics in cynomolgus monkeys after a single IV bolus injection for polypeptide complexes of this disclosure.
Figure 10B:
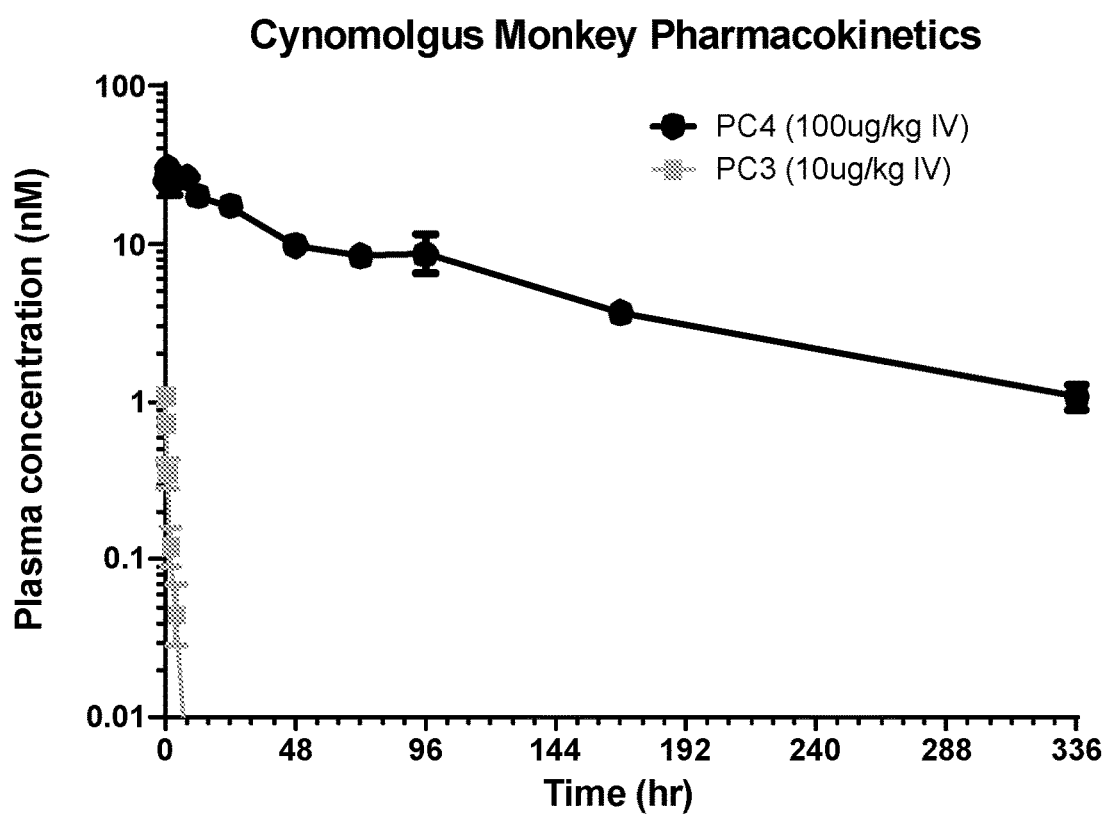
Figure 11A:
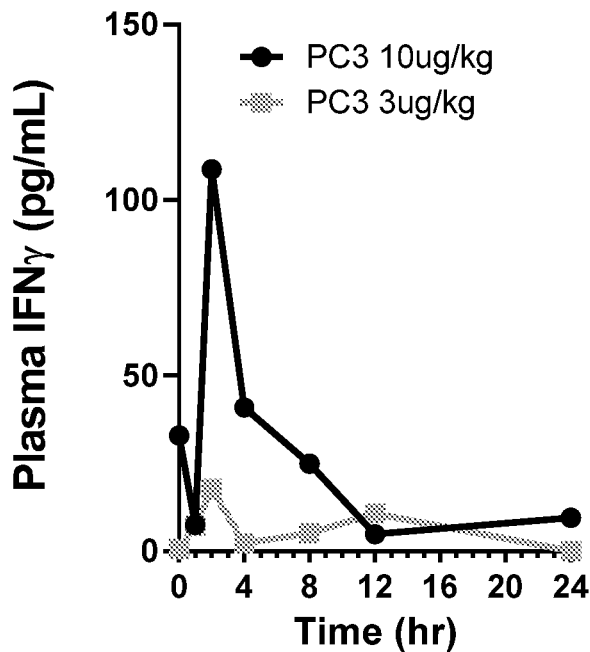
FIGS. 11A-11L illustrate cytokine release in cynomolgus monkeys after single IV bolus for polypeptide complexes of this disclosure.
Figure 11B:
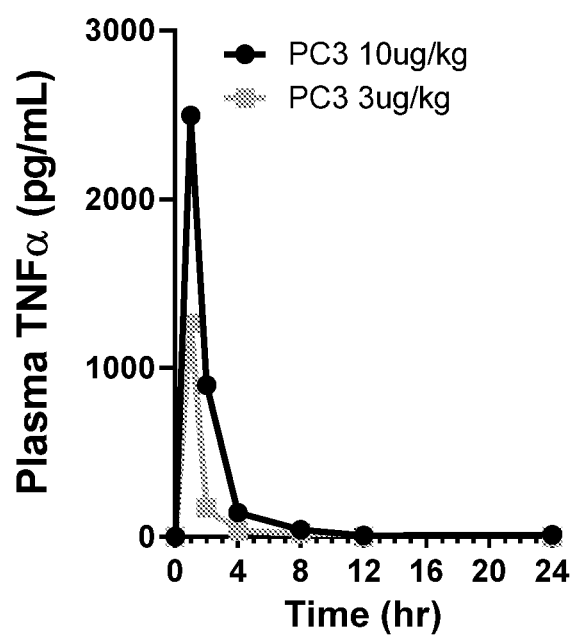
Figure 11C:
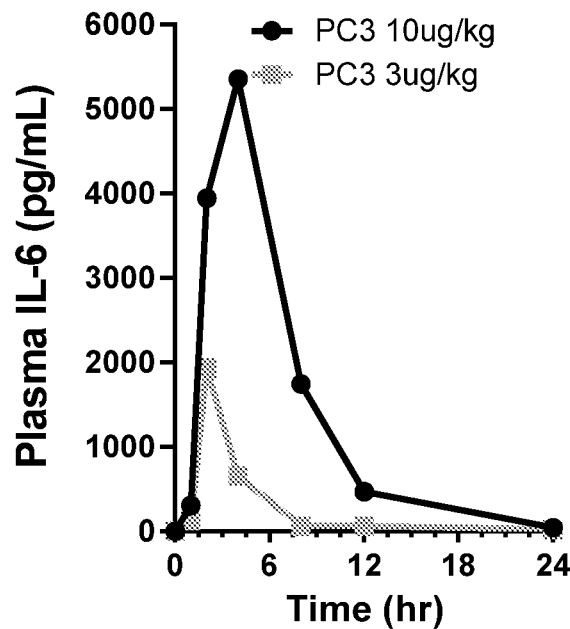
Figure 11D:
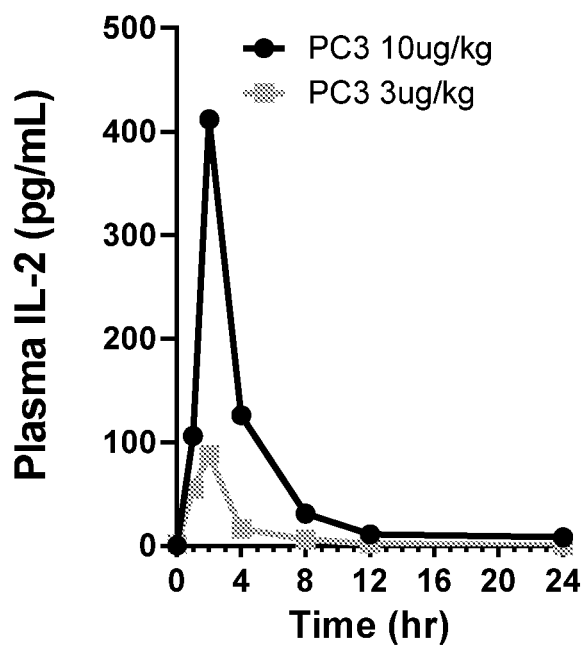
Figure 11E:
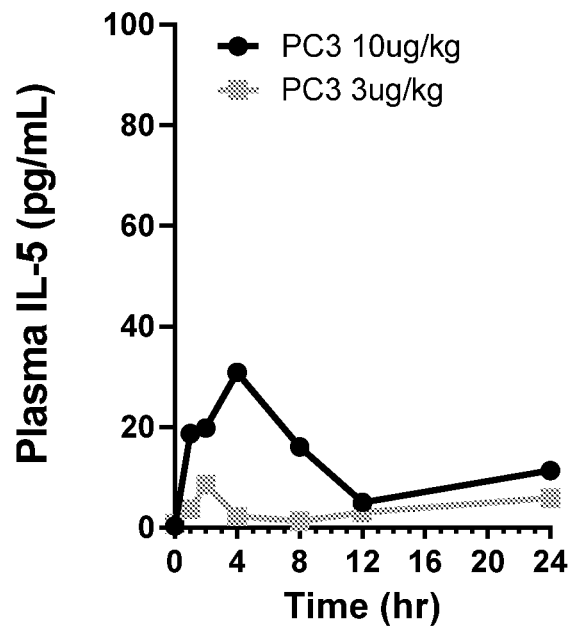
Figure 11F:
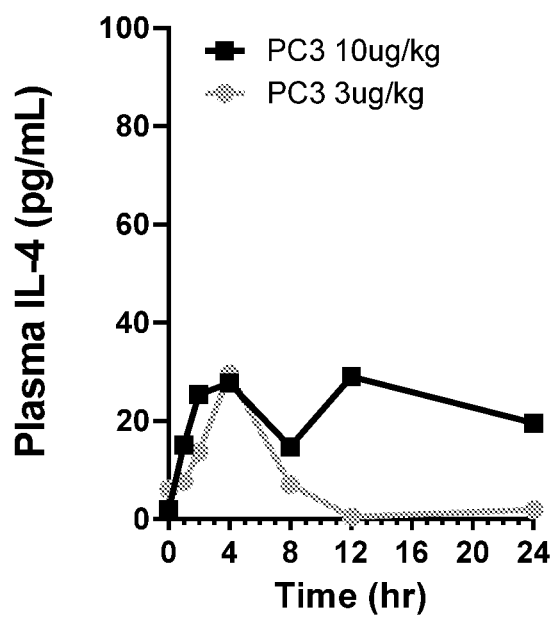
Figure 11G:
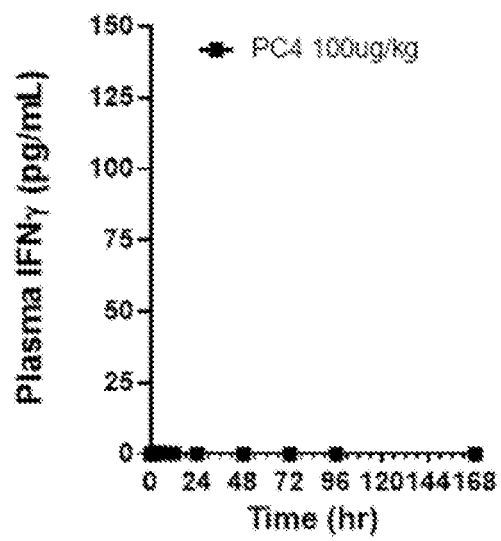
Figure 11H:
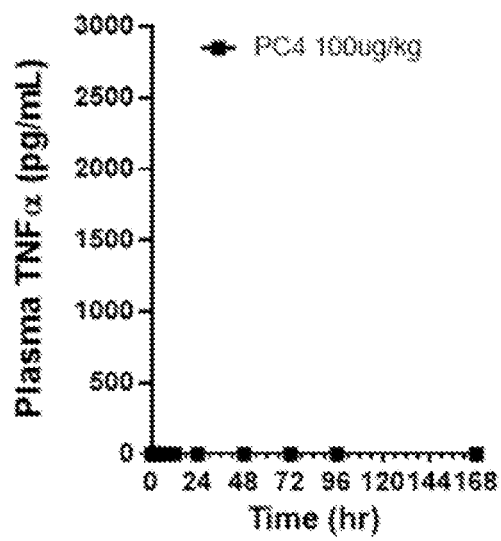
Figure 11I:
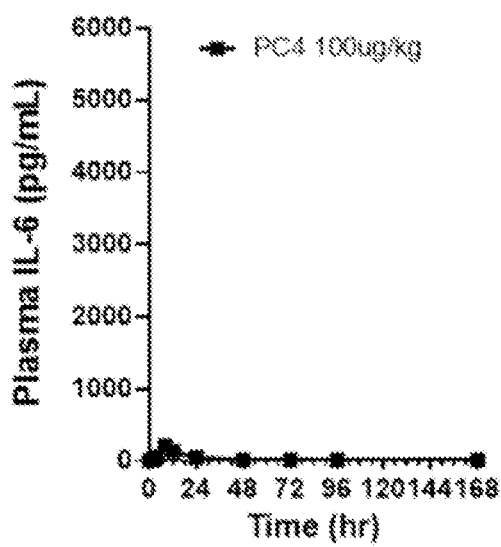
Figure 11J:
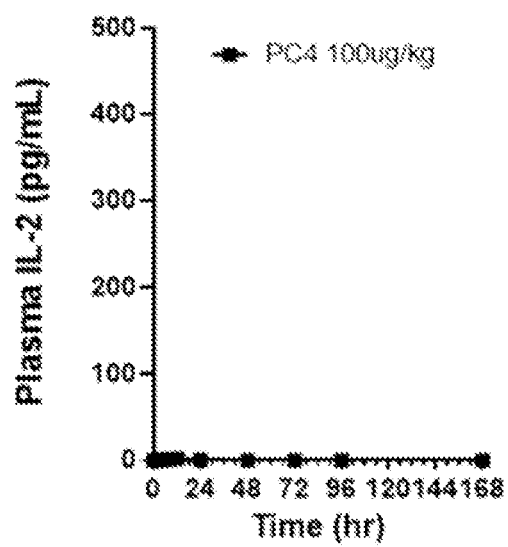
Figure 11K:
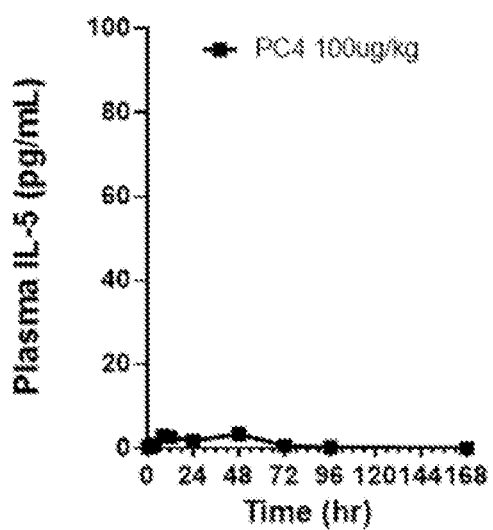
Figure 11L:
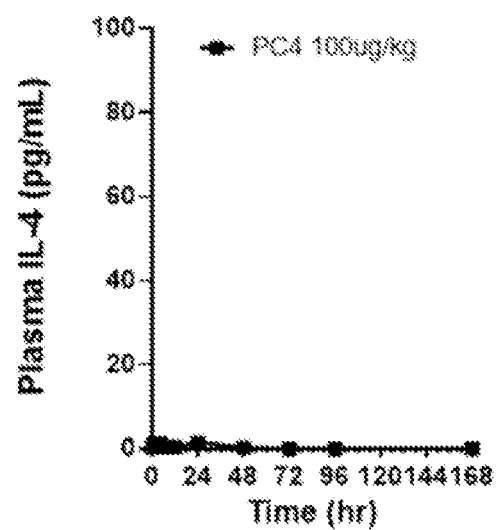

Pharmacokinetics and exploratory safety of polypeptide molecules were evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cyno plasma. Plasma concentration curves were fit to a standard two phase exponential equation representing distribution and elimination phases. Fitting of pharmacokinetics enabled the calculation of Cmax, half-life, volume of distribution, clearance, and 7 day area under the curve (AUC) shown in Tables 9-10. Measured pharmacokinetics in cynomolgus supports once weekly dosing in humans. Data is seen in FIGS. 10A-10B. FIG. 10A demonstrates that the polypeptide complexes described herein comprising a mask was over 8,500 less potent at T cell-mediated killing of EGFR-expressing tumor cells than an equivalent unmasked TCE in an in vitro assay. As seen in FIG. 10B and Table 9 below PC4 (masked) exhibited a half-life of approximately 94 hours, which supports once-weekly dosing in humans, as compared to an unmasked polypeptide complex that exhibited a half-life of about an hour.

TABLE 9

|  | PC4 100 ug/kg | Units |
|---|---|---|
| $C_{MAX}$ | 27.05 | nM |
| $t_{1/2}$ | 94.47 | hr |
| Vd | 0.12 | L |
| VSS | 0.25 | L |
| CL | 0.28 | mL/hr/kg |
| BW | 3.00 | kg |
| 7 day AUC | 96.143 | nM · min |

TABLE 10

|  | Unmasked polypeptide 10 ug/kg | Units |
|---|---|---|
| $C_{MAX}$ | 1.66 | nM |
| $t_{1/2}$ | 1.30 | hr |
| Vd | 0.24 | L |
| VSS | 1.08 | L |
| CL | 41.72 | mL/hr/kg |
| BW | 3.00 | kg |
| 7 day AUC | 75 | nM · min |

Example 5: Polypeptide Complexes in Cynomolgus Cytokine Release

Figure 12:
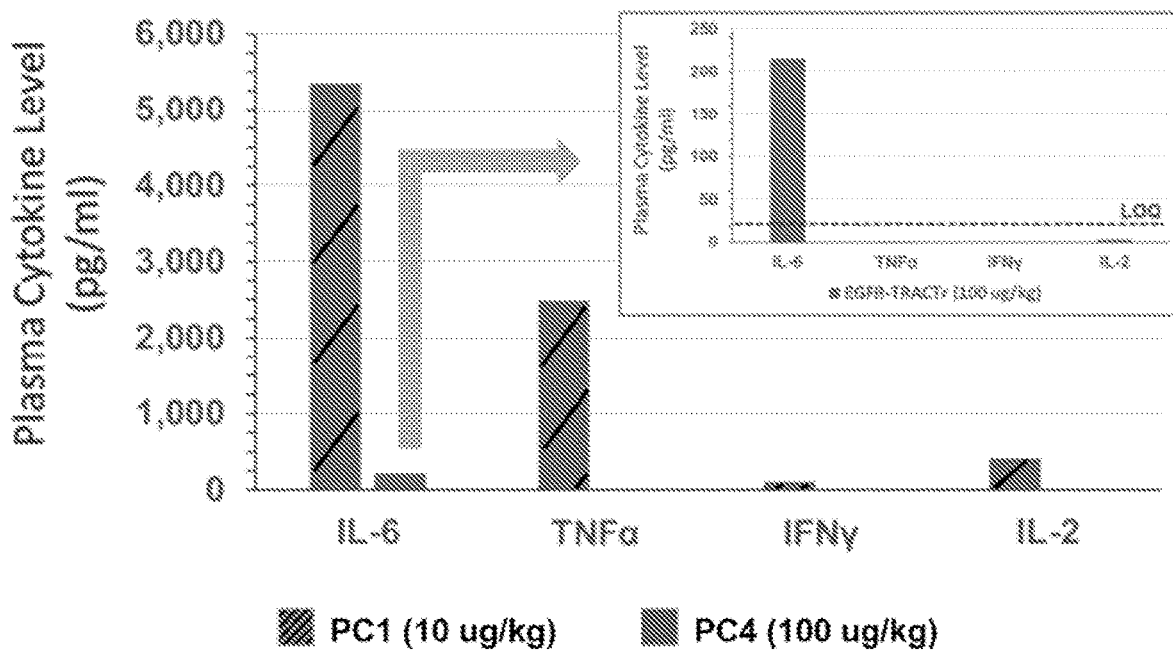
FIG. 12 illustrates dosing of polypeptide complexes of the disclosure on inflammatory cytokine levels.
Figure 13A:
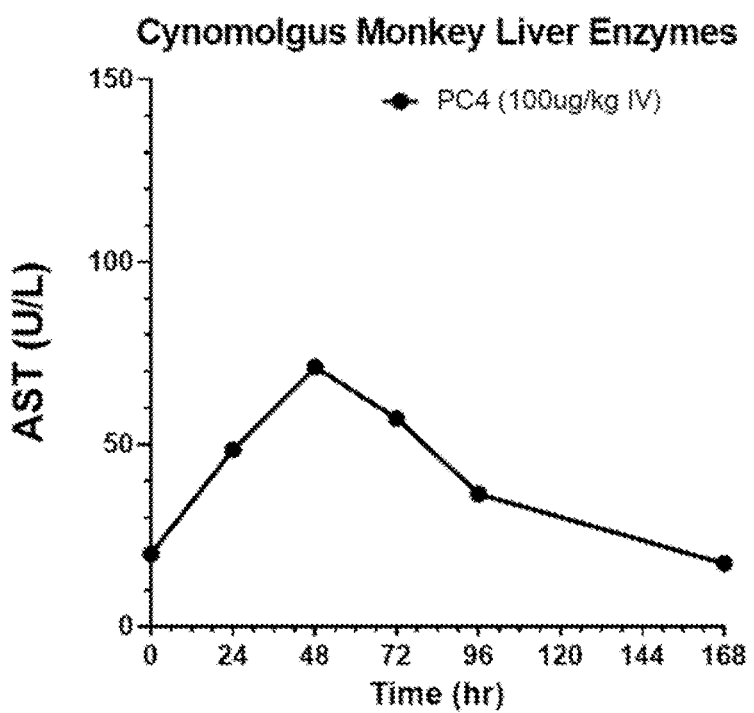
FIGS. 13A-13D illustrate serum liver enzymes in cynomolgus monkeys after single IV bolus for polypeptide complexes of this disclosure.
Figure 13B:
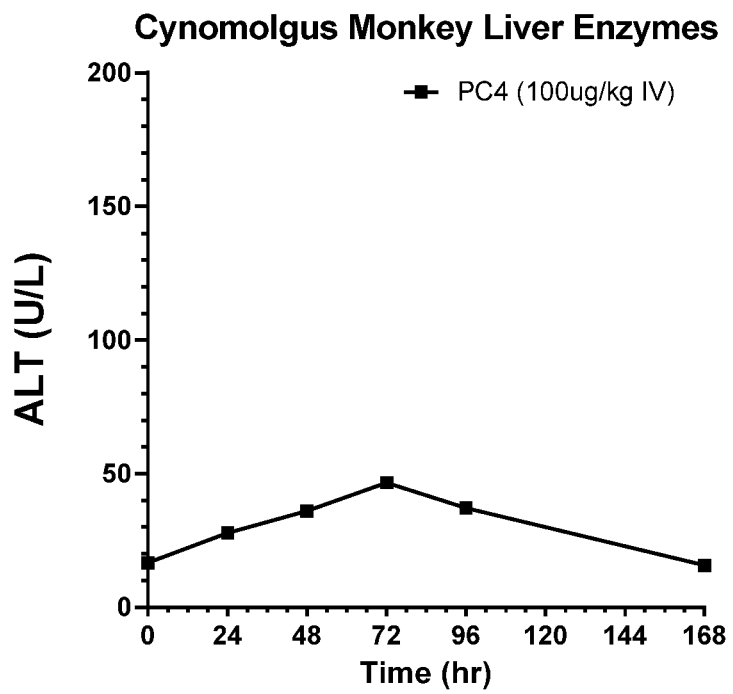
Figure 13C:
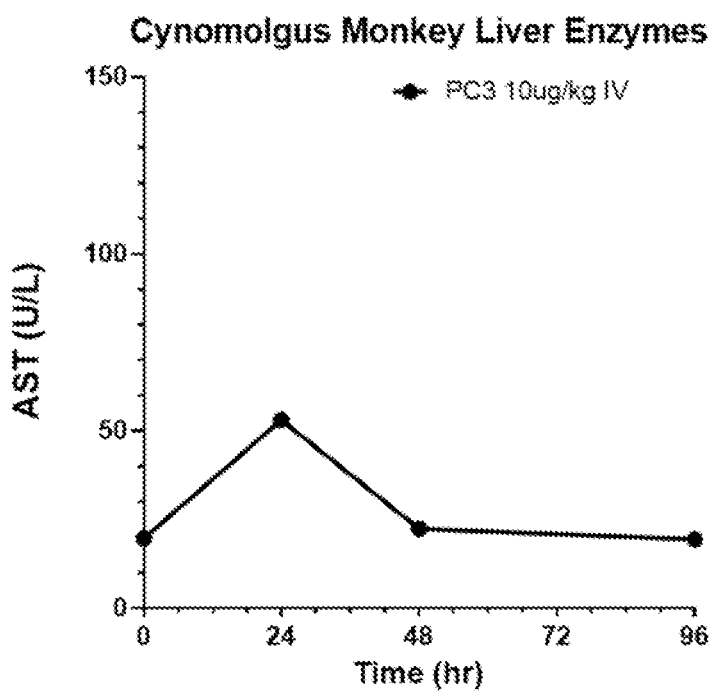
Figure 13D:
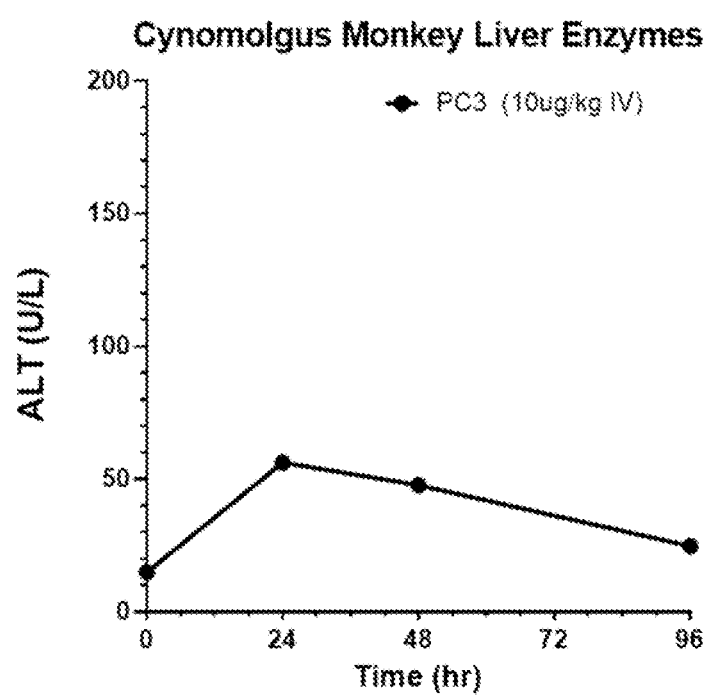

Cytokine release after polypeptide molecule administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for cytokines using a non-human primate cytometric Th1/Th2 bead array kit from BD biosciences following the manufacturer's instructions. Interferon gamma, tumor necrosis factor alpha, interleukin 6, interleukin 5, interleukin 4, and interleukin 2 levels in plasma were calculated relative to reference standards provided with the bead array kit. Data is seen in FIGS. 11A-11L and FIG. 12. FIG. 12 shows dosing of polypeptide complexes (EGFR TRACTr) described herein at 100 µg/kg resulted in minimal levels of inflammatory cytokine release, relative to an unmasked EGFR-TCE at 10 µg/kg, which led to a greater than 20-fold expression of IL-6.

Example 6: Polypeptide Complexes in Cynomolgus Toxicity

Systemic liver enzymes after polypeptide molecule administration by IV bolus was evaluated in cynomolgus monkeys. Briefly, cynomolgus monkeys of approximately 3 kg bodyweight were administered polypeptides as an IV bolus and observed daily for signs of adverse events. No in-life adverse events were observed. After dosing, blood was collected in K2 EDTA tubes at specific timepoints and processed to plasma. Plasma was stored frozen until analysis. Plasma samples were analyzed for the presence of liver enzymes aspartate transaminase (AST) and alanine aminotransferase (ALT) as signs of potential liver toxicity. AST and ALT levels were remained within the normal ranges for all timepoints tested after dosing suggesting a lack of liver toxicity. AST and ALT were quantified following the instructions provided in a commercially available kit from Millipore. AST and ALT levels were calculated according to manufacturer's instructions relative to a positive control reference standard. Data is seen in FIGS. 13A-13D.

Figure 14:
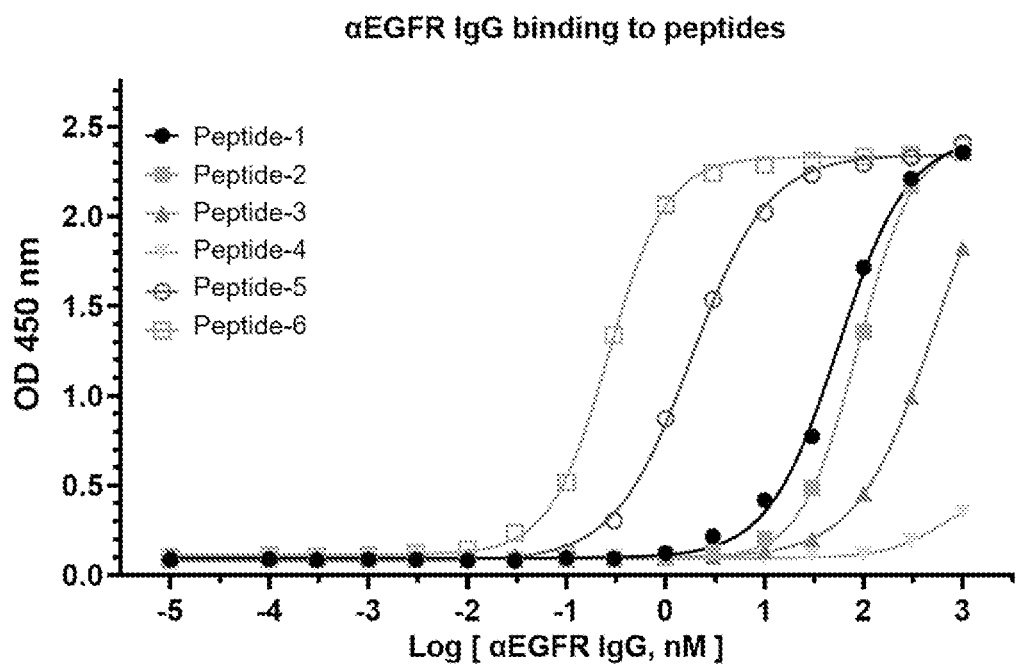
FIG. 14 illustrates binding curves for binding of αEGFR IgG by peptides of the present disclosure as measured by ELISA.

Example 7: Peptides Bind EGFR IgG and Inhibit EGFR IgG from Binding to the EGFR Antigen The peptide sequences (peptide-1 to peptide-6) of Table 11 were evaluated for binding to EGFR IgG (see Table 11) in an ELISA format. Briefly, biotinylated peptides were captured on neutravidin coated plates. EGFR IgG diluted in buffer was then added to the peptide coated plates. Bound EGFR IgG was detected using a standard horse radish peroxidase conjugate secondary antibody. The ELISA signal was plotted versus the log-scale antibody concentration. The concentrations of antibody required to observe half maximal binding signal ($EC_{50}$s) were calculated using Graphpad Prism software. FIG. 14 shows binding curves for peptide binding to EGFR IgG, and Table 12 provides the calculated $EC_{50}$s for peptide binding to EGFR IgG. Peptide-6 of SEQ ID NO: 76 showed the strongest binding to EGFR IgG (lowest $EC_{50}$) among the peptides tested in this series.

TABLE 11

Peptide sequences for EGFR IgG binding and EGFR IgG Sequence

| Description | Amino Acid Sequence (N to C) | SEQ ID NO: |
|---|---|---|
| Peptide-1 | DWCRSLMSYTDLCP | 71 |
| Peptide-2 | TSCADAHLIAPSCS | 72 |
| Peptide-3 | NCQWDRVEHTYACS | 73 |
| Peptide-4 | WVSCHDGSHMTCFH | 74 |
| Peptide-5 | MNCLNRLWVEYCLV | 75 |
| Peptide-6 | YCGQDNTWVREGCF | 76 |
| EGFR IgG (Light chain) | DILLTQSPVILSVSPGERVSFSCRASQSIGTN IHWYQQRINGSPRLLIKYASESISGIPSRFSG SGSGTDFTLSINSVESEDIADYYCQQNNNW PTTFGAGTKLELKRTVAAPSVFIFPPSDEQL KSGTASVVCLLNNFYPREAKVQWKVDNA | 22 |

TABLE 11-continued

Peptide sequences for EGFR IgG binding and EGFR IgG Sequence

| Description | Amino Acid Sequence (N to C) | SEQ ID NO: |
|---|---|---|
| | LQSGNSQESVTEQDSKDSTYSLSSTLTLSK ADYEKHKVYACEVTHQGLSSPVTKSFNRG EC | |
| EGFR IgG (Heavy chain) | QVQLKQSGPGLVQPSQSLSITCTVSGFSLTN YGVHWVRQSPGKGLEWLGVIWSGGNTDY NTPFTSRLSINKDNSKSQVFFKMNSLQSND TAIYYCARALTYYDYEFAYWGQGTLVTVS AASTKGPSVFPLAPSSKSTSGGTAALGCLV KDYFPEPVTVSWNSGALTSGVHTFPAVLQ SSGLYSLSSVVTVPSSSLGTQTYICNVNHKP SNTKVDKKVEPKSCDKTHTCPPCPAPELLG GPSVFLFPPKPKDTLMISRTPEVTCVVVDV SHEDPEVKFNWYVDGVEVHNAKTKPREE QYNSTYRVVSVLTVLHQDWLNGKEYKCK VSNKALPAPIEKTISKAKGQPREPQVYTLPP SRDELTKNQVSLTCLVKGFYPSDIAVEWES NGQPENNYKTTPPVLDSDGSFFLYSKLTVD KSRWQQGNVFSCSVMHEALHNHYTQKSL SLSPGK | 842 |

TABLE 12

EC$_{50}$s for peptide binding to EGFR IgG

| | Peptide-1 | Peptide-2 | Peptide-3 | Peptide-4 | Peptide-5 | Peptide-6 |
|---|---|---|---|---|---|---|
| EC$_{50}$ (nM) | 52 | 84 | 413 | >1000 | 2 | 0.3 |

Figure 15:
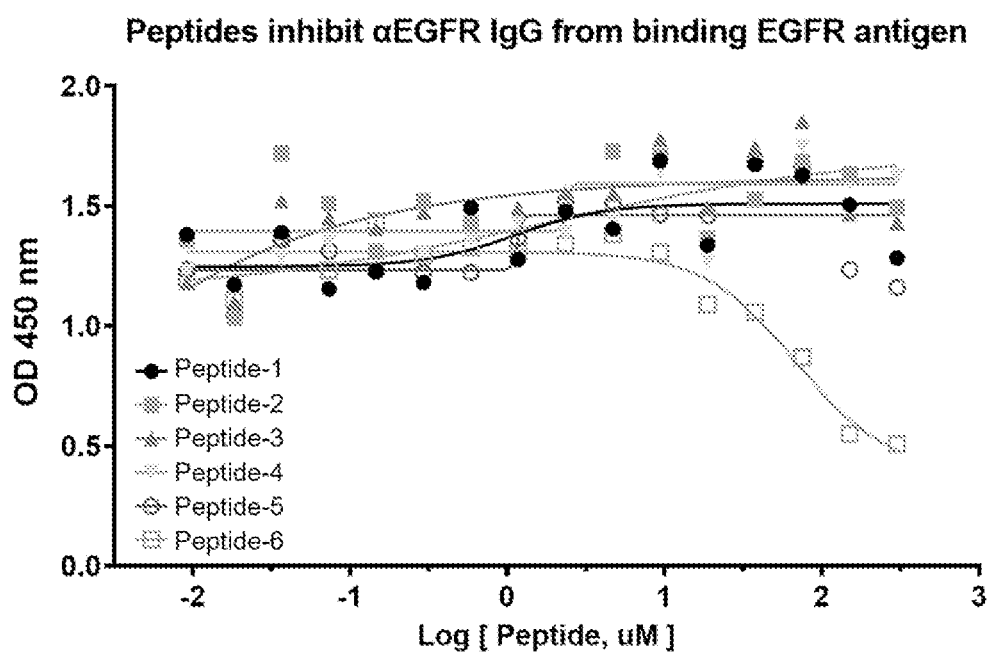
FIG. 15 illustrates inhibition of αEGFR IgG binding to the EGFR antigen by peptides of the present disclosure as measured by ELISA.

For a peptide to function as a mask, it must also inhibit the antibody of interest from binding to its cognate antigen. As such, ELISA-based competitive inhibition studies were also used to test the ability of each peptide to inhibit EGFR IgG from binding to the EGFR antigen. Biotinylated antigen was captured on neutravidin coated plates, quenched using biocytin, and washed. Inhibitory peptides were titrated in a dilution series and pre-incubated with a constant concentration of antibody. Inhibitory peptide and antibody mixtures were then incubated on the antigen captured plates. A horseradish peroxidase conjugate secondary antibody was then used to detect the antibody binding to the plate-bound antigen. The ELISA signal was plotted versus log-scale peptide concentration (see FIG. 15). A dose dependent decrease of signal was indicative of peptides that compete for antibody binding to the cognate antigen. Graphpad Prism software was used to calculate the inhibitory concentrations of peptide required to achieve 50% maximal signal (ICsos). The IC$_{50}$ data is provided in Table 13. Of the peptides tested in this series, peptide-6 was the most effective at inhibiting EGFR IgG binding to the EGFR antigen.

TABLE 13

IC$_{50}$s for peptide inhibition of EGFR IgG binding to EGFR antigen

| | Peptide-1 | Peptide-2 | Peptide-3 | Peptide-4 | Peptide-5 | Peptide-6 |
|---|---|---|---|---|---|---|
| IC$_{50}$ (nM) | >300 | >300 | >300 | >300 | >300 | 50 |

Figure 16:
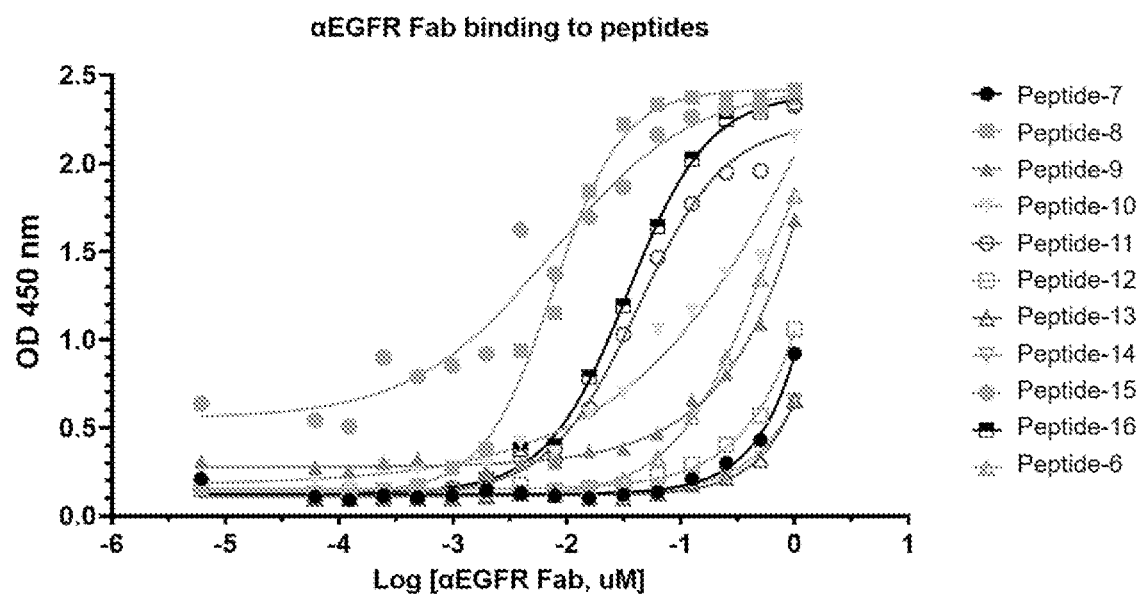
FIG. 16 illustrates binding curves for binding of αEGFR Fab by peptides of the present disclosure as measured by ELISA.

Example 8: Peptides Bind EGFR Fab and Inhibit EGFR Fab from Binding to the EGFR Antigen The peptide sequences of Table 14 were evaluated for binding to EGFR Fab in an ELISA format. Binding studies were carried out as described above in Example 7. Binding curves are shown in FIG. 16 and EC$_{50}$s for binding are provided in Tables 15-16. Peptide-8 and peptide-15 showed the strongest binding affinities (lowest EC$_{50}$s) for EGFR Fab among the peptides tested in this series.

TABLE 14

Peptide sequences for αEGFR IgG binding

| Description | Amino Acid Sequence (N to C) | SEQ ID NO: |
|---|---|---|
| Peptide-7 | WCTVWGDRQEVRCL | 77 |
| Peptide-8 | PCRSHIDVAKPICV | 26 |
| Peptide-9 | STCVHYWMQLRSCV | 78 |
| Peptide-10 | GGCAHWVMRLSWCQ | 79 |
| Peptide-11 | LGCQHFLMKLATCG | 80 |
| Peptide-12 | GCGDGLHRMVRMWC | 81 |
| Peptide-13 | ACTVMGARQEVRCV | 82 |
| Peptide-14 | PCPALIDVAEVICV | 83 |
| Peptide-15 | YCNSVWQRGQLYWC | 84 |
| Peptide-16 | ECSHMEGTRWPLCS | 85 |

TABLE 15

EC$_{50}$s for peptide binding to EGFR Fab

| | Peptide-7 | Peptide-8 | Peptide-9 | Peptide-10 | Peptide-11 | Peptide-12 |
|---|---|---|---|---|---|---|
| EC$_{50}$ (nM) | >1000 | 8 | >1000 | >1000 | 42 | >1000 |

TABLE 16

EC$_{50}$s for peptide binding to αEGFR Fab

|  | Peptide-13 | Peptide-14 | Peptide-15 | Peptide-16 | Peptide-6 |
|---|---|---|---|---|---|
| EC$_{50}$ (nM) | >1000 | >1000 | 7 | 34 | 458 |

Figure 17:
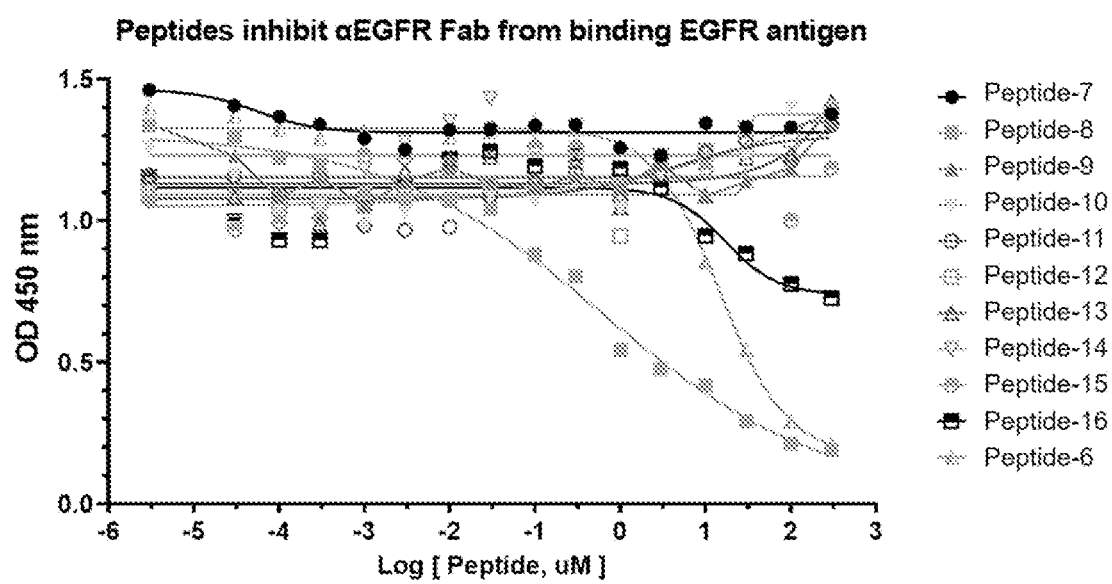
FIG. 17 illustrates inhibition of αEGFR Fab binding to the EGFR antigen by peptides of the present disclosure as measured by ELISA.

Competitive inhibition studies were also used to test the ability of each peptide to inhibit EGFR Fab from binding to the EGFR antigen in an ELISA format. Competitive inhibition measurements were carried out as described above in Example 7. Dose-dependent peptide inhibition of EGFR Fab binding to the EGFR antigen is shown in FIG. 17, and IC$_{50}$ data is provided in Tables 17-18. Notably, peptide-8 (SEQ ID NO: 26) was the most effective at inhibiting EGFR Fab binding to the EGFR antigen.

TABLE 17

IC$_{50}$s for peptide inhibition of αEGFR Fab binding to EGFR antigen

|  | Peptide-7 | Peptide-8 | Peptide-9 | Peptide-10 | Peptide-11 | Peptide-12 |
|---|---|---|---|---|---|---|
| IC$_{50}$ (nM) | >300 | 0.3 | >300 | >300 | >300 | >300 |

TABLE 18

IC$_{50}$s for peptide inhibition of αEGFR Fab binding to EGFR antigen

|  | Peptide-13 | Peptide-14 | Peptide-15 | Peptide-16 | Peptide-6 |
|---|---|---|---|---|---|
| IC$_{50}$ (nM) | >300 | >300 | >300 | >300 | 13 |

Example 9: Sequence Activity Relationships—EGFR Fab Peptide

Sequence activity relationships (SAR) were established for peptide-8 which was found to exhibit strong binding to EGFR Fab and inhibition of EGFR Fab binding to the EFGR antigen. The sequence activity relationships were established by mutating individual residues within the peptide to alanine and measuring the influence of each mutation on the ability of the peptide to inhibit EGFR Fab binding to the EGFR antigen. The alanine scanning sequences are provided in Table 19.

TABLE 19

Alanine scan peptide sequences

| Description | Amino Acid Sequence (N to C) | SEQ ID NO: |
|---|---|---|
| Peptide-8 (wild type) | PCRSHIDVAKPICV | 26 |
| Peptide-17 | ACRSHIDVAKPICV | 86 |
| Peptide-18 | PCASHIDVAKPICV | 87 |
| Peptide-19 | PCRAHIDVAKPICV | 88 |
| Peptide-20 | PCRSAIDVAKPICV | 89 |
| Peptide-21 | PCRSHADVAKPICV | 90 |
| Peptide-22 | PCRSHIAVAKPICV | 91 |
| Peptide-23 | PCRSHIDAAKPICV | 92 |
| Peptide-24 | PCRSHIDVAAPICV | 93 |
| Peptide-25 | PCRSHIDVAKAICV | 94 |
| Peptide-26 | PCRSHIDVAKPACV | 95 |
| Peptide-27 | PCRSHIDVAKPICA | 96 |

Figure 18:
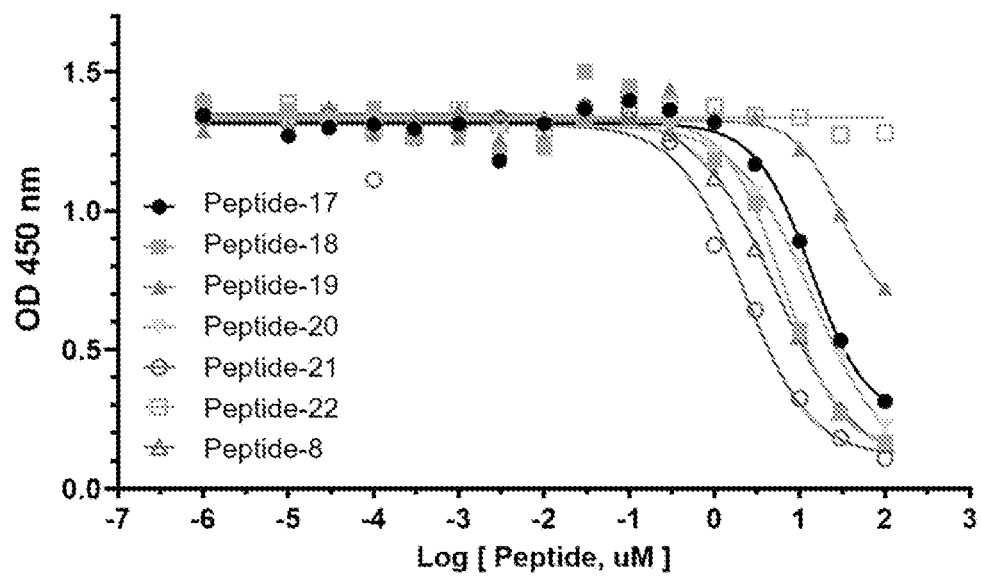
FIG. 18 illustrates inhibition of αEGFR Fab binding to the EGFR antigen by alanine scanning peptides of peptide-8 as measured by ELISA.
Figure 19:
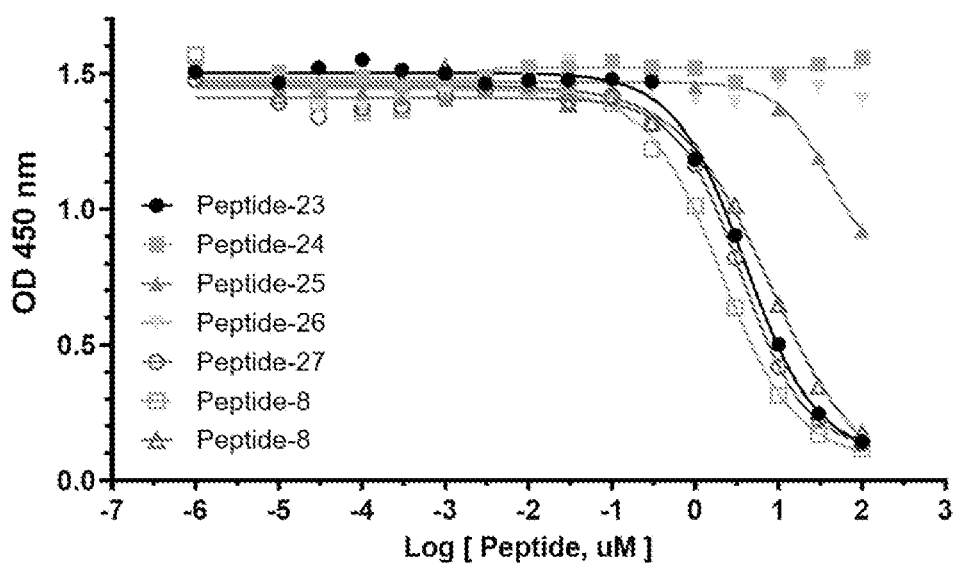
FIG. 19 illustrates inhibition of αEGFR Fab binding to the EGFR antigen by alanine scanning peptides of peptide-8 as measured by ELISA.
Figure 20:
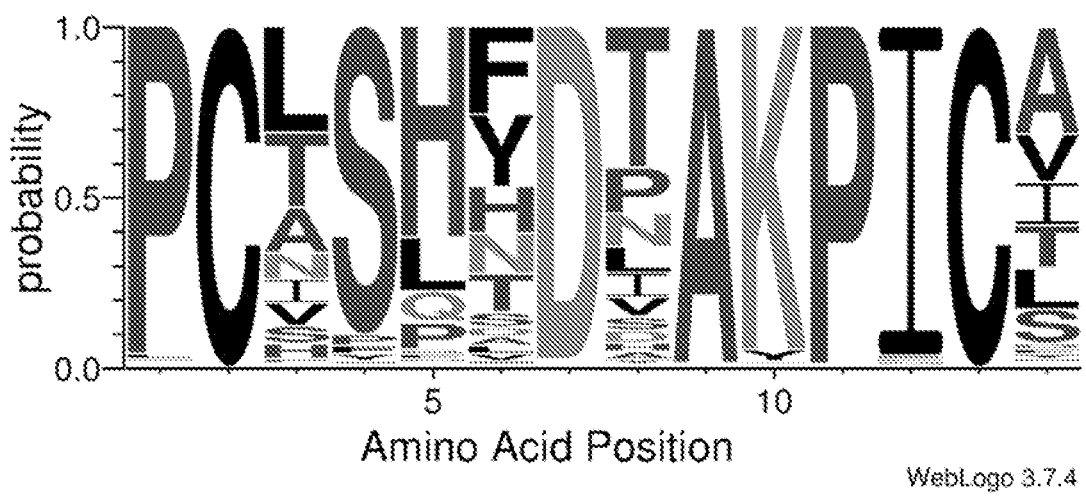
FIG. 20 illustrates a consensus sequence of optimized αEGFR Fab peptide-8 generated using WebLogo 3.7.4.

Inhibition measurements were carried out in an ELISA format as described above in Example 7. The competitive inhibition plots for the alanine scanning peptides are shown in FIGS. 18-19, and the calculated IC$_{50}$s are provided in Tables 20-21. Peptide residues whose alanine mutations significantly diminished the inhibitory activity (or significantly raised the IC$_{50}$) of the peptide were considered key residues where mutations were not tolerated (classified as not tolerated, or "NT"). Peptide residues whose alanine mutations only somewhat diminished the inhibitory activity of the peptide were considered somewhat tolerated (classified as somewhat tolerated, or "ST"). Peptide residues whose alanine mutations performed similarly to the non-mutated peptide-8 sequence were considered non-critical sites where mutations were indeed tolerated (classified as tolerated, or "T")

TABLE 20

Competitive inhibition and SAR data for peptide-8 alanine scanning mutants

| Peptide description | SEQ ID NO: | IC$_{50}$ (μM) | Fold shift in IC$_{50}$ relative to Peptide-8 (IC$_{50}$ Ala mutant/IC$_{50}$ Peptide-8) | Ala scan position | Mutation tolerated? |
|---|---|---|---|---|---|
| Peptide-8 (wild type) | 26 | 3.9 | — | — | — |
| Peptide-17 | 86 | 16 | 4.1 | Pro-1 | NT |
| Peptide-18 | 87 | 5.6 | 1.4 | Arg-3 | T |
| Peptide-19 | 88 | 93 | 24 | Ser-4 | NT |
| Peptide-20 | 89 | 11 | 2.8 | His-5 | ST |
| Peptide-21 | 90 | 1.95 | 0.5 | Ile-6 | T |
| Peptide-22 | 91 | >100 | ND | Asp-7 | NT |

TABLE 21

Competitive inhibition and SAR data for peptide-8 alanine scanning mutants

| Peptide description | SEQ ID NO: | IC$_{50}$ (μM) | Fold shift in IC$_{50}$ relative to Peptide-8 (IC$_{50}$ Ala mutant/IC$_{50}$ Peptide-8) | Ala scan position | Mutation tolerated? |
|---|---|---|---|---|---|
| Peptide-8 (wild type) | 26 | 1.4 | — | — | — |
| Peptide-23 | 92 | 3.8 | 2.7 | Val-8 | T |
| Peptide-24 | 93 | >100 | ND | Lys-10 | NT |
| Peptide-25 | 94 | >100 | ND | Pro-11 | NT |

TABLE 21-continued

Competitive inhibition and SAR data for peptide-8 alanine scanning mutants

| Peptide description | SEQ ID NO: | $IC_{50}$ (μM) | Fold shift in $IC_{50}$ relative to Peptide-8 ($IC_{50}$ Ala mutant/$IC_{50}$ Peptide-8) | Ala scan position | Mutation tolerated? |
|---|---|---|---|---|---|
| Peptide-26 | 95 | >100 | ND | Ile-12 | NT |
| Peptide-27 | 96 | 3.1 | 2.2 | Val-14 | T |

As can be seen from Tables 20-21, alanine mutations at Asp-7, Lys-10, Pro-11, and Ile-12 of peptide-8 were the most poorly tolerated, suggesting that these residues are key residues for inhibiting EGFR Fab binding to the EGFR antigen. The mutation studies indicate that Pro-1 and Ser-4 may also be important for binding inhibition. Additionally, the results indicate that Arg-3, Ile-6, Val-8, and Val-14 are non-critical residues for inhibition of EGFR binding to the EGFR antigen.

Example 10: Optimized Phage Library Construction of Peptide-8

Using the peptide sequence activity relationships of Example 9, DNA oligo libraries were constructed where codons encoding critical residues within peptide-8 were minimally mutated, and codons encoding non-critical residues that were tolerated in the alanine scanning mutation studies (e.g., Arg-3, Ile-6, Val-8, and Val-14) were heavily mutated. The resulting oligos were cloned into bacteriophage vectors used to display the SAR guided peptides via fusion to the pIII filament of the bacteriophage. The relevant vectors were then used to produce the phage optimization libraries via amplification in bacteria using standard techniques in the field.

Example 11: Panning of the Optimized Phage Library

Once the phage optimization libraries were completed, phage libraries were bio-panned using EGFR Fab loaded beads. Multiple rounds of panning were performed where bacteriophage was allowed to bind to EGFR Fab loaded beads, washed, eluted, and amplified. Additional selective pressure was included during each round of panning using a fixed concentration of EGFR antigen or peptide-8. After panning, phage infected bacteria were plated out and colonies picked into 96 well blocks. Clonal phage was then amplified and separated from bacterial cells via centrifugation. Phage containing supernatants were tested in binding ELISAs against EGFR Fab coated plates in the presence or absence of saturating concentrations of EGFR antigen. Phage able to bind EGFR Fab were selected for sequence analysis if the binding signal was reduced in the presence of pEGFR.

Example 12: Panning ELISAs—EGFR Fab Peptides

Clonal phage were harvested as crude supernatants and screened via standard ELISAs. Briefly, biotinylated EGFR Fab was captured on neutravidin coated plates. Prior to the addition of clonal phage, wells were incubated with blocking buffer and EGFR antigen or blocking buffer alone. Without washing or aspirating, clonal phage supernatants were then added to the wells and incubated for a short time. Wells were then washed followed by detection of bound phage using a horse radish conjugated anti-M13 antibody. Clonal phage of interest were then sent for sequence analysis.

Phage panning results of peptide-8 library sequences are shown in Table 22. 679 clonal phage sequences were identified. A consensus sequence was calculated from all the sequences of Table 22 using WebLogo 3.7.4. The consensus sequence is shown in FIG. 20.

TABLE 22

Phage panning results of αEGFR Fab peptide-8 library sequences. (—) indicates the same amino acid as in aEGFR Fab peptide-8 corresponding position.

| Phage | Amino acid position sequence | | | | | | | | | | | | | | Phage binding ELISA | | | |
|---|---|---|---|---|---|---|---|---|---|---|---|---|---|---|---|---|---|---|
| Phage number | 1 | 2 | 3 | 4 | 5 | 6 | 7 | 8 | 9 | 10 | 11 | 12 | 13 | 14 | Backgroud signal | EGFR Fab signal | EGFR Fab signal in presence of EGFR | SEQ ID NO: |
| Phage-1 | P | C | R | S | H | I | D | V | A | K | P | I | C | V | 0.071 | 2.596 | 0.084 | 98 |
| Phage-2 | — | — | L | — | P | F | — | T | — | — | — | — | — | A | 0.067 | 2.525 | 0.078 | 99 |
| Phage-3 | — | — | T | — | — | F | — | T | — | — | — | — | — | T | 0.068 | 2.592 | 0.082 | 100 |
| Phage-4 | — | — | T | — | — | F | — | T | — | — | — | — | — | I | 0.070 | 2.595 | 0.093 | 101 |
| Phage-5 | — | — | L | — | — | F | — | T | — | — | — | — | — | L | 0.078 | 2.582 | 0.077 | 102 |
| Phage-6 | — | — | L | — | — | T | — | T | — | — | — | — | — | A | 0.071 | 2.523 | 0.070 | 103 |
| Phage-7 | — | — | L | — | — | H | — | T | — | — | — | — | — | A | 0.069 | 2.599 | 0.076 | 104 |
| Phage-8 | — | — | L | — | — | F | — | T | — | — | — | — | — | A | 0.070 | 2.543 | 0.077 | 105 |
| Phage-9 | — | — | L | — | — | F | — | T | — | — | — | — | — | — | 0.073 | 2.513 | 0.083 | 106 |
| Phage-10 | — | — | L | — | — | N | — | P | — | — | — | — | — | S | 0.064 | 2.564 | 0.078 | 107 |
| Phage-11 | — | — | T | — | Q | H | — | T | — | — | — | — | — | I | 0.072 | 2.590 | 0.090 | 108 |
| Phage-12 | — | — | T | — | — | F | — | T | — | — | — | — | — | A | 0.073 | 2.503 | 0.091 | 109 |
| Phage-13 | — | — | L | — | — | T | — | T | — | — | — | — | — | — | 0.068 | 2.517 | 0.076 | 110 |
| Phage-14 | — | — | L | — | — | N | — | P | — | — | — | — | — | A | 0.066 | 2.589 | 0.068 | 111 |
| Phage-15 | — | — | L | — | — | Y | — | T | — | — | — | — | — | A | 0.074 | 2.584 | 0.086 | 112 |
| Phage-16 | — | — | N | — | — | Y | — | L | — | — | — | — | — | T | 0.082 | 2.545 | 0.084 | 113 |
| Phage-17 | — | — | N | — | — | F | — | I | — | — | — | — | — | L | 0.067 | 2.606 | 0.090 | 114 |
| Phage-18 | — | — | A | Y | — | N | — | P | — | — | — | — | — | S | 0.075 | 2.577 | 0.089 | 115 |
| Phage-19 | — | — | L | F | — | F | — | P | — | — | — | — | — | S | 0.077 | 2.590 | 0.126 | 116 |
| Phage-20 | — | — | T | — | — | F | — | P | — | — | — | — | — | A | 0.071 | 2.625 | 0.376 | 117 |

TABLE 22-continued Phage panning results of αEGFR Fab peptide-8 library sequences. (—) indicates the same amino acid as in aEGFR Fab peptide-8 corresponding position.

| Phage number | 1 | 2 | 3 | 4 | 5 | 6 | 7 | 8 | 9 | 10 | 11 | 12 | 13 | 14 | Backgroud signal | EGFR Fab signal | EGFR Fab signal in presence of EGFR | SEQ ID NO: |
|---|---|---|---|---|---|---|---|---|---|---|---|---|---|---|---|---|---|---|
| Phage-21 | — | — | T | — | — | N | — | N | — | — | — | — | — | A | 0.087 | 2.679 | 0.175 | 118 |
| Phage-22 | — | — | L | — | — | F | — | T | — | — | — | — | — | I | 0.074 | 2.588 | 0.070 | 119 |
| Phage-23 | — | — | T | — | — | T | — | L | — | — | — | — | — | — | 0.075 | 2.488 | 0.072 | 120 |
| Phage-24 | — | — | L | — | Q | F | — | T | — | — | — | — | — | S | 0.128 | 2.485 | 0.113 | 121 |
| Phage-25 | — | — | L | — | L | F | — | T | — | — | — | — | — | I | 0.096 | 2.475 | 0.085 | 122 |
| Phage-26 | — | — | L | — | — | F | — | N | — | — | — | — | — | — | 0.123 | 2.463 | 0.119 | 123 |
| Phage-27 | — | — | I | — | — | F | — | T | — | — | — | — | — | A | 0.097 | 2.461 | 0.085 | 124 |
| Phage-28 | — | — | I | — | — | Y | — | P | — | — | — | — | — | S | 0.078 | 2.501 | 0.078 | 125 |
| Phage-29 | — | — | L | — | — | H | — | P | — | — | — | — | — | A | 0.076 | 2.597 | 0.072 | 126 |
| Phage-30 | — | — | L | — | — | F | — | D | — | — | — | — | — | A | 0.078 | 2.596 | 0.073 | 127 |
| Phage-31 | — | — | A | — | — | F | — | T | — | — | — | — | — | I | 0.083 | 2.595 | 0.079 | 128 |
| Phage-32 | — | — | L | — | — | H | — | T | — | — | — | — | — | — | 0.071 | 2.595 | 0.071 | 129 |
| Phage-33 | — | — | T | — | R | F | — | T | — | — | — | — | — | A | 0.083 | 2.593 | 0.081 | 130 |
| Phage-34 | — | — | L | — | — | Y | — | L | — | — | — | — | — | I | 0.089 | 2.576 | 0.078 | 131 |
| Phage-35 | — | — | T | — | — | H | — | L | — | — | — | — | — | — | 0.083 | 2.575 | 0.079 | 132 |
| Phage-36 | — | — | L | — | — | F | — | I | — | — | — | — | — | A | 0.068 | 2.567 | 0.066 | 133 |
| Phage-37 | — | — | V | — | — | Y | — | T | — | — | — | — | — | A | 0.070 | 2.533 | 0.068 | 134 |
| Phage-38 | — | — | L | — | — | H | — | A | — | — | — | — | — | L | 0.069 | 2.513 | 0.068 | 135 |
| Phage-39 | — | — | — | — | L | N | — | T | — | — | — | — | — | — | 0.071 | 2.505 | 0.071 | 136 |
| Phage-40 | — | — | L | — | Q | F | — | T | — | — | — | — | — | A | 0.076 | 2.503 | 0.072 | 137 |
| Phage-41 | — | — | L | — | L | F | — | T | — | Q | — | — | — | — | 0.092 | 2.503 | 0.089 | 138 |
| Phage-42 | — | — | T | — | — | H | — | T | — | — | — | — | — | — | 0.079 | 2.500 | 0.079 | 139 |
| Phage-43 | — | — | N | — | — | Y | — | L | — | — | — | — | — | I | 0.071 | 2.496 | 0.067 | 140 |
| Phage-44 | — | — | L | — | L | Y | — | N | — | — | — | — | — | L | 0.071 | 2.494 | 0.070 | 141 |
| Phage-45 | — | — | L | — | — | D | — | T | — | — | — | — | — | T | 0.106 | 2.494 | 0.083 | 142 |
| Phage-46 | — | — | A | — | — | F | — | — | — | — | — | — | — | A | 0.075 | 2.493 | 0.068 | 143 |
| Phage-47 | — | — | P | F | — | F | — | P | — | — | — | — | — | — | 0.086 | 2.492 | 0.080 | 144 |
| Phage-48 | — | — | A | — | — | N | — | L | — | — | — | — | — | A | 0.073 | 2.487 | 0.071 | 145 |
| Phage-49 | — | — | I | — | Q | F | — | T | — | — | — | — | — | A | 0.109 | 2.481 | 0.080 | 146 |
| Phage-50 | — | — | I | — | L | Y | — | T | — | — | — | — | — | — | 0.077 | 2.476 | 0.076 | 147 |
| Phage-51 | — | — | L | — | L | T | — | P | — | — | — | — | — | A | 0.085 | 2.474 | 0.073 | 148 |
| Phage-52 | — | — | T | — | — | H | — | T | — | — | — | — | — | A | 0.104 | 2.473 | 0.088 | 149 |
| Phage-53 | — | — | L | Y | — | H | — | P | — | — | — | — | — | A | 0.099 | 2.472 | 0.092 | 150 |
| Phage-54 | — | — | H | — | — | Y | — | T | — | — | — | — | — | A | 0.074 | 2.470 | 0.072 | 151 |
| Phage-55 | — | — | L | — | — | S | — | P | — | — | — | — | — | S | 0.112 | 2.470 | 0.108 | 152 |
| Phage-56 | — | — | L | — | — | T | — | I | — | — | — | — | — | L | 0.120 | 2.468 | 0.117 | 153 |
| Phage-57 | — | — | L | F | — | F | — | P | — | — | — | — | — | A | 0.112 | 2.464 | 0.097 | 154 |
| Phage-58 | — | — | L | — | — | F | — | P | — | — | — | — | — | A | 0.110 | 2.463 | 0.105 | 155 |
| Phage-59 | — | — | L | — | P | H | — | T | — | — | — | — | — | L | 0.076 | 2.462 | 0.073 | 156 |
| Phage-60 | — | — | T | — | — | F | — | L | — | — | — | — | — | — | 0.106 | 2.461 | 0.084 | 157 |
| Phage-61 | — | — | V | — | L | Y | — | T | — | — | — | — | — | L | 0.103 | 2.461 | 0.095 | 158 |
| Phage-62 | — | — | T | — | — | L | — | T | — | — | — | — | — | A | 0.123 | 2.459 | 0.114 | 159 |
| Phage-63 | — | — | L | — | L | F | — | D | — | — | — | — | — | A | 0.081 | 2.456 | 0.079 | 160 |
| Phage-64 | — | — | N | — | — | H | — | L | — | — | — | — | — | — | 0.074 | 2.448 | 0.074 | 161 |
| Phage-65 | — | — | I | — | — | Y | — | T | — | — | — | — | — | I | 0.142 | 2.446 | 0.132 | 162 |
| Phage-66 | — | — | A | — | — | F | — | — | — | — | — | — | — | L | 0.103 | 2.445 | 0.097 | 163 |
| Phage-67 | — | — | T | — | — | F | — | S | — | — | — | — | — | I | 0.069 | 2.442 | 0.066 | 164 |
| Phage-68 | — | — | T | — | — | F | — | S | — | — | — | — | — | S | 0.132 | 2.433 | 0.124 | 165 |
| Phage-69 | — | — | T | — | L | V | — | T | — | — | — | — | — | A | 0.132 | 2.424 | 0.120 | 166 |
| Phage-70 | — | — | L | — | L | N | — | P | — | — | — | — | — | A | 0.153 | 2.423 | 0.136 | 167 |
| Phage-71 | — | — | I | — | — | N | — | T | — | — | — | — | — | A | 0.114 | 2.419 | 0.113 | 168 |
| Phage-72 | — | — | V | — | — | F | — | T | — | — | — | — | — | A | 0.122 | 2.415 | 0.102 | 169 |
| Phage-73 | — | — | N | — | P | F | — | T | — | — | — | — | — | — | 0.109 | 2.369 | 0.087 | 170 |
| Phage-74 | — | — | V | — | — | N | — | — | — | — | — | — | — | A | 0.108 | 2.358 | 0.093 | 171 |
| Phage-75 | — | — | L | — | — | V | — | P | — | — | — | — | — | — | 0.092 | 2.349 | 0.089 | 172 |
| Phage-76 | — | — | L | — | — | S | — | D | — | — | — | — | — | A | 0.074 | 2.331 | 0.071 | 173 |
| Phage-77 | — | — | T | — | — | H | — | — | — | — | — | — | — | — | 0.109 | 2.316 | 0.085 | 174 |
| Phage-78 | — | — | L | — | F | Y | — | L | — | — | — | — | — | S | 0.127 | 2.263 | 0.127 | 175 |
| Phage-79 | — | — | S | — | — | Y | — | T | — | — | — | — | — | F | 0.074 | 2.199 | 0.073 | 176 |
| Phage-80 | — | — | A | — | — | V | — | T | — | — | — | — | — | — | 0.069 | 2.170 | 0.068 | 177 |
| Phage-81 | — | — | L | — | L | D | — | P | — | — | — | — | — | A | 0.073 | 2.166 | 0.072 | 178 |
| Phage-82 | — | — | L | — | — | — | — | D | — | — | — | — | — | — | 0.154 | 2.150 | 0.139 | 179 |
| Phage-83 | — | — | T | — | — | A | — | T | — | N | — | — | — | A | 0.074 | 2.132 | 0.071 | 180 |
| Phage-84 | — | — | L | — | L | T | — | H | — | — | — | — | — | I | 0.088 | 2.125 | 0.075 | 181 |
| Phage-85 | — | — | F | — | — | H | — | P | — | — | — | — | — | — | 0.100 | 2.121 | 0.088 | 182 |
| Phage-86 | — | — | S | — | — | F | — | N | — | — | — | — | — | A | 0.081 | 2.086 | 0.078 | 183 |
| Phage-87 | — | — | A | — | L | T | — | T | — | — | — | — | — | A | 0.128 | 1.993 | 0.123 | 184 |
| Phage-88 | — | — | S | — | — | H | — | S | — | — | — | — | — | T | 0.069 | 1.993 | 0.067 | 185 |
| Phage-89 | — | — | T | — | P | Y | — | — | — | — | — | — | — | I | 0.077 | 1.983 | 0.075 | 186 |

TABLE 22-continued

Phage panning results of αEGFR Fab peptide-8 library sequences. (—) indicates the same amino acid as in aEGFR Fab peptide-8 corresponding position.

| Phage number | 1 | 2 | 3 | 4 | 5 | 6 | 7 | 8 | 9 | 10 | 11 | 12 | 13 | 14 | Backgroud signal | EGFR Fab signal | EGFR Fab signal in presence of EGFR | SEQ ID NO: |
|---|---|---|---|---|---|---|---|---|---|---|---|---|---|---|---|---|---|---|
| Phage-90 | — | — | L | — | P | L | — | S | — | — | — | — | — | A | 0.114 | 1.980 | 0.096 | 187 |
| Phage-91 | — | — | L | — | — | T | — | T | — | — | — | — | — | I | 0.072 | 1.972 | 0.071 | 188 |
| Phage-92 | — | — | L | — | L | F | — | T | — | — | — | — | — | H | 0.083 | 1.969 | 0.079 | 189 |
| Phage-93 | — | — | A | — | — | Y | — | D | — | — | — | — | — | S | 0.091 | 1.804 | 0.073 | 190 |
| Phage-94 | — | — | S | — | — | Y | — | — | — | — | — | — | — | A | 0.091 | 1.785 | 0.083 | 191 |
| Phage-95 | — | — | A | — | — | F | — | N | — | — | — | — | — | A | 0.092 | 1.688 | 0.076 | 192 |
| Phage-96 | — | — | T | — | Q | Y | — | T | — | — | — | — | — | T | 0.074 | 1.676 | 0.074 | 193 |
| Phage-97 | — | — | A | — | — | H | — | L | — | — | — | — | — | I | 0.080 | 1.670 | 0.080 | 194 |
| Phage-98 | — | — | I | — | Q | Y | — | T | — | — | — | — | — | T | 0.075 | 1.469 | 0.073 | 195 |
| Phage-99 | — | — | A | — | L | Y | — | — | — | — | — | — | — | A | 0.093 | 1.462 | 0.082 | 196 |
| Phage-100 | — | — | L | — | — | S | — | A | — | — | — | — | — | — | 0.123 | 1.428 | 0.087 | 197 |
| Phage-101 | — | — | A | — | — | H | — | T | — | — | — | — | — | L | 0.078 | 1.428 | 0.076 | 198 |
| Phage-102 | — | — | L | — | — | N | — | S | — | — | — | — | — | H | 0.081 | 1.394 | 0.078 | 199 |
| Phage-103 | — | — | — | — | — | L | — | P | — | — | — | — | — | S | 0.078 | 1.164 | 0.074 | 200 |
| Phage-104 | — | — | L | — | Q | T | — | D | — | — | — | — | — | — | 0.080 | 1.138 | 0.075 | 201 |
| Phage-105 | — | — | S | — | P | Y | — | S | — | — | — | — | — | A | 0.106 | 1.008 | 0.090 | 202 |
| Phage-106 | — | — | V | — | — | F | Y | T | — | Y | — | — | — | — | 0.098 | 0.968 | 0.083 | 203 |
| Phage-107 | — | — | T | — | L | H | — | N | — | — | — | — | — | T | 0.077 | 0.635 | 0.075 | 204 |
| Phage-108 | — | — | V | — | — | A | — | P | — | — | — | — | — | A | 0.072 | 0.459 | 0.072 | 205 |
| Phage-109 | — | — | A | — | L | S | — | D | — | — | — | — | — | I | 0.075 | 0.329 | 0.067 | 206 |
| Phage-110 | W | — | H | P | Q | S | — | P | — | Y | — | — | — | D | 0.094 | 0.265 | 0.070 | 207 |
| Phage-111 | — | — | A | — | Q | H | — | L | — | — | — | — | — | I | 0.085 | 0.213 | 0.081 | 208 |
| Phage-112 | L | — | H | P | Q | N | — | A | — | Y | — | N | — | F | 0.081 | 0.071 | 0.090 | 209 |
| Phage-113 | F | — | H | P | Q | A | — | L | — | Y | — | M | — | — | 0.076 | 0.069 | 0.081 | 210 |
| Phage-114 | W | — | H | P | Q | N | — | F | — | Y | — | M | — | D | 0.078 | 0.067 | 0.086 | 211 |
| Phage-115 | — | — | L | — | — | T | — | L | — | — | — | — | — | L | 0.074 | 2.491 | 0.074 | 212 |
| Phage-116 | — | — | A | — | — | Y | — | T | — | — | — | — | — | I | 0.074 | 2.485 | 0.074 | 213 |
| Phage-117 | — | — | V | — | — | Y | — | T | — | — | — | — | — | T | 0.091 | 2.455 | 0.091 | 214 |
| Phage-118 | — | — | V | — | — | T | — | T | — | — | — | — | — | S | 0.070 | 2.362 | 0.070 | 215 |
| Phage-119 | — | — | T | G | P | Y | — | T | — | — | — | — | — | A | 0.090 | 2.129 | 0.090 | 216 |
| Phage-120 | — | — | N | — | M | Y | — | T | — | — | — | — | — | A | 0.068 | 2.496 | 0.068 | 217 |
| Phage-121 | — | — | L | — | L | H | — | D | — | — | — | — | — | L | 0.072 | 2.430 | 0.073 | 218 |
| Phage-122 | — | — | T | — | — | — | — | T | — | — | — | — | — | I | 0.070 | 2.169 | 0.070 | 219 |
| Phage-123 | — | — | N | — | — | Y | — | L | — | — | — | — | — | — | 0.069 | 2.479 | 0.069 | 220 |
| Phage-124 | — | — | T | — | — | Y | — | L | — | — | — | — | — | T | 0.097 | 2.440 | 0.098 | 221 |
| Phage-125 | — | — | I | G | P | Y | — | T | — | — | — | — | — | A | 0.072 | 2.576 | 0.073 | 222 |
| Phage-126 | — | — | T | — | — | F | — | P | — | — | — | — | — | S | 0.072 | 2.562 | 0.073 | 223 |
| Phage-127 | — | — | L | — | — | H | — | N | — | — | — | — | — | A | 0.070 | 2.528 | 0.071 | 224 |
| Phage-128 | — | — | P | — | — | F | — | T | — | — | — | — | — | S | 0.081 | 2.509 | 0.082 | 225 |
| Phage-129 | — | — | S | — | L | F | — | T | — | — | — | — | — | I | 0.067 | 2.479 | 0.068 | 226 |
| Phage-130 | — | — | V | — | — | Y | — | T | — | — | — | — | — | — | 0.110 | 2.445 | 0.111 | 227 |
| Phage-131 | — | — | T | — | — | H | — | T | — | — | — | — | — | L | 0.088 | 2.485 | 0.090 | 228 |
| Phage-132 | — | — | T | — | P | Y | — | T | — | — | — | — | — | T | 0.071 | 2.472 | 0.073 | 229 |
| Phage-133 | — | — | T | — | — | F | — | — | — | — | — | — | — | A | 0.107 | 2.395 | 0.108 | 230 |
| Phage-134 | — | — | T | — | — | N | — | T | — | — | — | — | — | A | 0.080 | 2.037 | 0.082 | 231 |
| Phage-135 | — | — | T | — | — | F | — | I | — | — | — | — | — | A | 0.079 | 2.649 | 0.081 | 232 |
| Phage-136 | — | — | L | — | — | A | — | T | — | — | — | — | — | I | 0.072 | 2.589 | 0.074 | 233 |
| Phage-137 | — | — | T | — | — | V | — | T | — | — | — | — | — | A | 0.070 | 2.517 | 0.072 | 234 |
| Phage-138 | — | — | L | — | — | N | — | T | — | — | — | — | — | — | 0.071 | 2.482 | 0.072 | 235 |
| Phage-139 | — | — | L | — | — | T | — | T | — | — | — | — | — | T | 0.082 | 2.161 | 0.083 | 236 |
| Phage-140 | — | — | L | Y | P | S | — | P | — | — | — | — | — | A | 0.073 | 2.483 | 0.075 | 237 |
| Phage-141 | — | — | P | — | — | H | — | S | — | — | — | — | — | — | 0.072 | 1.781 | 0.073 | 238 |
| Phage-142 | — | — | N | — | — | T | — | N | — | — | — | — | — | T | 0.077 | 2.601 | 0.079 | 239 |
| Phage-143 | — | — | N | — | — | F | — | S | — | — | — | — | — | A | 0.077 | 2.006 | 0.079 | 240 |
| Phage-144 | — | — | A | — | L | H | — | T | — | — | — | — | — | S | 0.076 | 2.481 | 0.078 | 241 |
| Phage-145 | — | — | S | — | L | Y | — | A | — | — | — | — | — | — | 0.068 | 2.581 | 0.070 | 242 |
| Phage-146 | — | — | T | — | — | T | — | T | — | — | — | — | — | I | 0.074 | 2.395 | 0.076 | 243 |
| Phage-147 | — | — | T | — | — | Y | — | H | — | — | — | — | — | A | 0.118 | 2.404 | 0.120 | 244 |
| Phage-148 | — | — | N | — | L | H | — | T | — | — | — | — | — | — | 0.070 | 2.506 | 0.072 | 245 |
| Phage-149 | — | — | L | — | L | T | — | T | — | — | — | — | — | T | 0.067 | 2.600 | 0.070 | 246 |
| Phage-150 | — | — | A | — | — | F | — | P | — | — | — | — | — | F | 0.107 | 2.340 | 0.110 | 247 |
| Phage-151 | — | — | T | — | — | F | — | I | — | — | — | — | — | L | 0.073 | 2.628 | 0.076 | 248 |
| Phage-152 | — | — | L | — | — | V | — | T | — | — | — | — | — | A | 0.127 | 2.419 | 0.130 | 249 |
| Phage-153 | — | — | T | — | — | H | — | P | — | — | — | — | — | I | 0.076 | 2.473 | 0.079 | 250 |
| Phage-154 | — | — | L | F | — | H | — | T | — | — | — | — | — | L | 0.093 | 2.485 | 0.096 | 251 |
| Phage-155 | — | — | T | — | — | Y | — | T | — | — | — | — | — | A | 0.068 | 2.546 | 0.072 | 252 |
| Phage-156 | — | — | L | — | L | F | — | — | — | — | — | — | — | L | 0.073 | 2.449 | 0.076 | 253 |
| Phage-157 | — | — | I | — | L | V | — | T | — | — | — | — | — | — | 0.070 | 2.234 | 0.073 | 254 |
| Phage-158 | — | — | L | — | — | Y | — | N | — | — | — | — | — | I | 0.069 | 2.491 | 0.072 | 255 |

TABLE 22-continued

Phage panning results of αEGFR Fab peptide-8 library sequences. (—) indicates the same amino acid as in aEGFR Fab peptide-8 corresponding position.

| Phage number | 1 | 2 | 3 | 4 | 5 | 6 | 7 | 8 | 9 | 10 | 11 | 12 | 13 | 14 | Backgroud signal | EGFR Fab signal | EGFR Fab signal in presence of EGFR | SEQ ID NO: |
|---|---|---|---|---|---|---|---|---|---|---|---|---|---|---|---|---|---|---|
| Phage-159 | — | — | N | — | — | F | — | T | — | — | — | — | — | T | 0.073 | 1.550 | 0.075 | 256 |
| Phage-160 | — | — | L | — | L | T | — | — | — | — | — | — | — | S | 0.072 | 2.152 | 0.075 | 257 |
| Phage-161 | — | — | L | — | — | D | — | D | — | — | — | — | — | A | 0.084 | 2.459 | 0.088 | 258 |
| Phage-162 | — | — | T | — | — | — | — | T | — | — | — | — | — | A | 0.073 | 2.498 | 0.077 | 259 |
| Phage-163 | — | — | L | — | — | H | — | N | — | — | — | — | — | S | 0.075 | 2.483 | 0.079 | 260 |
| Phage-164 | — | — | S | — | — | N | — | P | — | — | — | — | — | S | 0.072 | 2.575 | 0.076 | 261 |
| Phage-165 | — | — | T | G | P | F | — | T | — | — | — | — | — | A | 0.073 | 2.512 | 0.078 | 262 |
| Phage-166 | — | — | N | — | L | F | — | D | — | — | — | — | — | — | 0.068 | 2.396 | 0.072 | 263 |
| Phage-167 | — | — | V | — | — | H | — | P | — | — | — | — | — | A | 0.072 | 2.021 | 0.076 | 264 |
| Phage-168 | — | — | T | — | — | F | — | — | — | — | — | — | — | T | 0.070 | 2.581 | 0.074 | 265 |
| Phage-169 | — | — | T | — | P | Y | — | T | — | — | — | — | — | — | 0.130 | 2.419 | 0.134 | 266 |
| Phage-170 | — | — | T | — | P | Y | — | T | — | — | — | — | — | S | 0.074 | 2.478 | 0.078 | 267 |
| Phage-171 | — | — | T | — | — | T | — | T | — | — | — | — | — | — | 0.073 | 2.525 | 0.078 | 268 |
| Phage-172 | — | — | T | — | — | H | — | L | — | — | — | — | — | A | 0.071 | 2.440 | 0.076 | 269 |
| Phage-173 | — | — | T | — | L | D | — | T | — | — | — | — | — | T | 0.073 | 2.238 | 0.078 | 270 |
| Phage-174 | — | — | A | — | L | F | — | T | — | — | — | — | — | A | 0.070 | 2.403 | 0.075 | 271 |
| Phage-175 | — | — | N | — | — | Y | — | T | — | — | — | — | — | S | 0.072 | 2.496 | 0.078 | 272 |
| Phage-176 | — | — | T | G | P | H | — | — | — | — | — | — | — | A | 0.074 | 2.465 | 0.080 | 273 |
| Phage-177 | — | — | P | F | — | N | — | P | — | — | — | — | — | A | 0.073 | 2.593 | 0.078 | 274 |
| Phage-178 | — | — | L | — | — | Y | — | T | — | — | — | — | — | — | 0.073 | 2.504 | 0.078 | 275 |
| Phage-179 | — | — | A | Y | — | N | — | P | — | — | — | — | — | A | 0.073 | 2.508 | 0.079 | 276 |
| Phage-180 | — | — | L | — | — | H | — | T | — | — | — | — | — | I | 0.102 | 2.526 | 0.108 | 277 |
| Phage-181 | — | — | S | — | — | T | — | P | — | — | — | — | — | A | 0.071 | 1.659 | 0.075 | 278 |
| Phage-182 | — | — | L | — | — | T | — | T | — | Q | — | — | — | — | 0.109 | 2.458 | 0.115 | 279 |
| Phage-183 | — | — | A | — | N | Y | — | L | — | — | — | — | — | T | 0.077 | 2.344 | 0.082 | 280 |
| Phage-184 | — | — | T | — | — | T | — | D | — | — | — | — | — | — | 0.073 | 1.572 | 0.076 | 281 |
| Phage-185 | — | — | A | F | G | N | — | P | — | — | — | — | — | S | 0.065 | 2.489 | 0.072 | 282 |
| Phage-186 | — | — | L | — | — | A | — | T | — | — | — | — | — | T | 0.070 | 2.504 | 0.077 | 283 |
| Phage-187 | — | — | L | — | — | N | — | T | — | — | — | — | — | I | 0.071 | 2.449 | 0.078 | 284 |
| Phage-188 | — | — | L | — | N | T | — | — | — | — | — | — | — | I | 0.090 | 0.618 | 0.092 | 285 |
| Phage-189 | — | — | T | — | — | F | — | T | — | — | — | — | — | L | 0.074 | 2.574 | 0.080 | 286 |
| Phage-190 | — | — | L | — | — | A | — | P | — | — | — | — | — | A | 0.108 | 2.494 | 0.115 | 287 |
| Phage-191 | — | — | L | — | — | H | — | S | — | — | — | — | — | S | 0.077 | 2.473 | 0.084 | 288 |
| Phage-192 | — | — | L | F | P | H | — | P | — | — | — | — | — | A | 0.074 | 2.477 | 0.081 | 289 |
| Phage-193 | — | — | T | — | — | S | — | — | — | — | — | — | — | A | 0.077 | 1.708 | 0.081 | 290 |
| Phage-194 | — | — | L | — | L | H | — | T | — | — | — | — | — | T | 0.085 | 2.485 | 0.092 | 291 |
| Phage-195 | — | — | A | — | — | T | — | T | — | — | — | — | — | — | 0.082 | 2.466 | 0.090 | 292 |
| Phage-196 | — | — | V | — | — | F | — | L | — | — | — | — | — | L | 0.067 | 2.482 | 0.074 | 293 |
| Phage-197 | — | — | T | — | — | H | — | — | — | — | — | — | — | T | 0.070 | 2.576 | 0.077 | 294 |
| Phage-198 | — | — | I | — | — | Y | — | T | — | — | — | — | — | L | 0.071 | 2.481 | 0.079 | 295 |
| Phage-199 | — | — | I | — | — | F | — | T | — | — | — | — | — | — | 0.070 | 2.442 | 0.078 | 296 |
| Phage-200 | — | — | L | — | — | A | — | T | — | — | — | — | — | A | 0.069 | 2.456 | 0.077 | 297 |
| Phage-201 | — | — | T | — | — | H | — | — | — | — | — | — | — | T | 0.076 | 2.616 | 0.084 | 298 |
| Phage-202 | — | — | T | — | — | F | — | L | — | — | — | — | — | A | 0.069 | 2.505 | 0.076 | 299 |
| Phage-203 | — | — | T | — | — | A | — | T | — | — | — | — | — | T | 0.071 | 2.537 | 0.079 | 300 |
| Phage-204 | — | — | A | — | P | Y | — | D | — | — | — | — | — | T | 0.068 | 1.894 | 0.074 | 301 |
| Phage-205 | — | — | L | — | P | V | — | T | — | — | — | — | — | A | 0.071 | 2.410 | 0.079 | 302 |
| Phage-206 | — | — | A | — | L | N | — | T | — | — | — | — | — | — | 0.070 | 2.553 | 0.079 | 303 |
| Phage-207 | — | — | L | — | — | N | — | N | — | — | — | — | — | A | 0.072 | 2.564 | 0.081 | 304 |
| Phage-208 | — | — | L | — | M | T | — | T | — | — | — | — | — | T | 0.070 | 2.480 | 0.078 | 305 |
| Phage-209 | — | — | L | — | L | F | — | I | — | — | — | — | — | I | 0.072 | 2.505 | 0.081 | 306 |
| Phage-210 | — | — | T | — | — | F | — | L | — | — | — | — | — | — | 0.072 | 2.498 | 0.080 | 307 |
| Phage-211 | — | — | — | — | Y | F | H | S | P | — | — | — | — | A | 0.083 | 2.504 | 0.092 | 308 |
| Phage-212 | — | — | T | — | P | F | — | T | — | — | — | — | — | I | 0.074 | 2.354 | 0.082 | 309 |
| Phage-213 | — | — | S | — | L | F | — | L | — | — | — | — | — | S | 0.080 | 2.502 | 0.089 | 310 |
| Phage-214 | — | — | V | — | — | S | — | T | — | — | — | — | — | A | 0.068 | 1.836 | 0.075 | 311 |
| Phage-215 | — | — | N | — | — | F | — | T | — | — | — | — | — | A | 0.068 | 2.519 | 0.077 | 312 |
| Phage-216 | — | — | A | — | — | F | — | N | — | — | — | — | — | S | 0.082 | 2.570 | 0.092 | 313 |
| Phage-217 | — | — | — | — | R | Y | — | T | — | — | — | — | — | — | 0.067 | 2.077 | 0.075 | 314 |
| Phage-218 | — | — | S | — | — | T | — | L | — | — | — | — | — | — | 0.076 | 0.724 | 0.078 | 315 |
| Phage-219 | — | — | T | — | — | L | — | T | — | — | — | — | — | F | 0.067 | 2.602 | 0.077 | 316 |
| Phage-220 | — | — | L | — | — | S | — | N | — | — | — | — | — | F | 0.070 | 2.376 | 0.080 | 317 |
| Phage-221 | — | — | A | — | — | H | — | T | — | — | — | — | — | A | 0.070 | 2.594 | 0.081 | 318 |
| Phage-222 | — | — | V | — | — | F | — | P | — | — | — | — | — | F | 0.074 | 2.491 | 0.084 | 319 |
| Phage-223 | — | — | L | — | — | Y | — | H | — | — | — | — | — | S | 0.074 | 2.463 | 0.084 | 320 |
| Phage-224 | — | — | T | — | — | N | — | L | — | — | — | — | — | — | 0.071 | 2.477 | 0.081 | 321 |
| Phage-225 | — | — | T | — | — | F | — | A | — | — | — | — | — | S | 0.073 | 2.380 | 0.083 | 322 |
| Phage-226 | — | — | L | — | — | V | — | — | — | — | — | — | — | T | 0.075 | 2.445 | 0.085 | 323 |
| Phage-227 | — | — | L | — | Q | Y | — | D | — | — | — | — | — | A | 0.079 | 2.412 | 0.090 | 324 |

TABLE 22-continued

Phage panning results of αEGFR Fab peptide-8 library sequences. (—) indicates the same amino acid as in aEGFR Fab peptide-8 corresponding position.

| Phage number | \multicolumn{14}{c}{Amino acid position sequence} | | | | | | | | | | | | | | Backgroud signal | EGFR Fab signal | EGFR Fab signal in presence of EGFR | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-228 | — | — | H | — | — | T | — | T | — | — | — | — | — | L | 0.072 | 2.269 | 0.082 | 325 |
| Phage-229 | — | — | T | — | Q | Y | — | T | — | — | — | — | — | — | 0.070 | 2.450 | 0.081 | 326 |
| Phage-230 | — | — | N | — | — | T | — | T | — | — | — | — | — | — | 0.085 | 2.472 | 0.096 | 327 |
| Phage-231 | — | — | L | — | — | L | — | T | — | — | — | — | — | T | 0.073 | 2.495 | 0.084 | 328 |
| Phage-232 | — | — | S | — | L | Y | — | T | — | — | — | — | — | Y | 0.065 | 1.908 | 0.074 | 329 |
| Phage-233 | — | — | A | — | L | F | — | N | — | — | — | — | — | I | 0.070 | 2.119 | 0.080 | 330 |
| Phage-234 | — | — | T | — | — | LL | — | L | — | — | — | — | — | T | 0.081 | 2.483 | 0.092 | 331 |
| Phage-235 | — | — | L | — | Q | H | — | D | — | — | — | — | — | — | 0.069 | 0.848 | 0.072 | 332 |
| Phage-236 | — | — | V | — | P | F | — | T | — | — | — | — | — | L | 0.074 | 2.641 | 0.087 | 333 |
| Phage-237 | — | — | L | — | — | T | — | S | — | — | — | — | — | — | 0.124 | 2.441 | 0.136 | 334 |
| Phage-238 | R | — | S | — | — | H | — | T | — | — | I | — | — | G | 0.071 | 2.472 | 0.083 | 335 |
| Phage-239 | — | — | L | — | — | H | — | Y | — | — | — | — | — | L | 0.074 | 2.572 | 0.087 | 336 |
| Phage-240 | — | — | N | — | — | Y | — | T | — | — | — | — | — | A | 0.093 | 2.501 | 0.106 | 337 |
| Phage-241 | — | — | L | F | — | Y | — | P | — | — | — | — | — | S | 0.075 | 2.502 | 0.088 | 338 |
| Phage-242 | — | — | L | F | — | N | — | P | — | — | — | — | — | Y | 0.074 | 2.535 | 0.087 | 339 |
| Phage-243 | — | — | T | — | — | F | — | A | — | — | — | — | — | A | 0.074 | 2.289 | 0.086 | 340 |
| Phage-244 | — | — | A | — | — | H | — | N | — | — | — | — | — | L | 0.071 | 2.348 | 0.083 | 341 |
| Phage-245 | — | — | N | — | — | F | — | T | — | — | — | — | — | L | 0.068 | 2.588 | 0.081 | 342 |
| Phage-246 | — | — | L | — | — | F | — | Y | — | — | — | — | — | T | 0.066 | 2.449 | 0.079 | 343 |
| Phage-247 | — | V | C | L | S | F | R | Y | R | Q | A | D | L | C | 0.130 | 2.417 | 0.142 | 344 |
| Phage-248 | — | — | I | — | P | F | — | T | — | — | — | — | — | A | 0.069 | 2.617 | 0.082 | 345 |
| Phage-249 | — | — | L | — | P | F | — | N | — | — | — | — | — | T | 0.100 | 2.362 | 0.113 | 346 |
| Phage-250 | — | — | T | — | — | F | — | N | — | — | — | — | — | L | 0.072 | 2.507 | 0.085 | 347 |
| Phage-251 | — | — | L | — | — | S | — | T | — | — | — | — | — | I | 0.068 | 1.565 | 0.077 | 348 |
| Phage-252 | — | — | L | — | — | S | — | T | — | — | — | — | — | L | 0.067 | 2.496 | 0.080 | 349 |
| Phage-253 | — | — | T | — | P | F | — | L | — | — | — | — | — | T | 0.084 | 0.883 | 0.088 | 350 |
| Phage-254 | — | — | T | — | P | Y | — | — | — | — | — | — | — | A | 0.073 | 1.856 | 0.083 | 351 |
| Phage-255 | — | — | A | — | — | Y | — | T | — | — | — | — | — | S | 0.071 | 2.369 | 0.084 | 352 |
| Phage-256 | — | — | P | — | — | T | — | T | — | — | — | — | — | — | 0.069 | 2.503 | 0.084 | 353 |
| Phage-257 | — | — | L | — | — | S | — | S | — | — | — | — | — | — | 0.080 | 2.231 | 0.093 | 354 |
| Phage-258 | — | — | T | — | L | F | — | T | — | — | — | — | — | T | 0.069 | 2.597 | 0.084 | 355 |
| Phage-259 | — | — | L | — | — | V | — | N | — | — | — | — | — | — | 0.070 | 1.452 | 0.079 | 356 |
| Phage-260 | — | — | L | — | Q | Y | — | N | — | — | — | — | — | A | 0.070 | 1.384 | 0.078 | 357 |
| Phage-261 | — | — | L | G | P | F | — | T | — | — | — | — | — | S | 0.076 | 2.322 | 0.090 | 358 |
| Phage-262 | — | — | I | — | — | T | — | P | — | — | — | — | — | I | 0.076 | 2.462 | 0.091 | 359 |
| Phage-263 | — | — | T | — | — | Y | — | S | — | — | — | — | — | A | 0.067 | 2.375 | 0.082 | 360 |
| Phage-264 | — | — | L | — | F | T | — | — | — | — | — | — | — | S | 0.093 | 2.466 | 0.108 | 361 |
| Phage-265 | — | — | L | — | — | S | — | N | — | — | — | — | — | T | 0.082 | 1.920 | 0.094 | 362 |
| Phage-266 | — | — | T | — | — | F | — | N | — | — | — | — | — | A | 0.081 | 2.458 | 0.096 | 363 |
| Phage-267 | — | — | T | — | — | N | — | T | — | — | — | — | — | S | 0.070 | 2.476 | 0.086 | 364 |
| Phage-268 | — | — | V | — | L | Y | — | T | — | — | — | — | — | T | 0.080 | 2.494 | 0.096 | 365 |
| Phage-269 | — | — | L | — | L | T | — | S | — | — | — | — | — | A | 0.072 | 2.320 | 0.087 | 366 |
| Phage-270 | — | — | T | — | — | Y | — | — | — | — | — | — | — | L | 0.076 | 2.572 | 0.093 | 367 |
| Phage-271 | — | — | L | — | — | F | — | P | — | — | — | — | — | I | 0.115 | 2.428 | 0.131 | 368 |
| Phage-272 | — | — | T | — | — | S | — | N | — | — | — | — | — | A | 0.073 | 2.492 | 0.090 | 369 |
| Phage-273 | — | — | A | Y | — | N | — | P | — | — | T | — | — | S | 0.072 | 2.468 | 0.089 | 370 |
| Phage-274 | — | — | L | — | P | H | — | T | — | — | — | — | — | A | 0.070 | 2.473 | 0.087 | 371 |
| Phage-275 | — | — | I | — | L | T | — | N | — | — | — | — | — | S | 0.075 | 1.899 | 0.089 | 372 |
| Phage-276 | — | — | A | — | Q | F | — | N | — | — | — | — | — | A | 0.090 | 1.979 | 0.104 | 373 |
| Phage-277 | — | — | T | — | L | T | — | T | — | — | — | — | — | — | 0.077 | 2.492 | 0.095 | 374 |
| Phage-278 | — | — | L | — | — | Y | — | L | — | — | — | — | — | A | 0.075 | 2.489 | 0.094 | 375 |
| Phage-279 | — | — | I | — | P | Y | — | N | — | — | — | — | — | I | 0.084 | 0.989 | 0.091 | 376 |
| Phage-280 | — | — | I | — | Q | T | — | T | — | — | — | — | — | A | 0.074 | 1.579 | 0.086 | 377 |
| Phage-281 | — | — | T | — | L | H | — | T | — | — | — | — | — | T | 0.070 | 2.573 | 0.091 | 378 |
| Phage-282 | — | — | S | — | F | D | N | P | T | Q | — | — | — | A | 0.080 | 2.480 | 0.100 | 379 |
| Phage-283 | — | — | N | — | — | H | — | T | — | — | — | — | — | A | 0.077 | 2.485 | 0.097 | 380 |
| Phage-284 | — | — | P | — | — | Y | — | A | — | — | — | — | — | — | 0.068 | 2.552 | 0.090 | 381 |
| Phage-285 | — | — | I | — | — | Y | — | T | — | — | — | — | — | A | 0.073 | 2.412 | 0.093 | 382 |
| Phage-286 | — | — | L | — | — | Y | — | P | — | — | — | — | — | A | 0.075 | 2.512 | 0.098 | 383 |
| Phage-287 | — | — | V | — | L | T | — | T | — | — | — | — | — | A | 0.072 | 2.466 | 0.096 | 384 |
| Phage-288 | — | — | T | — | L | A | — | P | — | — | — | — | — | I | 0.074 | 1.189 | 0.085 | 385 |
| Phage-289 | — | — | T | — | L | LL | — | D | — | — | — | — | — | T | 0.071 | 1.094 | 0.082 | 386 |
| Phage-290 | — | — | A | — | P | Y | — | T | — | — | — | — | — | T | 0.106 | 2.374 | 0.130 | 387 |
| Phage-291 | — | — | A | — | P | Y | — | L | — | — | — | — | — | T | 0.080 | 2.529 | 0.106 | 388 |
| Phage-292 | — | — | L | — | — | N | — | S | — | — | — | — | — | A | 0.112 | 2.417 | 0.136 | 389 |
| Phage-293 | — | — | T | — | L | T | — | T | — | — | — | — | — | T | 0.071 | 2.478 | 0.097 | 390 |
| Phage-294 | — | — | L | — | — | N | — | H | S | — | — | — | — | S | 0.075 | 2.502 | 0.101 | 391 |
| Phage-295 | — | — | T | — | — | F | — | — | — | — | — | — | — | — | 0.071 | 1.560 | 0.088 | 392 |
| Phage-296 | — | — | L | Y | L | N | — | P | — | — | — | — | — | L | 0.079 | 2.295 | 0.103 | 393 |

TABLE 22-continued

Phage panning results of αEGFR Fab peptide-8 library sequences. (—) indicates the same amino acid as in aEGFR Fab peptide-8 corresponding position.

| Phage number | \| Amino acid position sequence | | | | | | | | | | | | | | Phage binding ELISA | | | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | Backgroud signal | EGFR Fab signal | EGFR Fab signal in presence of EGFR | |
| Phage-297 | — | — | L | — | — | F | — | T | — | — | — | — | — | S | 0.066 | 2.624 | 0.095 | 394 |
| Phage-298 | — | — | N | Y | — | N | — | P | — | — | — | — | — | A | 0.070 | 2.418 | 0.097 | 395 |
| Phage-299 | — | — | A | — | Q | Y | — | T | — | — | — | — | — | T | 0.089 | 1.848 | 0.110 | 396 |
| Phage-300 | — | — | T | — | L | H | — | D | — | — | — | — | — | L | 0.077 | 1.446 | 0.095 | 397 |
| Phage-301 | — | — | T | — | — | N | N | N | — | — | — | — | — | A | 0.074 | 2.486 | 0.108 | 398 |
| Phage-302 | — | — | L | F | — | N | — | P | — | Q | — | — | — | A | 0.076 | 2.597 | 0.112 | 399 |
| Phage-303 | — | — | L | — | — | D | — | A | — | — | — | — | — | P | 0.105 | 2.443 | 0.139 | 400 |
| Phage-304 | — | — | L | — | — | Y | — | N | — | — | — | — | — | T | 0.072 | 2.525 | 0.110 | 401 |
| Phage-305 | — | — | A | — | — | A | — | T | — | — | — | — | — | A | 0.098 | 2.443 | 0.140 | 402 |
| Phage-306 | — | — | T | — | — | H | — | P | S | — | — | — | — | — | 0.126 | 2.443 | 0.168 | 403 |
| Phage-307 | — | — | T | — | L | Y | — | T | — | — | — | — | — | T | 0.068 | 2.484 | 0.121 | 404 |
| Phage-308 | — | — | A | — | — | F | — | N | — | — | — | — | — | — | 0.075 | 0.831 | 0.093 | 405 |
| Phage-309 | — | — | S | — | P | F | — | T | — | — | — | — | — | A | 0.072 | 2.633 | 0.169 | 406 |
| Phage-310 | — | — | S | — | P | F | — | P | — | — | — | — | — | A | 0.063 | 2.617 | 0.264 | 407 |
| Phage-311 | — | — | A | — | — | H | — | — | — | — | — | — | — | L | 0.073 | 0.121 | 0.079 | 408 |
| Phage-312 | L | — | F | L | — | P | E | D | — | S | — | F | — | F | 0.070 | 0.074 | 0.071 | 409 |
| Phage-313 | — | — | H | P | Q | N | — | T | — | Y | — | F | — | S | 0.089 | 0.088 | 0.071 | 410 |
| Phage-314 | H | — | H | P | Q | F | H | S | — | Y | — | F | — | A | 0.081 | 0.077 | 0.075 | 411 |
| Phage-315 | — | — | T | — | — | T | — | I | — | — | — | — | — | L | 0.079 | 2.573 | 0.079 | 412 |
| Phage-316 | — | — | A | — | — | Y | — | T | — | — | — | — | — | A | 0.073 | 2.558 | 0.066 | 413 |
| Phage-317 | — | — | T | — | — | T | — | T | — | — | — | — | — | A | 0.069 | 2.537 | 0.067 | 414 |
| Phage-318 | — | — | L | — | — | D | — | T | — | — | — | — | — | A | 0.092 | 2.531 | 0.091 | 415 |
| Phage-319 | — | — | T | — | — | H | — | N | — | — | — | — | — | H | 0.086 | 2.510 | 0.076 | 416 |
| Phage-320 | — | — | T | — | — | F | — | T | — | — | — | — | — | — | 0.072 | 2.655 | 0.073 | 417 |
| Phage-321 | — | — | A | — | — | H | — | T | — | — | — | — | — | I | 0.074 | 2.497 | 0.075 | 418 |
| Phage-322 | — | — | L | — | L | N | — | N | — | — | — | — | — | S | 0.076 | 2.624 | 0.079 | 419 |
| Phage-323 | — | — | L | — | — | F | — | T | — | — | — | — | — | T | 0.069 | 2.518 | 0.074 | 420 |
| Phage-324 | — | — | L | — | — | S | — | T | — | — | — | — | — | A | 0.074 | 2.576 | 0.080 | 421 |
| Phage-325 | — | — | N | — | L | Y | — | T | — | — | — | — | — | L | 0.064 | 2.590 | 0.070 | 422 |
| Phage-326 | — | — | A | — | — | D | — | T | — | — | — | — | — | A | 0.069 | 2.434 | 0.076 | 423 |
| Phage-327 | — | — | T | — | — | H | — | L | — | — | — | — | — | T | 0.070 | 2.471 | 0.077 | 424 |
| Phage-328 | — | — | L | F | L | N | — | P | — | — | — | — | — | A | 0.106 | 2.519 | 0.114 | 425 |
| Phage-329 | — | — | L | — | — | F | — | — | — | — | — | — | — | A | 0.066 | 2.492 | 0.074 | 426 |
| Phage-330 | — | — | A | — | — | Y | — | N | — | — | — | — | — | — | 0.084 | 2.342 | 0.092 | 427 |
| Phage-331 | — | — | L | — | L | F | — | T | — | — | — | — | — | A | 0.070 | 2.586 | 0.079 | 428 |
| Phage-332 | — | — | L | — | — | N | — | T | — | — | — | — | — | A | 0.068 | 2.611 | 0.078 | 429 |
| Phage-333 | — | — | I | — | — | F | — | T | — | — | — | — | — | L | 0.070 | 2.509 | 0.080 | 430 |
| Phage-334 | — | — | L | — | P | F | — | T | — | — | — | — | — | I | 0.104 | 2.468 | 0.115 | 431 |
| Phage-335 | — | — | T | — | — | Y | — | T | — | — | — | — | — | S | 0.070 | 2.494 | 0.081 | 432 |
| Phage-336 | — | — | L | — | L | Y | — | T | — | — | — | — | — | I | 0.067 | 2.607 | 0.079 | 433 |
| Phage-337 | — | — | A | — | — | T | — | T | — | — | — | — | — | T | 0.067 | 2.461 | 0.083 | 434 |
| Phage-338 | — | — | L | — | — | Y | — | T | — | — | — | — | — | I | 0.068 | 2.541 | 0.084 | 435 |
| Phage-339 | — | — | T | — | — | Y | — | T | — | — | — | — | — | — | 0.085 | 2.513 | 0.107 | 436 |
| Phage-340 | — | — | N | — | L | Y | — | T | — | — | — | — | — | I | 0.073 | 2.502 | 0.095 | 437 |
| Phage-341 | — | — | T | — | — | H | — | T | — | — | — | — | — | — | 0.074 | 2.592 | 0.069 | 438 |
| Phage-342 | — | — | L | — | — | Y | — | T | — | — | — | — | — | — | 0.085 | 2.587 | 0.076 | 439 |
| Phage-343 | — | — | A | — | — | T | — | T | — | — | — | — | — | A | 0.067 | 2.509 | 0.066 | 440 |
| Phage-344 | — | — | L | — | — | Y | — | T | — | — | — | — | — | T | 0.088 | 2.497 | 0.075 | 441 |
| Phage-345 | — | — | L | — | — | H | — | T | — | — | — | — | — | L | 0.068 | 2.603 | 0.070 | 442 |
| Phage-346 | — | — | L | — | — | T | — | T | — | — | — | — | — | L | 0.072 | 2.600 | 0.075 | 443 |
| Phage-347 | — | — | N | — | — | Y | — | T | — | — | — | — | — | L | 0.075 | 2.499 | 0.083 | 444 |
| Phage-348 | — | — | L | Y | — | N | — | P | — | — | — | — | — | A | 0.071 | 2.519 | 0.097 | 445 |
| Phage-349 | — | — | L | F | — | N | — | P | — | — | — | — | — | A | 0.074 | 2.678 | 0.124 | 446 |
| Phage-350 | — | — | T | — | — | Y | — | T | — | — | — | — | — | L | 0.073 | 2.586 | 0.072 | 447 |
| Phage-351 | — | — | L | — | — | Y | — | T | — | — | — | — | — | L | 0.072 | 2.584 | 0.069 | 448 |
| Phage-352 | — | — | T | — | — | Y | — | T | — | — | — | — | — | T | 0.093 | 2.552 | 0.089 | 449 |
| Phage-353 | — | — | N | — | — | Y | — | L | — | — | — | — | — | L | 0.070 | 2.612 | 0.101 | 450 |
| Phage-354 | — | — | L | — | — | F | — | P | — | — | — | — | — | S | 0.082 | 2.592 | 0.075 | 451 |
| Phage-355 | — | — | L | — | — | Y | — | I | — | — | — | — | — | A | 0.093 | 2.583 | 0.077 | 452 |
| Phage-356 | — | — | A | Y | — | H | — | P | — | — | — | — | — | A | 0.084 | 2.573 | 0.083 | 453 |
| Phage-357 | — | — | N | — | L | H | — | T | — | — | — | — | — | L | 0.090 | 2.564 | 0.074 | 454 |
| Phage-358 | — | — | T | — | — | Y | — | — | — | — | — | — | — | A | 0.073 | 2.558 | 0.064 | 455 |
| Phage-359 | — | — | A | — | — | F | — | l | — | — | — | — | — | — | 0.085 | 2.550 | 0.070 | 456 |
| Phage-360 | — | — | A | — | — | Y | — | T | — | — | — | — | — | L | 0.072 | 2.532 | 0.069 | 457 |
| Phage-361 | — | — | V | — | — | T | — | T | — | — | — | — | — | L | 0.082 | 2.523 | 0.082 | 458 |
| Phage-362 | — | — | N | — | — | F | — | N | — | — | — | — | — | A | 0.071 | 2.483 | 0.069 | 459 |
| Phage-363 | — | — | A | — | L | F | — | N | — | — | — | — | — | T | 0.104 | 2.479 | 0.093 | 460 |
| Phage-364 | — | — | L | — | — | F | — | — | — | — | — | — | — | i | 0.104 | 2.474 | 0.092 | 461 |
| Phage-365 | — | — | V | — | — | N | — | T | — | — | — | — | — | L | 0.089 | 2.471 | 0.075 | 462 |

TABLE 22-continued

Phage panning results of αEGFR Fab peptide-8 library sequences. (—) indicates the same amino acid as in aEGFR Fab peptide-8 corresponding position.

| Phage number | 1 | 2 | 3 | 4 | 5 | 6 | 7 | 8 | 9 | 10 | 11 | 12 | 13 | 14 | Backgroud signal | EGFR Fab signal | EGFR Fab signal in presence of EGFR | SEQ ID NO: |
|---|---|---|---|---|---|---|---|---|---|---|---|---|---|---|---|---|---|---|
| Phage-366 | — | — | L | — | — | D | — | P | — | — | — | — | — | L | 0.092 | 2.465 | 0.089 | 463 |
| Phage-367 | — | — | I | — | — | Y | — | T | — | — | — | — | — | — | 0.080 | 2.457 | 0.073 | 464 |
| Phage-368 | — | — | N | — | — | N | — | P | — | — | — | — | — | A | 0.071 | 2.456 | 0.067 | 465 |
| Phage-369 | — | — | T | — | — | H | — | T | — | — | — | — | — | S | 0.101 | 2.455 | 0.101 | 466 |
| Phage-370 | — | — | L | — | — | F | — | N | — | — | — | — | — | A | 0.077 | 2.455 | 0.071 | 467 |
| Phage-371 | — | — | L | — | — | S | — | P | — | — | — | — | — | A | 0.075 | 2.454 | 0.070 | 468 |
| Phage-372 | — | — | T | — | L | H | — | T | — | — | — | — | — | L | 0.092 | 2.446 | 0.086 | 469 |
| Phage-373 | — | — | N | — | L | H | — | T | — | — | — | — | — | I | 0.084 | 2.445 | 0.076 | 470 |
| Phage-374 | — | — | L | — | Q | Y | — | T | — | — | — | — | — | A | 0.126 | 2.435 | 0.111 | 471 |
| Phage-375 | — | — | L | — | — | H | — | T | — | — | — | — | — | S | 0.107 | 2.432 | 0.091 | 472 |
| Phage-376 | — | — | L | — | P | F | — | D | — | — | — | — | — | A | 0.127 | 2.430 | 0.123 | 473 |
| Phage-377 | — | — | A | — | — | A | — | T | — | — | — | — | — | T | 0.073 | 2.428 | 0.073 | 474 |
| Phage-378 | — | — | T | — | — | N | — | P | — | — | — | — | — | I | 0.089 | 2.425 | 0.075 | 475 |
| Phage-379 | — | — | A | — | P | Y | — | T | — | — | — | — | — | A | 0.083 | 2.423 | 0.071 | 476 |
| Phage-380 | — | — | L | — | — | H | — | I | — | — | — | — | — | S | 0.140 | 2.422 | 0.121 | 477 |
| Phage-381 | — | — | A | — | — | H | — | T | — | — | — | — | — | — | 0.092 | 2.419 | 0.090 | 478 |
| Phage-382 | — | — | T | — | — | Y | — | P | — | — | — | — | — | S | 0.066 | 2.419 | 0.065 | 479 |
| Phage-383 | — | — | P | — | — | Y | — | T | — | — | — | — | — | A | 0.146 | 2.413 | 0.126 | 480 |
| Phage-384 | — | — | S | — | P | Y | — | T | — | — | — | — | — | L | 0.082 | 2.412 | 0.077 | 481 |
| Phage-385 | — | — | T | — | — | Y | — | N | — | — | — | — | — | S | 0.075 | 2.406 | 0.073 | 482 |
| Phage-386 | — | — | V | — | — | T | — | S | — | — | — | — | — | — | 0.086 | 2.398 | 0.078 | 483 |
| Phage-387 | — | — | V | — | — | F | — | — | — | — | — | — | — | A | 0.096 | 2.372 | 0.077 | 484 |
| Phage-388 | — | — | L | — | — | — | — | P | — | — | — | — | — | A | 0.070 | 2.367 | 0.069 | 485 |
| Phage-389 | — | — | L | — | — | F | — | L | — | — | — | — | — | L | 0.107 | 2.367 | 0.081 | 486 |
| Phage-390 | L | — | Y | — | — | H | W | I | — | — | L | — | — | H | 2.341 | 2.360 | 2.220 | 487 |
| Phage-391 | — | — | T | — | — | A | — | — | — | — | — | — | — | A | 0.105 | 2.357 | 0.090 | 488 |
| Phage-392 | — | — | T | — | L | N | — | T | — | — | — | — | — | T | 0.149 | 2.343 | 0.139 | 489 |
| Phage-393 | — | — | N | — | P | Y | — | T | — | — | — | — | — | A | 0.072 | 2.341 | 0.069 | 490 |
| Phage-394 | — | — | T | — | — | T | — | N | — | — | — | — | — | T | 0.142 | 2.334 | 0.128 | 491 |
| Phage-395 | V | — | L | A | Y | R | S | R | Q | A | D | L | — | R | 0.082 | 2.309 | 0.079 | 492 |
| Phage-396 | — | N | — | L | Y | — | T | — | — | — | — | — | — | A | 0.079 | 2.253 | 0.072 | 493 |
| Phage-397 | — | — | I | — | — | N | — | N | — | — | — | — | — | A | 0.071 | 2.246 | 0.069 | 494 |
| Phage-398 | — | — | A | — | — | D | — | T | — | — | — | — | — | T | 0.072 | 2.238 | 0.069 | 495 |
| Phage-399 | — | — | A | — | P | F | — | T | — | — | — | — | — | Y | 0.104 | 2.230 | 0.085 | 496 |
| Phage-400 | — | — | A | — | — | N | — | T | — | — | — | — | — | I | 0.090 | 2.208 | 0.085 | 497 |
| Phage-401 | — | — | T | — | Q | T | — | I | — | — | — | — | — | A | 0.078 | 2.192 | 0.074 | 498 |
| Phage-402 | — | — | L | — | — | S | — | N | — | — | — | — | — | L | 0.074 | 2.185 | 0.072 | 499 |
| Phage-403 | — | — | L | — | — | N | — | S | — | — | — | — | — | T | 0.145 | 2.170 | 0.129 | 500 |
| Phage-404 | — | — | L | — | — | F | — | D | — | — | — | — | — | — | 0.115 | 2.159 | 0.103 | 501 |
| Phage-405 | — | — | T | — | L | T | — | N | — | — | — | — | — | T | 0.076 | 2.128 | 0.070 | 502 |
| Phage-406 | — | — | A | — | P | H | — | T | — | — | — | — | — | L | 0.073 | 2.112 | 0.066 | 503 |
| Phage-407 | — | — | N | — | Q | Y | — | T | — | — | — | — | — | A | 0.116 | 2.094 | 0.116 | 504 |
| Phage-408 | — | — | A | — | — | F | — | S | — | — | — | — | — | — | 0.083 | 2.093 | 0.076 | 505 |
| Phage-409 | — | — | A | — | — | F | — | A | — | — | — | — | — | A | 0.073 | 2.082 | 0.073 | 506 |
| Phage-410 | — | — | S | — | Q | Y | — | I | — | — | — | — | — | A | 0.104 | 2.053 | 0.084 | 507 |
| Phage-411 | — | — | L | — | — | Y | — | S | — | — | — | — | — | A | 0.071 | 1.973 | 0.070 | 508 |
| Phage-412 | — | — | L | — | Q | Y | — | T | — | — | — | — | — | I | 0.092 | 1.967 | 0.090 | 509 |
| Phage-413 | — | — | V | — | — | Y | — | — | — | — | — | — | — | A | 0.086 | 1.927 | 0.077 | 510 |
| Phage-414 | — | — | T | — | — | — | — | I | — | — | — | — | — | A | 0.152 | 1.856 | 0.120 | 511 |
| Phage-415 | — | — | V | — | — | N | — | T | — | — | — | — | — | T | 0.071 | 1.812 | 0.068 | 512 |
| Phage-416 | — | — | V | — | L | T | — | N | — | — | — | — | — | T | 0.084 | 1.715 | 0.072 | 513 |
| Phage-417 | — | — | V | — | L | T | — | N | — | — | — | — | — | L | 0.070 | 1.621 | 0.068 | 514 |
| Phage-418 | V | — | L | — | V | R | S | R | Q | A | D | L | — | R | 0.130 | 1.558 | 0.126 | 515 |
| Phage-419 | — | — | H | — | — | H | — | T | — | — | — | — | — | T | 0.095 | 1.527 | 0.088 | 516 |
| Phage-420 | — | — | L | — | P | Y | — | — | — | — | — | — | — | — | 0.086 | 1.518 | 0.069 | 517 |
| Phage-421 | — | — | N | — | — | D | — | T | — | — | — | — | — | S | 0.092 | 1.421 | 0.089 | 518 |
| Phage-422 | — | — | A | Y | Q | N | — | P | — | — | — | — | — | S | 0.106 | 1.313 | 0.105 | 519 |
| Phage-423 | — | — | S | — | — | F | — | L | — | — | — | — | — | — | 0.106 | 1.297 | 0.105 | 520 |
| Phage-424 | — | — | I | — | — | H | — | A | — | — | — | — | — | A | 0.112 | 1.252 | 0.097 | 521 |
| Phage-425 | — | — | H | — | R | H | — | T | — | — | — | — | — | A | 0.119 | 1.244 | 0.076 | 522 |
| Phage-426 | — | — | T | — | — | F | — | H | — | — | — | — | — | T | 0.084 | 1.196 | 0.080 | 523 |
| Phage-427 | — | — | I | — | L | Y | — | H | — | — | — | — | — | — | 0.097 | 1.055 | 0.092 | 524 |
| Phage-428 | — | — | L | — | — | T | — | T | — | — | — | — | — | S | 0.097 | 0.952 | 0.089 | 525 |
| Phage-429 | — | — | I | A | — | N | — | P | — | — | — | — | — | A | 0.076 | 0.927 | 0.071 | 526 |
| Phage-430 | — | — | L | — | — | N | — | T | — | — | — | — | — | T | 0.111 | 0.918 | 0.094 | 527 |
| Phage-431 | — | — | A | — | Q | Y | — | N | — | — | — | — | — | A | 0.103 | 0.879 | 0.083 | 528 |
| Phage-432 | — | — | L | — | L | S | — | P | — | — | — | — | — | T | 0.082 | 0.848 | 0.078 | 529 |
| Phage-433 | — | — | A | — | — | F | — | L | — | — | — | — | — | T | 0.154 | 0.759 | 0.123 | 530 |
| Phage-434 | — | — | L | — | — | N | — | L | — | — | — | — | — | — | 0.088 | 0.746 | 0.085 | 531 |

TABLE 22-continued

Phage panning results of αEGFR Fab peptide-8 library sequences. (—) indicates the same amino acid as in aEGFR Fab peptide-8 corresponding position.

| Phage number | \multicolumn{14}{c}{Amino acid position sequence} | Backgroud signal | EGFR Fab signal | EGFR Fab signal in presence of EGFR | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-435 | — | — | S | — | — | N | — | N | — | — | — | — | — | L | 0.080 | 0.712 | 0.075 | 532 |
| Phage-436 | — | — | A | — | N | H | — | D | — | — | — | — | — | L | 0.079 | 0.686 | 0.075 | 533 |
| Phage-437 | — | — | N | — | P | Y | — | T | — | — | — | — | — | F | 0.105 | 0.613 | 0.092 | 534 |
| Phage-438 | — | — | A | — | — | F | — | F | — | — | — | — | — | A | 0.070 | 0.600 | 0.069 | 535 |
| Phage-439 | — | — | I | — | — | N | — | H | — | — | — | — | — | I | 0.069 | 0.580 | 0.069 | 536 |
| Phage-440 | — | — | V | — | N | F | — | T | — | — | — | — | — | T | 0.072 | 0.472 | 0.070 | 537 |
| Phage-441 | — | — | A | — | — | H | — | T | — | — | — | — | — | Y | 0.093 | 0.426 | 0.076 | 538 |
| Phage-442 | T | — | T | — | — | F | — | T | — | — | — | — | — | — | 0.065 | 0.422 | 0.065 | 539 |
| Phage-443 | — | — | L | — | — | T | — | T | — | — | — | — | — | Y | 0.084 | 0.397 | 0.079 | 540 |
| Phage-444 | — | — | N | — | — | T | — | — | — | — | — | — | — | Y | 0.078 | 0.254 | 0.077 | 541 |
| Phage-445 | — | — | L | — | Q | F | — | T | — | — | — | — | — | L | 0.120 | 0.218 | 0.086 | 542 |
| Phage-446 | — | — | F | — | — | H | — | P | — | — | — | — | — | A | 0.077 | 0.189 | 0.077 | 543 |
| Phage-447 | — | — | T | — | — | T | — | — | — | — | — | — | — | — | 0.094 | 0.165 | 0.090 | 544 |
| Phage-448 | — | — | A | — | M | Y | — | D | — | — | — | — | — | H | 0.078 | 0.137 | 0.074 | 545 |
| Phage-449 | — | — | V | — | P | F | — | T | — | — | — | — | — | I | 0.102 | 0.135 | 0.093 | 546 |
| Phage-450 | — | — | N | — | L | Y | — | N | — | — | — | — | — | — | 0.066 | 0.133 | 0.065 | 547 |
| Phage-451 | — | — | L | — | L | N | — | P | — | — | — | — | — | T | 0.076 | 0.126 | 0.074 | 548 |
| Phage-452 | — | — | L | — | L | H | — | I | — | — | — | — | — | A | 0.070 | 0.117 | 0.070 | 549 |
| Phage-453 | T | — | S | L | Q | H | Q | Y | — | Y | — | M | — | I | 0.114 | 0.105 | 0.146 | 550 |
| Phage-454 | — | — | A | — | — | H | — | Y | — | — | — | — | — | T | 0.081 | 0.087 | 0.069 | 551 |
| Phage-455 | — | — | V | — | — | N | — | I | — | — | — | — | — | L | 0.076 | 0.080 | 0.075 | 552 |
| Phage-456 | M | — | H | P | Q | N | — | A | — | Y | — | F | — | D | 0.091 | 0.075 | 0.107 | 553 |
| Phage-457 | — | — | N | — | — | A | — | — | — | — | — | — | — | I | 0.073 | 0.074 | 0.067 | 554 |
| Phage-458 | — | — | N | — | — | T | — | S | — | — | — | — | — | A | 0.072 | 0.072 | 0.069 | 555 |
| Phage-459 | L | — | H | P | Q | N | — | A | — | Y | — | M | — | D | 0.076 | 0.072 | 0.088 | 556 |
| Phage-460 | G | — | F | — | — | P | Q | N | — | H | — | S | — | F | 0.073 | 0.069 | 0.077 | 557 |
| Phage-461 | L | — | H | P | Q | F | — | F | — | Y | — | M | — | D | 0.070 | 0.067 | 0.076 | 558 |
| Phage-462 | W | — | H | P | Q | H | — | A | — | Y | — | F | — | S | 0.068 | 0.066 | 0.073 | 559 |
| Phage-463 | W | — | H | P | Q | F | — | Y | — | Y | — | M | — | D | 0.071 | 0.065 | 0.078 | 560 |
| Phage-464 | F | — | H | P | Q | N | — | — | — | Y | — | — | — | A | 0.067 | 0.064 | 0.073 | 561 |
| Phage-465 | — | — | V | — | — | T | — | T | — | — | — | — | — | — | 0.082 | 1.564 | 0.082 | 562 |
| Phage-466 | — | — | N | — | F | T | — | T | — | — | — | — | — | A | 0.074 | 2.351 | 0.074 | 563 |
| Phage-467 | L | — | L | A | L | R | — | R | Q | A | D | L | — | R | 0.072 | 2.482 | 0.072 | 564 |
| Phage-468 | — | — | L | — | — | N | — | I | — | — | — | — | — | A | 0.089 | 2.287 | 0.090 | 565 |
| Phage-469 | — | — | L | — | — | H | — | — | — | — | — | — | — | — | 0.067 | 2.426 | 0.068 | 566 |
| Phage-470 | — | — | I | — | — | H | — | T | — | — | — | — | — | L | 0.068 | 2.419 | 0.069 | 567 |
| Phage-471 | — | — | L | Y | — | D | — | P | — | — | — | — | — | S | 0.131 | 2.417 | 0.132 | 568 |
| Phage-472 | — | — | L | — | N | Y | — | T | — | — | — | — | — | S | 0.067 | 2.347 | 0.068 | 569 |
| Phage-473 | — | — | S | — | — | H | — | T | — | — | — | — | — | L | 0.078 | 2.569 | 0.079 | 570 |
| Phage-474 | — | — | A | — | P | F | — | T | — | — | — | — | — | — | 0.073 | 1.500 | 0.073 | 571 |
| Phage-475 | — | — | V | — | — | N | — | I | — | — | — | — | — | A | 0.093 | 1.127 | 0.093 | 572 |
| Phage-476 | — | — | T | — | — | D | — | N | — | — | — | — | — | — | 0.071 | 0.993 | 0.071 | 573 |
| Phage-477 | — | — | T | — | L | V | — | — | — | — | — | — | — | L | 0.067 | 2.455 | 0.069 | 574 |
| Phage-478 | — | — | A | — | Q | F | — | L | — | — | — | — | — | T | 0.065 | 2.367 | 0.067 | 575 |
| Phage-479 | — | — | S | — | — | Y | — | T | — | — | — | — | — | L | 0.066 | 2.428 | 0.068 | 576 |
| Phage-480 | — | — | T | — | L | H | — | P | — | — | — | — | — | A | 0.076 | 2.589 | 0.078 | 577 |
| Phage-481 | — | — | A | Y | — | G | — | N | — | — | — | — | — | L | 0.071 | 2.556 | 0.073 | 578 |
| Phage-482 | — | — | I | — | — | N | — | H | — | — | — | — | — | S | 0.078 | 2.542 | 0.080 | 579 |
| Phage-483 | — | — | L | Y | — | Y | — | P | — | — | — | — | — | S | 0.072 | 0.531 | 0.073 | 580 |
| Phage-484 | — | — | S | — | — | Y | — | T | — | — | — | — | — | — | 0.069 | 2.426 | 0.071 | 581 |
| Phage-485 | — | — | T | — | R | F | — | I | — | — | — | — | — | A | 0.071 | 1.940 | 0.073 | 582 |
| Phage-486 | — | — | L | — | P | N | — | I | — | — | — | — | — | A | 0.091 | 1.291 | 0.092 | 583 |
| Phage-487 | — | — | T | — | L | Y | — | T | — | — | — | — | — | I | 0.071 | 2.445 | 0.073 | 584 |
| Phage-488 | — | — | S | — | — | Y | — | T | — | — | — | — | — | A | 0.073 | 2.388 | 0.075 | 585 |
| Phage-489 | — | — | T | — | N | F | — | T | — | — | — | — | — | A | 0.106 | 2.064 | 0.107 | 586 |
| Phage-490 | — | — | S | — | — | F | — | L | — | — | — | — | — | T | 0.105 | 2.314 | 0.107 | 587 |
| Phage-491 | — | — | T | — | — | L | — | P | — | — | — | — | — | A | 0.083 | 2.377 | 0.086 | 588 |
| Phage-492 | — | — | A | — | — | T | — | T | — | — | — | — | — | I | 0.066 | 2.513 | 0.068 | 589 |
| Phage-493 | — | — | I | — | — | N | — | P | — | — | — | — | — | S | 0.085 | 2.563 | 0.087 | 590 |
| Phage-494 | — | — | L | — | — | F | — | P | — | — | — | — | — | L | 0.074 | 2.534 | 0.077 | 591 |
| Phage-495 | — | — | V | — | L | Y | — | T | — | — | — | — | — | — | 0.072 | 2.466 | 0.075 | 592 |
| Phage-496 | — | — | L | — | — | F | — | A | — | — | — | — | — | I | 0.110 | 2.253 | 0.113 | 593 |
| Phage-497 | — | — | T | — | L | Y | — | T | — | — | — | — | — | — | 0.084 | 2.605 | 0.087 | 594 |
| Phage-498 | — | — | V | — | L | T | — | T | — | — | — | — | — | I | 0.115 | 2.249 | 0.117 | 595 |
| Phage-499 | — | — | — | — | — | L | — | I | — | — | — | — | — | A | 0.067 | 2.420 | 0.071 | 596 |
| Phage-500 | — | — | A | — | — | F | — | H | — | — | — | — | — | L | 0.074 | 2.332 | 0.077 | 597 |
| Phage-501 | — | — | T | — | L | F | — | N | — | — | — | — | — | A | 0.074 | 2.278 | 0.077 | 598 |
| Phage-502 | — | — | T | — | — | H | — | P | — | — | — | — | — | A | 0.071 | 2.487 | 0.075 | 599 |
| Phage-503 | — | — | A | — | — | T | — | N | — | — | — | — | — | A | 0.076 | 1.934 | 0.079 | 600 |

TABLE 22-continued

Phage panning results of αEGFR Fab peptide-8 library sequences. (—) indicates the same amino acid as in aEGFR Fab peptide-8 corresponding position.

| Phage number | \ | \ | \ | \ | Amino acid position sequence | \ | \ | \ | \ | \ | \ | \ | \ | \ | Backgroud signal | EGFR Fab signal | EGFR Fab signal in presence of EGFR | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-504 | — | — | T | — | L | S | — | T | — | — | — | — | — | T | 0.073 | 2.406 | 0.077 | 601 |
| Phage-505 | — | — | I | — | — | S | — | T | — | — | — | — | — | I | 0.103 | 1.750 | 0.106 | 602 |
| Phage-506 | — | — | V | — | Q | Y | — | L | — | — | — | — | — | — | 0.073 | 2.406 | 0.077 | 603 |
| Phage-507 | — | — | A | — | — | F | — | L | — | — | — | — | — | I | 0.106 | 2.411 | 0.110 | 604 |
| Phage-508 | — | — | L | — | R | F | — | — | — | — | — | — | — | T | 0.068 | 2.030 | 0.071 | 605 |
| Phage-509 | — | — | S | — | — | F | — | P | — | — | — | — | — | — | 0.067 | 2.255 | 0.072 | 606 |
| Phage-510 | — | — | N | — | — | Y | — | T | — | — | — | — | — | I | 0.081 | 2.466 | 0.085 | 607 |
| Phage-511 | — | — | P | — | — | F | — | T | — | — | — | — | — | I | 0.068 | 2.413 | 0.072 | 608 |
| Phage-512 | — | — | L | — | — | T | — | I | — | — | — | — | — | A | 0.069 | 2.453 | 0.074 | 609 |
| Phage-513 | — | — | A | — | — | T | — | L | — | — | — | — | — | T | 0.070 | 2.442 | 0.075 | 610 |
| Phage-514 | — | — | I | — | P | H | — | L | — | — | — | — | — | S | 0.068 | 0.963 | 0.070 | 611 |
| Phage-515 | — | — | T | — | — | Y | — | F | — | — | — | — | — | I | 0.066 | 2.224 | 0.070 | 612 |
| Phage-516 | — | — | — | — | — | Y | — | N | — | — | — | — | — | L | 0.072 | 2.240 | 0.076 | 613 |
| Phage-517 | — | — | S | — | — | F | — | T | — | — | — | — | — | A | 0.094 | 2.477 | 0.099 | 614 |
| Phage-518 | — | — | N | — | L | S | E | T | — | — | — | — | — | — | 0.082 | 2.453 | 0.088 | 615 |
| Phage-519 | — | — | L | — | — | D | — | — | — | — | — | — | — | T | 0.073 | 2.229 | 0.078 | 616 |
| Phage-520 | — | — | T | — | — | Y | — | — | — | — | — | — | — | — | 0.065 | 2.170 | 0.070 | 617 |
| Phage-521 | — | — | A | — | — | F | — | T | — | — | — | — | — | A | 0.081 | 2.451 | 0.086 | 618 |
| Phage-522 | — | — | T | — | L | F | — | T | — | — | — | — | — | S | 0.066 | 2.509 | 0.072 | 619 |
| Phage-523 | — | — | N | — | R | Y | — | T | — | — | — | — | — | A | 0.063 | 1.794 | 0.067 | 620 |
| Phage-524 | — | — | T | — | — | A | — | I | — | — | — | — | — | T | 0.070 | 1.982 | 0.075 | 621 |
| Phage-525 | — | — | L | — | R | F | — | T | — | — | — | — | — | I | 0.072 | 2.517 | 0.079 | 622 |
| Phage-526 | — | — | L | G | P | T | — | N | — | — | — | — | — | A | 0.071 | 2.571 | 0.077 | 623 |
| Phage-527 | — | — | T | — | Q | Y | — | — | — | — | — | — | — | A | 0.071 | 2.441 | 0.077 | 624 |
| Phage-528 | — | — | L | — | Q | F | — | — | — | — | — | — | — | A | 0.068 | 1.852 | 0.073 | 625 |
| Phage-529 | — | — | V | — | L | F | — | T | — | — | — | — | — | L | 0.070 | 2.465 | 0.076 | 626 |
| Phage-530 | — | — | S | — | — | T | — | T | — | — | — | — | — | I | 0.071 | 2.421 | 0.078 | 627 |
| Phage-531 | — | — | T | — | N | F | — | T | — | — | — | — | — | S | 0.080 | 0.848 | 0.082 | 628 |
| Phage-532 | — | — | L | — | — | T | — | N | — | — | — | — | — | I | 0.063 | 2.493 | 0.069 | 629 |
| Phage-533 | — | — | I | — | — | S | — | P | — | — | — | — | — | I | 0.070 | 2.320 | 0.077 | 630 |
| Phage-534 | — | — | L | — | — | L | — | T | — | — | — | — | — | A | 0.069 | 2.432 | 0.076 | 631 |
| Phage-535 | — | — | L | — | F | N | — | T | — | — | — | — | — | A | 0.069 | 2.324 | 0.075 | 632 |
| Phage-536 | — | — | N | — | — | T | — | T | — | — | — | — | — | I | 0.067 | 1.804 | 0.072 | 633 |
| Phage-537 | — | — | T | — | — | L | — | N | — | — | — | — | — | A | 0.068 | 2.491 | 0.075 | 634 |
| Phage-538 | — | — | A | — | — | Y | — | N | — | — | — | — | — | A | 0.066 | 2.253 | 0.073 | 635 |
| Phage-539 | — | — | T | — | L | F | — | T | — | — | — | — | — | — | 0.064 | 2.207 | 0.070 | 636 |
| Phage-540 | — | — | T | — | — | F | — | — | — | — | — | — | — | S | 0.067 | 2.536 | 0.075 | 637 |
| Phage-541 | — | — | L | — | L | V | — | T | — | — | — | — | — | I | 0.068 | 2.505 | 0.076 | 638 |
| Phage-542 | — | — | L | — | L | F | — | P | — | — | — | — | — | A | 0.073 | 2.596 | 0.081 | 639 |
| Phage-543 | — | — | I | — | — | S | — | T | — | — | — | — | — | A | 0.071 | 1.410 | 0.075 | 640 |
| Phage-544 | — | — | I | — | — | F | — | T | — | — | — | — | — | S | 0.068 | 1.927 | 0.075 | 641 |
| Phage-545 | — | — | N | — | L | Y | — | I | — | — | — | — | — | A | 0.073 | 2.447 | 0.082 | 642 |
| Phage-546 | — | — | L | F | — | H | — | P | — | — | — | — | — | N | 0.070 | 2.269 | 0.078 | 643 |
| Phage-547 | — | — | S | — | — | T | — | P | — | — | — | — | — | I | 0.070 | 1.596 | 0.076 | 644 |
| Phage-548 | — | — | N | — | — | H | — | T | — | — | — | — | — | I | 0.066 | 2.530 | 0.075 | 645 |
| Phage-549 | — | — | V | — | — | S | — | T | — | — | — | — | — | — | 0.074 | 2.290 | 0.081 | 646 |
| Phage-550 | — | — | N | — | L | F | — | T | — | — | — | — | — | L | 0.071 | 2.585 | 0.080 | 647 |
| Phage-551 | — | — | A | — | — | F | — | — | — | — | — | — | — | I | 0.083 | 2.221 | 0.091 | 648 |
| Phage-552 | — | — | L | — | L | N | — | N | — | — | — | — | — | — | 0.070 | 2.273 | 0.078 | 649 |
| Phage-553 | — | — | I | — | A | T | — | T | — | — | — | — | — | — | 0.070 | 0.950 | 0.073 | 650 |
| Phage-554 | — | — | A | F | L | N | — | P | — | — | — | — | — | S | 0.068 | 2.580 | 0.078 | 651 |
| Phage-555 | — | — | L | — | P | T | — | T | — | — | — | — | — | A | 0.068 | 0.956 | 0.071 | 652 |
| Phage-556 | — | — | T | — | — | H | — | Y | — | — | — | — | — | L | 0.070 | 2.403 | 0.079 | 653 |
| Phage-557 | — | — | A | — | — | Y | — | L | — | — | — | — | — | I | 0.073 | 2.576 | 0.083 | 654 |
| Phage-558 | — | — | T | — | P | Y | — | T | — | — | — | — | — | A | 0.068 | 2.333 | 0.077 | 655 |
| Phage-559 | — | — | L | — | — | V | — | T | — | — | — | — | — | S | 0.073 | 2.465 | 0.082 | 656 |
| Phage-560 | — | — | V | — | — | Y | — | L | — | — | — | — | — | L | 0.076 | 2.392 | 0.085 | 657 |
| Phage-561 | — | — | A | — | — | Y | — | P | — | — | — | — | — | S | 0.066 | 2.137 | 0.074 | 658 |
| Phage-562 | — | — | S | — | Q | F | — | T | — | — | — | — | — | A | 0.069 | 2.455 | 0.079 | 659 |
| Phage-563 | — | — | L | — | — | N | — | N | — | — | — | — | — | L | 0.069 | 2.460 | 0.079 | 660 |
| Phage-564 | — | — | L | — | L | L | — | T | — | — | — | — | — | I | 0.082 | 2.213 | 0.091 | 661 |
| Phage-565 | — | — | T | — | L | F | — | I | — | — | — | — | — | — | 0.068 | 2.597 | 0.079 | 662 |
| Phage-566 | — | — | A | — | — | Y | — | S | — | — | — | — | — | T | 0.085 | 1.380 | 0.091 | 663 |
| Phage-567 | — | — | V | — | L | L | — | T | — | — | — | — | — | I | 0.069 | 2.333 | 0.079 | 664 |
| Phage-568 | — | — | T | — | L | F | — | D | — | — | — | — | — | A | 0.069 | 2.414 | 0.080 | 665 |
| Phage-569 | — | — | A | — | — | F | — | T | — | — | — | — | — | L | 0.071 | 2.498 | 0.082 | 666 |
| Phage-570 | — | — | L | — | L | F | — | T | — | — | — | — | — | T | 0.065 | 2.565 | 0.076 | 667 |
| Phage-571 | — | — | L | — | Q | Y | — | I | — | — | — | — | — | L | 0.118 | 2.285 | 0.128 | 668 |
| Phage-572 | — | — | L | — | — | F | — | — | — | — | — | — | — | L | 0.071 | 2.496 | 0.082 | 669 |

TABLE 22-continued

Phage panning results of αEGFR Fab peptide-8 library sequences. (—) indicates the same amino acid as in aEGFR Fab peptide-8 corresponding position.

| Phage number | \multicolumn{14}{c|}{Amino acid position sequence} | Backgroud signal | EGFR Fab signal | EGFR Fab signal in presence of EGFR | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-573 | — | — | L | — | — | F | — | D | — | — | — | — | — | S | 0.119 | 2.388 | 0.130 | 670 |
| Phage-574 | — | — | A | — | L | T | — | T | — | — | — | — | — | T | 0.069 | 2.582 | 0.081 | 671 |
| Phage-575 | — | — | L | — | F | N | — | P | — | — | — | — | — | A | 0.071 | 2.478 | 0.083 | 672 |
| Phage-576 | — | — | T | — | Q | F | — | T | — | — | — | — | — | A | 0.065 | 2.577 | 0.078 | 673 |
| Phage-577 | — | — | L | — | — | Y | — | Y | — | — | — | — | — | S | 0.089 | 1.403 | 0.096 | 674 |
| Phage-578 | — | — | P | F | L | N | — | P | — | — | — | — | — | A | 0.071 | 2.465 | 0.083 | 675 |
| Phage-579 | — | — | N | — | — | F | — | — | — | — | — | — | — | — | 0.081 | 2.294 | 0.092 | 676 |
| Phage-580 | — | — | N | — | — | F | — | N | — | — | — | — | — | L | 0.073 | 2.412 | 0.085 | 677 |
| Phage-581 | — | — | N | — | — | F | — | H | — | — | — | — | — | I | 0.072 | 2.289 | 0.084 | 678 |
| Phage-582 | — | — | L | — | Q | N | — | P | — | — | — | — | — | A | 0.074 | 2.498 | 0.087 | 679 |
| Phage-583 | — | — | A | — | — | T | — | T | — | — | — | — | — | S | 0.075 | 1.392 | 0.082 | 680 |
| Phage-584 | — | — | S | — | Q | F | — | — | — | — | — | — | — | A | 0.081 | 0.877 | 0.085 | 681 |
| Phage-585 | — | — | H | — | L | F | — | L | — | — | — | — | — | A | 0.068 | 0.178 | 0.069 | 682 |
| Phage-586 | — | — | L | — | — | T | — | — | — | — | — | — | — | A | 0.066 | 2.605 | 0.080 | 683 |
| Phage-587 | — | — | L | — | L | H | — | P | — | — | — | — | — | — | 0.070 | 1.851 | 0.080 | 684 |
| Phage-588 | — | — | I | — | L | D | — | T | — | — | — | — | — | L | 0.072 | 1.357 | 0.079 | 685 |
| Phage-589 | — | — | V | — | — | L | — | T | — | — | — | — | — | A | 0.074 | 2.463 | 0.088 | 686 |
| Phage-590 | — | — | N | — | L | F | — | T | — | — | — | — | — | A | 0.073 | 2.367 | 0.086 | 687 |
| Phage-591 | — | — | N | — | L | T | — | T | — | — | — | — | — | S | 0.066 | 2.419 | 0.079 | 688 |
| Phage-592 | — | — | L | — | — | L | — | P | — | — | — | — | — | A | 0.129 | 2.446 | 0.143 | 689 |
| Phage-593 | — | — | A | — | — | H | — | S | — | — | — | — | — | — | 0.071 | 2.599 | 0.086 | 690 |
| Phage-594 | — | — | T | — | — | F | — | H | — | — | — | — | — | L | 0.073 | 2.488 | 0.087 | 691 |
| Phage-595 | — | — | L | — | L | H | — | T | — | — | — | — | — | A | 0.068 | 2.596 | 0.083 | 692 |
| Phage-596 | — | — | L | — | — | N | — | H | — | — | — | — | — | T | 0.069 | 2.505 | 0.084 | 693 |
| Phage-597 | — | — | S | — | — | F | — | A | — | — | — | — | — | Y | 0.075 | 2.447 | 0.089 | 694 |
| Phage-598 | — | — | T | — | — | T | — | P | — | — | — | — | — | A | 0.071 | 2.576 | 0.087 | 695 |
| Phage-599 | — | — | V | — | — | Y | — | T | — | — | — | — | — | I | 0.072 | 2.064 | 0.084 | 696 |
| Phage-600 | — | — | L | — | L | V | — | N | — | — | — | — | — | A | 0.072 | 1.402 | 0.080 | 697 |
| Phage-601 | — | — | A | — | P | F | — | L | — | — | — | — | — | S | 0.080 | 1.785 | 0.092 | 698 |
| Phage-602 | — | — | I | — | — | F | — | T | — | — | — | — | — | N | 0.071 | 1.154 | 0.078 | 699 |
| Phage-603 | — | — | L | — | F | T | — | P | — | — | — | — | — | A | 0.075 | 2.448 | 0.091 | 700 |
| Phage-604 | — | — | N | — | Q | Y | — | T | — | — | — | — | — | L | 0.068 | 2.259 | 0.083 | 701 |
| Phage-605 | — | — | I | — | — | Y | — | L | — | — | — | — | — | L | 0.068 | 2.443 | 0.085 | 702 |
| Phage-606 | — | — | T | — | — | H | — | H | — | — | — | — | — | L | 0.067 | 2.506 | 0.085 | 703 |
| Phage-607 | — | — | A | — | — | Y | — | L | — | — | — | — | — | S | 0.067 | 2.453 | 0.085 | 704 |
| Phage-608 | — | — | T | — | — | H | — | D | — | — | — | — | — | A | 0.072 | 1.237 | 0.080 | 705 |
| Phage-609 | — | — | A | — | R | Y | — | I | — | — | — | — | — | — | 0.072 | 1.337 | 0.081 | 706 |
| Phage-610 | — | — | N | — | — | F | — | L | — | — | — | — | — | A | 0.075 | 2.358 | 0.093 | 707 |
| Phage-611 | — | — | A | — | — | H | — | L | — | — | — | — | — | — | 0.069 | 1.799 | 0.083 | 708 |
| Phage-612 | — | — | V | — | F | Y | — | T | — | — | — | — | — | A | 0.068 | 2.489 | 0.088 | 709 |
| Phage-613 | — | — | T | — | — | N | — | T | — | — | — | — | — | — | 0.070 | 2.289 | 0.088 | 710 |
| Phage-614 | — | — | I | — | Q | Y | — | T | — | — | — | — | — | I | 0.094 | 2.107 | 0.11: | 711 |
| Phage-615 | — | — | L | — | — | H | — | P | — | — | — | — | — | H | 0.089 | 2.055 | 0.105 | 712 |
| Phage-616 | — | — | T | — | — | A | — | T | — | — | — | — | — | A | 0.070 | 1.392 | 0.080 | 713 |
| Phage-617 | — | — | L | — | — | D | — | — | — | — | — | — | — | — | 0.076 | 2.166 | 0.094 | 714 |
| Phage-618 | — | — | L | — | P | H | — | I | — | — | — | — | — | A | 0.077 | 2.354 | 0.096 | 715 |
| Phage-619 | — | — | T | — | — | Y | — | T | — | — | — | — | — | I | 0.067 | 2.586 | 0.089 | 716 |
| Phage-620 | — | — | T | — | — | N | — | T | — | — | — | — | — | T | 0.074 | 0.454 | 0.078 | 717 |
| Phage-621 | — | — | L | — | P | Y | — | N | — | — | — | — | — | A | 0.070 | 1.177 | 0.080 | 718 |
| Phage-622 | — | — | I | — | L | S | — | P | — | — | — | — | — | — | 0.072 | 2.281 | 0.092 | 719 |
| Phage-623 | — | — | L | — | — | Y | — | I | — | — | — | — | — | I | 0.079 | 2.302 | 0.099 | 720 |
| Phage-624 | — | — | V | — | — | Y | — | H | — | — | — | — | — | L | 0.093 | 2.448 | 0.115 | 721 |
| Phage-625 | — | — | T | — | — | H | — | N | — | — | — | — | — | A | 0.077 | 2.600 | 0.101 | 722 |
| Phage-626 | — | — | T | — | — | Y | — | N | — | — | — | — | — | T | 0.070 | 2.248 | 0.091 | 723 |
| Phage-627 | — | — | I | — | P | F | — | T | — | — | — | — | — | Y | 0.074 | 2.357 | 0.097 | 724 |
| Phage-628 | — | — | T | — | P | F | — | — | — | — | — | — | — | L | 0.119 | 2.272 | 0.141 | 725 |
| Phage-629 | — | — | L | — | — | T | — | L | — | — | — | — | — | I | 0.077 | 2.071 | 0.097 | 726 |
| Phage-630 | — | — | V | — | Q | H | — | T | — | — | — | — | — | A | 0.070 | 0.213 | 0.072 | 727 |
| Phage-631 | — | — | A | — | — | N | — | T | — | — | — | — | — | A | 0.074 | 2.132 | 0.096 | 728 |
| Phage-632 | — | — | V | — | — | F | — | H | — | — | — | — | — | — | 0.083 | 0.839 | 0.091 | 729 |
| Phage-633 | — | — | L | — | N | F | — | P | — | — | — | — | — | I | 0.078 | 1.955 | 0.099 | 730 |
| Phage-634 | L | — | L | A | S | R | Y | R | Q | A | D | L | — | R | 0.071 | 0.641 | 0.078 | 731 |
| Phage-635 | — | — | H | — | P | F | — | D | — | — | — | — | — | A | 0.066 | 0.345 | 0.070 | 732 |
| Phage-636 | — | — | I | — | — | N | — | N | — | — | — | — | — | T | 0.068 | 1.430 | 0.084 | 733 |
| Phage-637 | — | — | V | — | — | Y | — | T | — | — | — | — | — | L | 0.072 | 0.496 | 0.077 | 734 |
| Phage-638 | — | — | L | — | L | D | — | P | — | — | — | — | — | — | 0.077 | 1.281 | 0.092 | 735 |
| Phage-639 | — | — | H | — | — | F | — | S | — | — | — | — | — | S | 0.070 | 1.420 | 0.087 | 736 |
| Phage-640 | — | — | L | — | Q | T | — | — | — | — | — | — | — | A | 0.074 | 1.644 | 0.094 | 737 |
| Phage-641 | — | — | T | — | P | Y | — | P | — | — | — | — | — | A | 0.113 | 1.701 | 0.133 | 738 |

TABLE 22-continued

Phage panning results of αEGFR Fab peptide-8 library sequences. (—) indicates the same amino acid as in aEGFR Fab peptide-8 corresponding position.

| Phage number | \multicolumn{14}{c|}{Amino acid position sequence} | Background signal | EGFR Fab signal | EGFR Fab signal in presence of EGFR | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-642 | — | — | H | — | — | H | — | N | — | — | — | — | — | A | 0.067 | 1.062 | 0.080 | 739 |
| Phage-643 | — | — | V | — | — | F | — | N | — | — | — | — | — | A | 0.065 | 1.098 | 0.080 | 740 |
| Phage-644 | — | — | V | — | — | H | — | T | — | — | — | — | — | L | 0.083 | 0.335 | 0.087 | 741 |
| Phage-645 | — | — | S | — | — | F | — | — | — | — | — | — | — | L | 0.067 | 0.696 | 0.076 | 742 |
| Phage-646 | — | — | I | — | — | F | — | T | — | — | — | — | — | T | 0.070 | 0.882 | 0.082 | 743 |
| Phage-647 | — | — | I | — | — | D | — | P | — | — | — | — | — | T | 0.090 | 0.642 | 0.100 | 744 |
| Phage-648 | — | — | L | — | — | D | — | — | — | — | — | — | — | — | 0.081 | 0.847 | 0.096 | 745 |
| Phage-649 | — | — | L | — | — | N | — | L | — | — | — | — | — | A | 0.069 | 0.713 | 0.082 | 746 |
| Phage-650 | — | — | T | — | Q | T | — | T | — | — | — | — | — | I | 0.064 | 1.454 | 0.108 | 747 |
| Phage-651 | — | — | N | — | — | F | — | L | — | — | — | — | — | I | 0.111 | 0.134 | 0.112 | 748 |
| Phage-652 | — | — | A | F | L | N | — | P | — | — | — | — | — | A | 0.067 | 0.469 | 0.081 | 749 |
| Phage-653 | — | — | H | — | — | S | — | T | — | — | — | — | — | — | 0.084 | 0.153 | 0.086 | 750 |
| Phage-654 | — | — | L | — | Q | Y | — | I | — | — | — | — | — | I | 0.082 | 0.411 | 0.096 | 751 |
| Phage-655 | — | — | T | — | Q | Y | — | — | — | — | — | — | — | T | 0.075 | 0.309 | 0.085 | 752 |
| Phage-656 | — | — | L | — | — | N | — | T | — | — | — | — | — | T | 0.079 | 0.299 | 0.091 | 753 |
| Phage-657 | — | — | T | — | — | S | — | T | — | — | — | — | — | T | 0.069 | 0.287 | 0.084 | 754 |
| Phage-658 | — | — | L | — | — | F | — | N | — | — | — | — | — | L | 0.076 | 0.167 | 0.087 | 755 |
| Phage-659 | — | — | T | G | P | S | E | N | — | — | — | — | — | A | 0.076 | 0.206 | 0.092 | 756 |
| Phage-660 | — | — | — | — | Q | Y | — | T | — | — | — | — | — | A | 0.065 | 0.113 | 0.071 | 757 |
| Phage-661 | F | — | H | P | Q | F | — | H | — | Y | — | N | — | Y | 0.107 | 0.081 | 0.103 | 758 |
| Phage-662 | — | — | T | — | L | Y | — | S | — | — | — | — | — | — | 0.069 | 0.126 | 0.083 | 759 |
| Phage-663 | — | — | T | — | — | L | — | T | — | — | — | — | — | T | 0.089 | 0.110 | 0.094 | 760 |
| Phage-664 | — | — | H | P | Q | F | H | A | — | Y | — | — | — | D | 0.111 | 0.079 | 0.103 | 761 |
| Phage-665 | — | — | T | — | L | Y | — | T | — | — | — | — | — | H | 0.066 | 0.088 | 0.074 | 762 |
| Phage-666 | L | — | H | P | Q | N | — | T | — | Y | — | — | — | D | 0.118 | 0.097 | 0.110 | 763 |
| Phage-667 | — | — | L | — | R | F | — | H | — | — | — | — | — | T | 0.094 | 0.073 | 0.085 | 764 |
| Phage-668 | — | — | T | — | M | V | — | S | — | — | — | — | — | T | 0.071 | 0.106 | 0.089 | 765 |
| Phage-669 | F | — | H | P | Q | A | — | I | — | Y | — | L | — | N | 0.098 | 0.077 | 0.086 | 766 |
| Phage-670 | — | — | H | P | Q | F | H | P | — | Y | — | L | — | D | 0.097 | 0.079 | 0.086 | 767 |
| Phage-671 | — | — | L | F | — | N | — | I | — | — | — | — | — | A | 0.114 | 0.150 | 0.144 | 768 |
| Phage-672 | S | — | H | P | Q | A | — | I | — | Y | — | Y | — | D | 0.083 | 0.070 | 0.071 | 769 |
| Phage-673 | — | — | A | — | — | V | — | L | — | — | — | — | — | T | 0.123 | 0.110 | 0.111 | 770 |
| Phage-674 | — | — | V | — | — | N | — | T | — | — | — | — | — | S | 0.130 | 0.116 | 0.114 | 771 |
| Phage-675 | — | — | A | — | — | L | — | P | — | — | — | — | — | L | 0.122 | 0.113 | 0.086 | 772 |
| Phage-676 | — | — | I | — | L | T | — | T | — | — | — | — | — | T | 0.070 | 0.091 | 0.092 | 773 |
| Phage-677 | L | — | H | P | Q | A | — | I | — | F | — | F | — | N | 0.069 | 0.073 | 0.075 | 774 |
| Phage-678 | F | — | H | P | Q | N | — | S | — | Y | — | — | — | D | 0.074 | 0.072 | 0.068 | 775 |
| Phage-679 | L | — | H | P | Q | S | — | I | — | Y | — | F | — | D | 0.066 | 0.071 | 0.072 | 776 |

Figure 21:
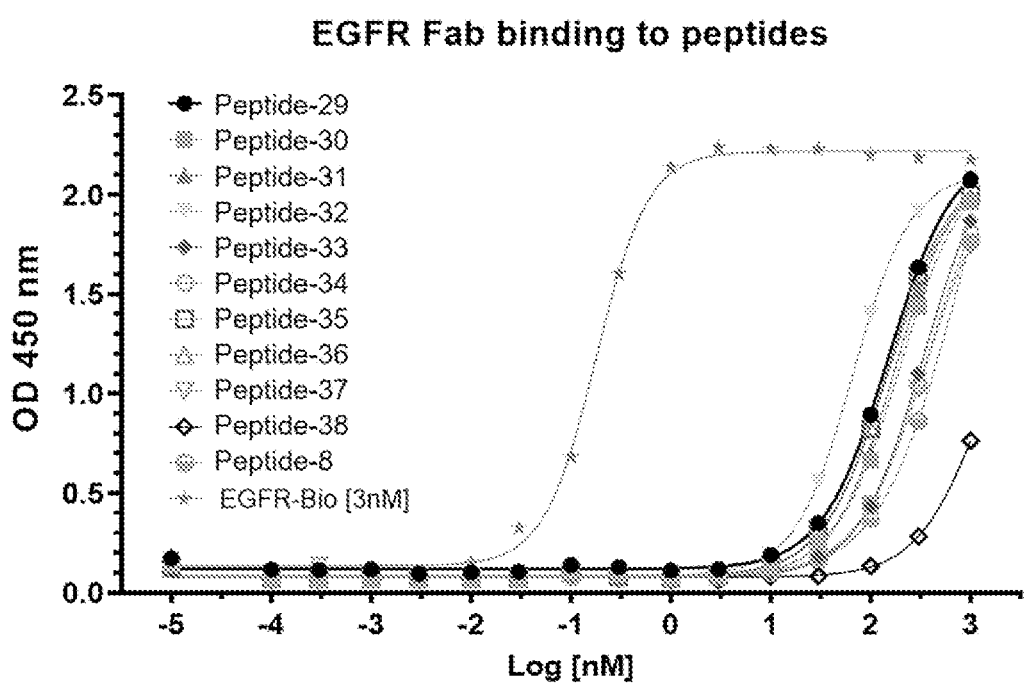
FIG. 21 illustrates αEGFR Fab binding by peptides identified by phage display.
Figure 22:
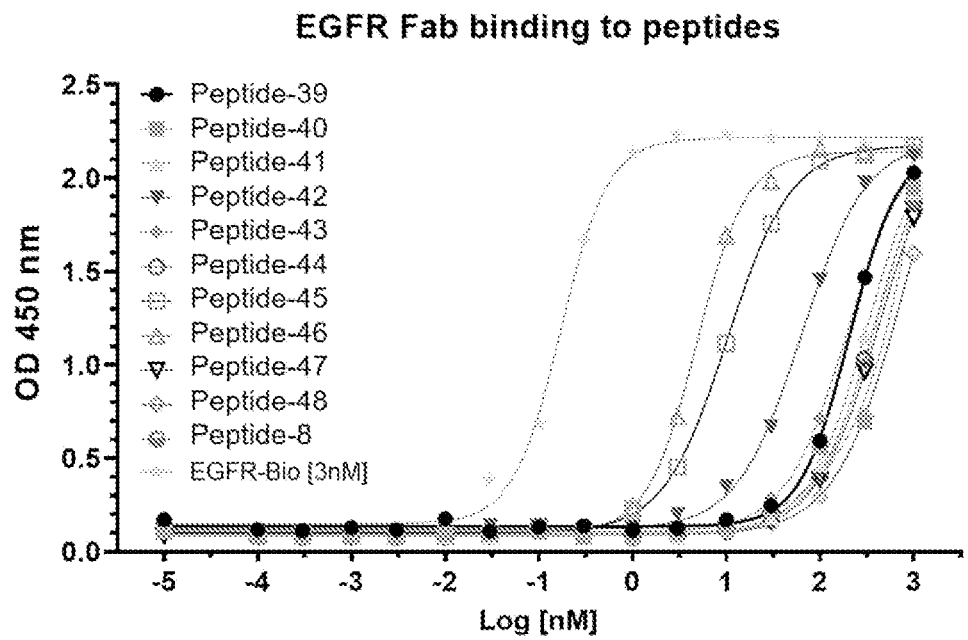
FIG. 22 illustrates αEGFR Fab binding by peptides identified by phage display.
Figure 23:
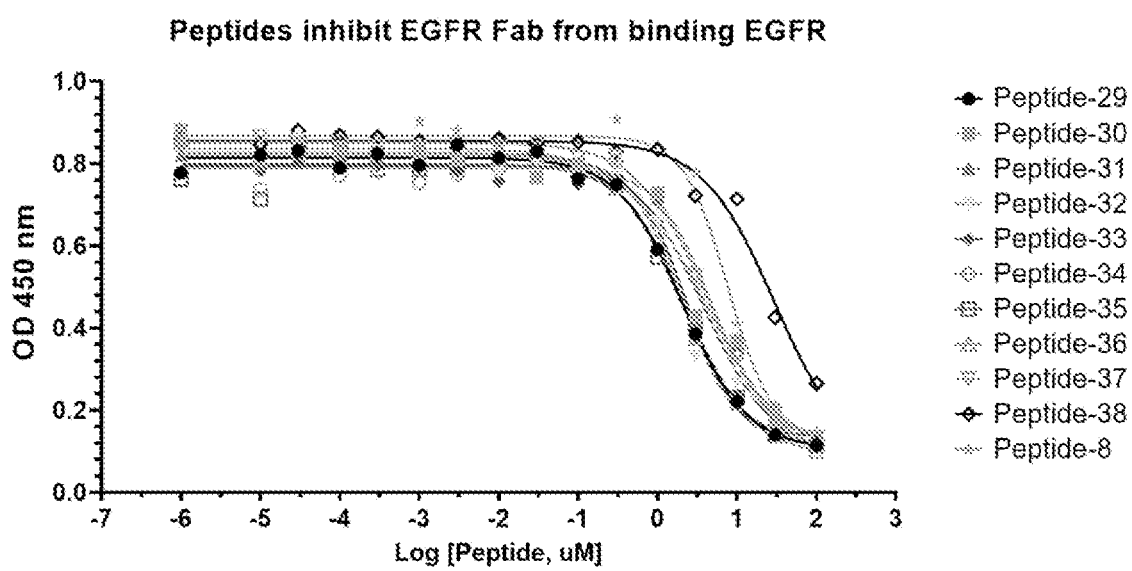
FIG. 23 illustrates inhibition of αEGFR Fab binding to EGFR by peptides identified phage display.
Figure 24:
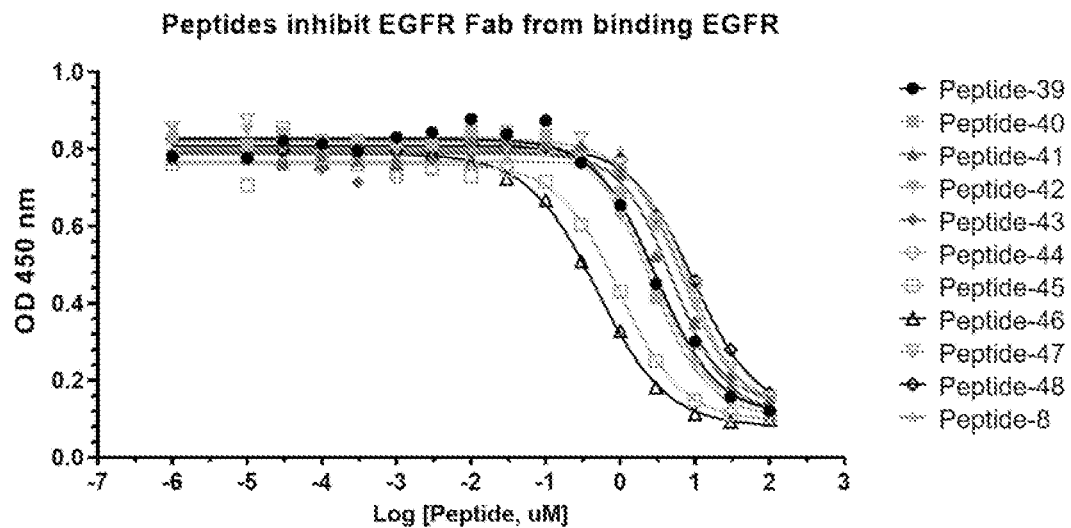
FIG. 24 illustrates inhibition of αEGFR Fab binding to EGFR by peptides identified by phage display.
Figure 25:
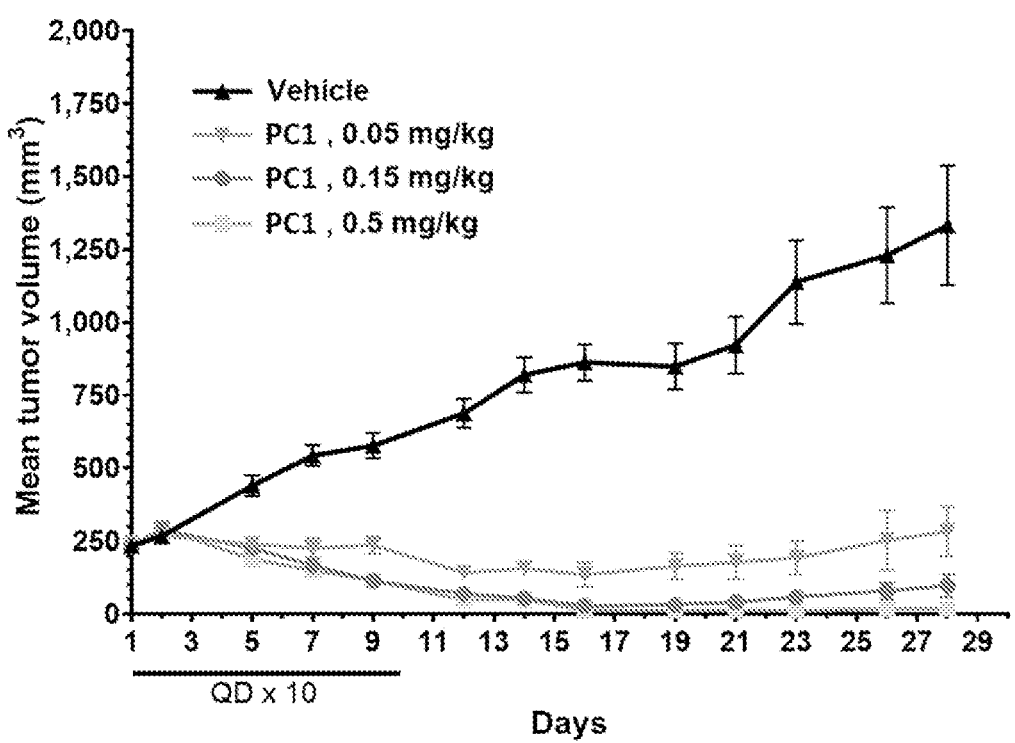
FIG. 25 shows in vivo tumor growth inhibition with different amounts of PC1 in human PBMC engrafted NCG mice bearing HCT116 xenograft tumors.
Figure 26:
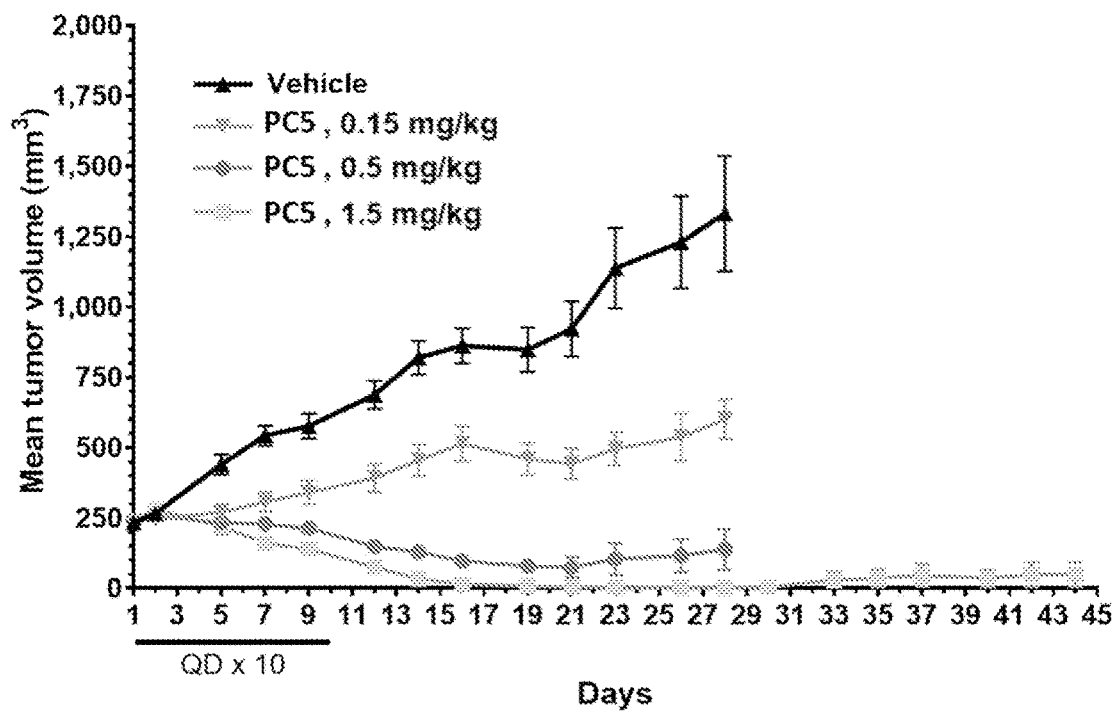
FIG. 26 shows in vivo tumor growth inhibition with different amounts of PC5 in human PBMC engrafted NCG mice bearing HCT116 xenograft tumors.
Figure 27:
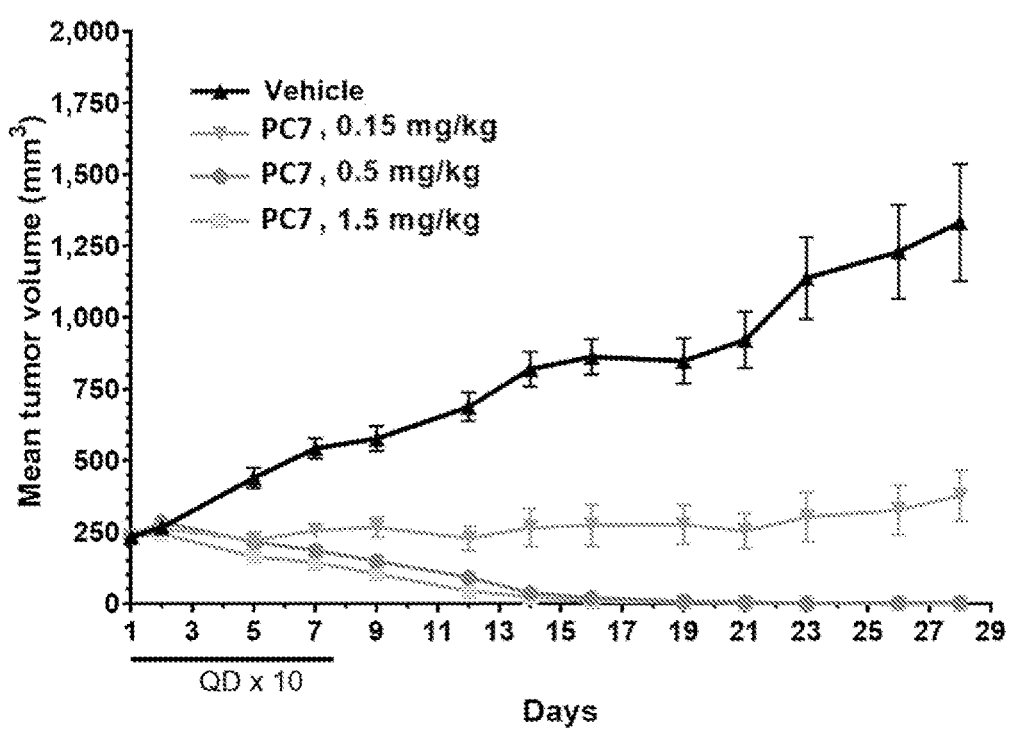
FIG. 27 shows in vivo tumor growth inhibition with different amounts of PC7 in human PBMC engrafted NCG mice bearing HCT116 xenograft tumors.

Of the 679 clonal phage, 20 were selected for peptide synthesis and evaluated for binding and inhibition of EGFR Fab. The sequences of the peptides that were selected for synthesis are shown in Table 23. Binding curves for binding of the peptides to EGFR Fab as measured by ELISA are shown in FIGS. 21-22, and EC$_{50}$s relative to peptide-8 and EGFR-Bio are provided in Tables 24-25. FIGS. 23-24 show dose-dependent inhibition of EGFR Fab binding to the EGFR antigen by the peptides as measured by ELISA. IC$_{50}$ data for binding inhibition by the peptides relative to peptide-8 is provided in Tables 26-27. The binding and inhibition data demonstrate that the phage library identified more potent peptide masks such as peptide-45 and peptide-46.

TABLE 23

Peptide sequences selected for synthesis (EGFR Fab Peptide-8 Optimization)

| Description | Amino Acid Sequence (N to C) | SEQ ID NO: |
|---|---|---|
| Peptide-29 | PCLSPFDTAKPICA | 99 |
| Peptide-30 | PCTSHFDTAKPICT | 100 |
| Peptide-31 | PCTSHFDTAKPICI | 101 |
| Peptide-32 | PCLSHFDTAKPICL | 102 |
| Peptide-33 | PCLSHTDTAKPICA | 103 |
| Peptide-34 | PCLSHHDTAKPICA | 104 |
| Peptide-35 | PCLSHFDTAKPICA | 105 |
| Peptide-36 | PCLSHFDTAKPICV | 106 |
| Peptide-37 | PCLSHNDPAKPICS | 107 |
| Peptide-38 | PCTSQHDTAKPICI | 108 |
| Peptide-39 | PCTSHFDTAKPICA | 109 |

TABLE 23-continued

Peptide sequences selected for synthesis (EGFR Fab Peptide-8 Optimization)

| Description | Amino Acid Sequence (N to C) | SEQ ID NO: |
|---|---|---|
| Peptide-40 | PCLSHTDTAKPICV | 110 |
| Peptide-41 | PCLSHNDPAKPICA | 111 |
| Peptide-42 | PCLSHYDTAKPICA | 112 |
| Peptide-43 | PCNSHYDLAKPICT | 113 |
| Peptide-44 | PCNSHFDIAKPICL | 114 |
| Peptide-45 | PCAYHNDPAKPICS | 115 |
| Peptide-46 | PCLFHFDPAKPICS | 116 |
| Peptide-47 | PCTSHFDPAKPICA | 117 |
| Peptide-48 | PCTSHNDNAKPICA | 118 |

TABLE 24

$EC_{50}$s for peptide binding to αEGFR Fab

| Peptide | $EC_{50}$ (nM) |
|---|---|
| EGFR-Bio (3 nM) | 0.17 |
| Peptide-8 | 699.6 |
| Peptide-29 | 150.6 |
| Peptide-30 | 194.0 |
| Peptide-31 | 171.8 |
| Peptide-32 | 66.55 |
| Peptide-33 | 340.2 |
| Peptide-34 | 377.5 |
| Peptide-35 | 149.2 |
| Peptide-36 | 154.2 |
| Peptide-37 | 358.0 |
| Peptide-38 | 1294 |

TABLE 25

$EC_{50}$s for peptide binding to αEGFR Fab

| Peptide | $EC_{50}$ (nM) |
|---|---|
| EGFR-Bio (3 nM) | 0.17 |
| Peptide-8 | 340.3 |
| Peptide-39 | 206.2 |
| Peptide-40 | 413.7 |
| Peptide-41 | 292.2 |
| Peptide-42 | 63.58 |
| Peptide-43 | 186.4 |
| Peptide-44 | 340.9 |
| Peptide-45 | 10.3 |
| Peptide-46 | 4.9 |
| Peptide-47 | 379.9 |
| Peptide-48 | 536 |

TABLE 26

$IC_{50}$s for peptide inhibition of αEGFR Fab binding to EGFR antigen

| Peptide | $IC_{50}$ (µM) |
|---|---|
| Peptide-8 | 7.76 |
| Peptide-29 | 2.08 |
| Peptide-30 | 4.55 |
| Peptide-31 | 3.72 |
| Peptide-32 | 2.08 |
| Peptide-33 | 2.30 |
| Peptide-34 | 4.91 |
| Peptide-35 | 2.22 |
| Peptide-36 | 1.97 |
| Peptide-37 | 4.16 |
| Peptide-38 | 29.9 |

TABLE 27

$IC_{50}$s for peptide inhibition of αEGFR Fab binding to EGFR antigen

| Peptide | $IC_{50}$ (µM) |
|---|---|
| Peptide-8 | 6.29 |
| Peptide-39 | 2.79 |
| Peptide-40 | 2.66 |
| Peptide-41 | 4.25 |
| Peptide-42 | 2.22 |
| Peptide-43 | 4.23 |
| Peptide-44 | 6.57 |
| Peptide-45 | 0.543 |
| Peptide-46 | 0.300 |
| Peptide-47 | 6.25 |
| Peptide-48 | 8.03 |

Example 13: Anti-Tumor Efficacy in a Mouse Model of Colorectal Cancer

Figure 28:
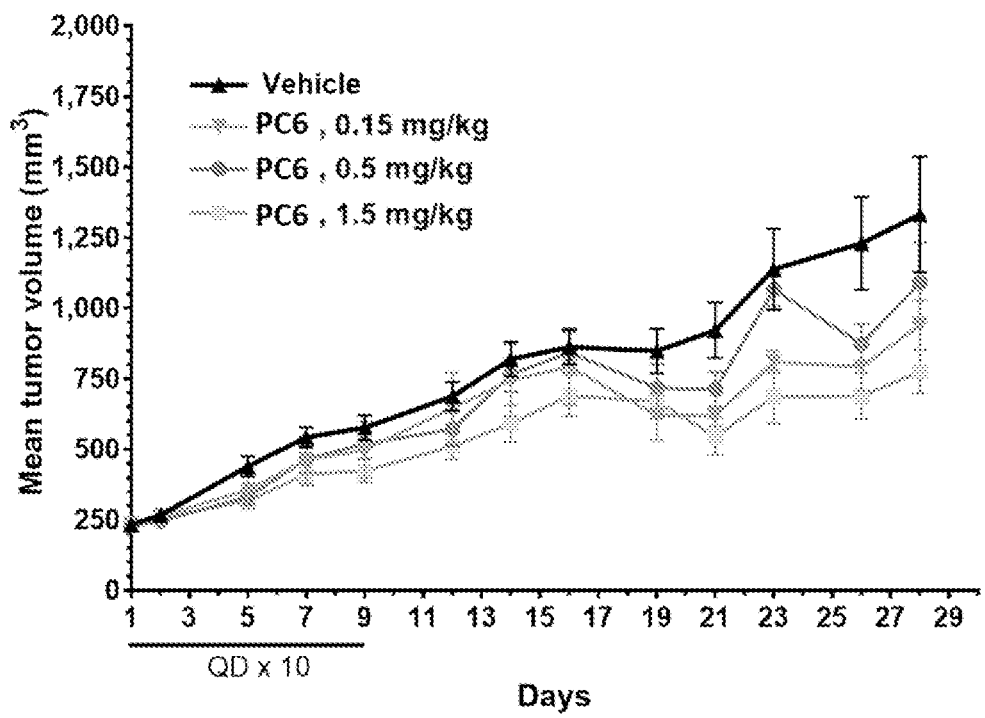
FIG. 28 shows in vivo tumor growth inhibition with different amounts of PC6 in human PBMC engrafted NCG mice bearing HCT116 xenograft tumors.

Female mice were subcutaneously implanted with 5 million HCT116 colorectal tumor cells in 50% matrigel. 20 million human PBMCs were engrafted via the tail vein the same day as HCT116 inoculation. When tumors reached 250 mm³, mice were randomized into groups and compounds were dosed intravenously every day for 10 days. Tumor volume was measured every two to three days and plotted overtime. The tumor volume growth kinetics indicate anti-tumor activity of masked EGFR targeted bispecific compounds. The anti-tumor activity observed was protease dependent in that the compound lacking the protease substrate within the cleavable linker was equivalent to vehicle controls. FIGS. 25-28 show the in vivo tumor growth inhibition data with different dosing amounts of PC1 (FIG. 25), PC5 (FIG. 26), PC7 (FIG. 27), and PC6 (FIG. 28).

Figure 29:
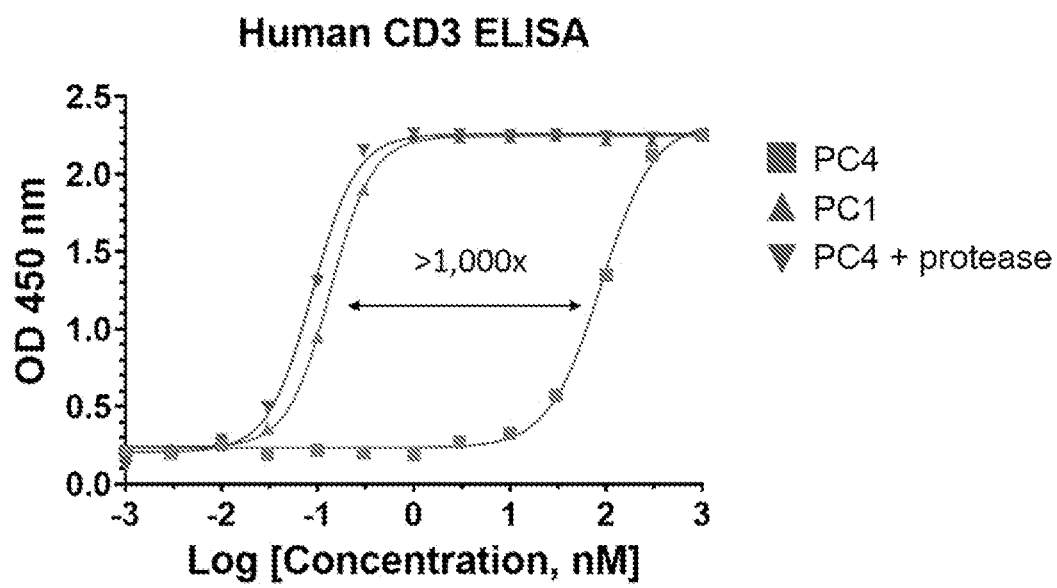
FIG. 29 shows PC1 and PC4 binding to human CD3ε as measured by ELISA. PC4 was treated with protease where indicated.
Figure 30:
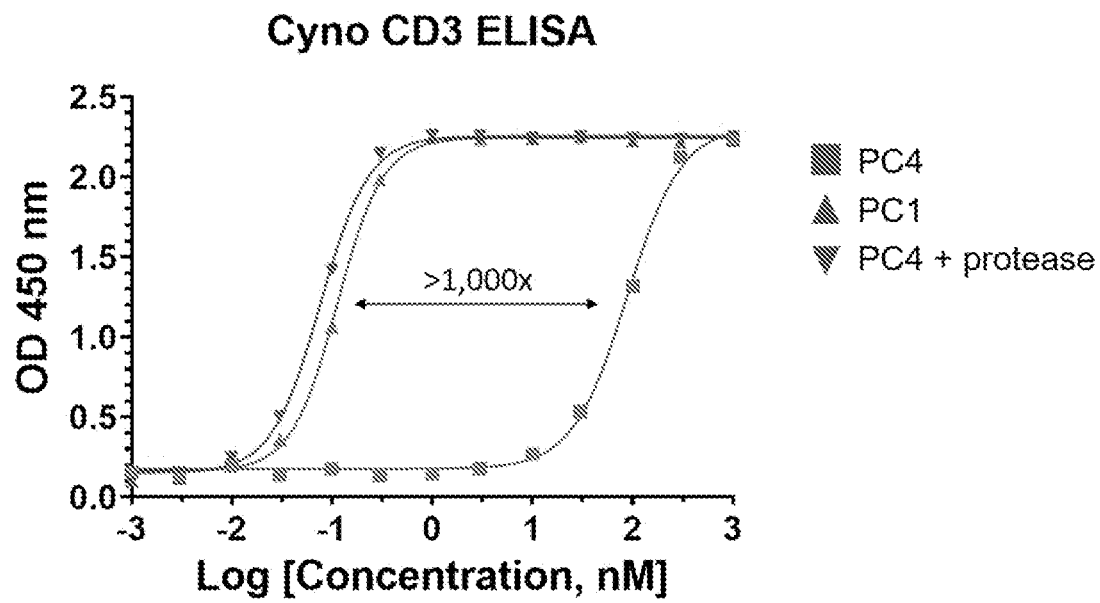
FIG. 30 shows PC1 and PC4 binding to cynomolgus monkey CD3ε as measure by ELISA. PC4 was treated with protease where indicated.
Figure 31:
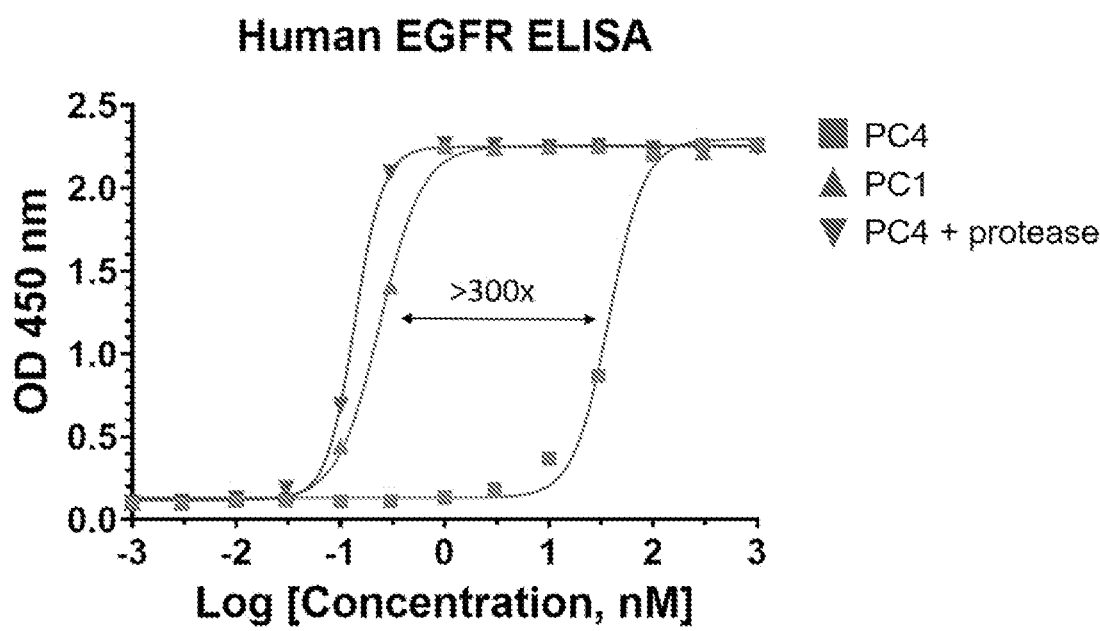
FIG. 31 shows PC1 and PC4 binding to human EGFR as measured by ELISA. PC4 was treated with protease where indicated.
Figure 32:
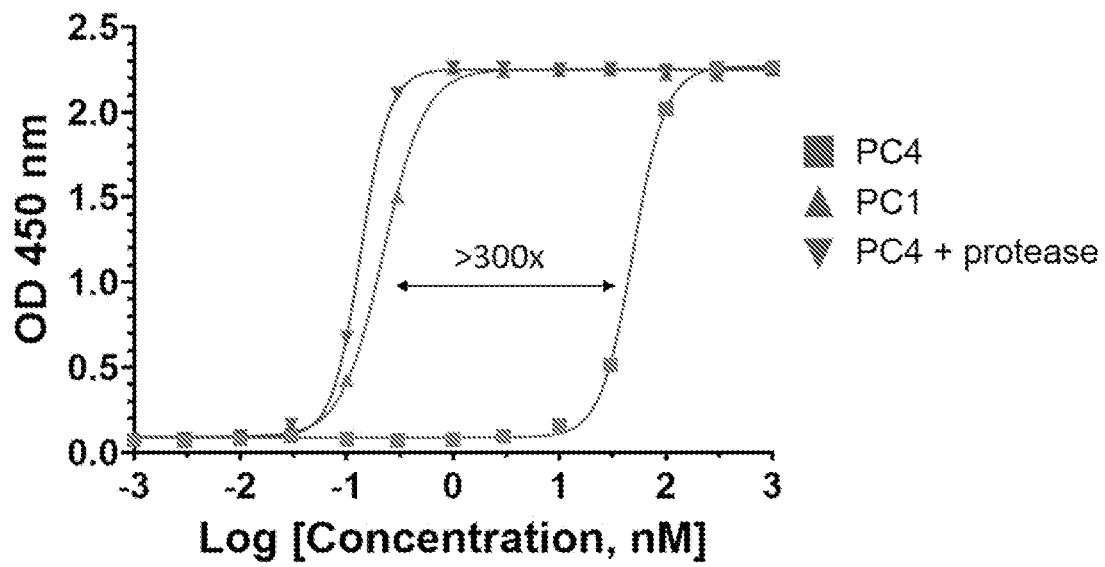
FIG. 32 shows PC1 and PC4 binding to cynomolgus EGFR as measured by ELISA. PC4 was treated with protease where indicated.
Figure 33:
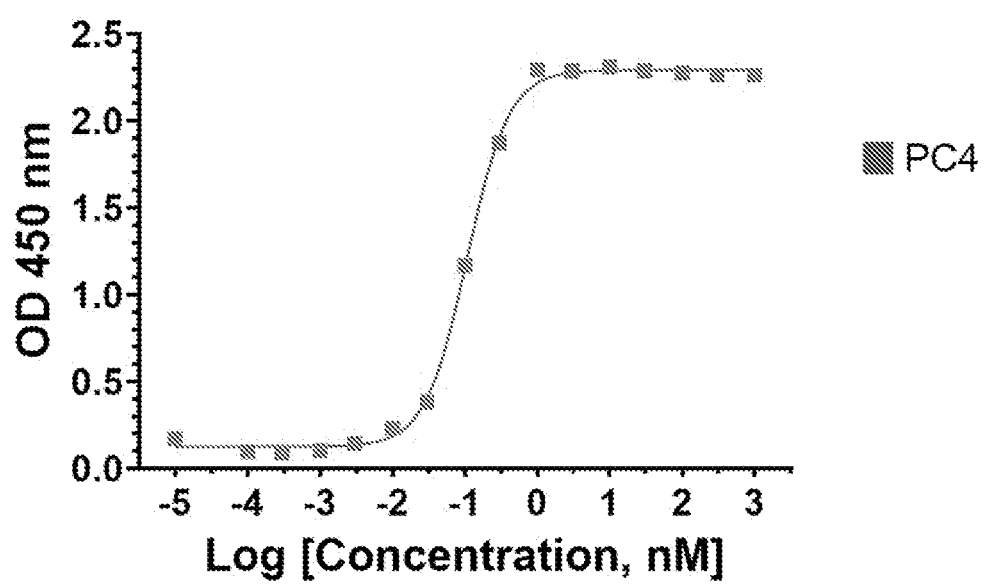
FIG. 33 shows PC4 binding to human albumin as measured by ELISA.
Figure 34:
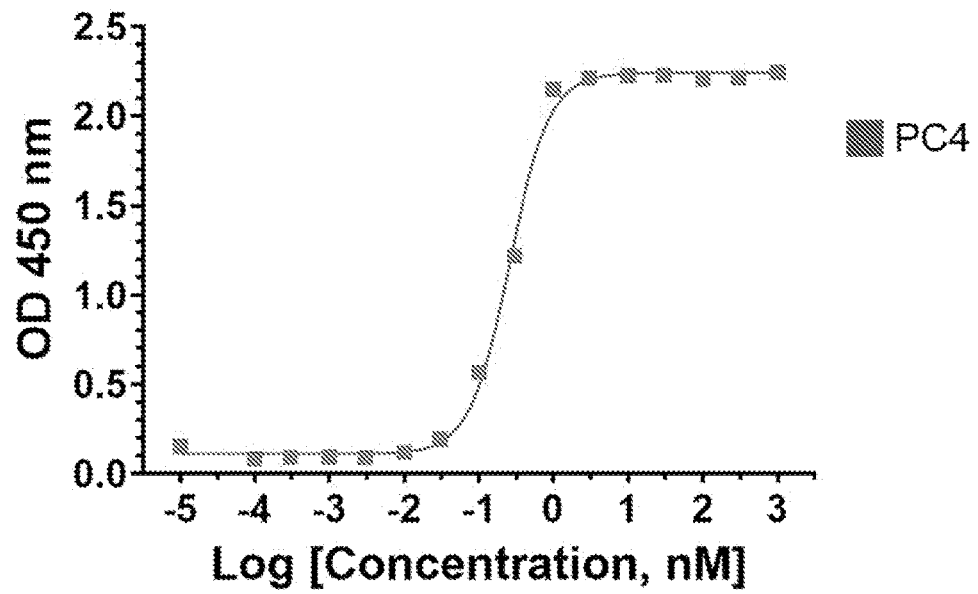
FIG. 34 shows PC4 binding to cynomolgus monkey albumin as measured by ELISA.

Example 14: Binding of PC1 and PC4 to Human and Cynomolgus CD3R, EGFR, and Albumin Polypeptide complexes PC1 and PC4 were evaluated for binding to human and cynomolgus monkey CD3ε, EGFR, and albumin by ELISA. Briefly, biotinylated antigen was captured on neutravidin coated plates. Polypeptide complex molecules were treated with active protease where indicated. Polypeptide complex molecules diluted in buffer were then added to the antigen coated plates. Bound polypeptide complex was detected using a standard horse radish peroxidase conjugate secondary antibody. Binding curves were fit using Graphpad Prism software. Binding curves for PC1 and PC4 binding to human and cynomolgus monkey CD3ε are shown in FIGS. 29 and 30, respectively. Binding curves for PC1 and PC4 binding to human and cynomolgus monkey EGFR are shown in FIGS. 31 and 32, respectively. As can be seen from the curves, target engagement is cleavage dependent as masking reduces CD3ε and EGFR binding by more than 1000-fold and more than 300-fold, respectively. Treatment of PC4 with protease enzyme enables potent antigen binding comparable to non-masked PC1. Binding curves for PC4 binding to human and cynomolgus monkey albumin are shown in FIGS. 33 and 34, respectively. As can be seen, PC4 exhibits potent binding to both human and monkey albumin.

Example 15: Polypeptide Complex Mediated Tumor Cytotoxicity and T Cell Activation (A549 Cells)

Figure 35:
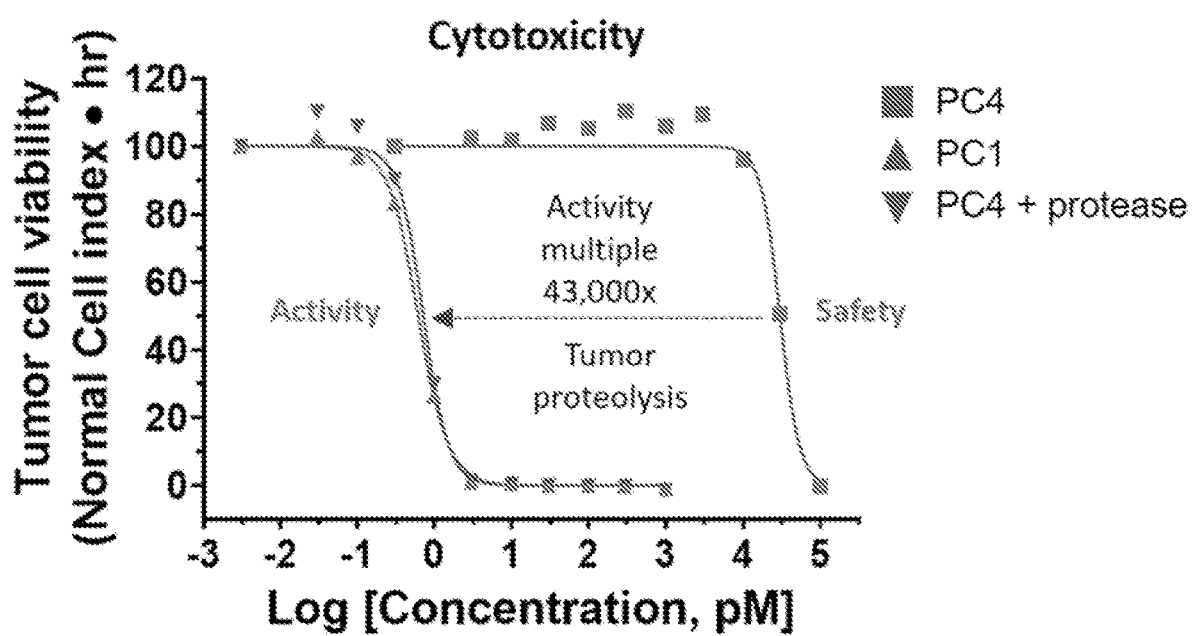
FIG. 35 shows PC1 and PC4 mediated killing of A549 cells in the presence of peripheral blood mononuclear cells (PBMCs). PC4 was treated with protease where indicated.
Figure 36:
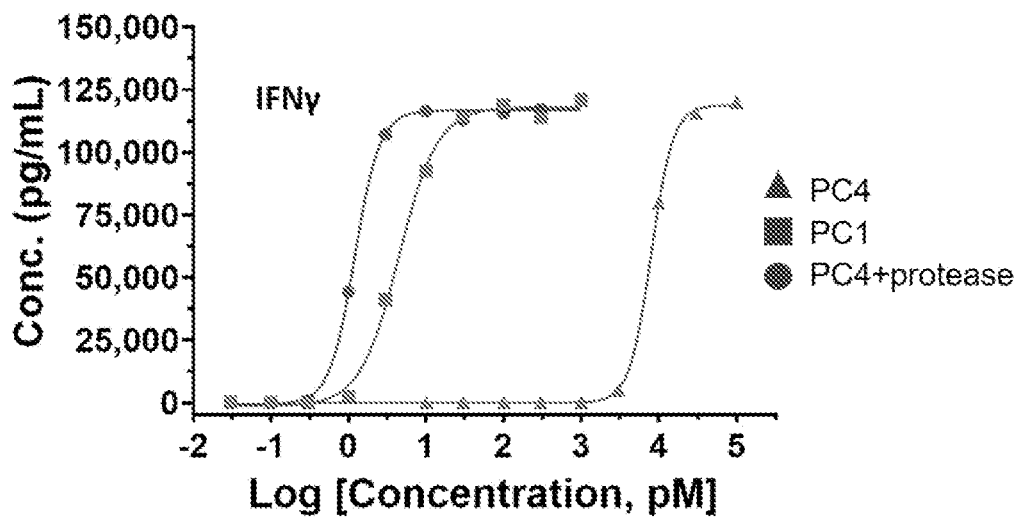
FIG. 36 shows IFNγ cytokine levels in EGFR positive HCT116 tumor cells with increasing concentrations of PC4 and PC1. PC4 was protease treated where indicated.
Figure 37:
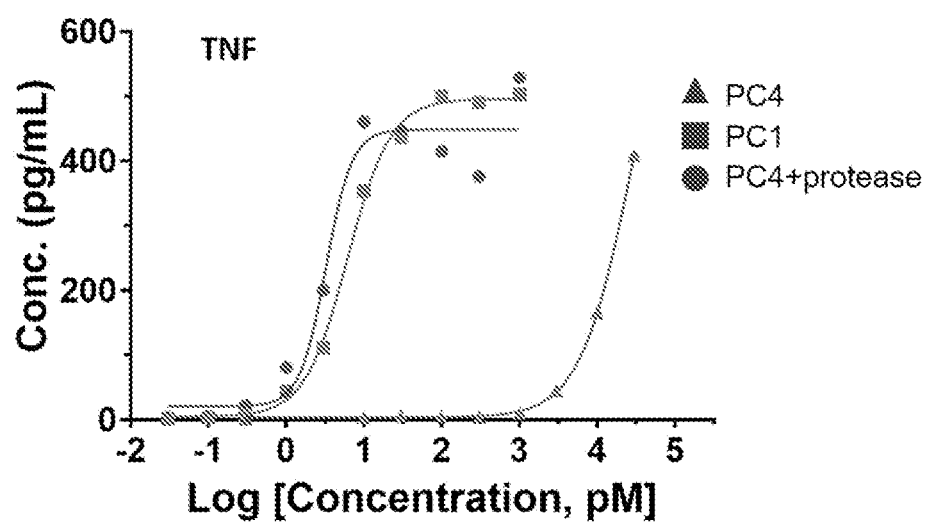
FIG. 37 shows TNF cytokine levels in EGFR positive HCT116 tumor cells with increasing concentrations of PC4 and PC1. PC4 was protease treated where indicated.

Polypeptide complexes were evaluated in a functional in vitro tumor cell killing assay using the EGFR positive tumor cell line A549. Tumor cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. Tumor cells were added per well and allowed to adhere overnight on a 96 well E-Plate. The following day polypeptide complexes titrated in human serum supplemented medium along with human PBMCs were added to the wells. Cell index measurements were taken every 10 minutes for an additional 72 hours. The cell index times number of hours (tumor cell growth kinetics) was then plotted versus logarithmic concentration of polypeptide complex where the concentration required to reduce the tumor growth 50% ($IC_{50}$) was calculated using Graphpad Prism software. FIG. 35 shows a graph of PC1 and PC4 mediated A549 tumor cell killing in the presence of PBMCs. PC4 was treated with protease where indicated. Protease treatment increased the activity of PC4 by about 43000-fold relative to untreated PC4. The activity level of protease treated PC4 was comparable to that of non-masked PC1 (see FIG. 35).

Figure 38:
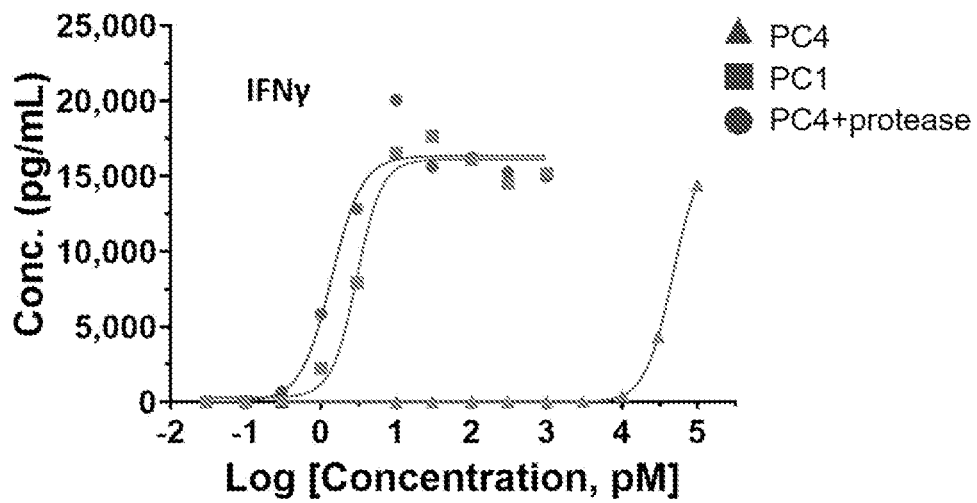
FIG. 38 shows IFNγ cytokine levels in EGFR positive A549 tumor cells with increasing concentrations of PC4 and PC1. PC4 was protease treated where indicated.
Figure 39:
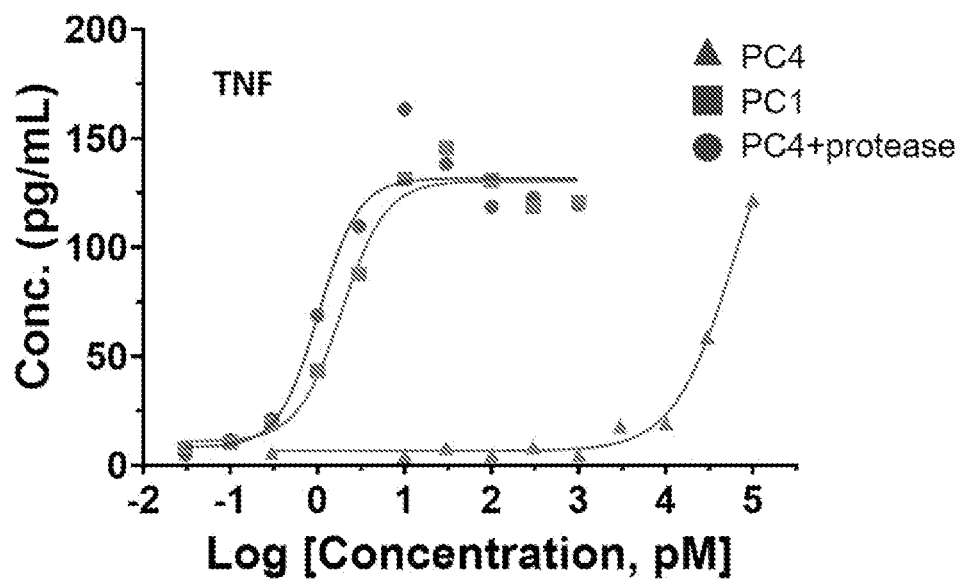
FIG. 39 shows TNF cytokine levels in EGFR positive A549 tumor cells with increasing concentrations of PC4 and PC1. PC4 was protease treated where indicated.

Example 16: Evaluation of Polypeptide Complex in an In Vitro Cytokine Induction Assay Polypeptide complexes PC1 and PC4 were evaluated in a functional in vitro cytokine induction assay using the EGFR positive tumor cell lines HCT116 (colorectal cancer (CRC) cells—KRAS and PIK3CA mutant) and A549 (non-small cell lung cancer (NSCLC) cells—KRAS mutant). T cell cytokine induction was measured using an Meso Scale Discovery (MSD) electrochemiluminescence instrument. Tumor cells were added to wells and allowed to adhere overnight on a 96 well. The following day polypeptide complexes titrated in human serum supplemented medium along with human PBMCs. Supernatants were harvested 72 hours later and measured for cytokine levels (interferon gamma (IFNγ) and tumor necrosis factor (TNF)). Cytokine levels were then plotted versus logarithmic concentration of polypeptide complex where the concentration required to induce 50% ($EC_{50}$) of the maximum was calculated using Graphpad Prism software. FIGS. 36-39 show cytokine levels with increasing concentrations of PC1 and PC4 in HCT116 cells (FIGS. 36-37) and in A549 cells (FIGS. 38-39). PC4 was treated with protease where indicated. Masking of PC4 EGFR and CD3 binding domains reduces the capacity to induce cytokine release. Additionally, the functional activity against KRAS mutant anti-EGFR resistant CRC and NSCLC cell lines in T cell co-culture assays was found to be cleavage dependent. Protease-treated PC4 exhibits similar potency relative to non-masked PC1.

Example 17: Activity in HCT116 Mouse Tumor Model

Figure 40:
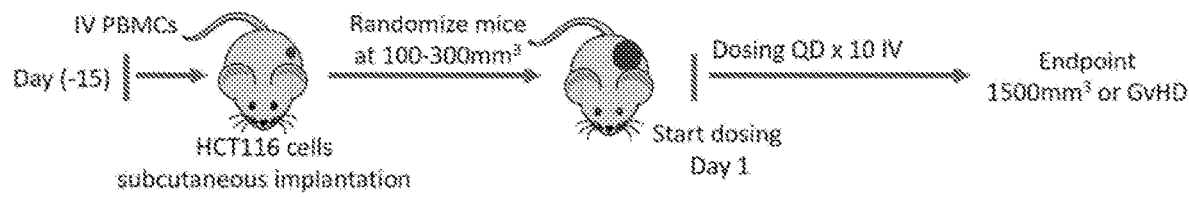
FIG. 40 shows a schematic representation of a HCT116 mouse tumor model study of the present disclosure.
Figure 41:
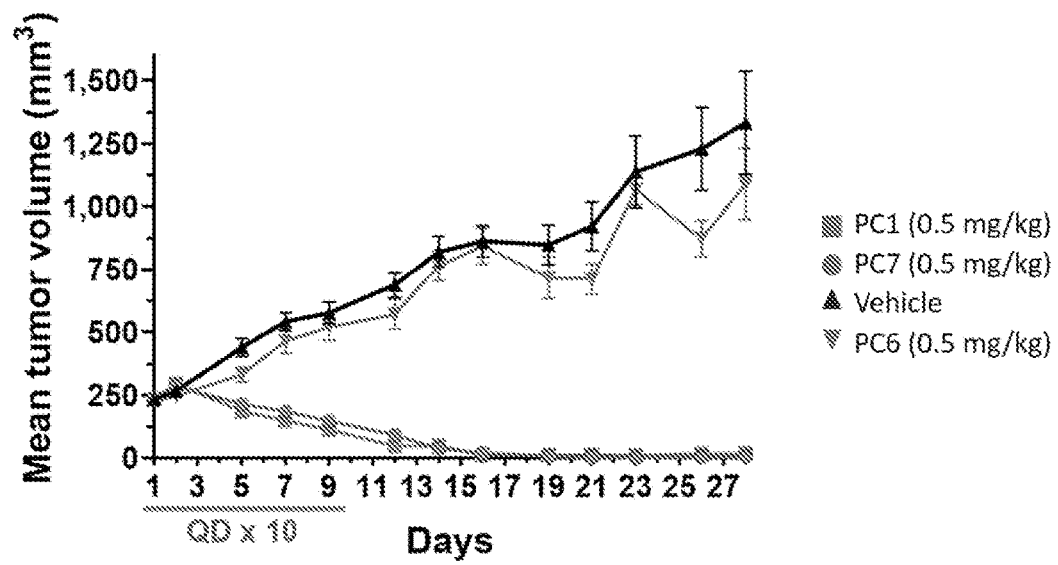
FIG. 41 shows mean tumor volume versus days of treatment with PC1, PC7, and PC6 in PBMC engrafted mice implanted with HCT116 tumor cells.
Figure 42:
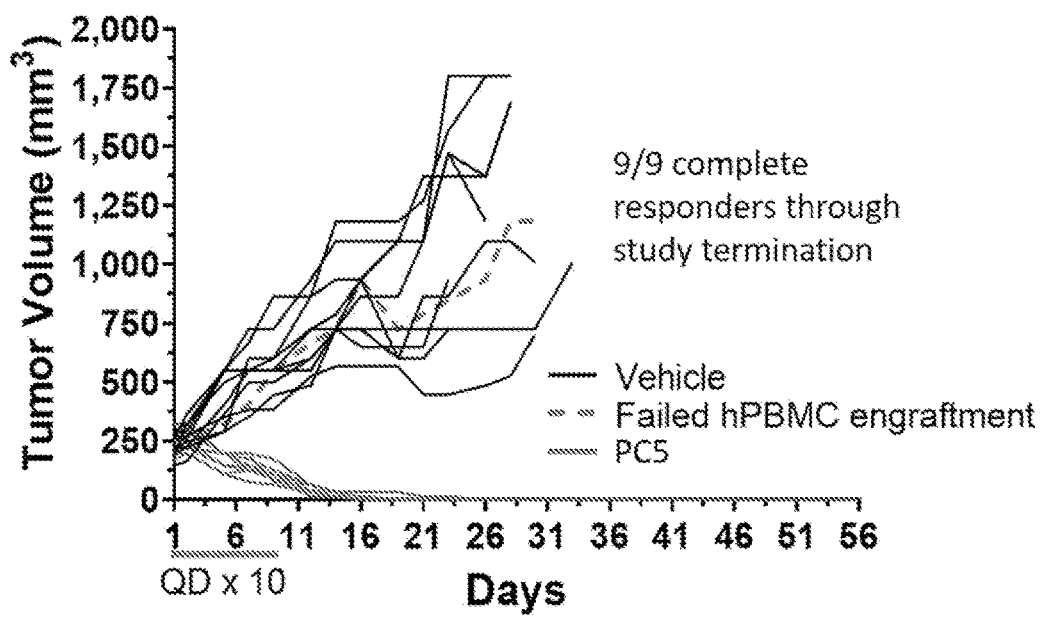
FIG. 42 shows tumor volume versus days of treatment with PC5 and vehicle in PBMC engrafted mice implanted with HCT116 tumor cells.
Figure 43:
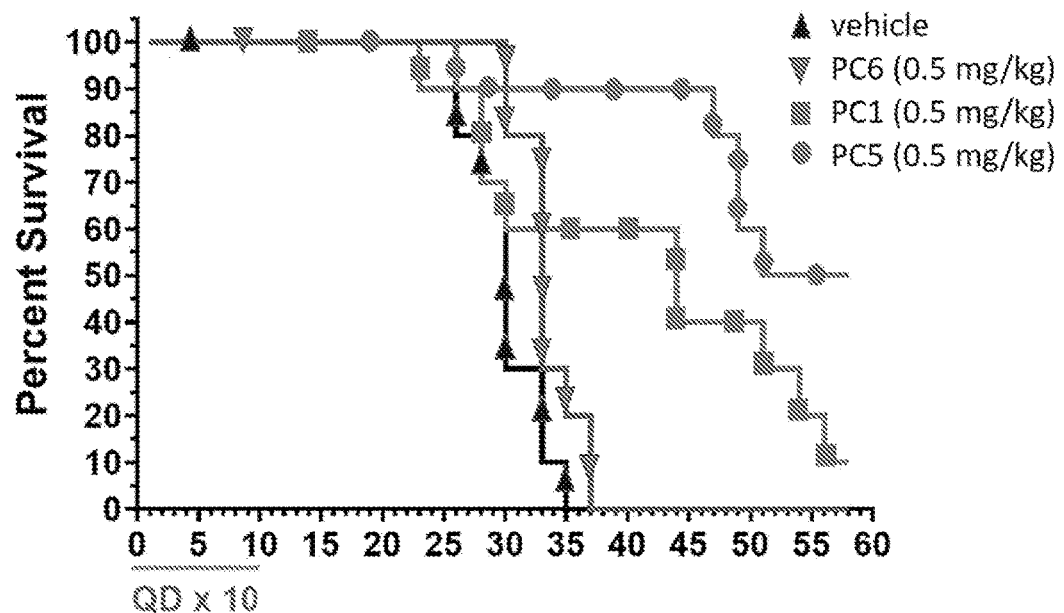
FIG. 43 shows percent survival in PBMC engrafted mice implanted with HCT116 tumor cells with treatment with PC1, PC5, and PC6.

Polypeptide complexes were evaluated in a mouse tumor model study. Female mice were subcutaneously implanted with 5 million HCT116 colorectal tumor cells in 50% matrigel. 20 million human PBMCs were engrafted via the tail vein the same day as HCT116 inoculation. When tumors reached 250 mm$^3$, mice were randomized into groups and compounds were dosed intravenously every day for 10 days (see FIG. 40). Tumor volume was measured every two to three days and plotted overtime. The tumor volume growth kinetics indicate that anti-tumor activity of masked EGFR targeted bispecific compounds is similar to that of the non-masked compound. The anti-tumor activity observed was protease dependent in that the compound lacking the protease substrate within the cleavable linker (non-cleavable) was equivalent to vehicle controls. Survival plots were generated based on number of mice alive in the study versus time. FIG. 41 shows a plot of mean tumor volume versus days of treatment for PC1 (0.5 mg/kg), PC7 (0.5 mg/kg), non-cleavable PC6 (0.5 mg/kg), and vehicle treated mice. FIG. 42 shows a plot of tumor volume versus days of treatment for vehicle and PC5 treated mice. Percent survival of mice versus days of treatment with PC1 (0.5 mg/kg), PC5 (0.5 mg/kg), non-cleavable PC6 (0.5 mg/kg), and vehicle is shown in FIG. 43. Cleavable PC7 and PC1 at equivalent dose levels were found to induce complete tumor eradication in human PBMC engrafted mice implanted with anti-EGFR resistant KRAS- and PIK3CA-mutant HCT116 human tumor cells (see FIG. 41).

Figure 44:
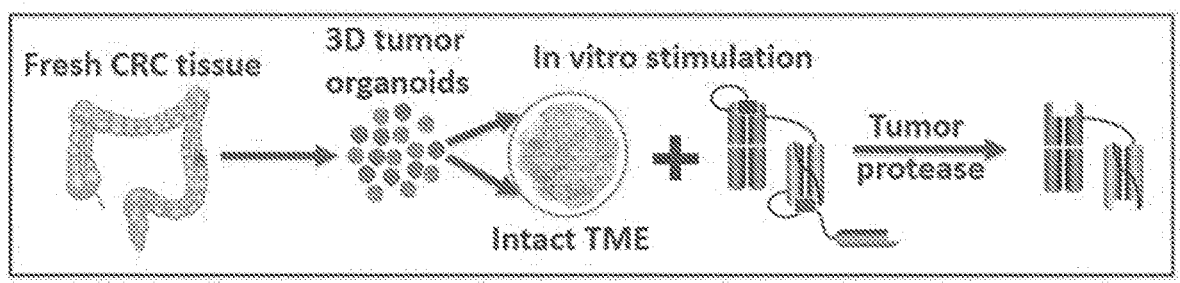
FIG. 44 shows a schematic representation a human colorectal cancer (CRC) organoid study of the present disclosure.
Figure 45:
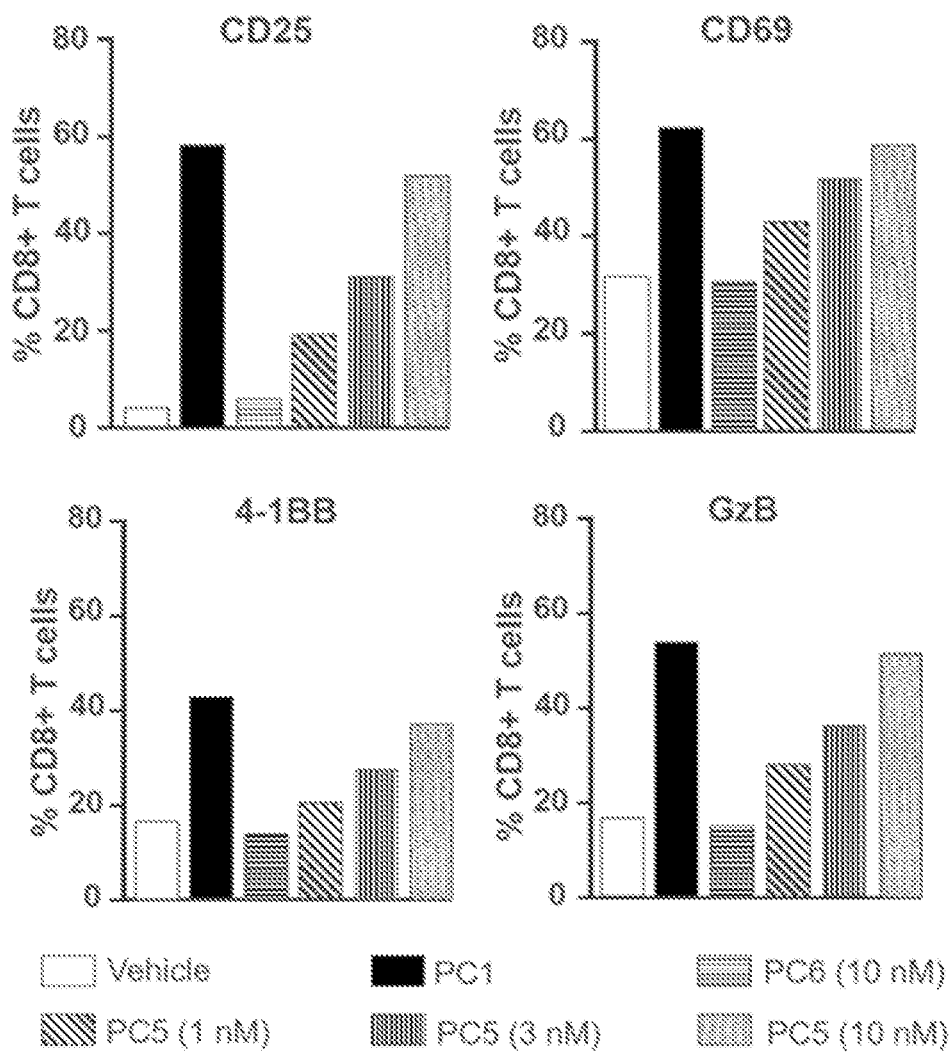
FIG. 45 shows induction of activation markers CD25, CD69, 4-1BB, and Granzyme with PC1 and PC5 in human colorectal cancer tumoroids.

Example 18: Cleavage-Dependent Activity in Human Colorectal Cancer (CRC) Organoids Fresh tumor tissue was procured from colorectal cancer patients, separated into small three-dimensional tumoroids without disruption of the underlying immune compartment or tumor microenvironment, and distributed to 96 well plates. Fresh tumoroids were treated with polypeptide complexes and maintained in culture for 24 to 72 hours (see FIG. 44). At the end of the study, tumoroids were digested and stained using fluorescently labeled antibodies that bind cell markers CD25, CD69, 4-1BB, and Granzyme-B (GzB). Stained cells were run via flow cytometry and fluorescent signals were gated on live cells. Percent of positively stained cells for a given marker were plotted for each polypeptide treatment condition. Referring to FIG. 45, upregulation of CD25, CD69, 4-1BB, and Granzyme was protease cleavage dependent where the polypeptide complex PC6 lacking cleavable substrate (non-cleavable) was inactive and equivalent to vehicle control. The cleavable and non-masked polypeptide complexes were active and able to induce activation markers within the tumor resident immune compartment in these primary human colorectal cancer tumoroids (see FIG. 45). Furthermore, concentration-dependent activity of PC5 was observed (see FIG. 45).

Example 19: Non-Human Primate (NHP) Toxicity Studies

Figure 46:
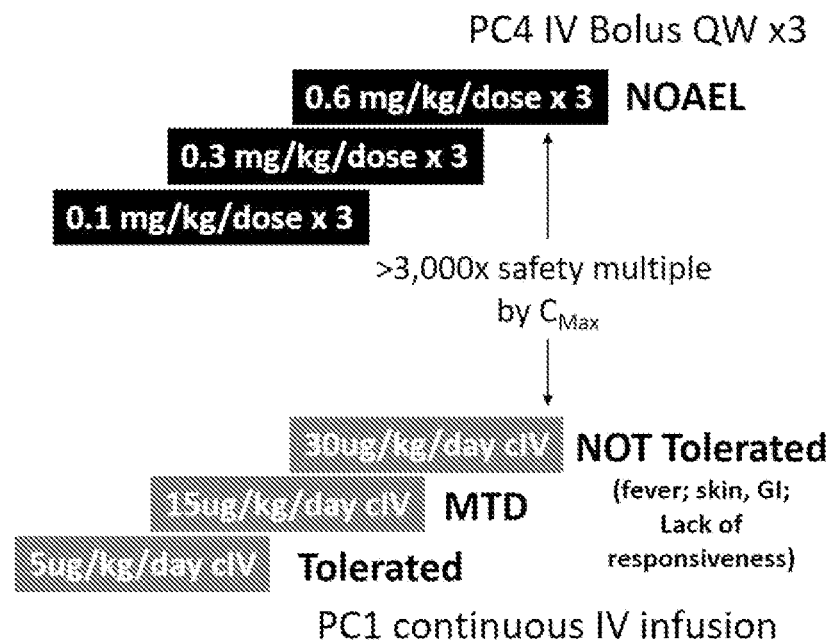
FIG. 46 shows maximum tolerated dose (MTD) for PC1 and no observed adverse effect level (NOAEL) for PC4 in cynomolgus monkeys.
Figure 47:
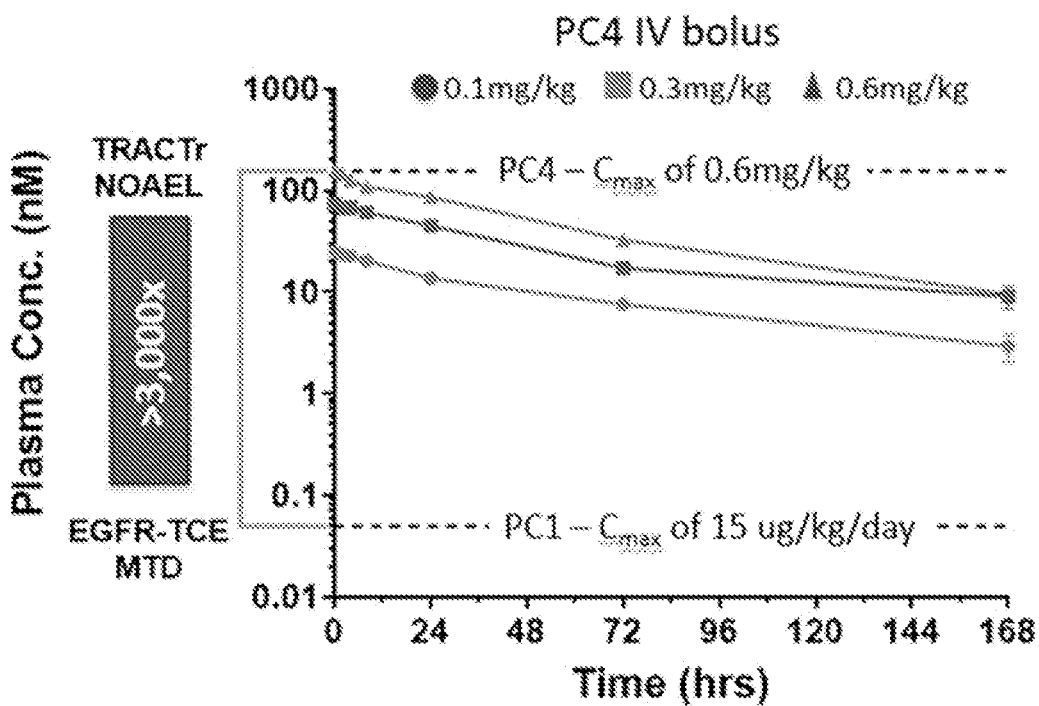
FIG. 47 shows pharmacokinetics in cynomolgus monkeys with different dosing amounts of PC4 after IV bolus injections.

Pharmacokinetics and exploratory safety of polypeptide molecules PC1 and PC4 were evaluated in cynomolgus monkeys. Briefly, cynomolgus monkeys of approximately 3 kg bodyweight were administered polypeptides as an IV bolus once weekly for three weeks or via continuous IV infusion. Animals were observed daily for signs of adverse events. PC1 was dosed at 5 µg/kg/day, 15 µg/kg/day, and 30 µg/kg/day via continuous IV (cIV) infusion. Dosing amounts of 0.1 mg/kg/dose, 0.3 mg/kg/dose, and 0.6 mg/kg/dose was used for PC4 via IV bolus injections. After dosing, blood was collected in K2 EDTA tubes at specific timepoints and processed to plasma. Plasma was stored frozen until analysis. Concentration of polypeptide molecules in plasma was measured via standard ELISA techniques relative to a reference standard diluted in control cynomolgus monkey plasma. Maximum plasma concentrations achieved in animals for masked polypeptide complex PC4 were compared to those achieved using the non-masked polypeptide complex PC1. Comparison of the maximum plasma concentration achieved with the masked polypeptide complex compared to the maximum tolerated plasma concentration for the non-masked polypeptide complex revealed a >3,000× multiple (see FIGS. 46-47). The masked polypeptide complex had no adverse events in the animals at the highest dose tested of 0.6 mg/kg/dose (see FIG. 46). The maximum tolerated dose (MTD) of the non-masked polypeptide complex PC1 was 15 µg/kg/day by continuous IV infusion. Animals dosed with 30 µg/kg/day continuous IV infusion of the non-masked polypeptide complex was not tolerated due to severe adverse events (see FIG. 46). The PC4 toxicity studies support its enhances pharmacokinetics, safety, and design. Notably, PC4 administered once weekly for three weeks was well tolerated without clinical observations or notable changes in clinical chemistry, hematology, or pathology. In contrast, PC1 dosed by continuous IV infusion at 15 µg/kg/day had increased body temperature and increased liver enzymes. Treatment with PC1 at 30 µg/kg/day by continuous IV infusion had to be terminated 24 hrs after dosing due to severe adverse events, including fever, skin rash, GI toxicities, and lack of responsiveness in the animals (see FIG. 46). Clinical observations, body temperature, and clinical pathology measurements support the large safety multiple (>3,000×) for PC4 relative to non-masked PC1. PC4 was found to reduce cytokine release and healthy tissue toxicities (GI, Liver, skin) at high exposures in cynomolgus monkeys despite broad tissue expression of EGFR. The NOAEL (no observed adverse effect level) for PC4 is ≥0.6 mg/kg/dose weekly IV bolus for three weeks (see FIG. 46).

Example 20: EGFR Polypeptide Complex Binding of PC10 and PC11

The EGFR-CD3 polypeptide complexes were evaluated for EGFR and CD3ε binding.

Briefly, the polypeptide complex molecules were evaluated for their ability to bind EGFR as well as CD3 in a standard enzyme linked immunosorbent assay (ELISA) format. Polypeptide complex binding of EGFR or CD3 were measured before and after protease treatment. Briefly, biotinylated antigen was captured on neutravidin coated plates. Polypeptide complex molecules were treated with active matriptase (MTSP1) where indicated. Polypeptide complex molecules diluted in buffer were then added to the antigen coated plates. Bound polypeptide complex was detected using a standard horse radish peroxidase conjugate secondary antibody. The concentration of polypeptide complex required to achieve 50% maximal signal (EC50) was calculated using Graphpad Prism software.

Figure 48:
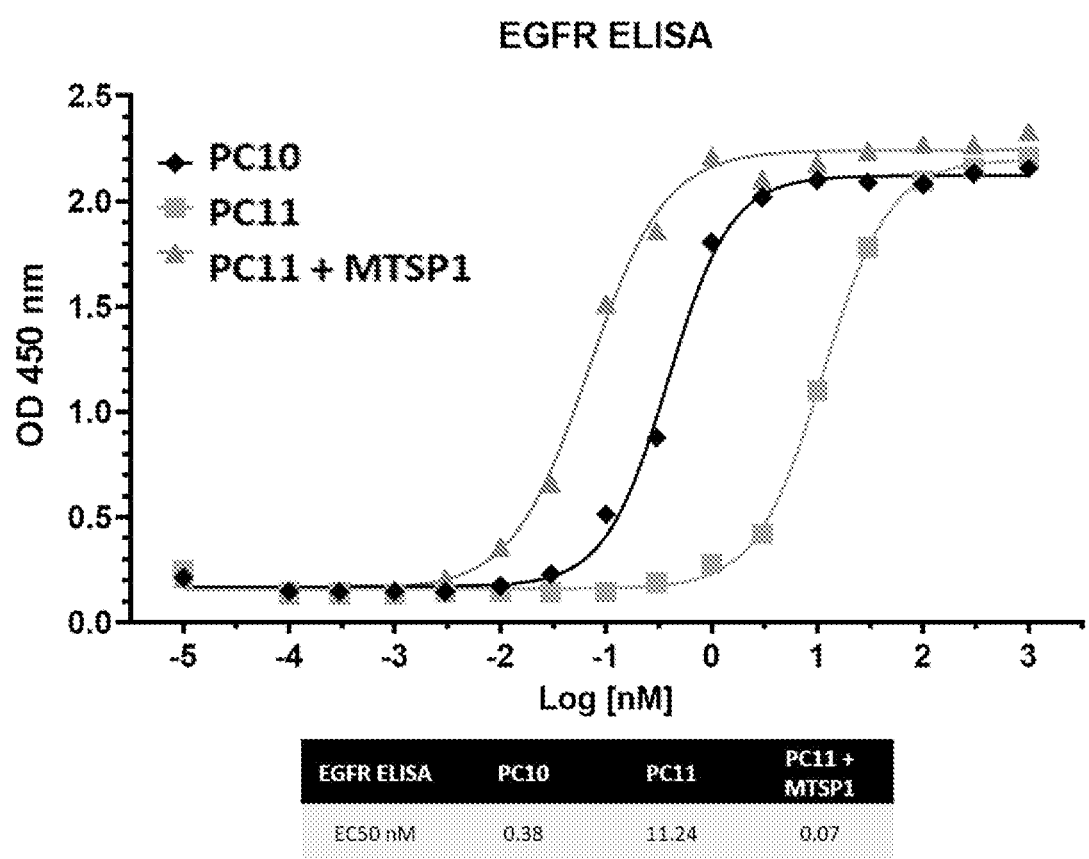
FIG. 48 shows PC10 and PC11 binding to EGFR measured by ELISA.

FIG. 48 shows PC10 and PC11 binding to EGFR measured by ELISA.

Figure 49:
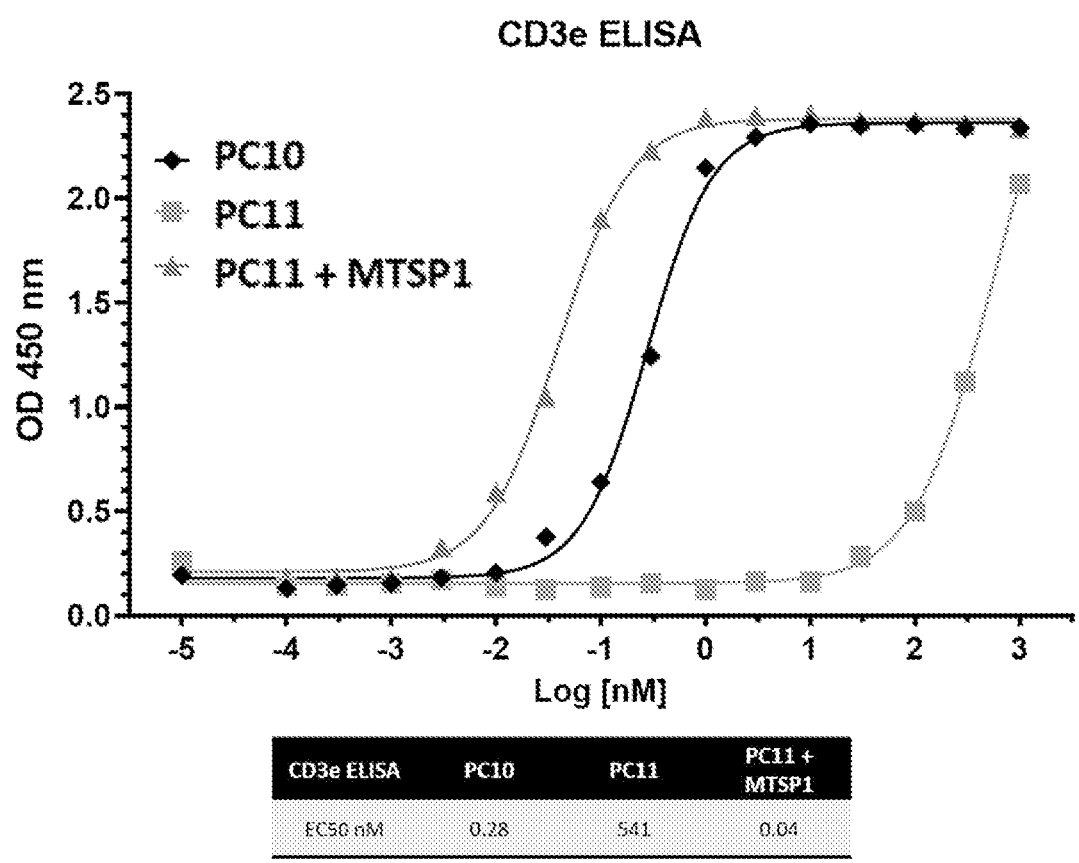
FIG. 49 shows PC10 and PC11 binding to CD3 measured by ELISA.

FIG. 49 shows PC10 and PC11 binding to CD3 measured by ELISA.

Example 21: PC10 and PC11 Mediated Tumor Cytotoxicity and T Cell Activation

Polypeptide complexes PC10 and PC11 were evaluated in a functional in vitro tumor cell killing assay using the EGFR positive tumor cell line HCT116. Tumor cell killing was measured using an xCelligence real time cell analyzer from Agilent that relies on sensor impedance measurements (cell index) that increased as tumor cells adhere, spread, and expand on the surface of the sensor. Likewise, as the tumor cells were killed the impedance decreased. 10,000 tumor cells were added per well and allowed to adhere overnight on a 96 well E-Plate. The following day polypeptide complexes titrated in human serum supplemented medium along with 30,000 CD8+ T cells were added to the wells. Cell index measurements were taken every 10 minutes for an additional 72 hours. The cell index times number of hours (tumor cell growth kinetics) was then plotted versus concentration of polypeptide complex where the concentration required to reduce the tumor growth 50% ($IC_{50}$) was calculated using Graphpad Prism software.

Figure 50:
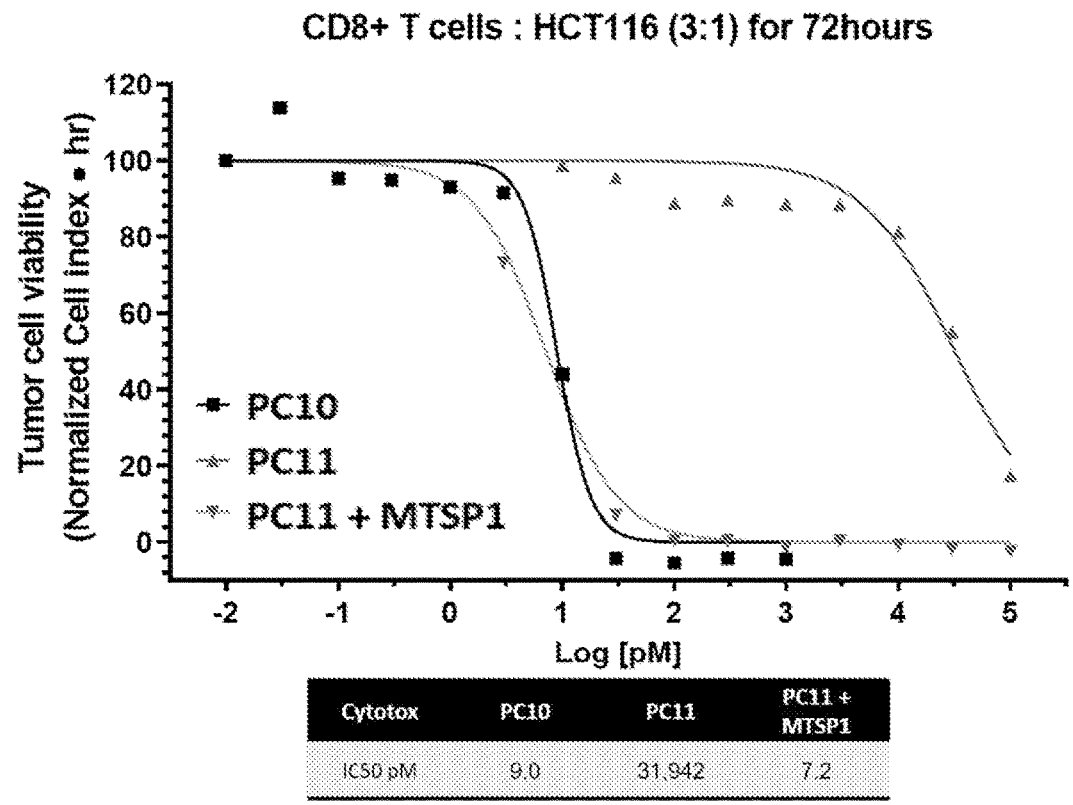
FIG. 50 shows a graph of PC10 and PC11 mediated HCT116 tumor cell killing in the presence of CD8+ T cells.

FIG. 50 shows a graph of PC10 and PC11 mediated HCT116 tumor cell killing in the presence of CD8+ T cells.

Example 22: Optimized Phase Library Construction—CD3 scFv Peptides

Sequence activity relationships (SAR) were established for Peptide-A and Peptide-B by mutating each individual residue within the peptide to alanine and measuring binding and inhibition against SP34.185 scFv. Peptide residues whose alanine mutations significantly weakened binding and inhibition can be considered critical residues where mutations were not tolerated. Peptide residues whose alanine mutations performed similarly to the non-mutated sequence can be considered non-critical sites where mutations were indeed tolerated. Using the peptide SAR, DNA oligo libraries were constructed where codons encoding critical residues within each peptide sequence were minimally mutated and codons encoding non-critical residues were heavily mutated. The resulting oligos were cloned into bacteriophage vectors used to display the SAR guided peptides via fusion to the pIII filament of the bacteriophage. The relevant vectors were then used to produce the phage optimization libraries via amplification in bacteria using standard techniques in the field.

Peptides were evaluated for their ability to bind SP34.185 scFv by standard enzyme linked immunosorbent assays (ELISAs). Briefly, biotinylated peptides were captured on neutravidin coated plates, quenched with biocytin followed by a washing step. SP34.185 scFv was then titrated onto the peptide captured plates. Plates were then washed and bound SP34.185 scFv was detected using a secondary horse radish peroxidase antibody conjugate. After washing again, plates were developed using standard ELISA techniques and stopped using acid. The concentration of SP34.185 scFv required to achieve 50% maximal signal or $EC_{50}$ was calculated using Graphpad prism. Data is shown in FIGS. 51A-51F and summarized in Tables 28A-28D. Peptide Sequences of CD3 Ala Scan Peptides for Peptide A and Peptide-B are shown in Table 30.

TABLE 28A

Figure 51A:
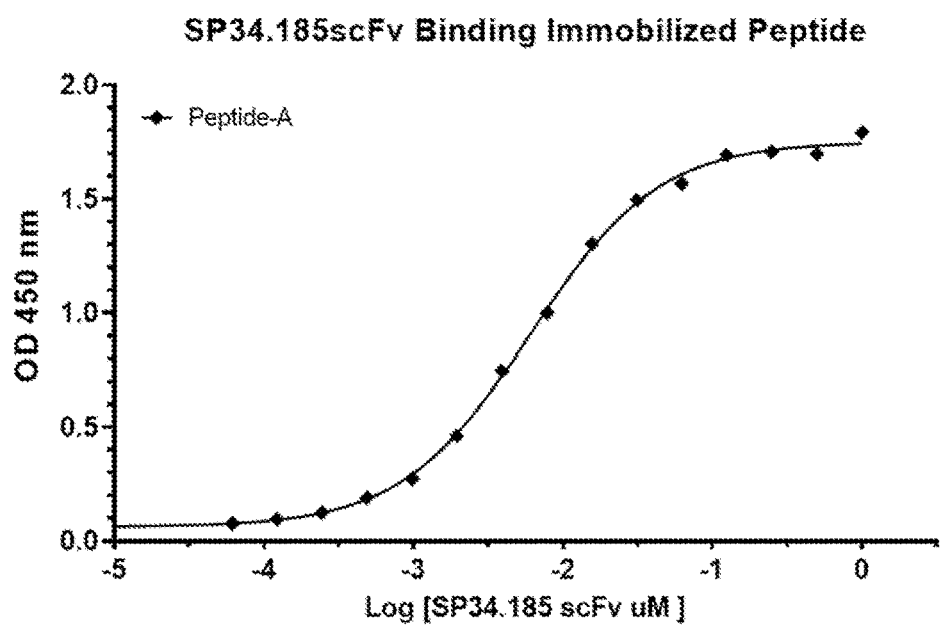
FIGS. 51A-51F illustrate anti-CD3 scFv binding by alanine scanning peptides of anti-CD3 scFv Peptide-A and Peptide-B as measured by ELISA.
Figure 51B:
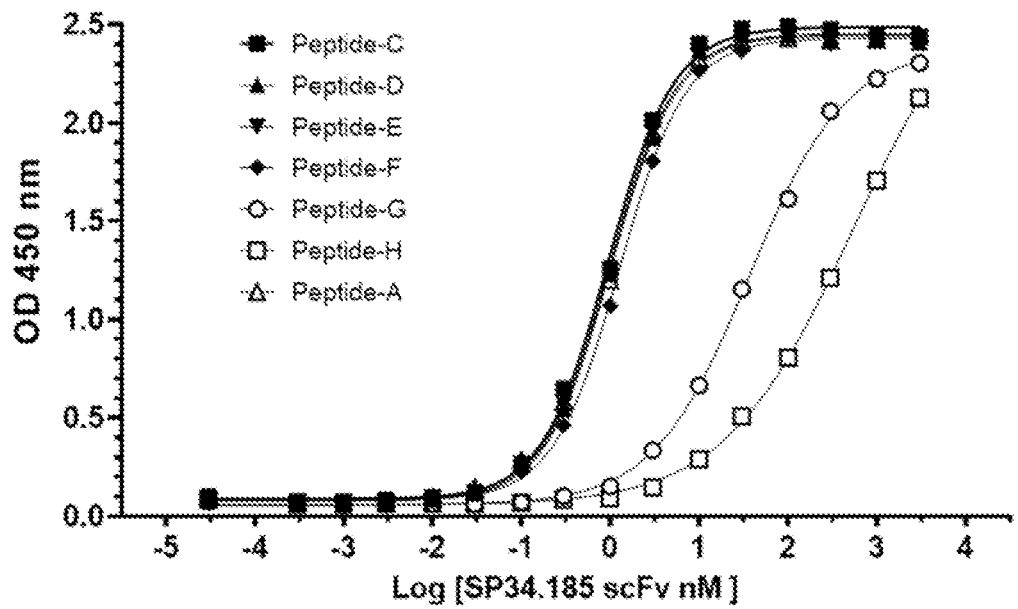

Summary of FIG. 51B

| ELISA | Peptide-A | Peptide-C | Peptide-D | Peptide-E | Peptide-F | Peptide-G | Peptide-H |
|---|---|---|---|---|---|---|---|
| $EC_{50}$ nM | 1.013 | 0.9429 | 1.018 | 0.9738 | 1.27 | 47.5 | 346.2 |

TABLE 28B

Figure 51C:
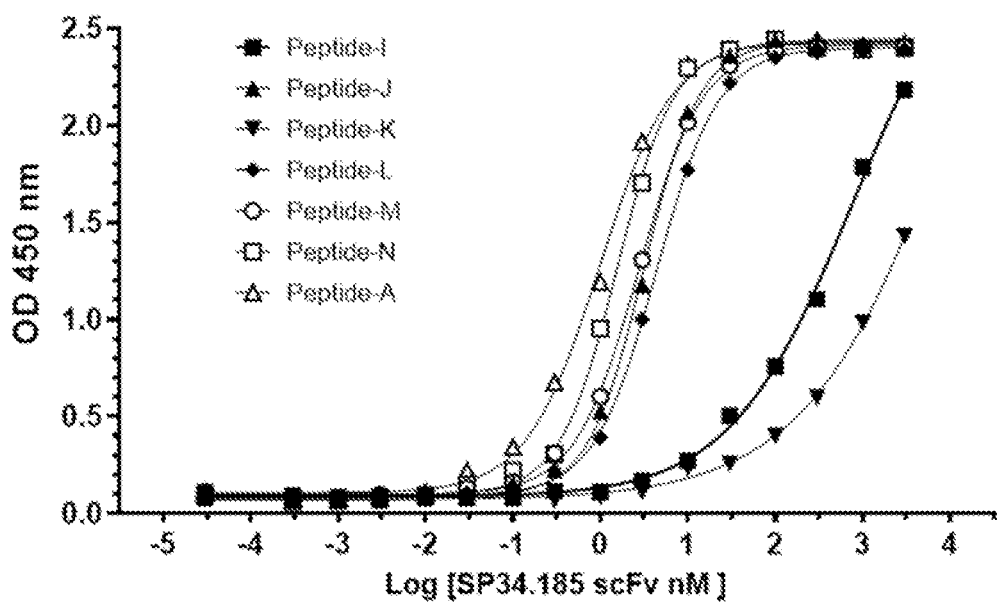
Figure 51D:
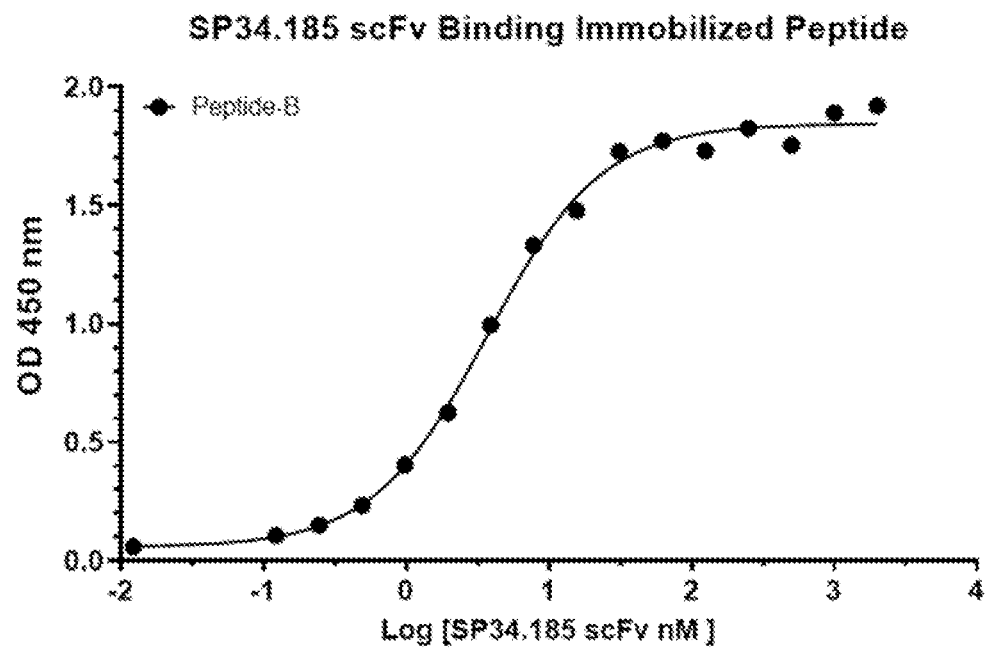

Summary of FIG. 51C

| ELISA | Peptide-A | Peptide-I | Peptide-J | Peptide-K | Peptide-L | Peptide-M | Peptide-N |
|---|---|---|---|---|---|---|---|
| $EC_{50}$ nM | 0.986 | 310.8 | 3.134 | 1,960 | 4.363 | 2.76 | 1.546 |

TABLE 28C

Figure 51E:
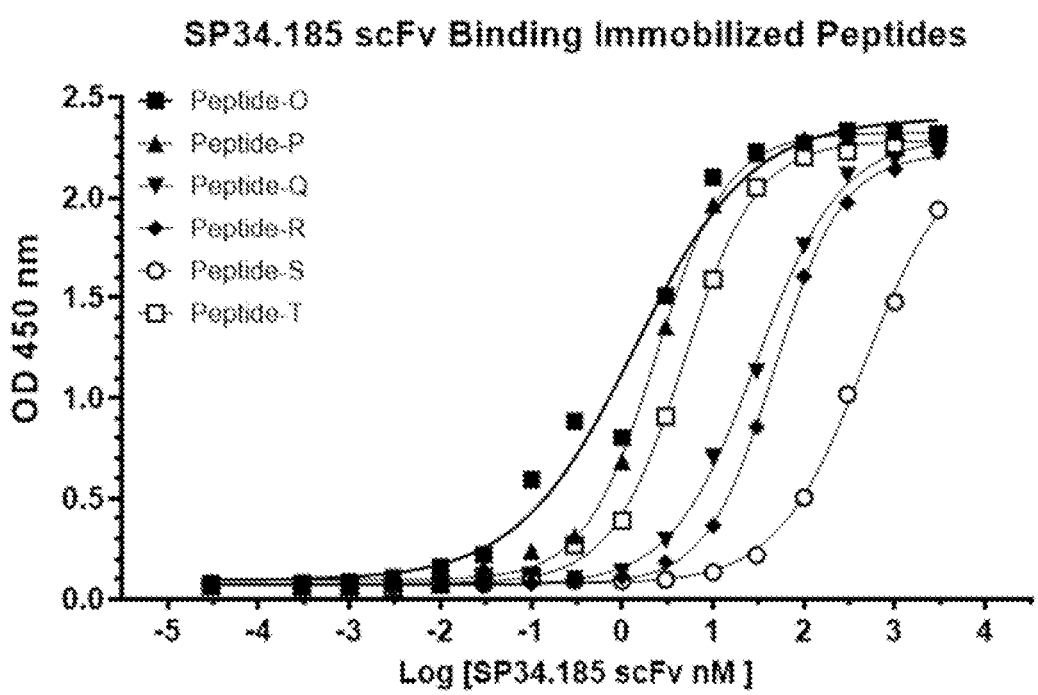

Summary of FIG. 51E

| ELISA | Peptide-O | Peptide-P | Peptide-Q | Peptide-R | Peptide-S | Peptide-T |
|---|---|---|---|---|---|---|
| $EC_{50}$ nM | 1.356 | 2.359 | 30.04 | 47.50 | 457.1 | 4.762 |

TABLE 28D

Figure 51F:
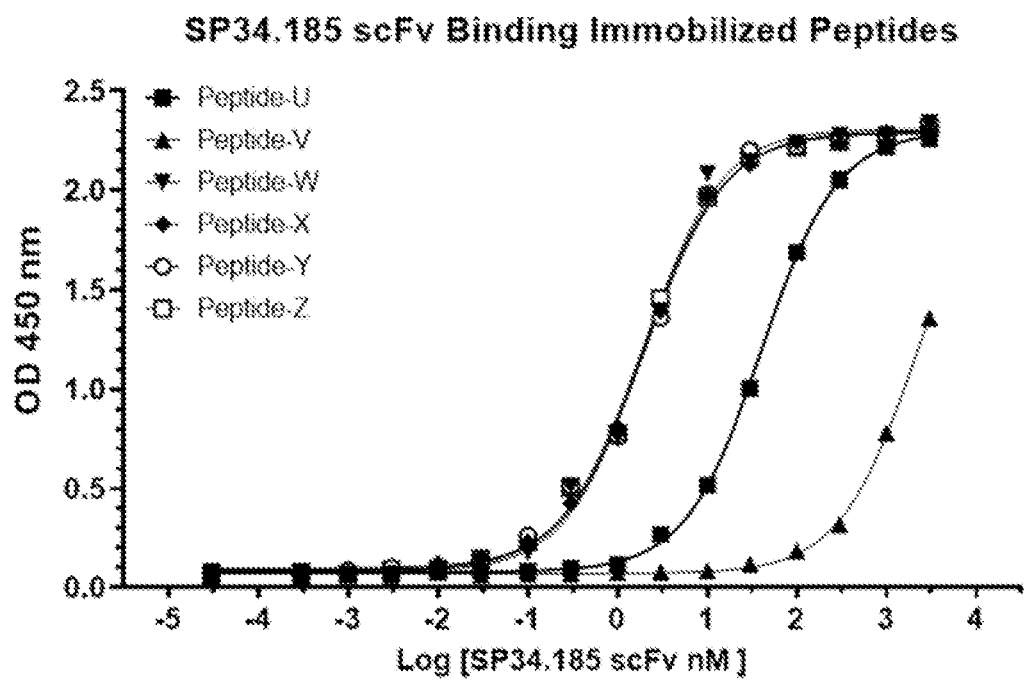
Figure 52A:
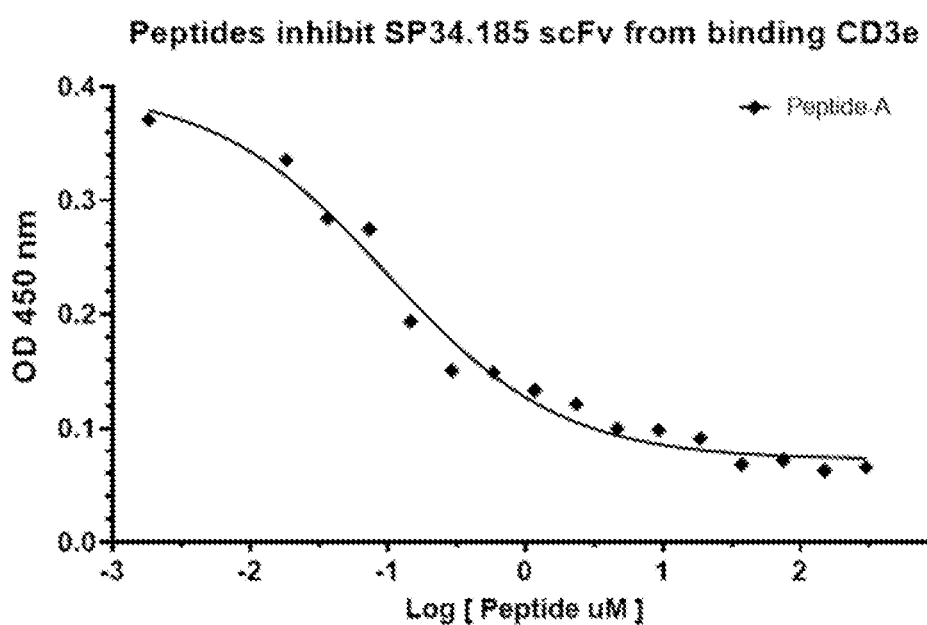
FIGS. 52A-52F illustrate inhibition of anti-CD3 scFv binding to CD3 by alanine scanning peptides of anti-CD3 scFv Peptide-A and Peptide-B as measured by ELISA.
Figure 52B:
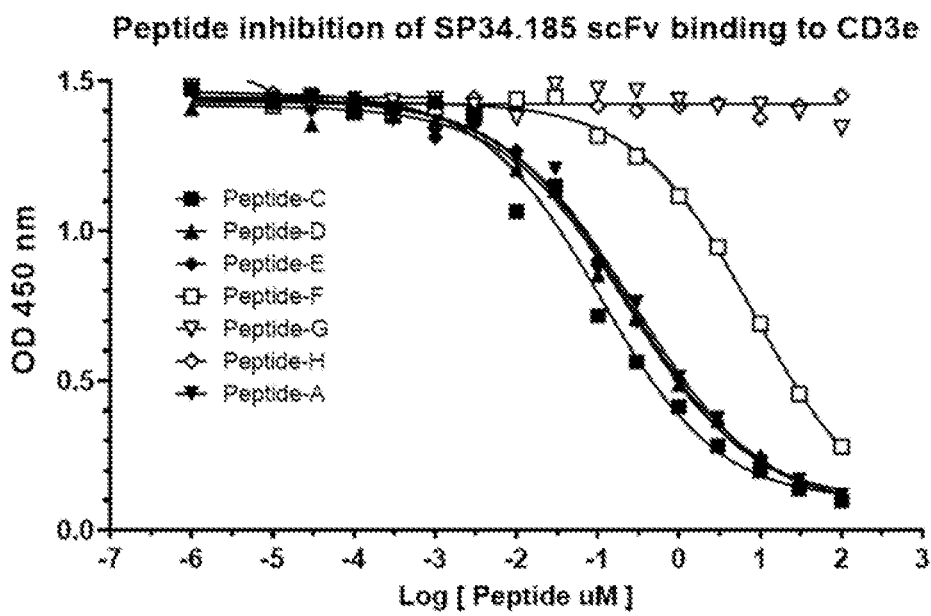
Figure 52C:
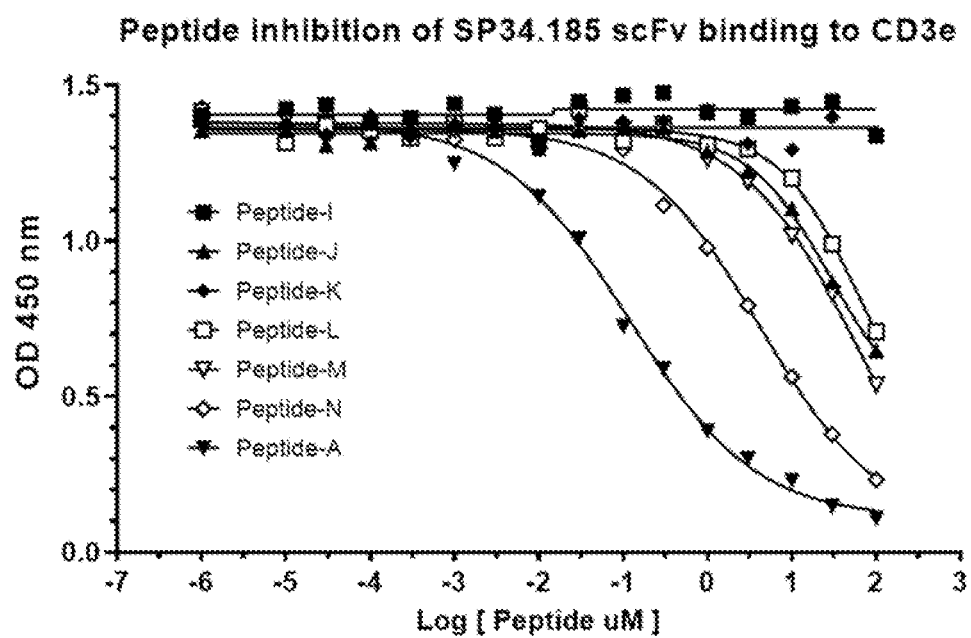
Figure 52D:
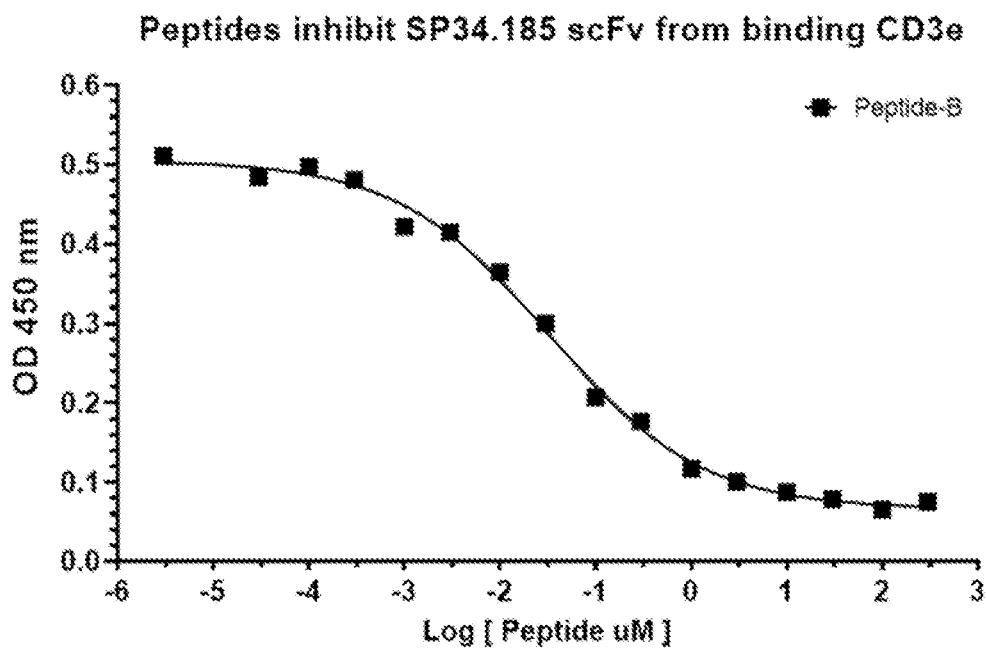
Figure 52E:
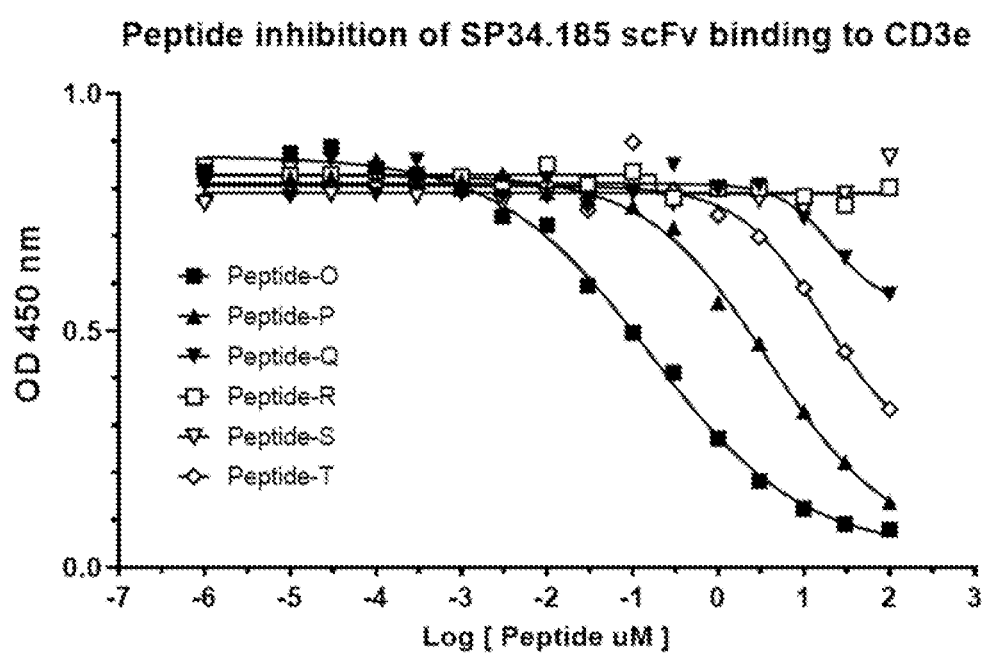
Figure 52F:
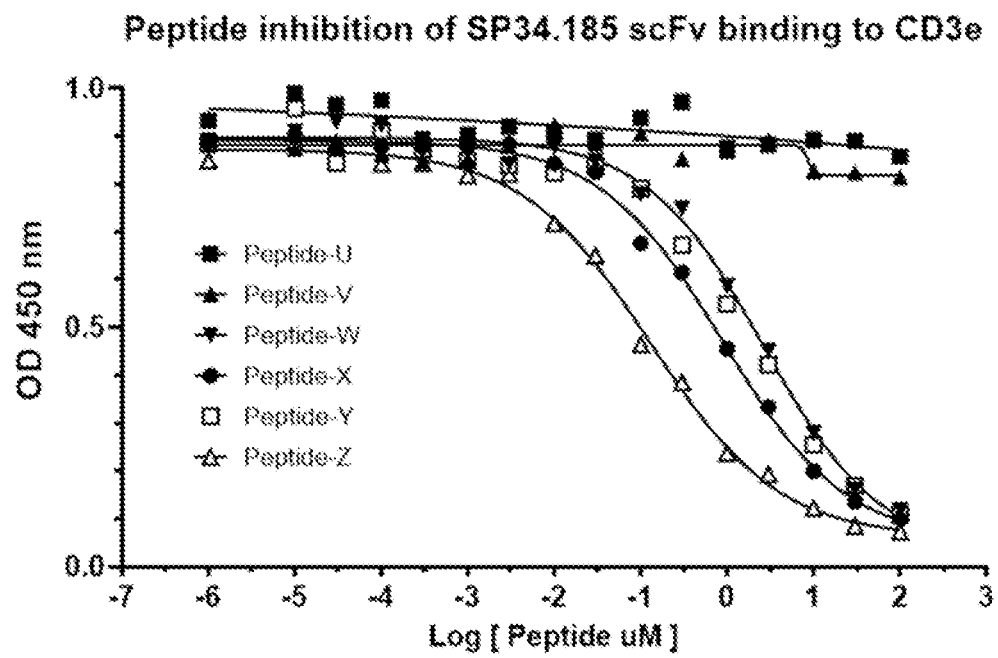

Summary of FIG. 51F

| ELISA | Peptide-U | Peptide-V | Peptide-W | Peptide-X | Peptide-Y | Peptide-Z |
|---|---|---|---|---|---|---|
| $EC_{50}$ nM | 39.90 | 2168 | 1.916 | 1.948 | 2.012 | 1.833 |

Peptides were evaluated for their ability to inhibit SP34.185 scFv from binding CD3ε by standard enzyme linked immunosorbent assays (ELISAs). Briefly, a fixed concentration of SP34.185 scFv was incubated with varying concentrations of peptides in solution. SP34.185scFv and peptide solutions were incubated for 1 hr prior to addition to CD3 coated plates. Binding was allowed to proceed for 30 min prior to washing. After washing, bound SP34.185 scFv using a secondary horse radish peroxidase antibody conjugate. After washing again, plates were developed using standard ELISA techniques and stopped using acid. The concentration of peptide required to inhibit 50% of the SP34.185 scFv CD3 binding signal ($IC_{50}$) was calculated using Graphpad prism. Data is shown in FIGS. 52A-52F and summarized in Tables 29A-29D.

TABLE 29A

| Summary of FIG. 52B | | | | | | | |
|---|---|---|---|---|---|---|---|
| ELISA | Peptide-A | Peptide-C | Peptide-D | Peptide-E | Peptide-F | Peptide-G | Peptide-H |
| $IC_{50}$ uM | 0.1926 | 0.1025 | 0.2318 | 0.1905 | 5.484 | >100 | >100 |

TABLE 29B

| Summary of FIG. 52C | | | | | | | |
|---|---|---|---|---|---|---|---|
| ELISA | Peptide-A | Peptide-I | Peptide-10 | Peptide-K | Peptide-L | Peptide-M | Peptide-N |
| $IC_{50}$ uM | 0.1138 | >100 | 63.18 | >100 | 86.78 | 36.66 | 3.009 |

TABLE 29C

| Summary of FIG. 52E | | | | | | |
|---|---|---|---|---|---|---|
| ELISA | Peptide-O | Peptide-P | Peptide-Q | Peptide-R | Peptide-S | Peptide-T |
| $IC_{50}$ uM | 0.1473 | 3.333 | >100 | >100 | >100 | 41.46 |

TABLE 29D

| Summary of FIG. 52F | | | | | | |
|---|---|---|---|---|---|---|
| ELISA | Peptide-U | Peptide-V | Peptide-W | Peptide-X | Peptide-Y | Peptide-Z |
| $IC_{50}$ uM | >100 | >100 | 1.912 | 0.6992 | 1.456 | 0.1180 |

TABLE 30

| CD3 Ala Scan Sequences-Peptide-A and Peptide-B | | | |
|---|---|---|---|
| Peptide-ID | anti-CD3 Panned target | Sequence | SEQ ID NO: |
| Peptide-A | SP34.185 | GSQCLGPEWEVCPY | 797 |
| Peptide-C | SP34.185 | ASQCLGPEWEVCPY | 798 |
| Peptide-D | SP34.185 | GAQCLGPEWEVCPY | 799 |
| Peptide-E | SP34.185 | GSACLGPEWEVCPY | 800 |
| Peptide-F | SP34.185 | GSQCAGPEWEVCPY | 801 |
| Peptide-G | SP34.185 | GSQCLAPEWEVCPY | 802 |
| Peptide-H | SP34.185 | GSQCLGAEWEVCPY | 803 |
| Peptide-I | SP34.185 | GSQCLGPAWEVCPY | 804 |
| Peptide-J | SP34.185 | GSQCLGPEAEVCPY | 805 |
| Peptide-K | SP34.185 | GSQCLGPEWAVCPY | 806 |
| Peptide-L | SP34.185 | GSQCLGPEWEACPY | 807 |
| Peptide-M | SP34.185 | GSQCLGPEWEVCAY | 808 |
| Peptide-N | SP34.185 | GSQCLGPEWEVCPA | 809 |
| Peptide-A | SP34.185 | GSQCLGPEWEVCPY | 810 |
| Peptide-B | SP34.185 | VYCGPEFDESVGCM | 811 |
| Peptide-O | SP34.185 | AYCGPEFDESVGCM | 812 |
| Peptide-P | SP34.185 | VACGPEFDESVGCM | 813 |
| Peptide-Q | SP34.185 | VYCAPEFDESVGCM | 814 |
| Peptide-R | SP34.185 | VYCGAEFDESVGCM | 815 |

TABLE 30-continued CD3 Ala Scan Sequences-Peptide-A and Peptide-B

| Peptide-ID | anti-CD3 Panned target | Sequence | SEQ ID NO: |
|---|---|---|---|
| Peptide-S | SP34.185 | VYCGPAFDESVGCM | 816 |
| Peptide-T | SP34.185 | VYCGPEADESVGCM | 817 |
| Peptide-U | SP34.185 | VYCGPEFAESVGCM | 818 |
| Peptide-V | SP34.185 | VYCGPEFDASVGCM | 819 |
| Peptide-W | SP34.185 | VYCGPEFDEAVGCM | 820 |
| Peptide-X | SP34.185 | VYCGPEFDESAGCM | 821 |
| Peptide-Y | SP34.185 | VYCGPEFDESVACM | 822 |
| Peptide-Z | SP34.185 | VYCGPEFDESVGCA | 823 |

Example 23: Panning of the Optimized Phage Library Construction—CD3 scFv Peptides Once the phage optimization libraries were completed, phage libraries were bio-panned using SP34.185 scFv loaded beads. Multiple rounds of panning were performed where bacteriophage was allowed to bind to SP34.185 scFv loaded beads, washed, eluted, and amplified. Additional selective pressure was included during each round of panning using a fixed concentration of CD3, Peptide-A, or Peptide-B. After panning, phage infected bacteria were plated out and colonies picked into 96 well blocks. Clonal phage was then amplified and separated from bacterial cells via centrifugation. Phage containing supernatants were tested in binding ELISAs against SP34.185 scFv coated plates in the presence or absence of saturating concentration of CD3. Phage able to bind SP34.185 scFv were selected for sequence analysis if the binding signal was reduced in the presence of CD3.

Example 24: Panning ELISAs—CD3 scFv Peptides

Clonal phages were harvested as crude supernatants and screened via standard enzyme linked immunosorbent assays (ELISAs). Briefly, biotinylated SP34.185 scFv was captured on neutravidin coated plates. Prior to the addition of clonal phage, wells were incubated with blocking buffer and CD3 or blocking buffer alone. Without washing or aspirating, clonal phage supernatants were then added to the wells and incubated for a short time. Wells were then washed followed by detection of bound phage using a horse radish peroxidase conjugated anti-M13 antibody. Clonal phage of interest was then sent for sequence analysis.

Figure 53A:
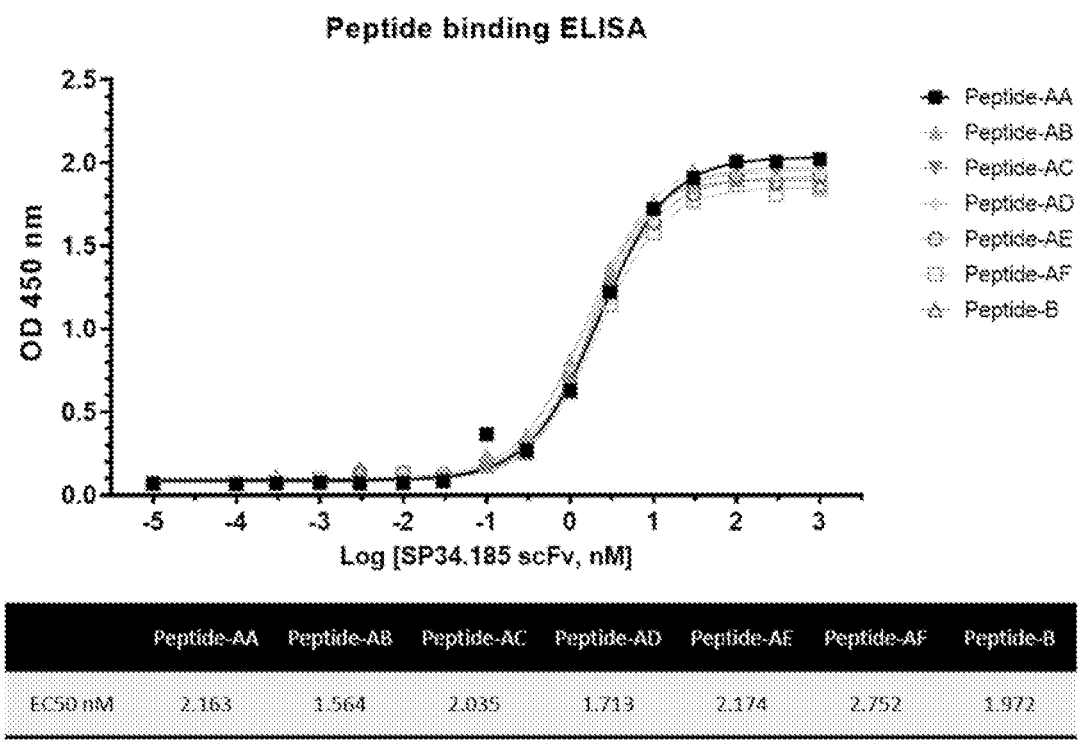
FIGS. 53A-53B illustrate anti-CD3 scFv binding by optimized anti-CD3 scFv Peptide-B sequences as measured by ELISA.
Figure 53B:
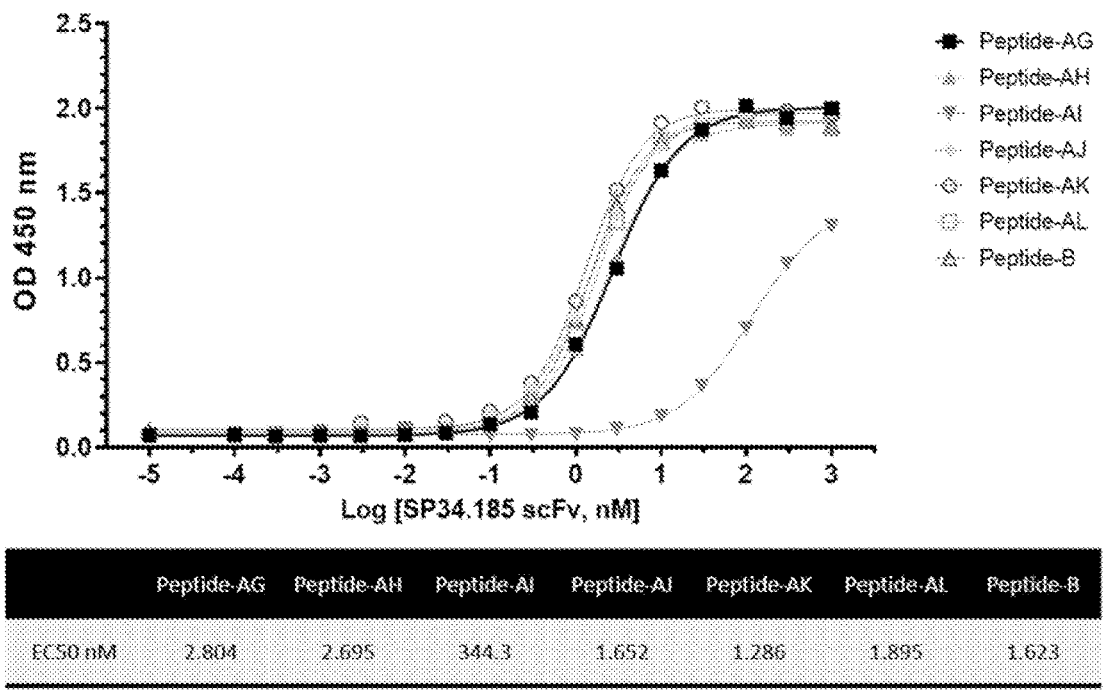
Figure 54A:
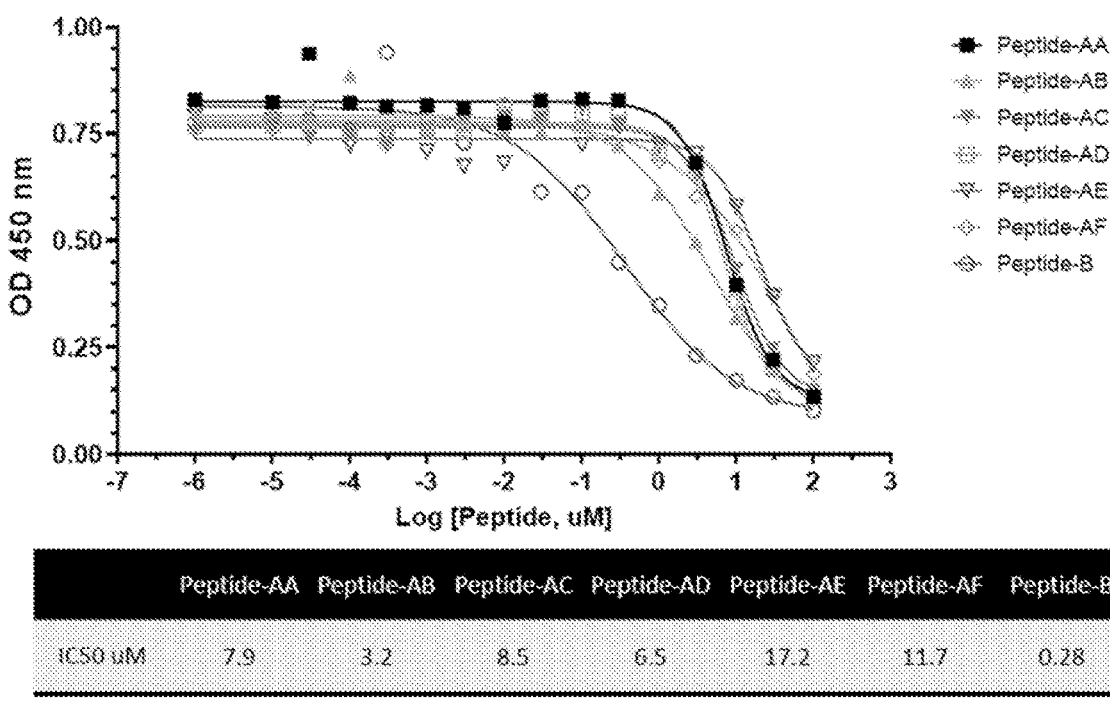
FIGS. 54A-54B illustrate inhibition of anti-CD3 scFv binding to CD3 by optimized anti-CD3 scFv Peptide-B sequences as measured by ELISA.
Figure 54B:
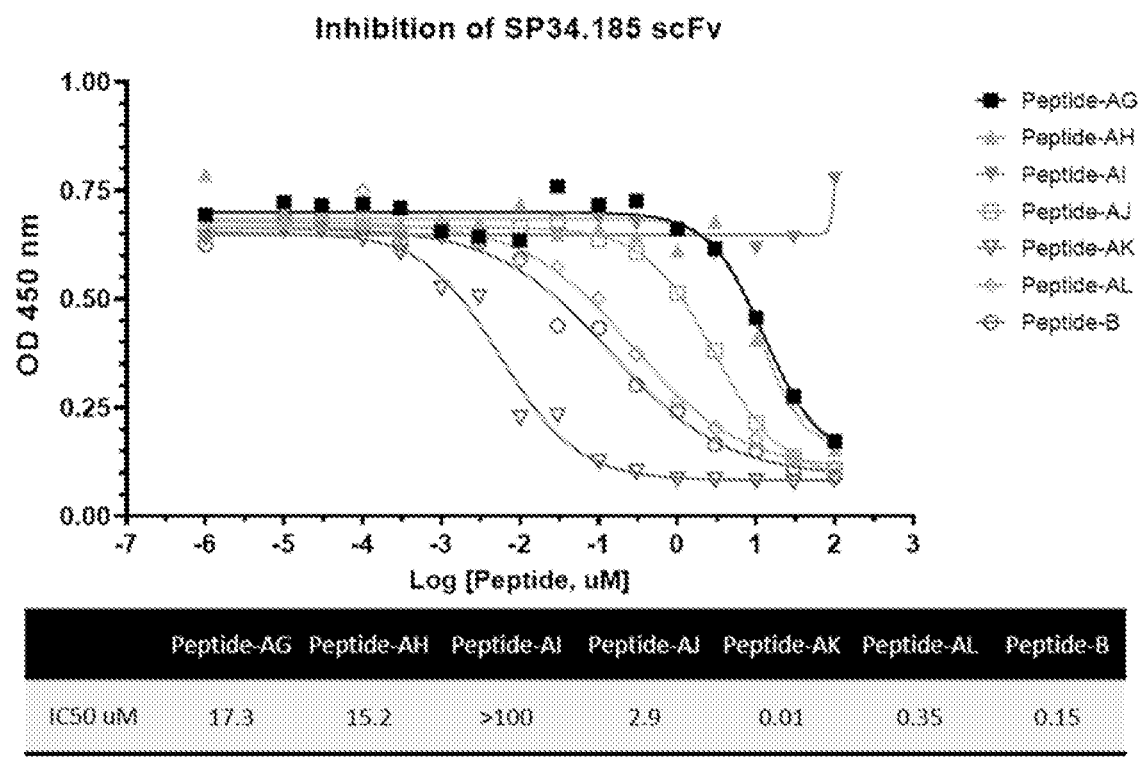
Figure 55:
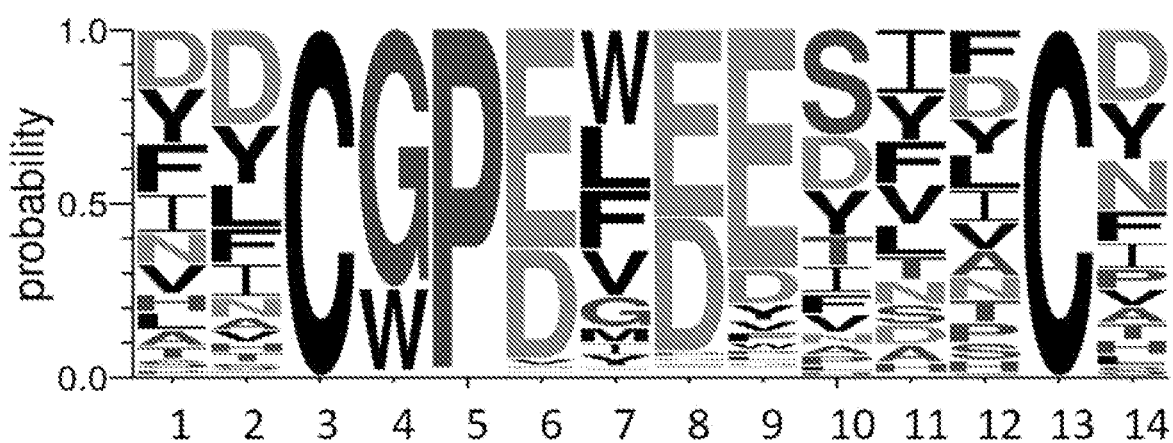
FIG. 55 illustrates the core sequence motif of optimized anti-CD3 scFv Peptide-B sequences generated using WebLogo 3.7.4.

Phage panning results of CD3 scFv Peptide-B library sequences are shown in Table 31. The sequences of those peptides selected for synthesis are shown in Table 32, and further evaluated for binding to anti-CD3 scFv (FIGS. 53A-53B) and inhibition of anti-CD3 scFv binding to CD3 (FIGS. 54A-54B). The consensus sequence shown in FIG. 55 was calculated from all the sequences shown in Table 31 and was generated using WebLogo 3.7.4.

TABLE 31

Clonal Phage Peptide Sequences from the Peptide-B Optimization Library Panning (—) indicates same amino acid as in CD3 scFv Peptide-B corresponding position (e.g. Phage-1 position).

| Phage ID | Amino acid position sequence 1 | 2 | 3 | 4 | 5 | 6 | 7 | 8 | 9 | 10 | 11 | 12 | 13 | 14 | Phage binding ELISA Backgroud signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-1/ Peptide B | V | Y | C | G | P | E | F | D | E | S | V | G | C | M | 0.06 | 2.79 | 0.09 | 25 |
| Phage-2 | D | D | — | W | — | D | W | E | F | D | F | A | — | A | 0.08 | 2.75 | 0.09 | 824 |
| Phage-3 | Y | I | — | — | L | D | — | P | D | F | L | Y | — | D | 0.08 | 2.88 | 0.10 | 825 |
| Phage-4 | F | D | — | W | — | D | W | E | — | Y | F | V | — | D | 0.08 | 2.79 | 0.09 | 826 |
| Phage-5 | Y | I | — | W | — | D | W | E | — | Y | F | D | — | D | 0.08 | 2.74 | 0.09 | 827 |
| Phage-6 | N | I | — | W | — | D | W | E | D | D | Y | F | — | F | 0.09 | 2.54 | 0.09 | 828 |
| Phage-7 | N | F | — | W | — | D | W | E | Y | I | Y | P | — | I | 0.07 | 2.77 | 0.09 | 829 |
| Phage-8 | — | D | — | W | — | D | W | E | — | D | F | L | — | I | 0.08 | 2.54 | 0.08 | 830 |
| Phage-9 | H | A | — | W | — | D | W | E | — | Y | F | P | — | N | 0.08 | 2.85 | 0.09 | 831 |
| Phage-10 | Y | D | — | — | — | D | V | — | — | — | Y | V | — | V | 0.09 | 2.63 | 0.10 | 832 |
| Phage-11 | I | D | — | W | — | D | W | E | D | D | T | F | — | Y | 0.09 | 2.73 | 0.08 | 833 |
| Phage-12 | Y | L | — | — | — | D | G | — | — | T | L | A | — | Y | 0.08 | 2.66 | 0.15 | 834 |
| Phage-13 | — | D | — | — | — | D | G | — | — | — | I | L | — | Y | 0.11 | 2.13 | 0.08 | 835 |
| Phage-14 | F | I | — | W | — | D | W | E | — | D | Y | F | — | A | 0.07 | 2.44 | 0.09 | 843 |
| Phage-15 | G | D | — | W | — | D | W | E | W | D | F | Y | — | D | 0.07 | 2.71 | 0.07 | 844 |
| Phage-16 | Y | L | — | W | — | D | W | E | Y | I | D | L | — | D | 0.12 | 2.67 | 0.08 | 845 |
| Phage-17 | S | F | — | W | — | D | W | E | — | Y | F | D | — | D | 0.10 | 2.60 | 0.07 | 846 |
| Phage-18 | D | D | — | W | — | D | W | E | — | Y | A | S | — | D | 0.09 | 2.57 | 0.07 | 847 |
| Phage-19 | N | L | — | W | — | D | W | E | Y | P | F | F | — | D | 0.09 | 2.52 | 0.09 | 848 |
| Phage-20 | F | D | — | W | — | D | W | E | — | — | F | V | — | D | 0.08 | 2.34 | 0.09 | 849 |
| Phage-21 | D | I | — | — | — | D | G | — | — | T | I | I | — | D | 0.13 | 2.30 | 0.10 | 850 |
| Phage-22 | D | D | — | W | — | D | W | E | Y | Y | A | V | — | D | 0.09 | 2.28 | 0.09 | 851 |
| Phage-23 | Y | D | — | W | — | D | W | E | — | Y | S | N | — | D | 0.10 | 2.17 | 0.08 | 852 |
| Phage-24 | I | N | — | W | — | D | W | E | D | Y | F | F | — | D | 0.07 | 2.16 | 0.07 | 853 |
| Phage-25 | N | I | — | W | — | D | W | E | D | D | T | F | — | F | 0.06 | 2.87 | 0.07 | 854 |
| Phage-26 | N | I | — | W | — | D | W | E | P | N | S | F | — | F | 0.09 | 2.87 | 0.08 | 855 |
| Phage-27 | Y | D | — | — | — | — | M | — | — | — | I | D | — | F | 0.09 | 2.39 | 0.08 | 856 |
| Phage-28 | D | F | — | W | — | D | W | E | F | P | F | I | — | H | 0.11 | 2.73 | 0.12 | 857 |
| Phage-29 | D | F | — | — | — | — | M | — | — | — | I | T | — | I | 0.07 | 2.36 | 0.08 | 858 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \multicolumn{14}{c}{Amino acid position sequence} | Background signal | SP34.185 scFv signal | SP34.185 scFv signal in presence of CD3 | SEQ ID NO: |
|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 |  |  |  |  |
| Phage-30 | Y | D | — | — | — | — | — | — | — | — | T | V | — | I | 0.10 | 2.32 | 0.08 | 859 |
| Phage-31 | H | D | — | W | — | D | W | E | W | D | I | F | — | I | 0.07 | 2.26 | 0.08 | 860 |
| Phage-32 | H | A | — | W | — | D | W | E | — | Y | N | P | — | N | 0.11 | 2.71 | 0.11 | 861 |
| Phage-33 | D | V | — | W | — | D | W | E | W | D | F | F | — | N | 0.08 | 2.65 | 0.08 | 862 |
| Phage-34 | N | — | — | W | — | D | W | E | Y | Y | I | P | — | N | 0.10 | 2.57 | 0.08 | 863 |
| Phage-35 | I | I | — | W | — | D | W | E | F | I | D | Y | — | N | 0.08 | 2.10 | 0.07 | 864 |
| Phage-36 | S | L | — | W | — | D | W | E | Y | D | I | A | — | P | 0.07 | 2.53 | 0.08 | 865 |
| Phage-37 | D | L | — | — | — | — | L | — | — | — | I | F | — | P | 0.08 | 2.49 | 0.09 | 866 |
| Phage-38 | T | N | — | W | — | D | W | E | W | V | L | P | — | P | 0.14 | 2.47 | 0.10 | 867 |
| Phage-39 | I | E | — | W | — | D | W | E | P | N | Y | F | — | P | 0.13 | 2.29 | 0.09 | 868 |
| Phage-40 | I | F | — | W | — | D | W | E | D | Y | — | D | — | P | 0.07 | 2.28 | 0.07 | 869 |
| Phage-41 | I | D | — | W | — | D | W | E | Y | D | F | F | — | P | 0.07 | 2.26 | 0.08 | 870 |
| Phage-42 | L | F | — | W | — | D | W | E | D | — | F | F | — | P | 0.18 | 2.11 | 0.13 | 871 |
| Phage-43 | — | D | — | W | — | D | W | E | D | Y | A | D | — | T | 0.11 | 2.20 | 0.10 | 872 |
| Phage-44 | — | I | — | W | — | D | W | E | Q | Y | F | P | — | V | 0.11 | 2.34 | 0.09 | 873 |
| Phage-45 | I | E | — | W | — | D | W | E | P | I | Y | P | — | Y | 0.09 | 2.85 | 0.09 | 874 |
| Phage-46 | I | T | — | W | — | D | W | E | V | Y | F | P | — | Y | 0.07 | 2.55 | 0.08 | 875 |
| Phage-47 | I | D | — | W | — | D | W | E | Y | I | H | P | — | Y | 0.06 | 2.51 | 0.09 | 876 |
| Phage-48 | I | D | — | W | — | D | W | E | Y | I | N | P | — | Y | 0.12 | 2.50 | 0.12 | 877 |
| Phage-49 | A | D | — | W | — | D | W | E | — | A | F | P | — | Y | 0.09 | 2.44 | 0.09 | 878 |
| Phage-50 | I | D | — | W | — | D | W | E | Y | I | Y | P | — | Y | 0.09 | 2.31 | 0.07 | 879 |
| Phage-51 | N | I | — | W | — | D | W | E | D | D | N | F | — | F | 0.09 | 2.08 | 0.09 | 880 |
| Phage-52 | Y | D | — | W | — | D | W | E | Y | V | D | A | — | Y | 0.09 | 2.06 | 0.09 | 881 |
| Phage-53 | F | — | — | — | — | D | G | — | — | — | Y | V | — | D | 0.09 | 2.03 | 0.11 | 882 |
| Phage-54 | D | I | — | W | — | D | W | E | Y | I | N | I | — | S | 0.11 | 2.02 | 0.11 | 883 |
| Phage-55 | F | V | — | W | — | D | W | E | D | F | N | F | — | D | 0.07 | 2.01 | 0.08 | 884 |
| Phage-56 | F | A | — | W | — | D | W | E | D | Y | — | A | — | D | 0.07 | 2.01 | 0.09 | 885 |
| Phage-57 | D | N | — | W | — | D | W | E | Y | D | F | F | — | V | 0.08 | 1.99 | 0.09 | 886 |
| Phage-58 | Y | D | — | W | — | D | W | E | — | Y | N | D | — | A | 0.09 | 1.96 | 0.11 | 887 |
| Phage-59 | D | D | — | — | — | D | G | — | — | T | I | I | — | V | 0.07 | 1.91 | 0.09 | 888 |
| Phage-60 | F | P | — | W | — | D | W | E | — | Y | A | I | — | D | 0.10 | 1.89 | 0.10 | 889 |
| Phage-61 | P | D | — | — | — | D | G | — | — | — | L | F | — | T | 0.12 | 1.86 | 0.07 | 890 |
| Phage-62 | D | N | — | W | — | D | W | E | Y | D | Y | F | — | V | 0.07 | 1.83 | 0.07 | 891 |
| Phage-63 | I | F | — | W | — | D | W | E | — | F | Y | D | — | Y | 0.12 | 1.82 | 0.08 | 892 |
| Phage-64 | A | D | — | W | — | D | W | E | — | Y | F | P | — | N | 0.08 | 1.82 | 0.08 | 893 |
| Phage-65 | H | T | — | W | — | D | W | E | D | D | I | F | — | N | 0.12 | 1.81 | 0.10 | 894 |
| Phage-66 | F | A | — | W | — | D | W | E | — | A | F | L | — | L | 0.09 | 1.80 | 0.09 | 895 |
| Phage-67 | Y | D | — | — | — | — | L | — | — | — | I | A | — | D | 0.08 | 1.77 | 0.08 | 896 |
| Phage-68 | N | S | — | W | — | D | W | E | Y | D | I | I | — | D | 0.08 | 1.77 | 0.10 | 897 |
| Phage-69 | F | A | — | W | — | D | W | E | — | V | A | P | — | Y | 0.07 | 1.75 | 0.07 | 898 |
| Phage-70 | L | D | — | — | — | D | G | — | — | T | L | T | — | Y | 0.10 | 1.75 | 0.12 | 899 |
| Phage-71 | — | L | — | W | — | D | W | E | — | F | Y | D | — | P | 0.07 | 1.74 | 0.09 | 900 |
| Phage-72 | H | A | — | W | — | V | W | E | — | Y | F | P | — | N | 0.07 | 1.72 | 0.08 | 901 |
| Phage-73 | N | E | — | W | — | N | G | E | P | T | F | P | — | T | 0.08 | 1.71 | 0.07 | 902 |
| Phage-74 | L | T | — | — | — | D | G | — | — | T | L | Y | — | D | 0.08 | 1.70 | 0.07 | 903 |
| Phage-75 | Y | D | — | — | — | — | Y | — | — | — | — | P | — | I | 0.13 | 1.67 | 0.09 | 904 |
| Phage-76 | I | E | — | W | — | D | W | E | P | N | S | F | — | D | 0.09 | 1.66 | 0.08 | 905 |
| Phage-77 | Y | D | — | — | — | — | L | — | — | — | I | H | — | Y | 0.12 | 1.66 | 0.09 | 906 |
| Phage-78 | I | — | — | — | — | — | — | — | — | — | T | I | — | N | 0.08 | 1.63 | 0.08 | 907 |
| Phage-79 | I | — | — | — | — | — | V | E | — | A | Y | L | — | Y | 0.09 | 1.62 | 0.10 | 908 |
| Phage-80 | F | D | — | — | — | D | G | — | — | T | — | Y | — | D | 0.09 | 1.61 | 0.08 | 909 |
| Phage-81 | I | D | — | — | — | D | G | — | — | T | I | S | — | Y | 0.08 | 1.57 | 0.11 | 910 |
| Phage-82 | N | — | — | — | — | — | — | — | — | I | S | T | — | L | 0.10 | 1.55 | 0.11 | 911 |
| Phage-83 | Y | D | — | — | — | D | G | — | — | — | Y | F | — | D | 0.08 | 1.53 | 0.08 | 912 |
| Phage-84 | N | F | — | W | — | D | W | E | Y | F | N | D | — | N | 0.09 | 1.53 | 0.09 | 913 |
| Phage-85 | — | L | — | W | — | D | W | E | A | F | D | D | — | D | 0.07 | 1.47 | 0.07 | 914 |
| Phage-86 | I | — | — | — | — | — | W | E | W | P | — | A | — | N | 0.16 | 1.47 | 0.10 | 915 |
| Phage-87 | — | F | — | W | — | D | W | E | D | N | F | F | — | N | 0.08 | 1.46 | 0.10 | 916 |
| Phage-88 | — | V | — | W | — | D | W | E | T | F | F | P | — | D | 0.08 | 1.46 | 0.08 | 917 |
| Phage-89 | D | N | — | — | — | D | G | — | — | T | Y | I | — | N | 0.10 | 1.45 | 0.09 | 918 |
| Phage-90 | D | N | — | W | — | D | W | E | Y | N | F | F | — | V | 0.07 | 1.45 | 0.08 | 919 |
| Phage-91 | F | — | — | — | — | — | V | E | — | D | Y | L | — | I | 0.10 | 1.43 | 0.10 | 920 |
| Phage-92 | D | N | — | W | — | D | W | E | Y | D | I | F | — | V | 0.07 | 1.43 | 0.07 | 921 |
| Phage-93 | I | D | — | — | — | — | — | — | — | — | I | A | — | P | 0.08 | 1.42 | 0.08 | 922 |
| Phage-94 | Y | F | — | — | — | — | V | E | — | Y | T | L | — | F | 0.10 | 1.42 | 0.10 | 923 |
| Phage-95 | F | — | — | — | — | — | — | — | — | — | A | P | — | N | 0.06 | 1.37 | 0.08 | 924 |
| Phage-96 | F | D | — | — | — | — | V | E | — | Y | F | Y | — | A | 0.11 | 1.36 | 0.08 | 925 |
| Phage-97 | D | F | — | W | — | D | W | E | D | F | F | F | — | A | 0.18 | 1.35 | 0.12 | 926 |
| Phage-98 | F | F | — | — | — | — | D | G | — | — | T | L | S | — | N | 0.08 | 1.35 | 0.09 | 927 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \_ | \_ | \_ | \_ | Amino acid position sequence | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-99 | F | I | — | — | — | — | — | — | — | — | — | A | — | L | 0.14 | 1.35 | 0.09 | 928 |
| Phage-100 | Y | D | — | — | — | — | — | — | — | A | I | — | — | Y | 0.09 | 1.32 | 0.10 | 929 |
| Phage-101 | Y | T | — | W | — | D | W | E | — | Y | L | Y | — | P | 0.10 | 1.32 | 0.15 | 930 |
| Phage-102 | F | D | — | W | — | D | W | E | — | P | T | T | — | H | 0.08 | 1.31 | 0.08 | 931 |
| Phage-103 | Y | D | — | W | — | D | W | E | D | F | P | I | — | D | 0.14 | 1.31 | 0.10 | 932 |
| Phage-104 | — | V | — | W | — | D | W | E | Y | I | D | D | — | S | 0.08 | 1.30 | 0.07 | 933 |
| Phage-105 | I | N | — | W | — | D | W | E | V | I | S | F | — | D | 0.12 | 1.30 | 0.08 | 934 |
| Phage-106 | L | S | — | W | — | D | W | E | — | V | T | P | — | L | 0.10 | 1.29 | 0.10 | 935 |
| Phage-107 | F | A | — | W | — | D | W | E | — | V | D | I | — | Y | 0.09 | 1.28 | 0.08 | 936 |
| Phage-108 | Y | D | — | — | — | — | M | — | — | — | I | V | — | D | 0.10 | 1.25 | 0.08 | 937 |
| Phage-109 | Y | D | — | W | — | D | W | E | V | F | I | V | — | D | 0.06 | 1.25 | 0.07 | 938 |
| Phage-110 | D | N | — | W | — | D | W | E | H | N | F | F | — | V | 0.10 | 1.25 | 0.08 | 939 |
| Phage-111 | Y | D | — | — | — | D | G | — | — | — | I | Y | — | P | 0.07 | 1.23 | 0.08 | 940 |
| Phage-112 | Y | D | — | — | — | — | — | E | F | P | Y | Y | — | F | 0.12 | 1.23 | 0.12 | 941 |
| Phage-113 | A | D | — | — | — | — | Y | — | — | — | I | P | — | V | 0.11 | 1.22 | 0.09 | 942 |
| Phage-114 | F | L | — | — | — | — | V | E | — | V | H | Y | — | S | 0.08 | 1.22 | 0.10 | 943 |
| Phage-115 | T | D | — | W | — | D | W | E | Y | I | T | S | — | S | 0.08 | 1.22 | 0.08 | 944 |
| Phage-116 | A | F | — | — | — | — | L | — | — | — | I | T | — | D | 0.09 | 1.21 | 0.09 | 945 |
| Phage-117 | N | D | — | W | — | D | W | E | — | Y | F | S | — | Y | 0.09 | 1.19 | 0.09 | 946 |
| Phage-118 | F | D | — | — | — | — | W | E | I | V | T | D | — | Y | 0.08 | 1.19 | 0.09 | 947 |
| Phage-119 | N | L | — | — | — | — | M | — | — | — | I | I | — | P | 0.13 | 1.19 | 0.11 | 948 |
| Phage-120 | D | L | — | — | — | — | M | — | — | — | I | Y | — | D | 0.10 | 1.19 | 0.14 | 949 |
| Phage-121 | F | D | — | — | — | D | G | V | — | D | Y | I | — | D | 0.09 | 1.18 | 0.09 | 950 |
| Phage-122 | Y | A | — | W | — | D | W | E | — | D | F | A | — | Y | 0.11 | 1.18 | 0.08 | 951 |
| Phage-123 | H | D | — | — | — | — | M | — | — | — | I | V | — | V | 0.10 | 1.17 | 0.10 | 952 |
| Phage-124 | — | F | — | — | — | — | — | E | F | I | F | L | — | A | 0.07 | 1.17 | 0.08 | 953 |
| Phage-125 | Y | D | — | — | — | — | L | — | — | — | I | L | — | D | 0.08 | 1.16 | 0.09 | 954 |
| Phage-126 | S | V | — | W | — | D | W | E | — | F | Y | S | — | D | 0.11 | 1.16 | 0.10 | 955 |
| Phage-127 | P | — | — | — | — | D | G | — | — | T | A | I | — | T | 0.13 | 1.16 | 0.10 | 956 |
| Phage-128 | D | D | — | — | — | — | L | E | W | Y | Y | P | — | Y | 0.09 | 1.16 | 0.08 | 957 |
| Phage-129 | F | I | — | — | — | — | — | — | — | — | L | P | — | N | 0.08 | 1.14 | 0.09 | 958 |
| Phage-130 | I | D | — | — | — | — | — | — | — | I | L | P | — | D | 0.11 | 1.14 | 0.33 | 959 |
| Phage-131 | F | L | — | — | — | — | — | E | — | D | A | P | — | Y | 0.08 | 1.13 | 0.08 | 960 |
| Phage-132 | I | F | — | — | — | D | G | — | — | T | H | I | — | H | 0.10 | 1.13 | 0.07 | 961 |
| Phage-133 | — | F | — | W | — | D | W | E | Y | I | D | F | — | N | 0.10 | 1.11 | 0.21 | 962 |
| Phage-134 | I | F | — | — | — | — | Y | — | — | — | L | H | — | I | 0.12 | 1.11 | 0.11 | 963 |
| Phage-135 | H | L | — | W | — | D | W | E | W | Y | — | D | — | P | 0.08 | 1.11 | 0.10 | 964 |
| Phage-136 | F | I | — | — | — | — | M | — | — | — | I | A | — | N | 0.08 | 1.11 | 0.09 | 965 |
| Phage-137 | I | F | — | — | — | — | V | E | M | I | F | L | — | N | 0.09 | 1.10 | 0.08 | 966 |
| Phage-138 | Y | D | — | — | — | — | W | E | F | P | — | D | — | I | 0.11 | 1.09 | 0.11 | 967 |
| Phage-139 | N | L | — | — | — | — | L | — | — | — | I | T | — | F | 0.10 | 1.09 | 0.08 | 968 |
| Phage-140 | F | — | — | — | — | — | V | E | D | F | Y | F | — | Y | 0.08 | 1.09 | 0.08 | 969 |
| Phage-141 | D | I | — | — | — | — | — | — | — | — | L | I | — | N | 0.11 | 1.07 | 0.11 | 970 |
| Phage-142 | D | D | — | — | — | — | — | — | — | — | L | P | — | D | 0.08 | 1.07 | 0.08 | 971 |
| Phage-143 | A | I | — | — | — | — | L | — | — | — | I | A | — | P | 0.09 | 1.07 | 0.09 | 972 |
| Phage-144 | — | I | — | — | — | — | V | E | D | Y | N | L | — | Y | 0.08 | 1.07 | 0.09 | 973 |
| Phage-145 | H | T | — | W | — | D | W | E | D | Y | T | V | — | P | 0.10 | 1.06 | 0.09 | 974 |
| Phage-146 | S | D | — | W | — | D | W | E | Y | F | Y | D | — | N | 0.10 | 1.06 | 0.08 | 975 |
| Phage-147 | — | F | — | — | D | G | — | — | T | — | H | — | D | | 0.09 | 1.05 | 0.08 | 976 |
| Phage-148 | D | — | — | — | — | — | Y | — | — | — | — | H | — | I | 0.09 | 1.05 | 0.08 | 977 |
| Phage-149 | A | D | — | — | — | D | G | — | — | — | T | T | — | H | 0.07 | 1.05 | 0.08 | 978 |
| Phage-150 | F | — | — | — | — | — | L | — | — | — | L | T | — | V | 0.10 | 1.05 | 0.08 | 979 |
| Phage-151 | I | L | — | — | — | — | V | E | — | D | Y | Y | — | Y | 0.11 | 1.04 | 0.09 | 980 |
| Phage-152 | H | L | — | W | — | D | W | E | I | Y | H | S | — | D | 0.09 | 1.04 | 0.09 | 981 |
| Phage-153 | I | F | — | W | — | D | W | E | D | Y | N | F | — | T | 0.08 | 1.04 | 0.11 | 982 |
| Phage-154 | I | V | — | — | — | D | G | — | — | T | L | I | — | H | 0.12 | 1.04 | 0.11 | 983 |
| Phage-155 | A | D | — | W | — | D | W | E | W | D | Y | T | — | D | 0.12 | 1.03 | 0.11 | 984 |
| Phage-156 | I | T | — | — | — | — | — | — | — | — | T | T | — | N | 0.20 | 1.02 | 0.21 | 985 |
| Phage-157 | Y | H | — | W | — | D | W | E | — | Y | T | S | — | D | 0.20 | 1.02 | 0.09 | 986 |
| Phage-158 | N | — | — | — | — | — | V | E | — | Y | A | L | — | T | 0.11 | 1.01 | 0.10 | 987 |
| Phage-159 | F | I | — | — | — | — | M | — | — | — | I | H | — | D | 0.15 | 1.00 | 0.19 | 988 |
| Phage-160 | D | N | — | W | — | D | W | E | — | F | A | V | — | P | 0.14 | 1.00 | 0.10 | 989 |
| Phage-161 | Y | D | — | — | — | — | L | — | — | T | — | V | — | D | 0.10 | 1.00 | 0.09 | 990 |
| Phage-162 | Y | D | — | — | — | — | — | — | — | I | A | — | — | Y | 0.08 | 0.99 | 0.08 | 991 |
| Phage-163 | I | D | — | W | — | D | W | E | Y | T | — | H | — | D | 0.07 | 0.97 | 0.09 | 992 |
| Phage-164 | D | D | — | — | — | — | L | — | — | — | I | I | — | I | 0.09 | 0.96 | 0.09 | 993 |
| Phage-165 | — | — | — | — | — | — | Y | — | — | — | S | F | — | F | 0.09 | 0.91 | 0.08 | 994 |
| Phage-166 | F | N | — | W | — | D | W | E | D | P | Y | F | — | V | 0.09 | 0.86 | 0.07 | 995 |
| Phage-167 | Y | D | — | — | — | — | Y | — | — | — | S | Y | — | S | 0.08 | 0.82 | 0.07 | 996 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \_ | \_ | \_ | \_ | Amino acid position sequence | \_ | \_ | \_ | \_ | \_ | \_ | \_ | \_ | \_ | Background signal | Phage binding ELISA SP34.185 scFv signal | SP34.185 scFv signal in presence of CD3 | SEQ ID NO: |
|---|---|---|---|---|---|---|---|---|---|---|---|---|---|---|---|---|---|---|
|  | 1 | 2 | 3 | 4 | 5 | 6 | 7 | 8 | 9 | 10 | 11 | 12 | 13 | 14 |  |  |  |  |
| Phage-168 | — | A | — | W | — | D | W | E | Y | T | D | S | — | F | 0.13 | 0.79 | 0.09 | 997 |
| Phage-169 | T | D | — | — | — | — | — | — | — | — | — | A | — | Y | 0.10 | 0.77 | 0.09 | 998 |
| Phage-170 | T | D | — | W | — | D | W | E | F | Y | A | D | — | D | 0.07 | 0.75 | 0.08 | 999 |
| Phage-171 | Y | D | — | — | — | — | L | — | — | — | — | I | — | H | 0.09 | 0.69 | 0.09 | 1000 |
| Phage-172 | S | D | — | — | — | D | G | — | — | — | I | I | — | T | 0.07 | 0.69 | 0.07 | 1001 |
| Phage-173 | Y | — | — | — | — | — | — | — | — | — | I | D | — | D | 0.08 | 0.67 | 0.09 | 1002 |
| Phage-174 | F | F | — | — | — | — | I | — | — | — | I | A | — | V | 0.08 | 0.62 | 0.09 | 1003 |
| Phage-175 | D | — | — | — | — | — | — | — | — | — | T | F | — | D | 0.16 | 0.60 | 0.10 | 1004 |
| Phage-176 | Y | D | — | — | — | — | W | E | W | P | I | D | — | V | 0.10 | 0.59 | 0.10 | 1005 |
| Phage-177 | F | — | — | — | — | — | I | E | L | F | S | F | — | Y | 0.13 | 0.59 | 0.11 | 1006 |
| Phage-178 | Y | — | — | — | — | — | V | — | — | — | I | T | — | P | 0.15 | 0.42 | 0.11 | 1007 |
| Phage-179 | I | L | — | — | — | — | — | — | — | — | I | N | — | N | 0.09 | 0.37 | 0.25 | 1008 |
| Phage-180 | — | V | — | — | — | A | M | G | Q | H | Y | L | — | D | 0.08 | 0.09 | 0.08 | 1009 |
| Phage-181 | — | V | — | — | T | K | M | G | I | H | Y | S | — | Y | 0.08 | 0.08 | 0.08 | 1010 |
| Phage-182 | Y | D | — | W | — | D | W | E | Y | V | Y | A | — | Y | 0.08 | 0.98 | 0.08 | 1011 |
| Phage-183 | D | L | — | — | — | — | L | — | — | — | — | N | — | D | 0.09 | 0.98 | 0.08 | 1012 |
| Phage-184 | Y | — | — | — | — | — | — | — | — | — | T | V | — | Y | 0.14 | 0.97 | 0.16 | 1013 |
| Phage-185 | L | D | — | W | — | D | W | E | W | P | Y | S | — | N | 0.08 | 0.96 | 0.09 | 1014 |
| Phage-186 | F | I | — | W | — | D | W | E | D | D | F | F | — | Y | 0.08 | 0.96 | 0.09 | 1015 |
| Phage-187 | D | L | — | — | — | — | V | E | W | Y | F | F | — | N | 0.11 | 0.95 | 0.10 | 1016 |
| Phage-188 | Y | D | — | — | — | — | L | — | — | — | I | V | — | F | 0.07 | 0.94 | 0.08 | 1017 |
| Phage-189 | L | N | — | W | — | V | W | E | D | D | — | F | — | Y | 0.09 | 0.92 | 0.09 | 1018 |
| Phage-190 | F | N | — | W | — | D | W | E | D | P | N | F | — | V | 0.09 | 0.91 | 0.09 | 1019 |
| Phage-191 | — | I | — | W | — | D | W | E | D | D | Y | F | — | P | 0.10 | 0.91 | 0.13 | 1020 |
| Phage-192 | F | L | — | — | — | — | — | — | — | — | S | V | — | Y | 0.10 | 0.91 | 0.08 | 1021 |
| Phage-193 | Y | D | — | — | — | — | L | — | — | — | I | F | — | Y | 0.10 | 0.91 | 0.09 | 1022 |
| Phage-194 | H | L | — | — | — | D | G | — | — | — | F | T | — | F | 0.11 | 0.90 | 0.10 | 1023 |
| Phage-195 | Y | F | — | — | — | — | M | — | — | — | L | Y | — | I | 0.08 | 0.90 | 0.08 | 1024 |
| Phage-196 | Y | — | — | — | — | — | V | E | — | Y | A | N | — | Y | 0.07 | 0.90 | 0.07 | 1025 |
| Phage-197 | N | H | — | — | — | — | — | — | — | I | T | A | — | Y | 0.16 | 0.90 | 0.58 | 1026 |
| Phage-198 | I | D | — | W | — | D | W | E | — | A | F | N | — | Y | 0.09 | 0.90 | 0.08 | 1027 |
| Phage-199 | A | — | — | — | — | — | L | E | — | F | F | L | — | T | 0.09 | 0.89 | 0.08 | 1028 |
| Phage-200 | I | — | — | — | — | — | V | E | — | V | H | H | — | Y | 0.08 | 0.89 | 0.08 | 1029 |
| Phage-201 | F | F | — | — | — | — | — | — | — | — | A | — | — | D | 0.10 | 0.89 | 0.11 | 1030 |
| Phage-202 | Y | D | — | — | — | — | L | — | — | T | I | I | — | A | 0.08 | 0.89 | 0.08 | 1031 |
| Phage-203 | I | L | — | — | — | — | W | E | Y | P | L | D | — | S | 0.09 | 0.89 | 0.10 | 1032 |
| Phage-204 | F | I | — | — | — | — | — | — | — | — | T | T | — | N | 0.09 | 0.88 | 0.10 | 1033 |
| Phage-205 | F | — | — | — | — | — | L | — | — | — | — | S | — | D | 0.17 | 0.88 | 0.15 | 1034 |
| Phage-206 | H | L | — | — | — | — | L | — | — | — | — | T | — | F | 0.10 | 0.87 | 0.10 | 1035 |
| Phage-207 | L | I | — | — | — | — | V | E | D | Y | S | L | — | H | 0.09 | 0.87 | 0.09 | 1036 |
| Phage-208 | Y | F | — | — | — | — | M | — | — | — | — | Y | — | D | 0.08 | 0.87 | 0.08 | 1037 |
| Phage-209 | H | I | — | — | — | — | M | — | — | — | I | Y | — | I | 0.13 | 0.87 | 0.09 | 1038 |
| Phage-210 | F | D | — | — | — | — | L | — | — | — | I | N | — | Y | 0.08 | 0.87 | 0.09 | 1039 |
| Phage-211 | Y | — | — | — | — | — | V | F | I | Y | I | Y | — | T | 0.07 | 0.87 | 0.08 | 1040 |
| Phage-212 | L | A | — | W | — | V | R | E | — | I | N | A | — | I | 0.08 | 0.85 | 0.07 | 1041 |
| Phage-213 | I | D | — | W | — | D | W | E | D | I | T | F | — | D | 0.08 | 0.85 | 0.08 | 1042 |
| Phage-214 | I | V | — | — | — | — | L | — | — | — | I | T | — | P | 0.11 | 0.85 | 0.15 | 1043 |
| Phage-215 | F | — | — | — | — | — | — | E | L | P | A | D | — | D | 0.08 | 0.85 | 0.09 | 1044 |
| Phage-216 | F | D | — | — | — | — | — | — | — | — | N | P | — | F | 0.10 | 0.85 | 0.09 | 1045 |
| Phage-217 | D | A | — | W | — | D | W | E | — | Y | S | S | — | D | 0.10 | 0.83 | 0.10 | 1046 |
| Phage-218 | D | H | — | W | — | D | W | E | P | N | Y | F | — | V | 0.08 | 0.83 | 0.09 | 1047 |
| Phage-219 | D | — | — | W | — | D | W | E | I | N | Y | I | — | F | 0.09 | 0.83 | 0.10 | 1048 |
| Phage-220 | I | — | — | W | — | D | W | E | Y | V | Y | A | — | N | 0.10 | 0.82 | 0.09 | 1049 |
| Phage-221 | D | F | — | — | — | — | V | E | — | D | Y | L | — | D | 0.07 | 0.82 | 0.08 | 1050 |
| Phage-222 | H | D | — | — | — | D | G | R | — | D | Y | D | — | A | 0.11 | 0.82 | 0.09 | 1051 |
| Phage-223 | L | A | — | W | — | D | W | E | D | D | Y | F | — | V | 0.08 | 0.82 | 0.09 | 1052 |
| Phage-224 | D | I | — | W | — | D | W | E | D | Y | L | P | — | V | 0.10 | 0.82 | 0.10 | 1053 |
| Phage-225 | I | L | — | — | — | — | T | E | V | Y | A | L | — | P | 0.08 | 0.81 | 0.10 | 1054 |
| Phage-226 | I | F | — | — | — | — | W | E | F | — | — | L | — | N | 0.10 | 0.81 | 0.11 | 1055 |
| Phage-227 | T | — | — | — | — | — | V | E | D | F | S | L | — | V | 0.07 | 0.80 | 0.08 | 1056 |
| Phage-228 | F | I | — | I | — | — | W | E | F | V | D | A | — | F | 0.11 | 0.80 | 0.09 | 1057 |
| Phage-229 | F | A | — | W | — | D | W | E | — | D | S | P | — | D | 0.06 | 0.80 | 0.07 | 1058 |
| Phage-230 | I | L | — | — | — | — | V | E | — | L | I | F | — | P | 0.12 | 0.80 | 0.08 | 1059 |
| Phage-231 | F | — | — | — | — | — | V | E | — | Y | I | Y | — | Y | 0.08 | 0.80 | 0.08 | 1060 |
| Phage-232 | D | S | — | — | — | — | L | — | — | — | I | I | — | D | 0.10 | 0.79 | 0.09 | 1061 |
| Phage-233 | F | L | — | — | — | D | G | — | — | T | S | V | — | D | 0.11 | 0.79 | 0.08 | 1062 |
| Phage-234 | F | N | — | W | — | N | G | E | P | T | Y | F | — | V | 0.11 | 0.79 | 0.08 | 1063 |
| Phage-235 | L | A | — | W | — | V | W | E | Y | P | — | T | — | I | 0.09 | 0.78 | 0.09 | 1064 |
| Phage-236 | D | — | — | — | — | — | V | E | — | D | — | Y | — | Y | 0.09 | 0.78 | 0.09 | 1065 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \multicolumn{14}{c}{Amino acid position sequence} | | | | | | | | | | | | | | Phage binding ELISA | | | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | |
| Phage-237 | I | T | — | W | — | D | W | E | — | Y | A | N | — | T | 0.08 | 0.77 | 0.07 | 1066 |
| Phage-238 | F | F | — | — | — | D | G | — | — | T | Y | S | — | I | 0.15 | 0.77 | 0.13 | 1067 |
| Phage-239 | T | D | — | W | — | D | W | E | Y | A | T | S | — | D | 0.09 | 0.76 | 0.09 | 1068 |
| Phage-240 | F | N | — | — | — | D | G | Y | — | D | Y | L | — | D | 0.10 | 0.76 | 0.11 | 1069 |
| Phage-241 | Y | D | — | W | — | D | W | E | V | D | F | H | — | P | 0.11 | 0.76 | 0.08 | 1070 |
| Phage-242 | N | I | — | W | — | D | W | E | D | D | S | F | — | F | 0.08 | 0.76 | 0.08 | 1071 |
| Phage-243 | A | T | — | — | — | — | — | — | — | — | I | — | — | S | 0.13 | 0.75 | 0.09 | 1072 |
| Phage-244 | S | — | — | — | — | — | — | — | — | — | T | F | — | D | 0.10 | 0.74 | 0.09 | 1073 |
| Phage-245 | P | I | — | — | — | — | Y | — | — | — | D | V | — | A | 0.08 | 0.74 | 0.08 | 1074 |
| Phage-246 | Y | — | — | — | — | D | G | — | — | Y | N | S | — | I | 0.11 | 0.74 | 0.11 | 1075 |
| Phage-247 | — | D | — | W | — | D | W | E | V | F | I | A | — | D | 0.11 | 0.74 | 0.10 | 1076 |
| Phage-248 | D | L | — | — | — | — | V | E | — | V | N | L | — | L | 0.12 | 0.74 | 0.10 | 1077 |
| Phage-249 | F | D | — | — | — | — | M | — | — | — | T | T | — | F | 0.09 | 0.74 | 0.09 | 1078 |
| Phage-250 | N | F | — | W | — | D | W | E | P | I | Y | F | — | T | 0.13 | 0.74 | 0.14 | 1079 |
| Phage-251 | — | D | — | — | — | D | G | — | — | — | F | F | — | L | 0.08 | 0.73 | 0.08 | 1080 |
| Phage-252 | — | D | — | — | — | D | G | — | — | T | A | F | — | I | 0.10 | 0.73 | 0.09 | 1081 |
| Phage-253 | N | I | — | — | — | — | M | — | — | — | L | V | — | I | 0.10 | 0.73 | 0.09 | 1082 |
| Phage-254 | I | I | — | — | — | — | — | — | — | — | F | F | — | F | 0.08 | 0.73 | 0.09 | 1083 |
| Phage-255 | N | F | — | — | — | — | Y | — | — | — | I | S | — | I | 0.10 | 0.73 | 0.38 | 1084 |
| Phage-256 | H | L | — | — | — | — | T | E | — | A | D | T | — | N | 0.11 | 0.73 | 0.51 | 1085 |
| Phage-257 | D | — | — | — | — | — | V | E | — | D | Y | L | — | D | 0.08 | 0.72 | 0.09 | 1086 |
| Phage-258 | D | — | — | — | — | — | L | — | — | — | I | N | — | D | 0.11 | 0.72 | 0.10 | 1087 |
| Phage-259 | F | — | — | — | — | — | L | — | — | — | L | F | — | V | 0.09 | 0.72 | 0.08 | 1088 |
| Phage-260 | P | D | — | — | — | — | W | E | F | Y | — | T | — | N | 0.12 | 0.72 | 0.08 | 1089 |
| Phage-261 | F | D | — | — | — | — | — | E | Y | I | Y | A | — | T | 0.09 | 0.72 | 0.08 | 1090 |
| Phage-262 | D | — | — | — | — | — | I | — | — | — | S | I | — | N | 0.12 | 0.72 | 0.11 | 1091 |
| Phage-263 | D | F | — | — | — | I | V | E | — | Y | I | F | — | F | 0.08 | 0.72 | 0.07 | 1092 |
| Phage-264 | P | V | — | W | — | D | W | E | Y | V | S | S | — | D | 0.08 | 0.71 | 0.08 | 1093 |
| Phage-265 | Y | I | — | — | — | — | R | — | — | — | N | L | — | L | 0.09 | 0.71 | 0.09 | 1094 |
| Phage-266 | Y | D | — | — | — | — | L | — | — | — | I | V | — | D | 0.11 | 0.71 | 0.11 | 1095 |
| Phage-267 | H | D | — | W | — | D | W | E | D | F | Y | F | — | V | 0.09 | 0.71 | 0.08 | 1096 |
| Phage-268 | H | — | — | — | — | — | Y | — | — | — | I | D | — | Y | 0.12 | 0.71 | 0.10 | 1097 |
| Phage-269 | L | F | — | — | — | — | M | P | — | D | I | F | — | N | 0.08 | 0.71 | 0.08 | 1098 |
| Phage-270 | H | D | — | — | — | — | L | E | F | H | Y | A | — | Y | 0.10 | 0.71 | 0.12 | 1099 |
| Phage-271 | D | F | — | — | — | — | L | — | — | — | I | N | — | F | 0.08 | 0.70 | 0.08 | 1100 |
| Phage-272 | Y | F | — | — | — | — | L | — | — | — | I | A | — | N | 0.10 | 0.70 | 0.10 | 1101 |
| Phage-273 | T | D | — | W | — | D | W | E | A | D | I | I | — | D | 0.10 | 0.70 | 0.08 | 1102 |
| Phage-274 | Y | D | — | — | — | — | L | — | — | — | I | Y | — | F | 0.09 | 0.70 | 0.08 | 1103 |
| Phage-275 | Y | — | — | W | — | D | W | W | — | Y | — | T | — | D | 0.10 | 0.70 | 0.11 | 1104 |
| Phage-276 | P | I | — | — | — | — | L | E | — | — | Y | L | — | N | 0.13 | 0.69 | 0.52 | 1105 |
| Phage-277 | F | D | — | — | — | — | I | — | — | — | I | V | — | Y | 0.12 | 0.69 | 0.11 | 1106 |
| Phage-278 | I | L | — | — | — | D | G | I | — | F | F | D | — | P | 0.09 | 0.68 | 0.07 | 1107 |
| Phage-279 | A | — | — | — | — | — | Y | — | — | — | L | T | — | V | 0.07 | 0.68 | 0.07 | 1108 |
| Phage-280 | D | F | — | — | — | — | L | — | — | — | I | I | — | A | 0.14 | 0.68 | 0.14 | 1109 |
| Phage-281 | Y | D | — | — | — | — | — | — | — | — | L | D | — | N | 0.08 | 0.68 | 0.08 | 1110 |
| Phage-282 | A | T | — | — | — | — | — | — | — | — | — | A | — | D | 0.14 | 0.67 | 0.08 | 1111 |
| Phage-283 | L | L | — | — | — | D | G | V | — | D | F | F | — | D | 0.10 | 0.67 | 0.10 | 1112 |
| Phage-284 | N | F | — | — | — | — | L | P | — | D | I | F | — | F | 0.12 | 0.66 | 0.13 | 1113 |
| Phage-285 | F | I | — | — | — | — | V | E | — | V | S | L | — | N | 0.08 | 0.66 | 0.08 | 1114 |
| Phage-286 | Y | D | — | — | — | D | G | Y | — | A | F | Y | — | H | 0.12 | 0.66 | 0.10 | 1115 |
| Phage-287 | N | F | — | — | — | — | I | E | E | D | Y | L | — | D | 0.08 | 0.65 | 0.08 | 1116 |
| Phage-288 | D | — | — | — | — | D | G | V | — | D | F | I | — | N | 0.06 | 0.65 | 0.08 | 1117 |
| Phage-289 | T | D | — | W | — | D | W | E | Y | I | Y | S | — | S | 0.08 | 0.65 | 0.07 | 1118 |
| Phage-290 | F | — | — | — | — | — | — | E | — | I | T | N | — | I | 0.14 | 0.65 | 0.11 | 1119 |
| Phage-291 | F | D | — | W | — | D | W | E | — | — | F | F | — | H | 0.07 | 0.64 | 0.08 | 1120 |
| Phage-292 | D | F | — | — | — | D | G | — | — | — | F | F | — | P | 0.08 | 0.63 | 0.08 | 1121 |
| Phage-293 | H | N | — | — | — | — | L | — | — | — | L | V | — | D | 0.13 | 0.63 | 0.09 | 1122 |
| Phage-294 | I | — | — | — | — | D | G | A | — | D | Y | T | — | D | 0.07 | 0.63 | 0.07 | 1123 |
| Phage-295 | F | D | — | — | — | — | — | E | F | P | — | I | — | F | 0.08 | 0.62 | 0.08 | 1124 |
| Phage-296 | Y | N | — | — | — | — | L | — | — | — | L | T | — | D | 0.09 | 0.62 | 0.08 | 1125 |
| Phage-297 | F | D | — | — | — | — | L | — | — | — | I | H | — | A | 0.07 | 0.62 | 0.08 | 1126 |
| Phage-298 | D | I | — | — | — | — | V | E | — | Y | F | L | — | F | 0.15 | 0.61 | 0.10 | 1127 |
| Phage-299 | F | D | — | — | — | — | V | — | — | — | L | T | — | F | 0.10 | 0.61 | 0.09 | 1128 |
| Phage-300 | F | — | — | — | — | — | I | E | — | F | H | L | — | F | 0.08 | 0.61 | 0.08 | 1129 |
| Phage-301 | A | — | — | — | — | — | L | — | — | — | I | I | — | D | 0.12 | 0.61 | 0.10 | 1130 |
| Phage-302 | Y | N | — | — | — | — | L | — | — | — | I | T | — | N | 0.09 | 0.61 | 0.10 | 1131 |
| Phage-303 | F | D | — | W | — | D | W | E | — | P | — | D | — | L | 0.08 | 0.61 | 0.07 | 1132 |
| Phage-304 | D | V | — | — | — | — | L | — | — | — | — | L | — | P | 0.08 | 0.60 | 0.08 | 1133 |
| Phage-305 | N | — | — | — | — | — | L | — | — | — | L | P | — | P | 0.09 | 0.60 | 0.08 | 1134 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \multicolumn{14}{c|}{Amino acid position sequence} | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-306 | Y | — | — | W | — | D | W | E | Y | D | I | F | — | S | 0.08 | 0.60 | 0.10 | 1135 |
| Phage-307 | D | D | — | — | — | — | — | — | — | — | T | Y | — | N | 0.08 | 0.60 | 0.09 | 1136 |
| Phage-308 | F | — | — | — | — | — | E | — | V | F | H | — | — | Y | 0.09 | 0.60 | 0.09 | 1137 |
| Phage-309 | T | D | — | W | — | D | W | E | — | Y | F | L | — | D | 0.07 | 0.60 | 0.09 | 1138 |
| Phage-310 | — | — | — | — | — | — | W | E | — | — | Y | L | — | P | 0.09 | 0.60 | 0.09 | 1139 |
| Phage-311 | D | D | — | — | — | N | G | Y | A | T | F | I | — | Y | 0.06 | 0.59 | 0.08 | 1140 |
| Phage-312 | F | L | — | — | — | — | I | E | D | D | T | H | — | Y | 0.16 | 0.59 | 0.38 | 1141 |
| Phage-313 | F | A | — | W | — | D | W | E | — | T | I | P | — | H | 0.08 | 0.59 | 0.08 | 1142 |
| Phage-314 | — | L | — | — | — | — | — | — | — | — | Y | N | — | Y | 0.10 | 0.58 | 0.08 | 1143 |
| Phage-315 | Y | D | — | — | — | — | — | — | — | — | I | S | — | I | 0.09 | 0.58 | 0.09 | 1144 |
| Phage-316 | Y | D | — | — | — | — | — | — | — | — | — | N | — | Y | 0.12 | 0.57 | 0.10 | 1145 |
| Phage-317 | A | I | — | W | — | D | W | E | — | F | — | D | — | Y | 0.10 | 0.57 | 0.09 | 1146 |
| Phage-318 | L | T | — | W | — | V | R | E | — | I | F | A | — | D | 0.07 | 0.57 | 0.08 | 1147 |
| Phage-319 | — | L | — | — | — | — | — | — | — | — | Y | Y | — | N | 0.09 | 0.57 | 0.09 | 1148 |
| Phage-320 | N | V | — | — | — | — | Y | — | — | — | A | P | — | N | 0.07 | 0.56 | 0.08 | 1149 |
| Phage-321 | H | D | — | — | — | — | — | — | — | — | I | S | — | V | 0.11 | 0.55 | 0.09 | 1150 |
| Phage-322 | F | D | — | — | — | — | L | — | — | T | — | D | — | N | 0.12 | 0.55 | 0.41 | 1151 |
| Phage-323 | Y | F | — | — | — | — | V | E | — | H | F | Y | — | Y | 0.09 | 0.55 | 0.08 | 1152 |
| Phage-324 | D | — | — | — | — | — | L | — | — | — | I | I | — | H | 0.09 | 0.54 | 0.09 | 1153 |
| Phage-325 | D | D | — | — | — | — | V | P | — | D | I | T | — | Y | 0.11 | 0.54 | 0.08 | 1154 |
| Phage-326 | D | N | — | — | — | — | L | — | — | — | — | V | — | D | 0.10 | 0.54 | 0.08 | 1155 |
| Phage-327 | — | H | — | W | — | D | W | E | P | N | Y | Y | — | D | 0.10 | 0.54 | 0.08 | 1156 |
| Phage-328 | D | — | — | — | — | — | L | — | — | — | L | F | — | L | 0.09 | 0.53 | 0.09 | 1157 |
| Phage-329 | D | D | — | — | — | — | L | — | — | — | — | V | — | A | 0.08 | 0.53 | 0.11 | 1158 |
| Phage-330 | A | A | — | — | — | — | L | — | — | — | I | V | — | D | 0.13 | 0.53 | 0.09 | 1159 |
| Phage-331 | D | F | — | — | — | — | — | E | — | I | N | N | — | F | 0.14 | 0.52 | 0.48 | 1160 |
| Phage-332 | Y | — | — | — | — | — | — | — | — | — | N | A | — | Y | 0.08 | 0.52 | 0.07 | 1161 |
| Phage-333 | — | L | — | — | — | — | — | — | — | — | N | S | — | Y | 0.10 | 0.52 | 0.11 | 1162 |
| Phage-334 | Y | D | — | — | — | — | — | — | — | — | I | D | — | D | 0.09 | 0.52 | 0.09 | 1163 |
| Phage-335 | D | S | — | — | — | — | — | E | F | Y | Y | V | — | F | 0.11 | 0.52 | 0.14 | 1164 |
| Phage-336 | Y | I | — | — | — | — | L | — | — | — | L | I | — | N | 0.10 | 0.52 | 0.08 | 1165 |
| Phage-337 | F | D | — | — | — | — | V | E | — | D | Y | F | — | Y | 0.11 | 0.52 | 0.10 | 1166 |
| Phage-338 | F | D | — | — | — | — | Y | — | — | — | L | Y | — | F | 0.08 | 0.52 | 0.07 | 1167 |
| Phage-339 | — | L | — | — | — | D | G | — | — | Y | S | F | — | H | 0.10 | 0.51 | 0.10 | 1168 |
| Phage-340 | I | P | — | — | — | — | M | — | — | — | — | V | — | N | 0.12 | 0.51 | 0.09 | 1169 |
| Phage-341 | I | I | — | — | — | D | G | Y | — | D | F | T | — | D | 0.12 | 0.51 | 0.09 | 1170 |
| Phage-342 | I | F | — | — | — | — | L | — | — | — | I | I | — | Y | 0.11 | 0.51 | 0.08 | 1171 |
| Phage-343 | — | D | — | — | — | — | — | — | — | — | Y | D | — | Y | 0.18 | 0.51 | 0.18 | 1172 |
| Phage-344 | L | S | — | — | — | — | M | — | — | — | L | Y | — | D | 0.12 | 0.51 | 0.08 | 1173 |
| Phage-345 | Y | D | — | W | — | D | W | E | Y | N | I | D | — | T | 0.08 | 0.51 | 0.09 | 1174 |
| Phage-346 | N | H | — | — | — | D | G | — | — | T | T | V | — | F | 0.09 | 0.51 | 0.08 | 1175 |
| Phage-347 | N | F | — | — | — | — | L | — | — | — | I | P | — | H | 0.11 | 0.50 | 0.12 | 1176 |
| Phage-348 | F | H | — | — | — | — | I | E | — | Y | A | L | — | D | 0.08 | 0.50 | 0.09 | 1177 |
| Phage-349 | — | — | — | — | — | — | V | E | D | Y | N | L | — | Y | 0.07 | 0.50 | 0.08 | 1178 |
| Phage-350 | — | — | — | — | — | D | G | — | — | L | A | N | — | Y | 0.09 | 0.50 | 0.08 | 1179 |
| Phage-351 | L | I | — | — | — | V | I | A | — | D | L | P | — | N | 0.17 | 0.50 | 0.26 | 1180 |
| Phage-352 | D | I | — | — | — | — | I | P | — | D | — | S | — | D | 0.10 | 0.50 | 0.08 | 1181 |
| Phage-353 | I | — | — | — | — | — | W | E | — | A | D | Y | — | D | 0.11 | 0.50 | 0.45 | 1182 |
| Phage-354 | I | D | — | W | — | D | W | E | D | D | S | I | — | Y | 0.10 | 0.50 | 0.10 | 1183 |
| Phage-355 | — | L | — | — | — | — | V | E | D | F | T | L | — | D | 0.09 | 0.50 | 0.11 | 1184 |
| Phage-356 | L | — | — | — | — | V | I | E | — | I | Y | Y | — | Y | 0.09 | 0.49 | 0.09 | 1185 |
| Phage-357 | F | F | — | — | — | — | E | — | V | H | S | D | — | N | 0.14 | 0.49 | 0.38 | 1186 |
| Phage-358 | N | D | — | — | — | — | V | E | L | V | S | D | — | N | 0.10 | 0.49 | 0.08 | 1187 |
| Phage-359 | D | L | — | — | — | — | L | — | — | — | T | V | — | D | 0.09 | 0.49 | 0.08 | 1188 |
| Phage-360 | I | P | — | — | — | — | V | E | D | Y | N | L | — | N | 0.08 | 0.49 | 0.08 | 1189 |
| Phage-361 | Y | — | — | — | — | — | L | E | W | P | — | V | — | N | 0.10 | 0.49 | 0.10 | 1190 |
| Phage-362 | Y | D | — | — | — | — | L | — | — | — | — | I | — | N | 0.08 | 0.49 | 0.10 | 1191 |
| Phage-363 | — | — | — | — | — | D | G | — | — | — | F | D | — | A | 0.08 | 0.49 | 0.08 | 1192 |
| Phage-364 | N | D | — | — | — | — | W | E | D | T | Y | F | — | L | 0.08 | 0.49 | 0.10 | 1193 |
| Phage-365 | P | — | — | — | — | — | M | E | — | L | S | N | — | S | 0.13 | 0.48 | 0.16 | 1194 |
| Phage-366 | D | D | — | — | — | — | E | V | I | S | D | — | — | Y | 0.15 | 0.48 | 0.10 | 1195 |
| Phage-367 | D | L | — | — | — | — | P | — | D | — | P | — | — | D | 0.08 | 0.48 | 0.08 | 1196 |
| Phage-368 | I | — | — | — | — | — | — | — | — | — | F | V | — | Y | 0.11 | 0.48 | 0.10 | 1197 |
| Phage-369 | A | — | — | — | — | — | Y | E | V | F | A | D | — | N | 0.10 | 0.48 | 0.11 | 1198 |
| Phage-370 | I | D | — | — | — | — | Y | — | — | — | — | D | — | L | 0.09 | 0.48 | 0.09 | 1199 |
| Phage-371 | H | I | — | W | — | D | W | E | — | F | H | D | — | N | 0.07 | 0.48 | 0.08 | 1200 |
| Phage-372 | Y | D | — | — | — | — | L | — | — | T | I | T | — | L | 0.08 | 0.48 | 0.08 | 1201 |
| Phage-373 | Y | L | — | — | — | — | L | — | — | T | I | L | — | N | 0.09 | 0.48 | 0.08 | 1202 |
| Phage-374 | F | F | — | — | — | — | — | E | — | A | F | L | — | F | 0.10 | 0.48 | 0.14 | 1203 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-375 | I | L | — | — | — | — | L | — | — | — | F | T | — | A | 0.07 | 0.47 | 0.08 | 1204 |
| Phage-376 | F | H | — | — | — | — | V | E | L | Y | T | D | — | N | 0.09 | 0.47 | 0.08 | 1205 |
| Phage-377 | N | L | — | — | — | — | V | E | — | Y | N | F | — | Y | 0.08 | 0.47 | 0.08 | 1206 |
| Phage-378 | F | D | — | — | — | — | V | E | — | T | Y | Y | — | F | 0.21 | 0.47 | 0.09 | 1207 |
| Phage-379 | — | F | — | — | — | — | — | E | — | D | H | Y | — | Y | 0.12 | 0.47 | 0.37 | 1208 |
| Phage-380 | A | I | — | — | — | — | W | E | V | V | A | D | — | N | 0.11 | 0.47 | 0.11 | 1209 |
| Phage-381 | F | I | — | W | — | D | W | E | — | D | N | Y | — | N | 0.12 | 0.47 | 0.25 | 1210 |
| Phage-382 | I | — | — | — | — | — | — | — | — | — | F | I | — | D | 0.08 | 0.47 | 0.10 | 1211 |
| Phage-383 | N | L | — | — | — | — | V | E | D | V | Y | D | — | H | 0.12 | 0.47 | 0.43 | 1212 |
| Phage-384 | H | — | — | — | — | — | V | E | — | Y | H | N | — | N | 0.09 | 0.47 | 0.09 | 1213 |
| Phage-385 | D | I | — | — | — | — | Y | — | — | — | Y | S | — | T | 0.09 | 0.47 | 0.09 | 1214 |
| Phage-386 | D | — | — | — | — | — | L | — | — | T | L | I | — | A | 0.13 | 0.46 | 0.10 | 1215 |
| Phage-387 | I | A | — | — | — | — | M | P | — | D | I | D | — | Y | 0.12 | 0.46 | 0.09 | 1216 |
| Phage-388 | I | D | — | — | — | — | L | — | — | — | I | F | — | Y | 0.10 | 0.46 | 0.10 | 1217 |
| Phage-389 | Y | F | — | — | — | D | V | E | — | D | F | A | — | D | 0.11 | 0.46 | 0.11 | 1218 |
| Phage-390 | Y | N | — | — | — | — | W | E | Y | A | I | L | — | D | 0.12 | 0.46 | 0.34 | 1219 |
| Phage-391 | I | — | — | — | — | — | V | E | D | Y | I | V | — | N | 0.14 | 0.46 | 0.22 | 1220 |
| Phage-392 | Y | D | — | — | — | — | I | — | — | — | T | P | — | A | 0.07 | 0.46 | 0.07 | 1221 |
| Phage-393 | D | T | — | W | — | D | W | E | H | I | Y | A | — | D | 0.09 | 0.46 | 0.09 | 1222 |
| Phage-394 | D | I | — | — | — | — | M | — | — | — | T | — | — | N | 0.13 | 0.45 | 0.12 | 1223 |
| Phage-395 | Y | D | — | W | — | D | W | E | R | Y | F | P | — | I | 0.10 | 0.45 | 0.09 | 1224 |
| Phage-396 | H | L | — | — | — | — | L | — | — | — | — | A | — | S | 0.13 | 0.45 | 0.11 | 1225 |
| Phage-397 | Y | D | — | — | — | D | G | — | — | T | T | I | — | A | 0.09 | 0.45 | 0.09 | 1226 |
| Phage-398 | Y | — | — | — | — | — | Y | E | D | V | L | D | — | F | 0.07 | 0.45 | 0.08 | 1227 |
| Phage-399 | D | F | — | — | — | — | M | — | — | T | I | S | — | D | 0.14 | 0.45 | 0.10 | 1228 |
| Phage-400 | I | L | — | — | — | — | L | — | — | — | L | V | — | D | 0.08 | 0.44 | 0.07 | 1229 |
| Phage-401 | L | I | — | — | — | — | W | E | V | I | T | N | — | D | 0.12 | 0.44 | 0.40 | 1230 |
| Phage-402 | Y | D | — | — | — | — | — | — | — | Y | F | — | — | P | 0.09 | 0.44 | 0.09 | 1231 |
| Phage-403 | A | L | — | — | — | — | V | E | V | Y | D | V | — | V | 0.08 | 0.44 | 0.08 | 1232 |
| Phage-404 | Y | H | — | W | — | D | W | E | D | V | N | F | — | Y | 0.10 | 0.44 | 0.09 | 1233 |
| Phage-405 | F | L | — | — | — | M | G | G | L | T | F | Y | — | Y | 0.09 | 0.44 | 0.08 | 1234 |
| Phage-406 | I | I | — | — | — | — | — | — | — | Y | — | — | — | F | 0.09 | 0.43 | 0.19 | 1235 |
| Phage-407 | F | F | — | — | — | — | M | — | — | — | — | H | — | F | 0.11 | 0.43 | 0.09 | 1236 |
| Phage-408 | A | F | — | — | — | — | — | — | — | — | L | F | — | A | 0.09 | 0.43 | 0.09 | 1237 |
| Phage-409 | N | — | — | — | — | D | G | — | — | T | N | I | — | D | 0.08 | 0.43 | 0.08 | 1238 |
| Phage-410 | Y | L | — | — | — | — | W | E | W | V | H | N | — | L | 0.13 | 0.43 | 0.09 | 1239 |
| Phage-411 | A | T | — | — | — | D | G | — | — | — | H | I | — | A | 0.08 | 0.43 | 0.09 | 1240 |
| Phage-412 | — | — | — | — | — | — | V | E | V | L | D | Y | — | D | 0.07 | 0.42 | 0.08 | 1241 |
| Phage-413 | I | H | — | — | — | — | W | E | F | Y | T | D | — | D | 0.08 | 0.42 | 0.08 | 1242 |
| Phage-414 | D | D | — | — | — | — | L | — | — | T | — | A | — | D | 0.13 | 0.42 | 0.32 | 1243 |
| Phage-415 | Y | L | — | — | — | — | — | — | — | — | I | D | — | N | 0.11 | 0.42 | 0.17 | 1244 |
| Phage-416 | L | L | — | — | — | — | V | E | D | V | F | A | — | Y | 0.09 | 0.42 | 0.09 | 1245 |
| Phage-417 | Y | D | — | — | — | — | L | — | — | — | L | T | — | Y | 0.08 | 0.42 | 0.08 | 1246 |
| Phage-418 | F | D | — | — | — | — | L | — | — | T | — | N | — | Y | 0.09 | 0.41 | 0.09 | 1247 |
| Phage-419 | F | A | — | W | — | D | W | E | — | I | N | D | — | H | 0.08 | 0.41 | 0.09 | 1248 |
| Phage-420 | Y | — | — | — | — | — | Y | E | — | D | I | Y | — | N | 0.09 | 0.41 | 0.09 | 1249 |
| Phage-421 | N | V | — | — | — | — | V | E | D | Y | T | F | — | Y | 0.09 | 0.40 | 0.08 | 1250 |
| Phage-422 | A | — | — | — | — | — | L | E | — | Y | D | F | — | T | 0.12 | 0.40 | 0.08 | 1251 |
| Phage-423 | F | D | — | — | — | — | I | — | — | — | T | I | — | T | 0.08 | 0.40 | 0.09 | 1252 |
| Phage-424 | N | L | — | — | — | — | L | — | — | T | L | V | — | A | 0.10 | 0.40 | 0.09 | 1253 |
| Phage-425 | Y | S | — | W | — | D | W | E | — | Y | L | A | — | N | 0.08 | 0.40 | 0.08 | 1254 |
| Phage-426 | G | I | — | — | — | — | V | E | D | Y | N | Y | — | D | 0.09 | 0.40 | 0.10 | 1255 |
| Phage-427 | F | F | — | — | — | — | L | — | — | — | — | N | — | H | 0.07 | 0.40 | 0.07 | 1256 |
| Phage-428 | Y | — | — | — | — | — | Y | E | — | D | F | Y | — | F | 0.11 | 0.40 | 0.09 | 1257 |
| Phage-429 | L | — | — | — | — | — | Y | — | — | — | T | D | — | Y | 0.11 | 0.40 | 0.10 | 1258 |
| Phage-430 | D | I | — | — | — | — | V | E | — | D | F | L | — | Y | 0.10 | 0.40 | 0.08 | 1259 |
| Phage-431 | T | L | — | — | — | — | V | E | L | Y | I | F | — | D | 0.08 | 0.40 | 0.09 | 1260 |
| Phage-432 | F | — | — | — | — | — | — | E | Q | I | A | D | — | Y | 0.11 | 0.40 | 0.09 | 1261 |
| Phage-433 | D | D | — | — | — | — | V | E | — | Y | H | L | — | D | 0.11 | 0.40 | 0.18 | 1262 |
| Phage-434 | D | — | — | — | — | — | L | E | D | V | T | L | — | H | 0.13 | 0.39 | 0.09 | 1263 |
| Phage-435 | — | L | — | — | — | — | V | E | D | V | N | L | — | Y | 0.09 | 0.39 | 0.08 | 1264 |
| Phage-436 | D | I | — | — | — | — | L | — | — | T | I | D | — | Y | 0.09 | 0.39 | 0.09 | 1265 |
| Phage-437 | T | — | — | — | — | — | V | E | — | D | I | N | — | Y | 0.08 | 0.39 | 0.08 | 1266 |
| Phage-438 | I | V | — | W | — | D | W | E | — | Y | P | N | — | D | 0.08 | 0.39 | 0.08 | 1267 |
| Phage-439 | S | D | — | — | — | — | L | — | — | — | I | I | — | T | 0.11 | 0.39 | 0.10 | 1268 |
| Phage-440 | Y | D | — | — | — | — | L | P | — | D | Y | D | — | N | 0.15 | 0.39 | 0.10 | 1269 |
| Phage-441 | N | L | — | W | — | D | W | E | — | Y | Y | A | — | D | 0.12 | 0.39 | 0.17 | 1270 |
| Phage-442 | D | D | — | — | — | — | L | — | — | — | L | P | — | H | 0.10 | 0.39 | 0.08 | 1271 |
| Phage-443 | S | L | — | — | — | D | G | Q | — | D | Y | T | — | F | 0.08 | 0.39 | 0.08 | 1272 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \_ | \_ | \_ | \_ | Amino acid position sequence | \_ | \_ | \_ | \_ | \_ | \_ | \_ | \_ | \_ | Background signal | Phage binding ELISA SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-444 | L | I | — | W | — | D | W | E | — | Y | N | F | — | T | 0.13 | 0.39 | 0.11 | 1273 |
| Phage-445 | F | H | — | — | — | D | G | — | — | T | — | P | — | I | 0.08 | 0.39 | 0.08 | 1274 |
| Phage-446 | F | D | — | — | — | — | W | E | W | I | Y | D | — | F | 0.08 | 0.38 | 0.08 | 1275 |
| Phage-447 | I | — | — | — | — | — | W | — | — | — | L | D | — | D | 0.08 | 0.38 | 0.09 | 1276 |
| Phage-448 | L | I | — | — | — | — | I | — | — | — | A | S | — | N | 0.10 | 0.38 | 0.11 | 1277 |
| Phage-449 | T | S | — | W | V | D | W | E | — | F | S | D | — | I | 0.11 | 0.38 | 0.34 | 1278 |
| Phage-450 | Y | — | — | — | — | — | V | E | — | D | Y | V | — | D | 0.10 | 0.38 | 0.08 | 1279 |
| Phage-451 | D | D | — | — | — | — | Q | E | F | I | Y | A | — | I | 0.09 | 0.38 | 0.08 | 1280 |
| Phage-452 | A | D | — | W | — | D | W | E | — | Y | A | D | — | Y | 0.11 | 0.38 | 0.10 | 1281 |
| Phage-453 | Y | — | — | — | — | — | — | — | — | I | H | — | — | I | 0.08 | 0.38 | 0.07 | 1282 |
| Phage-454 | S | E | — | W | — | D | W | E | P | F | F | D | — | N | 0.08 | 0.37 | 0.09 | 1283 |
| Phage-455 | Y | H | — | — | — | — | M | — | — | — | L | I | — | T | 0.07 | 0.37 | 0.07 | 1284 |
| Phage-456 | S | D | — | W | — | D | W | E | D | A | Y | F | — | I | 0.09 | 0.37 | 0.07 | 1285 |
| Phage-457 | — | D | — | — | — | — | V | E | — | Y | Y | H | — | I | 0.08 | 0.37 | 0.08 | 1286 |
| Phage-458 | D | N | — | — | — | — | Y | — | — | — | T | A | — | N | 0.10 | 0.37 | 0.10 | 1287 |
| Phage-459 | L | — | — | — | — | V | — | E | F | Y | D | Y | — | Y | 0.08 | 0.37 | 0.10 | 1288 |
| Phage-460 | Y | T | — | — | — | — | M | — | — | — | T | — | — | I | 0.09 | 0.37 | 0.08 | 1289 |
| Phage-461 | N | F | — | W | — | D | W | E | V | N | S | F | — | D | 0.09 | 0.37 | 0.08 | 1290 |
| Phage-462 | N | A | — | W | — | D | W | E | Y | I | D | F | — | N | 0.12 | 0.36 | 0.09 | 1291 |
| Phage-463 | Y | N | — | — | — | — | M | — | — | — | I | F | — | S | 0.09 | 0.36 | 0.07 | 1292 |
| Phage-464 | L | D | — | — | — | — | L | — | — | — | I | T | — | Y | 0.08 | 0.36 | 0.09 | 1293 |
| Phage-465 | H | — | — | — | — | — | — | — | — | — | I | N | — | D | 0.11 | 0.36 | 0.08 | 1294 |
| Phage-466 | I | I | — | — | — | — | L | P | — | D | Y | V | — | T | 0.08 | 0.36 | 0.08 | 1295 |
| Phage-467 | D | I | — | — | — | — | — | — | — | — | I | D | — | S | 0.08 | 0.36 | 0.08 | 1296 |
| Phage-468 | P | — | — | — | — | — | — | — | — | — | — | L | — | F | 0.10 | 0.36 | 0.09 | 1297 |
| Phage-469 | — | F | — | — | — | — | — | — | — | — | — | D | — | Y | 0.07 | 0.36 | 0.08 | 1298 |
| Phage-470 | Y | D | — | W | — | D | W | E | — | A | L | P | — | A | 0.08 | 0.36 | 0.08 | 1299 |
| Phage-471 | D | D | — | W | — | D | W | E | D | Y | — | F | — | F | 0.10 | 0.36 | 0.10 | 1300 |
| Phage-472 | H | F | — | — | — | — | W | E | L | F | S | D | — | Y | 0.11 | 0.36 | 0.11 | 1301 |
| Phage-473 | I | T | — | W | — | D | W | E | V | N | F | P | — | Y | 0.07 | 0.35 | 0.07 | 1302 |
| Phage-474 | P | D | — | — | — | — | L | — | — | — | I | T | — | N | 0.20 | 0.35 | 0.16 | 1303 |
| Phage-475 | N | L | — | W | — | D | W | E | A | F | F | P | — | Y | 0.08 | 0.35 | 0.07 | 1304 |
| Phage-476 | F | — | — | — | — | — | — | E | Y | I | R | D | — | Y | 0.08 | 0.35 | 0.07 | 1305 |
| Phage-477 | F | F | — | — | — | — | — | — | — | — | I | I | — | D | 0.09 | 0.35 | 0.10 | 1306 |
| Phage-478 | — | L | — | — | — | — | K | G | G | P | T | Y | N | S | 0.08 | 0.35 | 0.10 | 1307 |
| Phage-479 | L | A | — | W | — | V | W | E | — | P | G | H | — | D | 0.11 | 0.35 | 0.10 | 1308 |
| Phage-480 | D | — | — | — | — | — | V | E | D | V | N | D | — | Y | 0.07 | 0.35 | 0.08 | 1309 |
| Phage-481 | D | — | — | — | — | — | — | E | — | A | H | Y | — | N | 0.08 | 0.35 | 0.07 | 1310 |
| Phage-482 | — | L | — | — | — | — | L | — | — | T | L | T | — | I | 0.08 | 0.35 | 0.07 | 1311 |
| Phage-483 | Y | — | — | — | — | — | I | E | D | Y | N | L | — | N | 0.10 | 0.34 | 0.09 | 1312 |
| Phage-484 | Y | I | — | — | — | — | V | E | — | Y | Y | N | — | F | 0.13 | 0.34 | 0.14 | 1313 |
| Phage-485 | D | I | — | — | — | — | L | — | — | — | I | F | — | F | 0.08 | 0.34 | 0.09 | 1314 |
| Phage-486 | D | I | — | — | — | — | V | E | — | D | Y | L | — | Y | 0.07 | 0.34 | 0.08 | 1315 |
| Phage-487 | T | L | — | — | — | — | — | E | — | D | A | P | — | I | 0.10 | 0.34 | 0.08 | 1316 |
| Phage-488 | N | — | — | W | — | D | W | E | Y | I | N | S | — | V | 0.14 | 0.34 | 0.09 | 1317 |
| Phage-489 | N | D | — | — | — | — | V | E | — | Y | Y | Y | — | T | 0.07 | 0.34 | 0.09 | 1318 |
| Phage-490 | I | T | — | — | — | — | M | — | — | — | I | D | — | N | 0.08 | 0.34 | 0.08 | 1319 |
| Phage-491 | Y | — | — | — | — | — | M | A | — | D | L | I | — | D | 0.10 | 0.34 | 0.29 | 1320 |
| Phage-492 | I | D | — | — | — | — | L | — | — | — | I | V | — | T | 0.11 | 0.33 | 0.09 | 1321 |
| Phage-493 | H | T | — | W | — | D | W | E | W | D | — | Y | — | D | 0.08 | 0.33 | 0.07 | 1322 |
| Phage-494 | I | H | — | — | — | — | W | E | L | I | D | D | — | L | 0.08 | 0.33 | 0.10 | 1323 |
| Phage-495 | Y | T | — | — | — | — | L | — | — | — | I | T | — | Y | 0.08 | 0.33 | 0.08 | 1324 |
| Phage-496 | F | H | — | — | — | — | V | E | — | T | — | Y | — | F | 0.11 | 0.33 | 0.09 | 1325 |
| Phage-497 | D | — | — | — | — | — | L | — | — | — | L | I | — | N | 0.07 | 0.33 | 0.08 | 1326 |
| Phage-498 | I | — | — | — | — | — | — | — | — | — | D | Y | — | I | 0.08 | 0.33 | 0.10 | 1327 |
| Phage-499 | D | L | — | — | — | — | I | E | — | D | L | V | — | T | 0.09 | 0.33 | 0.09 | 1328 |
| Phage-500 | N | I | — | — | — | — | L | Q | — | D | I | V | — | P | 0.09 | 0.33 | 0.09 | 1329 |
| Phage-501 | N | N | — | — | — | — | M | — | — | — | I | T | — | Y | 0.08 | 0.33 | 0.08 | 1330 |
| Phage-502 | H | T | — | — | — | — | L | — | — | — | I | V | — | V | 0.08 | 0.33 | 0.08 | 1331 |
| Phage-503 | Y | — | — | — | — | — | I | E | D | I | L | Y | — | T | 0.12 | 0.33 | 0.23 | 1332 |
| Phage-504 | N | T | — | — | — | — | — | E | F | V | H | L | — | P | 0.07 | 0.33 | 0.11 | 1333 |
| Phage-505 | D | I | — | — | — | — | M | — | — | — | T | V | — | D | 0.10 | 0.33 | 0.09 | 1334 |
| Phage-506 | A | I | — | — | — | — | V | E | I | V | N | Y | — | Y | 0.09 | 0.32 | 0.07 | 1335 |
| Phage-507 | H | L | — | — | — | — | V | E | D | P | T | A | — | V | 0.10 | 0.32 | 0.28 | 1336 |
| Phage-508 | A | D | — | — | — | — | L | — | — | — | I | S | — | T | 0.10 | 0.32 | 0.09 | 1337 |
| Phage-509 | F | D | — | — | — | — | L | — | — | — | — | I | — | D | 0.07 | 0.32 | 0.09 | 1338 |
| Phage-510 | D | V | — | — | — | — | — | — | — | — | I | D | — | N | 0.10 | 0.32 | 0.08 | 1339 |
| Phage-511 | Y | L | — | — | — | — | V | E | — | I | S | I | — | F | 0.08 | 0.32 | 0.07 | 1340 |
| Phage-512 | S | A | — | — | — | — | — | — | — | — | L | H | — | V | 0.10 | 0.31 | 0.30 | 1341 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \multicolumn{14}{c}{Amino acid position sequence} | | | | | | | | | | | | | | Background signal | Phage binding ELISA SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-513 | H | L | — | W | — | D | W | E | — | D | S | A | — | N | 0.08 | 0.31 | 0.08 | 1342 |
| Phage-514 | H | T | — | W | — | D | W | E | Y | D | Y | D | — | F | 0.10 | 0.31 | 0.08 | 1343 |
| Phage-515 | Y | D | — | — | — | — | W | E | — | V | A | L | — | N | 0.10 | 0.31 | 0.10 | 1344 |
| Phage-516 | T | L | — | — | — | — | I | E | — | Y | I | V | — | Y | 0.09 | 0.31 | 0.23 | 1345 |
| Phage-517 | S | — | — | — | — | — | — | — | — | — | I | F | — | T | 0.09 | 0.31 | 0.09 | 1346 |
| Phage-518 | D | I | — | — | — | — | — | — | — | — | L | H | — | Y | 0.08 | 0.31 | 0.08 | 1347 |
| Phage-519 | L | F | — | — | — | — | — | E | — | A | Y | L | — | I | 0.08 | 0.31 | 0.08 | 1348 |
| Phage-520 | I | F | — | — | — | — | I | E | — | D | F | V | — | T | 0.10 | 0.31 | 0.10 | 1349 |
| Phage-521 | D | D | — | — | — | — | W | E | Y | Y | — | A | — | V | 0.08 | 0.31 | 0.08 | 1350 |
| Phage-522 | D | D | — | — | — | — | L | — | — | T | T | I | — | Y | 0.10 | 0.31 | 0.09 | 1351 |
| Phage-523 | A | S | — | — | — | — | L | — | — | — | — | A | — | D | 0.10 | 0.31 | 0.09 | 1352 |
| Phage-524 | Y | L | — | — | — | — | V | E | D | Y | D | Y | — | Y | 0.08 | 0.31 | 0.09 | 1353 |
| Phage-525 | D | L | — | — | — | — | W | E | — | T | I | F | — | A | 0.12 | 0.30 | 0.09 | 1354 |
| Phage-526 | D | F | — | — | — | D | G | E | — | F | Y | I | — | P | 0.12 | 0.30 | 0.11 | 1355 |
| Phage-527 | — | — | — | — | — | — | V | E | — | N | I | L | — | H | 0.15 | 0.30 | 0.17 | 1356 |
| Phage-528 | D | — | — | — | — | — | V | E | — | N | Y | F | — | F | 0.12 | 0.30 | 0.21 | 1357 |
| Phage-529 | N | D | — | W | — | D | W | Y | — | F | L | S | — | D | 0.10 | 0.30 | 0.10 | 1358 |
| Phage-530 | R | D | — | W | — | D | W | E | V | P | Y | F | — | D | 0.08 | 0.30 | 0.09 | 1359 |
| Phage-531 | N | L | — | — | — | — | V | E | — | A | — | Y | — | Y | 0.10 | 0.30 | 0.13 | 1360 |
| Phage-532 | F | D | — | W | — | D | G | E | L | N | Y | L | — | T | 0.23 | 0.30 | 0.08 | 1361 |
| Phage-533 | Y | — | — | — | — | — | V | E | D | V | N | L | — | I | 0.18 | 0.30 | 0.10 | 1362 |
| Phage-534 | D | N | — | — | — | — | Y | — | — | — | I | T | — | L | 0.11 | 0.29 | 0.09 | 1363 |
| Phage-535 | L | N | — | W | — | D | W | E | — | D | Y | S | — | N | 0.09 | 0.29 | 0.09 | 1364 |
| Phage-536 | P | T | — | — | — | — | V | E | — | L | L | S | — | N | 0.12 | 0.29 | 0.26 | 1365 |
| Phage-537 | D | H | — | — | — | — | V | E | L | I | F | Y | — | H | 0.11 | 0.29 | 0.08 | 1366 |
| Phage-538 | F | H | — | — | — | — | L | — | — | — | I | F | — | Y | 0.08 | 0.29 | 0.08 | 1367 |
| Phage-539 | F | D | — | — | — | — | L | E | — | T | — | V | — | P | 0.16 | 0.29 | 0.16 | 1368 |
| Phage-540 | D | F | — | — | — | — | L | — | — | — | L | P | — | A | 0.08 | 0.29 | 0.08 | 1369 |
| Phage-541 | D | S | — | — | — | — | L | — | — | — | I | Y | — | D | 0.09 | 0.29 | 0.09 | 1370 |
| Phage-542 | A | D | — | W | — | D | W | E | — | F | L | L | — | F | 0.12 | 0.29 | 0.10 | 1371 |
| Phage-543 | I | L | — | — | — | — | V | E | — | L | D | F | — | N | 0.10 | 0.28 | 0.08 | 1372 |
| Phage-544 | F | F | — | — | — | — | — | E | — | I | F | L | — | Y | 0.09 | 0.28 | 0.07 | 1373 |
| Phage-545 | Y | N | — | — | — | D | G | — | — | — | Y | D | — | H | 0.07 | 0.28 | 0.07 | 1374 |
| Phage-546 | D | N | — | — | — | — | L | — | — | T | I | T | — | F | 0.11 | 0.28 | 0.11 | 1375 |
| Phage-547 | H | N | — | — | — | D | G | — | — | A | F | I | — | N | 0.09 | 0.28 | 0.23 | 1376 |
| Phage-548 | D | — | — | — | — | — | V | E | — | D | L | V | — | P | 0.10 | 0.28 | 0.23 | 1377 |
| Phage-549 | D | — | — | — | — | — | L | — | — | — | L | N | — | F | 0.08 | 0.28 | 0.07 | 1378 |
| Phage-550 | D | — | — | — | — | — | — | Q | — | D | F | H | — | H | 0.11 | 0.28 | 0.27 | 1379 |
| Phage-551 | Y | D | — | — | — | — | W | E | F | T | D | D | — | I | 0.10 | 0.28 | 0.18 | 1380 |
| Phage-552 | D | I | — | — | — | — | Y | E | — | D | I | I | — | Y | 0.14 | 0.28 | 0.19 | 1381 |
| Phage-553 | F | D | — | — | — | — | L | — | — | T | — | P | — | P | 0.11 | 0.28 | 0.08 | 1382 |
| Phage-554 | N | — | — | — | — | — | L | — | — | T | S | V | — | D | 0.09 | 0.28 | 0.26 | 1383 |
| Phage-555 | Y | — | — | — | — | — | W | E | F | — | F | D | — | D | 0.17 | 0.28 | 0.11 | 1384 |
| Phage-556 | Y | A | — | — | — | — | L | — | — | — | — | T | — | D | 0.09 | 0.28 | 0.08 | 1385 |
| Phage-557 | F | L | — | — | — | — | V | E | Q | D | Y | F | — | V | 0.08 | 0.28 | 0.10 | 1386 |
| Phage-558 | D | N | — | — | — | — | — | — | — | — | — | R | — | D | 0.09 | 0.27 | 0.26 | 1387 |
| Phage-559 | N | D | — | — | — | D | G | I | — | T | — | D | — | Y | 0.10 | 0.27 | 0.24 | 1388 |
| Phage-560 | Y | F | — | — | — | — | V | E | D | Y | N | D | — | F | 0.08 | 0.27 | 0.09 | 1389 |
| Phage-561 | N | L | — | — | — | — | — | — | — | — | I | F | — | Y | 0.10 | 0.27 | 0.07 | 1390 |
| Phage-562 | I | D | — | W | — | D | W | E | — | Y | I | P | — | T | 0.10 | 0.27 | 0.08 | 1391 |
| Phage-563 | I | — | — | — | — | D | G | — | — | — | F | I | — | A | 0.07 | 0.27 | 0.08 | 1392 |
| Phage-564 | D | — | — | — | — | — | — | — | — | — | V | — | — | Y | 0.08 | 0.27 | 0.07 | 1393 |
| Phage-565 | — | F | — | — | — | — | W | E | D | I | T | D | — | D | 0.13 | 0.27 | 0.09 | 1394 |
| Phage-566 | L | D | — | — | — | — | V | — | — | T | F | T | — | H | 0.08 | 0.26 | 0.08 | 1395 |
| Phage-567 | D | D | — | — | — | — | Y | — | — | — | F | A | — | H | 0.13 | 0.26 | 0.10 | 1396 |
| Phage-568 | I | — | — | — | — | — | Y | Q | — | D | L | P | — | N | 0.12 | 0.26 | 0.11 | 1397 |
| Phage-569 | L | D | — | — | — | — | V | E | — | Y | N | Y | — | V | 0.09 | 0.26 | 0.08 | 1398 |
| Phage-570 | Y | V | — | — | — | — | — | — | — | — | S | A | — | N | 0.14 | 0.26 | 0.08 | 1399 |
| Phage-571 | T | P | — | — | — | — | L | E | — | A | I | — | — | Y | 0.10 | 0.26 | 0.10 | 1400 |
| Phage-572 | Y | F | — | — | — | — | — | — | — | — | A | D | — | N | 0.08 | 0.26 | 0.08 | 1401 |
| Phage-573 | D | D | — | — | — | — | — | E | — | D | I | I | — | D | 0.12 | 0.26 | 0.25 | 1402 |
| Phage-574 | L | — | — | — | — | V | V | E | — | L | N | H | — | N | 0.08 | 0.26 | 0.09 | 1403 |
| Phage-575 | — | I | — | — | — | D | G | E | — | L | I | A | — | A | 0.09 | 0.26 | 0.27 | 1404 |
| Phage-576 | F | A | — | W | — | D | W | Q | — | T | Y | V | — | N | 0.09 | 0.25 | 0.08 | 1405 |
| Phage-577 | Y | I | — | — | — | — | V | E | F | L | F | F | — | N | 0.08 | 0.25 | 0.08 | 1406 |
| Phage-578 | T | Q | — | — | — | K | G | E | P | T | Y | H | — | Y | 0.12 | 0.25 | 0.12 | 1407 |
| Phage-579 | N | — | — | — | — | — | V | E | — | Y | H | N | — | D | 0.10 | 0.25 | 0.17 | 1408 |
| Phage-580 | — | — | — | — | — | — | W | E | F | F | S | D | — | A | 0.08 | 0.25 | 0.07 | 1409 |
| Phage-581 | F | — | — | — | — | — | L | E | — | — | F | F | — | Y | 0.10 | 0.25 | 0.22 | 1410 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | _____ Amino acid position sequence _____ | | | | | | | | | | | | | | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-582 | D | — | — | — | — | — | I | E | — | N | F | Y | — | Y | 0.13 | 0.25 | 0.09 | 1411 |
| Phage-583 | Y | A | — | — | — | — | V | E | — | Y | — | Y | — | A | 0.08 | 0.25 | 0.09 | 1412 |
| Phage-584 | — | D | — | — | — | — | L | — | — | I | I | — | — | D | 0.08 | 0.25 | 0.07 | 1413 |
| Phage-585 | N | D | — | — | — | — | M | — | — | I | A | — | — | Y | 0.07 | 0.25 | 0.07 | 1414 |
| Phage-586 | — | — | — | — | — | — | — | — | — | Y | L | A | — | A | 0.09 | 0.25 | 0.21 | 1415 |
| Phage-587 | — | I | — | — | — | — | — | — | — | A | N | — | — | D | 0.08 | 0.25 | 0.09 | 1416 |
| Phage-588 | L | T | — | W | — | D | W | E | — | D | F | F | — | N | 0.07 | 0.24 | 0.07 | 1417 |
| Phage-589 | F | — | — | — | — | — | Q | E | — | I | N | Y | — | Y | 0.10 | 0.24 | 0.23 | 1418 |
| Phage-590 | T | — | — | — | — | — | L | E | — | F | F | L | — | Y | 0.13 | 0.24 | 0.08 | 1419 |
| Phage-591 | P | D | — | — | — | — | L | — | — | — | A | — | — | H | 0.12 | 0.24 | 0.09 | 1420 |
| Phage-592 | N | D | — | — | — | — | — | E | — | I | I | F | — | V | 0.09 | 0.24 | 0.24 | 1421 |
| Phage-593 | Y | I | — | — | — | — | — | — | — | — | F | Y | — | N | 0.25 | 0.24 | 0.08 | 1422 |
| Phage-594 | H | A | — | — | — | — | L | — | — | — | L | L | — | N | 0.20 | 0.24 | 0.07 | 1423 |
| Phage-595 | Y | — | — | — | — | — | W | E | — | A | — | L | — | A | 0.09 | 0.24 | 0.21 | 1424 |
| Phage-596 | A | F | — | — | — | — | V | E | — | Y | D | L | — | N | 0.10 | 0.24 | 0.16 | 1425 |
| Phage-597 | Y | N | — | — | — | — | — | — | — | — | A | — | — | S | 0.15 | 0.23 | 0.09 | 1426 |
| Phage-598 | Y | L | — | — | — | — | V | E | D | D | T | L | — | A | 0.08 | 0.23 | 0.09 | 1427 |
| Phage-599 | A | V | — | — | — | — | — | — | — | — | N | — | — | D | 0.08 | 0.23 | 0.08 | 1428 |
| Phage-600 | N | — | — | — | — | — | W | E | V | Y | S | L | — | P | 0.13 | 0.23 | 0.08 | 1429 |
| Phage-601 | D | F | — | — | — | — | V | E | — | D | T | Y | — | H | 0.07 | 0.23 | 0.07 | 1430 |
| Phage-602 | I | S | — | — | — | — | Y | E | W | D | Y | A | — | N | 0.08 | 0.23 | 0.10 | 1431 |
| Phage-603 | — | N | — | — | — | — | L | — | — | — | T | I | — | Y | 0.08 | 0.23 | 0.08 | 1432 |
| Phage-604 | Y | D | — | — | — | — | — | — | — | T | A | P | — | Y | 0.07 | 0.23 | 0.08 | 1433 |
| Phage-605 | Y | L | — | — | — | — | — | E | — | N | F | L | — | T | 0.09 | 0.23 | 0.22 | 1434 |
| Phage-606 | F | D | — | — | — | — | V | — | — | — | — | D | — | A | 0.08 | 0.22 | 0.09 | 1435 |
| Phage-607 | Y | D | — | — | — | — | Q | E | — | I | S | F | — | N | 0.09 | 0.22 | 0.09 | 1436 |
| Phage-608 | T | D | — | — | — | — | I | E | L | Y | D | D | — | F | 0.09 | 0.22 | 0.09 | 1437 |
| Phage-609 | T | F | — | — | — | — | L | — | — | — | Y | — | — | Y | 0.08 | 0.22 | 0.07 | 1438 |
| Phage-610 | F | F | — | — | — | — | I | — | — | — | N | A | — | V | 0.09 | 0.22 | 0.07 | 1439 |
| Phage-611 | Y | H | — | W | — | D | W | E | P | I | Y | I | — | I | 0.12 | 0.22 | 0.10 | 1440 |
| Phage-612 | A | I | — | — | — | — | Y | E | — | D | H | Y | — | Y | 0.08 | 0.22 | 0.08 | 1441 |
| Phage-613 | P | L | — | — | — | D | G | F | — | N | Y | N | — | F | 0.12 | 0.22 | 0.08 | 1442 |
| Phage-614 | F | P | — | W | — | D | W | E | W | D | N | N | — | H | 0.09 | 0.22 | 0.09 | 1443 |
| Phage-615 | — | D | — | — | — | D | G | — | — | L | A | A | — | H | 0.10 | 0.22 | 0.11 | 1444 |
| Phage-616 | — | D | — | W | — | D | W | E | — | Y | Y | S | — | D | 0.08 | 0.22 | 0.07 | 1445 |
| Phage-617 | — | — | — | — | — | — | Y | — | — | — | Y | D | — | T | 0.07 | 0.21 | 0.10 | 1446 |
| Phage-618 | N | L | — | — | — | — | W | E | N | F | A | D | — | F | 0.08 | 0.21 | 0.08 | 1447 |
| Phage-619 | Y | I | — | — | — | — | L | E | V | F | F | V | — | D | 0.12 | 0.21 | 0.10 | 1448 |
| Phage-620 | I | F | — | — | — | — | L | E | D | Y | S | I | — | D | 0.09 | 0.21 | 0.08 | 1449 |
| Phage-621 | D | — | — | — | — | — | L | E | Q | Y | D | L | — | F | 0.09 | 0.21 | 0.08 | 1450 |
| Phage-622 | L | L | — | — | — | V | N | E | D | P | L | D | — | Y | 0.11 | 0.21 | 0.13 | 1451 |
| Phage-623 | I | D | — | — | — | — | — | — | — | — | F | — | — | Y | 0.08 | 0.21 | 0.08 | 1452 |
| Phage-624 | I | I | — | — | — | — | V | E | — | I | D | I | — | S | 0.08 | 0.21 | 0.08 | 1453 |
| Phage-625 | I | A | — | W | — | D | W | E | D | Y | S | S | — | P | 0.08 | 0.21 | 0.11 | 1454 |
| Phage-626 | Y | — | — | — | — | — | V | E | D | I | N | D | — | I | 0.09 | 0.21 | 0.07 | 1455 |
| Phage-627 | N | I | — | — | — | — | M | — | — | — | I | D | — | I | 0.08 | 0.21 | 0.07 | 1456 |
| Phage-628 | F | D | — | W | — | D | W | E | — | L | — | S | — | Y | 0.07 | 0.21 | 0.08 | 1457 |
| Phage-629 | Y | F | — | — | — | — | W | E | D | H | F | F | — | D | 0.09 | 0.21 | 0.19 | 1458 |
| Phage-630 | T | — | — | — | — | — | — | E | — | D | S | Y | — | D | 0.12 | 0.20 | 0.09 | 1459 |
| Phage-631 | N | L | — | — | — | — | V | E | L | I | D | I | — | S | 0.11 | 0.20 | 0.09 | 1460 |
| Phage-632 | D | N | — | — | — | — | W | E | — | V | Y | L | — | N | 0.08 | 0.20 | 0.08 | 1461 |
| Phage-633 | F | L | — | — | — | — | — | — | — | — | D | L | — | Y | 0.08 | 0.20 | 0.09 | 1462 |
| Phage-634 | H | I | — | — | — | — | Q | — | — | — | I | — | — | T | 0.09 | 0.20 | 0.19 | 1463 |
| Phage-635 | F | D | — | W | — | D | W | E | D | N | S | Y | — | D | 0.10 | 0.20 | 0.09 | 1464 |
| Phage-636 | T | A | — | — | — | — | W | E | F | D | F | N | — | D | 0.08 | 0.20 | 0.07 | 1465 |
| Phage-637 | H | H | — | W | — | D | W | E | D | Y | S | T | — | P | 0.10 | 0.20 | 0.11 | 1466 |
| Phage-638 | Y | — | — | — | — | — | — | — | — | — | N | — | — | F | 0.07 | 0.20 | 0.08 | 1467 |
| Phage-639 | L | H | — | W | — | D | W | E | — | I | D | I | — | D | 0.08 | 0.20 | 0.09 | 1468 |
| Phage-640 | D | I | — | — | — | D | G | Q | — | D | F | V | — | S | 0.08 | 0.20 | 0.09 | 1469 |
| Phage-641 | D | V | — | W | — | D | W | E | V | N | Y | F | — | D | 0.09 | 0.20 | 0.07 | 1470 |
| Phage-642 | — | N | — | — | — | — | M | — | — | — | I | D | — | A | 0.12 | 0.20 | 0.10 | 1471 |
| Phage-643 | D | N | — | — | — | — | — | — | — | A | T | V | — | N | 0.11 | 0.19 | 0.19 | 1472 |
| Phage-644 | D | L | — | — | — | — | — | E | — | V | H | N | — | N | 0.08 | 0.19 | 0.08 | 1473 |
| Phage-645 | — | N | — | — | — | — | — | — | — | — | S | Y | — | F | 0.13 | 0.19 | 0.09 | 1474 |
| Phage-646 | N | I | — | W | — | D | W | E | — | D | N | F | — | S | 0.08 | 0.19 | 0.08 | 1475 |
| Phage-647 | F | V | — | — | — | — | W | E | V | Y | D | — | — | D | 0.08 | 0.19 | 0.08 | 1476 |
| Phage-648 | A | — | — | — | — | — | L | E | V | V | H | L | — | V | 0.10 | 0.19 | 0.17 | 1477 |
| Phage-649 | P | F | — | — | — | — | M | — | — | T | I | D | — | Y | 0.07 | 0.19 | 0.09 | 1478 |
| Phage-650 | L | L | — | — | — | V | M | E | D | V | F | A | — | Y | 0.08 | 0.19 | 0.08 | 1479 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-651 | D | L | — | — | — | — | — | — | — | — | T | N | — | Y | 0.07 | 0.19 | 0.08 | 1480 |
| Phage-652 | H | D | — | — | — | — | M | E | — | Y | Y | L | — | P | 0.10 | 0.18 | 0.10 | 1481 |
| Phage-653 | T | D | — | — | — | — | Y | — | — | — | I | I | — | P | 0.08 | 0.18 | 0.09 | 1482 |
| Phage-654 | — | L | — | W | — | D | W | E | D | Y | A | D | — | N | 0.09 | 0.18 | 0.08 | 1483 |
| Phage-655 | N | D | — | — | — | — | L | — | — | — | L | T | — | D | 0.07 | 0.18 | 0.09 | 1484 |
| Phage-656 | I | — | — | — | — | — | L | — | — | — | I | A | — | Y | 0.11 | 0.18 | 0.08 | 1485 |
| Phage-657 | N | — | — | — | — | — | V | E | — | F | N | F | — | H | 0.11 | 0.18 | 0.14 | 1486 |
| Phage-658 | D | V | — | — | — | — | I | E | — | Y | S | F | — | I | 0.08 | 0.18 | 0.09 | 1487 |
| Phage-659 | D | L | — | — | — | — | V | E | — | I | T | D | — | A | 0.10 | 0.18 | 0.12 | 1488 |
| Phage-660 | H | D | — | — | — | — | — | — | — | — | — | F | — | I | 0.12 | 0.18 | 0.12 | 1489 |
| Phage-661 | P | L | — | — | — | V | L | E | — | D | I | Y | — | Y | 0.10 | 0.18 | 0.13 | 1490 |
| Phage-662 | D | L | — | — | — | — | — | E | D | I | I | D | — | N | 0.10 | 0.18 | 0.11 | 1491 |
| Phage-663 | D | — | — | — | — | — | V | E | V | P | S | N | — | N | 0.10 | 0.18 | 0.18 | 1492 |
| Phage-664 | I | I | — | — | — | — | L | — | — | — | T | A | — | D | 0.10 | 0.18 | 0.09 | 1493 |
| Phage-665 | D | H | — | — | — | — | — | — | — | — | — | N | — | D | 0.10 | 0.18 | 0.14 | 1494 |
| Phage-666 | F | D | — | — | — | — | — | — | — | — | L | Y | — | S | 0.07 | 0.18 | 0.07 | 1495 |
| Phage-667 | F | A | — | W | — | D | W | E | — | V | Y | I | — | Y | 0.08 | 0.18 | 0.08 | 1496 |
| Phage-668 | L | — | — | — | — | — | — | — | — | — | L | D | — | S | 0.08 | 0.18 | 0.09 | 1497 |
| Phage-669 | D | L | — | — | — | — | L | E | — | A | F | L | — | A | 0.09 | 0.18 | 0.08 | 1498 |
| Phage-670 | F | A | — | — | — | — | L | — | — | T | L | T | — | L | 0.10 | 0.18 | 0.08 | 1499 |
| Phage-671 | F | D | — | — | — | — | V | E | — | I | S | N | — | D | 0.17 | 0.18 | 0.10 | 1500 |
| Phage-672 | — | H | — | — | — | — | L | E | Y | P | F | D | — | N | 0.09 | 0.17 | 0.16 | 1501 |
| Phage-673 | A | — | — | — | — | — | — | E | — | H | T | T | — | N | 0.10 | 0.17 | 0.15 | 1502 |
| Phage-674 | L | — | — | — | — | V | S | E | Q | F | T | F | — | I | 0.08 | 0.17 | 0.08 | 1503 |
| Phage-675 | D | — | — | — | — | — | L | — | — | — | Y | D | — | N | 0.10 | 0.17 | 0.09 | 1504 |
| Phage-676 | F | — | — | — | — | — | W | — | F | D | V | — | — | I | 0.13 | 0.17 | 0.15 | 1505 |
| Phage-677 | F | T | — | — | — | — | V | E | — | Y | D | H | — | I | 0.08 | 0.17 | 0.09 | 1506 |
| Phage-678 | Y | N | — | — | — | — | — | — | — | — | T | — | — | F | 0.12 | 0.17 | 0.11 | 1507 |
| Phage-679 | A | V | — | — | — | — | N | — | — | — | N | S | — | A | 0.08 | 0.17 | 0.08 | 1508 |
| Phage-680 | I | — | — | W | — | D | W | E | V | P | N | D | — | A | 0.10 | 0.17 | 0.09 | 1509 |
| Phage-681 | Y | F | — | — | — | — | — | E | — | F | F | H | — | Y | 0.12 | 0.17 | 0.12 | 1510 |
| Phage-682 | Y | V | — | — | — | D | G | — | — | — | S | F | — | D | 0.12 | 0.17 | 0.12 | 1511 |
| Phage-683 | I | S | — | — | — | — | V | E | — | F | F | Y | — | Y | 0.10 | 0.17 | 0.08 | 1512 |
| Phage-684 | L | I | — | — | — | V | — | E | — | D | — | Y | — | D | 0.17 | 0.17 | 0.15 | 1513 |
| Phage-685 | — | — | — | — | — | — | V | E | D | H | N | Y | — | A | 0.14 | 0.17 | 0.16 | 1514 |
| Phage-686 | L | D | — | — | — | — | — | E | F | V | Y | I | — | A | 0.08 | 0.17 | 0.10 | 1515 |
| Phage-687 | Y | D | — | — | — | — | — | E | — | D | L | P | — | I | 0.17 | 0.17 | 0.11 | 1516 |
| Phage-688 | D | V | — | — | — | — | V | E | — | D | Y | Y | — | D | 0.10 | 0.17 | 0.14 | 1517 |
| Phage-689 | N | D | — | W | — | D | W | E | Y | D | N | V | — | V | 0.08 | 0.17 | 0.10 | 1518 |
| Phage-690 | D | L | — | — | — | — | — | E | V | A | N | D | — | N | 0.10 | 0.16 | 0.16 | 1519 |
| Phage-691 | H | D | — | — | — | — | L | — | — | — | I | S | — | N | 0.09 | 0.16 | 0.07 | 1520 |
| Phage-692 | L | D | — | W | — | D | W | E | — | T | T | H | — | D | 0.08 | 0.16 | 0.08 | 1521 |
| Phage-693 | I | — | — | — | — | — | V | E | — | D | D | Y | — | L | 0.09 | 0.16 | 0.09 | 1522 |
| Phage-694 | Y | — | — | W | — | D | W | E | — | V | I | I | — | D | 0.09 | 0.16 | 0.09 | 1523 |
| Phage-695 | F | D | — | — | — | — | I | — | — | Y | T | N | — | N | 0.12 | 0.16 | 0.09 | 1524 |
| Phage-696 | I | T | — | — | — | — | L | — | — | T | I | N | — | D | 0.08 | 0.16 | 0.11 | 1525 |
| Phage-697 | D | S | — | — | — | — | V | E | — | D | I | Y | — | I | 0.07 | 0.16 | 0.08 | 1526 |
| Phage-698 | Y | L | — | — | — | — | — | — | — | G | N | — | — | H | 0.07 | 0.16 | 0.08 | 1527 |
| Phage-699 | D | N | — | — | — | — | L | P | — | D | Y | F | — | D | 0.08 | 0.16 | 0.10 | 1528 |
| Phage-700 | — | L | — | — | — | — | — | E | — | V | S | N | — | N | 0.11 | 0.16 | 0.08 | 1529 |
| Phage-701 | — | D | — | W | — | D | W | E | — | D | I | V | — | D | 0.10 | 0.16 | 0.09 | 1530 |
| Phage-702 | — | — | — | W | — | D | W | E | D | N | F | P | — | Y | 0.07 | 0.16 | 0.07 | 1531 |
| Phage-703 | D | — | — | — | — | — | V | E | — | H | F | N | — | H | 0.08 | 0.16 | 0.08 | 1532 |
| Phage-704 | A | D | — | — | — | — | I | E | — | D | A | Y | — | Y | 0.12 | 0.16 | 0.09 | 1533 |
| Phage-705 | I | L | — | W | — | D | W | E | D | A | T | F | — | Y | 0.09 | 0.16 | 0.07 | 1534 |
| Phage-706 | I | H | — | W | — | D | W | E | D | F | N | I | — | P | 0.09 | 0.16 | 0.08 | 1535 |
| Phage-707 | T | I | — | — | — | — | V | E | D | Y | N | D | — | I | 0.07 | 0.16 | 0.07 | 1536 |
| Phage-708 | D | D | — | — | — | — | L | — | — | — | — | A | — | I | 0.08 | 0.16 | 0.08 | 1537 |
| Phage-709 | D | D | — | W | — | D | W | E | D | H | I | F | — | F | 0.13 | 0.16 | 0.08 | 1538 |
| Phage-710 | — | N | — | — | — | — | V | E | — | I | I | F | — | D | 0.12 | 0.15 | 0.12 | 1539 |
| Phage-711 | I | F | — | W | — | D | W | E | D | D | T | V | — | I | 0.08 | 0.15 | 0.09 | 1540 |
| Phage-712 | I | I | — | — | — | — | — | E | — | I | S | D | — | L | 0.12 | 0.15 | 0.15 | 1541 |
| Phage-713 | F | D | — | — | — | — | V | E | — | Y | N | D | — | D | 0.11 | 0.15 | 0.09 | 1542 |
| Phage-714 | N | D | — | — | — | — | L | — | — | — | T | L | — | I | 0.08 | 0.15 | 0.10 | 1543 |
| Phage-715 | A | I | — | — | — | — | L | E | — | D | I | S | — | N | 0.12 | 0.15 | 0.17 | 1544 |
| Phage-716 | H | L | — | — | — | — | — | — | — | — | T | N | — | Y | 0.07 | 0.15 | 0.07 | 1545 |
| Phage-717 | S | — | — | — | — | — | L | — | — | — | — | A | — | I | 0.10 | 0.15 | 0.11 | 1546 |
| Phage-718 | L | — | — | — | — | — | — | E | Q | L | A | D | — | T | 0.08 | 0.15 | 0.08 | 1547 |
| Phage-719 | I | D | — | — | — | — | L | — | — | — | I | A | — | N | 0.07 | 0.15 | 0.08 | 1548 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \multicolumn{14}{c}{Amino acid position sequence} | | | | | | | | | | | | | | Background signal | Phage binding ELISA SP34.185 scFv signal | SP34.185 scFv signal in presence of CD3 | SEQ ID NO: |
|---|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | | | | |
| Phage-720 | F | D | — | — | — | D | G | Q | — | D | L | V | — | N | 0.10 | 0.15 | 0.08 | 1549 |
| Phage-721 | N | L | — | — | — | — | — | E | — | F | F | D | — | Y | 0.09 | 0.15 | 0.15 | 1550 |
| Phage-722 | S | I | — | — | — | — | L | Q | — | D | I | V | — | P | 0.09 | 0.14 | 0.14 | 1551 |
| Phage-723 | N | P | — | — | — | — | Y | — | — | — | A | H | — | D | 0.08 | 0.14 | 0.08 | 1552 |
| Phage-724 | Y | D | — | — | — | — | L | — | — | Y | Y | N | — | N | 0.12 | 0.14 | 0.11 | 1553 |
| Phage-725 | — | D | — | — | — | — | L | — | — | T | I | F | — | N | 0.07 | 0.14 | 0.08 | 1554 |
| Phage-726 | D | N | — | — | — | — | L | — | — | — | T | T | — | T | 0.09 | 0.14 | 0.10 | 1555 |
| Phage-727 | — | D | — | — | — | — | L | — | — | — | S | Y | — | D | 0.10 | 0.14 | 0.13 | 1556 |
| Phage-728 | Y | — | — | — | — | — | — | E | F | I | D | F | — | F | 0.07 | 0.14 | 0.07 | 1557 |
| Phage-729 | Y | D | — | W | — | D | W | E | V | I | T | Y | — | N | 0.08 | 0.14 | 0.09 | 1558 |
| Phage-730 | F | D | — | — | — | — | I | E | — | D | F | F | — | V | 0.06 | 0.14 | 0.07 | 1559 |
| Phage-731 | I | F | — | W | — | D | W | — | D | I | N | F | — | D | 0.10 | 0.14 | 0.14 | 1560 |
| Phage-732 | N | F | — | — | — | — | L | P | — | D | I | T | — | Y | 0.37 | 0.14 | 0.09 | 1561 |
| Phage-733 | S | L | — | — | — | — | — | E | — | Y | Y | H | — | L | 0.09 | 0.14 | 0.07 | 1562 |
| Phage-734 | A | S | — | — | — | — | L | — | — | — | L | D | — | L | 0.12 | 0.14 | 0.13 | 1563 |
| Phage-735 | S | F | — | — | — | — | R | E | W | D | L | A | — | Y | 0.09 | 0.14 | 0.08 | 1564 |
| Phage-736 | H | L | — | — | — | — | — | E | D | V | L | D | — | I | 0.08 | 0.14 | 0.12 | 1565 |
| Phage-737 | L | D | — | — | — | D | G | — | — | F | Y | Y | — | N | 0.20 | 0.14 | 0.09 | 1566 |
| Phage-738 | D | N | — | W | — | D | W | E | — | D | I | A | — | T | 0.16 | 0.14 | 0.11 | 1567 |
| Phage-739 | S | D | — | — | — | — | L | — | — | T | I | H | — | I | 0.09 | 0.14 | 0.08 | 1568 |
| Phage-740 | N | S | — | — | — | D | G | — | — | — | — | D | — | L | 0.08 | 0.14 | 0.08 | 1569 |
| Phage-741 | D | L | — | — | — | — | L | — | — | — | T | L | — | L | 0.07 | 0.14 | 0.08 | 1570 |
| Phage-742 | F | D | — | — | — | — | S | — | — | — | F | N | — | Y | 0.09 | 0.14 | 0.11 | 1571 |
| Phage-743 | D | L | — | — | — | — | — | E | — | D | D | I | — | Y | 0.12 | 0.14 | 0.13 | 1572 |
| Phage-744 | H | A | — | — | — | — | — | E | — | D | T | Y | — | F | 0.10 | 0.14 | 0.14 | 1573 |
| Phage-745 | S | D | — | — | — | — | L | — | — | — | — | A | — | I | 0.11 | 0.14 | 0.08 | 1574 |
| Phage-746 | I | V | — | — | — | — | L | P | — | D | Y | N | — | Y | 0.09 | 0.13 | 0.11 | 1575 |
| Phage-747 | D | L | — | — | — | — | — | — | — | — | F | I | — | F | 0.09 | 0.13 | 0.08 | 1576 |
| Phage-748 | Y | D | — | — | — | — | — | — | — | T | L | T | — | N | 0.13 | 0.13 | 0.08 | 1577 |
| Phage-749 | Y | D | — | — | — | — | V | E | — | I | — | N | — | D | 0.11 | 0.13 | 0.12 | 1578 |
| Phage-750 | — | F | — | — | — | — | — | I | E | D | D | H | — | I | 0.07 | 0.13 | 0.07 | 1579 |
| Phage-751 | F | T | — | — | — | — | W | E | D | D | Y | A | — | S | 0.12 | 0.13 | 0.12 | 1580 |
| Phage-752 | N | F | — | — | — | — | — | — | — | — | — | — | — | N | 0.10 | 0.13 | 0.09 | 1581 |
| Phage-753 | N | L | — | — | — | — | V | E | — | I | L | I | — | D | 0.07 | 0.13 | 0.07 | 1582 |
| Phage-754 | D | S | — | — | — | — | V | E | — | Y | D | L | — | N | 0.11 | 0.13 | 0.08 | 1583 |
| Phage-755 | T | L | — | — | — | — | — | E | — | I | T | D | — | N | 0.09 | 0.13 | 0.08 | 1584 |
| Phage-756 | T | V | — | — | — | K | M | E | M | N | S | T | — | D | 0.09 | 0.13 | 0.09 | 1585 |
| Phage-757 | — | H | — | W | — | D | W | E | D | A | — | S | — | N | 0.10 | 0.12 | 0.11 | 1586 |
| Phage-758 | D | L | — | — | — | D | G | N | — | L | D | F | — | F | 0.08 | 0.12 | 0.08 | 1587 |
| Phage-759 | D | L | — | — | — | D | G | E | — | H | Y | Y | — | D | 0.09 | 0.12 | 0.07 | 1588 |
| Phage-760 | F | N | — | — | — | — | V | E | — | I | L | L | — | T | 0.11 | 0.12 | 0.12 | 1589 |
| Phage-761 | H | — | — | — | — | — | V | E | N | I | N | D | — | I | 0.09 | 0.12 | 0.07 | 1590 |
| Phage-762 | I | D | — | — | — | — | L | — | — | — | — | T | — | D | 0.09 | 0.12 | 0.08 | 1591 |
| Phage-763 | I | F | — | — | — | — | I | E | Q | P | A | L | — | Y | 0.08 | 0.12 | 0.09 | 1592 |
| Phage-764 | Y | D | — | — | — | — | — | Q | — | D | L | V | — | P | 0.10 | 0.12 | 0.08 | 1593 |
| Phage-765 | H | A | — | W | — | D | W | E | — | p | N | Y | — | D | 0.13 | 0.12 | 0.09 | 1594 |
| Phage-766 | N | V | — | W | — | D | W | E | — | D | Y | N | — | Y | 0.11 | 0.12 | 0.10 | 1595 |
| Phage-767 | S | F | — | — | Q | — | L | G | D | N | Y | D | — | I | 0.09 | 0.12 | 0.12 | 1596 |
| Phage-768 | D | D | — | — | — | — | L | — | — | T | T | V | — | Y | 0.08 | 0.12 | 0.09 | 1597 |
| Phage-769 | N | F | — | — | — | — | W | E | V | A | T | L | — | L | 0.09 | 0.12 | 0.14 | 1598 |
| Phage-770 | D | L | — | — | — | — | V | E | — | D | T | Y | — | N | 0.09 | 0.11 | 0.07 | 1599 |
| Phage-771 | A | L | — | — | — | — | V | E | Q | V | D | L | — | T | 0.08 | 0.11 | 0.08 | 1600 |
| Phage-772 | D | D | — | — | — | — | L | — | — | — | — | N | — | N | 0.08 | 0.11 | 0.08 | 1601 |
| Phage-773 | I | F | — | — | — | — | — | E | Q | I | I | Y | — | D | 0.09 | 0.11 | 0.11 | 1602 |
| Phage-774 | S | D | — | W | — | D | W | E | — | V | Y | Y | — | S | 0.09 | 0.11 | 0.10 | 1603 |
| Phage-775 | F | F | — | — | — | D | G | — | — | V | A | I | — | N | 0.09 | 0.11 | 0.07 | 1604 |
| Phage-776 | D | D | — | W | — | D | W | E | D | D | — | Y | — | Y | 0.11 | 0.11 | 0.07 | 1605 |
| Phage-777 | Y | D | — | — | — | — | — | — | — | T | — | V | — | P | 0.08 | 0.11 | 0.08 | 1606 |
| Phage-778 | S | — | — | — | — | — | L | — | — | — | — | N | — | V | 0.10 | 0.11 | 0.08 | 1607 |
| Phage-779 | A | F | — | V | S | F | Q | Q | S | L | P | H | — | D | 0.09 | 0.11 | 0.10 | 1608 |
| Phage-780 | — | N | — | — | — | — | V | E | — | Y | F | V | — | F | 0.09 | 0.11 | 0.09 | 1609 |
| Phage-781 | T | N | — | W | — | D | W | E | — | D | F | A | — | V | 0.07 | 0.11 | 0.08 | 1610 |
| Phage-782 | D | D | — | — | — | — | — | E | — | I | I | L | — | F | 0.08 | 0.10 | 0.08 | 1611 |
| Phage-783 | N | S | — | — | — | — | L | E | D | Y | H | L | — | P | 0.08 | 0.10 | 0.08 | 1612 |
| Phage-784 | I | H | — | — | — | D | S | — | G | F | D | F | — | D | 0.09 | 0.10 | 0.08 | 1613 |
| Phage-785 | F | D | — | — | — | — | L | E | — | D | H | L | — | F | 0.08 | 0.10 | 0.08 | 1614 |
| Phage-786 | T | V | — | W | — | D | — | E | — | Y | A | D | — | D | 0.10 | 0.10 | 0.08 | 1615 |
| Phage-787 | Y | F | — | W | — | D | W | E | — | A | A | D | — | L | 0.09 | 0.10 | 0.09 | 1616 |
| Phage-788 | — | S | — | — | — | — | — | — | — | — | — | D | — | I | 0.08 | 0.10 | 0.07 | 1617 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | SEQ ID NO: |
|---|---|---|---|---|---|---|---|---|---|---|---|---|---|---|---|---|---|---|
| Phage-789 | A | V | — | — | — | — | L | P | — | D | I | V | — | Y | 0.08 | 0.10 | 0.08 | 1618 |
| Phage-790 | — | L | — | — | — | — | V | E | — | Y | H | L | — | A | 0.08 | 0.10 | 0.30 | 1619 |
| Phage-791 | S | L | — | W | — | D | W | E | — | V | D | N | — | F | 0.12 | 0.10 | 0.11 | 1620 |
| Phage-792 | T | I | — | — | — | D | G | Q | — | D | Y | N | — | H | 0.07 | 0.10 | 0.07 | 1621 |
| Phage-793 | F | L | — | — | — | — | G | E | P | T | Y | L | — | T | 0.12 | 0.10 | 0.09 | 1622 |
| Phage-794 | D | D | — | W | L | — | Q | H | D | I | Y | V | — | A | 0.10 | 0.10 | 0.08 | 1623 |
| Phage-795 | I | F | — | — | — | — | V | E | — | V | A | F | — | F | 0.07 | 0.10 | 0.08 | 1624 |
| Phage-796 | A | L | — | — | — | — | V | E | D | D | Y | D | — | L | 0.09 | 0.10 | 0.09 | 1625 |
| Phage-797 | D | D | — | — | — | — | I | E | L | Y | L | T | — | A | 0.08 | 0.10 | 0.08 | 1626 |
| Phage-798 | T | D | — | W | — | D | W | E | D | D | S | I | — | D | 0.07 | 0.10 | 0.07 | 1627 |
| Phage-799 | S | I | — | — | — | — | L | E | — | I | F | L | — | N | 0.08 | 0.10 | 0.08 | 1628 |
| Phage-800 | N | D | — | — | — | — | L | E | — | D | I | L | — | F | 0.07 | 0.10 | 0.09 | 1629 |
| Phage-801 | D | D | — | — | — | — | L | — | — | T | Y | S | — | Y | 0.09 | 0.09 | 0.08 | 1630 |
| Phage-802 | F | V | — | — | — | — | W | E | — | I | D | L | — | I | 0.10 | 0.09 | 0.09 | 1631 |
| Phage-803 | Y | D | — | — | — | — | L | — | — | L | S | — | — | P | 0.07 | 0.09 | 0.07 | 1632 |
| Phage-804 | N | L | — | — | — | — | L | — | — | — | I | I | — | P | 0.08 | 0.09 | 0.08 | 1633 |
| Phage-805 | I | D | — | W | — | D | W | E | — | F | N | N | — | F | 0.08 | 0.09 | 0.09 | 1634 |
| Phage-806 | A | — | — | — | — | — | L | E | — | H | D | Y | — | Y | 0.08 | 0.09 | 0.09 | 1635 |
| Phage-807 | D | D | — | S | — | Q | — | — | Q | I | D | L | — | D | 0.14 | 0.09 | 0.09 | 1636 |
| Phage-808 | S | — | — | — | — | — | S | — | — | — | I | Y | — | Y | 0.08 | 0.09 | 0.07 | 1637 |
| Phage-809 | S | L | — | — | — | — | — | Q | — | D | A | P | — | N | 0.07 | 0.09 | 0.07 | 1638 |
| Phage-810 | D | A | — | — | — | — | L | — | — | T | T | H | — | D | 0.09 | 0.09 | 0.08 | 1639 |
| Phage-811 | N | D | — | — | — | — | V | E | — | V | A | D | — | F | 0.07 | 0.09 | 0.08 | 1640 |
| Phage-812 | Y | I | — | — | — | — | — | E | Q | D | Y | F | — | F | 0.08 | 0.09 | 0.08 | 1641 |
| Phage-813 | T | D | — | — | — | D | G | — | — | T | N | Y | — | F | 0.11 | 0.09 | 0.08 | 1642 |
| Phage-814 | Y | D | — | — | — | — | V | — | — | — | — | L | — | P | 0.08 | 0.09 | 0.08 | 1643 |
| Phage-815 | I | D | — | — | — | — | — | — | — | — | A | Y | — | T | 0.08 | 0.09 | 0.08 | 1644 |
| Phage-816 | F | D | — | — | — | — | — | E | — | F | F | H | — | Y | 0.09 | 0.09 | 0.09 | 1645 |
| Phage-817 | F | P | — | — | — | — | I | E | — | Y | D | Y | — | V | 0.09 | 0.09 | 0.08 | 1646 |
| Phage-818 | A | D | — | — | — | I | — | E | S | I | D | I | — | V | 0.09 | 0.09 | 0.07 | 1647 |
| Phage-819 | I | S | — | — | — | D | L | W | P | T | D | I | — | T | 0.10 | 0.09 | 0.10 | 1648 |
| Phage-820 | D | D | — | — | — | D | G | — | — | V | H | T | — | N | 0.09 | 0.09 | 0.07 | 1649 |
| Phage-821 | I | D | — | W | — | D | W | E | G | — | F | A | — | N | 0.09 | 0.09 | 0.08 | 1650 |
| Phage-822 | L | N | — | — | — | D | G | — | — | T | F | Y | — | D | 0.08 | 0.08 | 0.07 | 1651 |
| Phage-823 | I | H | — | — | — | — | L | G | A | Y | I | S | — | S | 0.08 | 0.08 | 0.09 | 1652 |
| Phage-824 | T | I | — | W | — | D | W | E | — | D | Y | F | — | Y | 0.08 | 0.08 | 0.08 | 1653 |
| Phage-825 | H | S | — | L | A | Q | — | — | Q | D | L | V | — | I | 0.07 | 0.08 | 0.07 | 1654 |
| Phage-826 | N | N | — | A | S | D | L | S | — | D | N | S | — | I | 0.07 | 0.08 | 0.08 | 1655 |
| Phage-827 | — | N | — | W | — | D | W | E | — | D | — | A | — | N | 0.09 | 0.08 | 0.07 | 1656 |
| Phage-828 | — | — | — | — | — | — | L | — | — | — | F | Y | — | F | 0.08 | 0.08 | 0.07 | 1657 |
| Phage-829 | L | F | — | — | T | V | L | — | — | F | F | D | — | D | 0.07 | 0.08 | 0.07 | 1658 |
| Phage-830 | F | D | — | — | — | — | L | — | — | — | S | — | — | A | 0.08 | 0.08 | 0.07 | 1659 |
| Phage-831 | Y | — | — | — | — | — | V | E | — | N | — | Y | — | I | 0.07 | 0.08 | 0.08 | 1660 |
| Phage-832 | D | — | — | — | — | — | L | — | D | — | T | I | — | H | 0.12 | 0.08 | 0.10 | 1661 |
| Phage-833 | — | F | — | — | — | Q | W | A | — | A | N | A | — | F | 0.09 | 0.08 | 0.07 | 1662 |
| Phage-834 | F | T | — | — | — | — | Y | — | — | — | I | T | — | P | 0.09 | 0.08 | 0.09 | 1663 |
| Phage-835 | L | N | — | — | — | — | V | N | — | — | S | V | — | I | 0.07 | 0.08 | 0.08 | 1664 |
| Phage-836 | A | I | — | W | — | D | W | E | — | F | S | D | — | H | 0.07 | 0.08 | 0.07 | 1665 |
| Phage-837 | Y | — | — | — | V | D | L | G | A | N | — | Y | — | Y | 0.10 | 0.08 | 0.09 | 1666 |
| Phage-838 | H | — | — | — | — | — | V | E | — | D | Y | H | — | D | 0.07 | 0.08 | 0.07 | 1667 |
| Phage-839 | N | D | — | — | S | L | Q | Y | D | I | P | T | — | V | 0.08 | 0.08 | 0.07 | 1668 |
| Phage-840 | Y | V | — | R | — | Q | L | — | V | Y | H | Y | — | N | 0.15 | 0.08 | 0.07 | 1669 |
| Phage-841 | H | D | — | — | — | D | G | — | — | — | I | I | — | S | 0.08 | 0.08 | 0.07 | 1670 |
| Phage-842 | F | D | — | — | — | — | L | — | — | T | I | I | — | P | 0.08 | 0.08 | 0.08 | 1671 |
| Phage-843 | — | D | — | — | S | D | R | G | — | N | A | A | — | H | 0.07 | 0.08 | 0.07 | 1672 |
| Phage-844 | N | I | — | L | A | Q | — | N | — | D | P | T | — | N | 0.07 | 0.08 | 0.08 | 1673 |
| Phage-845 | T | N | — | — | S | K | S | Q | V | — | D | H | — | I | 0.10 | 0.08 | 0.09 | 1674 |
| Phage-846 | N | H | — | H | — | Q | — | W | — | L | T | N | — | N | 0.09 | 0.07 | 0.07 | 1675 |
| Phage-847 | L | L | — | H | — | Q | G | — | L | Y | H | L | — | H | 0.09 | 0.07 | 0.08 | 1676 |
| Phage-848 | T | N | — | D | S | K | L | E | G | D | D | N | — | F | 0.09 | 0.07 | 0.07 | 1677 |
| Phage-849 | N | D | — | — | — | — | M | — | — | — | L | L | — | D | 0.08 | 0.07 | 0.07 | 1678 |
| Phage-850 | F | H | — | — | — | — | V | — | — | — | I | N | — | N | 0.07 | 0.07 | 0.07 | 1679 |
| Phage-851 | D | F | — | — | — | D | G | — | — | T | Y | V | — | S | 0.07 | 0.07 | 0.08 | 1680 |
| Phage-852 | — | S | — | — | — | Q | — | — | — | N | N | T | — | N | 0.07 | 0.07 | 0.08 | 1681 |
| Phage-853 | — | — | — | H | L | — | S | E | Q | F | D | I | — | I | 0.08 | 0.07 | 0.07 | 1682 |
| Phage-854 | D | D | — | — | — | — | W | E | F | V | F | F | — | D | 0.08 | 0.07 | 0.08 | 1683 |
| Phage-855 | Y | N | — | E | Q | Q | Q | — | — | D | P | S | — | I | 0.07 | 0.07 | 0.07 | 1684 |
| Phage-856 | N | T | — | — | T | — | Q | H | — | F | N | — | — | L | 0.08 | 0.07 | 0.08 | 1685 |
| Phage-857 | H | P | — | Q | — | G | I | E | — | V | D | Y | — | V | 0.08 | 0.07 | 0.08 | 1686 |

TABLE 31-continued

Clonal Phage Peptide Sequences from the Peptide-B Optimization Library Panning (—) indicates same amino acid as in CD3 scFv Peptide-B corresponding position (e.g. Phage-1 position).

| Phage ID | \_\_ | \_\_ | \_\_ | \_\_ | Amino acid position sequence | \_\_ | \_\_ | \_\_ | \_\_ | \_\_ | \_\_ | \_\_ | \_\_ | Phage binding ELISA | | | SEQ ID NO: |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | Background signal | SP34.185 scFv signal | SP34.185 scFv signal in presence of CD3 | |
| Phage-858 | — | A | — | S | R | Q | L | G | — | D | A | Y | — | N | 0.07 | 0.07 | 0.07 | 1687 |
| Phage-859 | D | I | — | — | A | Q | E | V | H | V | Y | T | — | P | 0.07 | 0.07 | 0.07 | 1688 |
| Phage-860 | F | F | — | E | G | N | L | — | A | Y | L | L | — | L | 0.08 | 0.07 | 0.08 | 1689 |
| Phage-861 | Y | — | — | — | — | D | G | E | — | N | I | V | — | D | 0.07 | 0.07 | 0.07 | 1690 |

TABLE 32

Sequences of those peptides selected for synthesis (CD3 scFv Peptide-B Optimization)

| Peptide-ID | Sequence | SEQ ID NO: |
|---|---|---|
| Peptide-AA | DDCWPDWEFDFACA | 824 |
| Peptide-AB | YICGLDFPDFLYCD | 825 |
| Peptide-AC | FDCWPDWEEYFVCD | 826 |
| Peptide-AD | YICWPDWEEYFDCD | 827 |
| Peptide-AE | NICWPDWEDDYFCF | 828 |
| Peptide-AF | NFCWPDWEYIYPCI | 829 |
| Peptide-AG | VDCWPDWEEDFLCI | 830 |
| Peptide-AH | HACWPDWEEYFPCN | 831 |
| Peptide-AI | YDCGPDVDESYVCV | 832 |
| Peptide-AJ | IDCWPDWEDDTFCY | 833 |
| Peptide-AK | YLCGPDGDETLACY | 834 |
| Peptide-AL | VDCGPDGDESILCY | 835 |

While preferred embodiments of the present disclosure have been shown and described herein, it will be obvious to those skilled in the art that such embodiments are provided by way of example only.

SEQUENCE LISTING

The patent contains a lengthy sequence listing. A copy of the sequence listing is available in electronic form from the USPTO web site (https://seqdata.uspto.gov/?pageRequest=docDetail&DocID=US12161724B2). An electronic copy of the sequence listing will also be available from the USPTO upon request and payment of the fee set forth in 37 CFR 1.19(b)(3).

What is claimed is:

1. An isolated polypeptide complex comprising an anti-epidermal growth factor receptor (EGFR) binding domain that is linked to a peptide that impairs binding of the anti-EGFR binding domain to EGFR, wherein the peptide comprises an amino acid sequence according to the formula:

$X_1$—C—$X_2$—$X_3$—$X_4$—$X_5$-D-$X_6$-A-$X_7$—P—$X_8$—C—$X_9$, (SEQ ID NO: 841) wherein $X_1$ is selected from the group consisting of: P and L;

$X_2$ is selected from the group consisting of: R, L, T, A, N, I, V, S, H, and P;

$X_3$ is selected from the group consisting of: S, P, F, and Y;

$X_4$ is selected from the group consisting of: H, L, Q, P, R, F, and N;

$X_5$ is selected from the group consisting of: I, F, Y, H, N, T, S, D, A, L, and V;

$X_6$ is selected from the group consisting of: T, P, N, L, I, V, S, D, H, A, and Y;

$X_7$ is selected from the group consisting of: K and Y;

$X_8$ is selected from the group consisting of: I, P, L, and M; and $X_9$ is selected from the group consisting of: A, V, I, T, L, S, D, F, V, and H, wherein the anti-EGFR binding domain comprises heavy chain complementarity determining regions HC-CDR1, HC-CDR2, and HC-CDR3, wherein the HC-CDR1, the HC-CDR2, and the HC-CDR3 comprise: HC-CDR1: SEQ ID NO: 18, HC-CDR2: SEQ ID NO: 19, and HC-CDR3: SEQ ID NO: 20; and the anti-EGFR binding domain comprises light chain complementarity determining regions: LC-CDR1, LC-CDR2, and LC-CDR3, wherein the LC-CDR1, the LC-CDR2, and the LC-CDR3 comprise LC-CDR1: SEQ ID NO: 15, LC-CDR2: SEQ ID NO: 16, and LC-CDR3: SEQ ID NO: 17.

2. The isolated polypeptide complex of claim 1, wherein
$X_1$ is selected from the group consisting of: P and L;
$X_2$ is selected from the group consisting of: R, L, T, A, and N;
$X_3$ is selected from the group consisting of: S, P, and F;
$X_4$ is selected from the group consisting of: H, L, Q, and P;
$X_5$ is selected from the group consisting of: I, F, Y, H, N, and T;
$X_6$ is selected from the group consisting of: T, P, N, L, I, and V;
$X_7$ is selected from the group consisting of: K;
$X_8$ is selected from the group consisting of: I; and
$X_9$ is selected from the group consisting of: A, V, I, T, L, and S.

3. The isolated polypeptide complex of claim 2, wherein
$X_1$ is selected from the group consisting of: P;
$X_2$ is selected from the group consisting of: R, L, and T;
$X_3$ is selected from the group consisting of: S;
$X_4$ is selected from the group consisting of: H, L, Q, and P;
$X_5$ is selected from the group consisting of: I, F, Y, and T;
$X_6$ is selected from the group consisting of: T, P, N, and V;
$X_7$ is selected from the group consisting of: K;
$X_8$ is selected from the group consisting of: I; and
$X_9$ is selected from the group consisting of: A, V, and I.

4. The isolated polypeptide complex of claim 1, wherein the peptide comprises the amino acid sequence according to any one of SEQ ID NOs: 99-118.

5. The isolated polypeptide complex of claim 1, wherein the peptide comprises the amino acid sequence according to SEQ ID NO: 115.

6. The isolated polypeptide complex of claim 1, wherein the peptide comprises the amino acid sequence according to SEQ ID NO: 116.

7. The isolated polypeptide complex of claim 1, wherein the peptide comprises the amino acid sequence according to any one of SEQ ID NOs: 26, 87, 90, 92, or 96.

8. The isolated polypeptide complex of claim 1, wherein the peptide comprises the amino acid sequence according to SEQ ID NO: 26.

9. The isolated polypeptide complex of claim 1, wherein the anti-EGFR binding domain comprises an antibody or an antibody fragment.

10. The isolated polypeptide complex of claim 9, wherein the antibody or antibody fragment comprises a single chain variable fragment, a single domain antibody, a Fab, or a Fab'.

11. The isolated polypeptide complex of claim 10, wherein the antibody or antibody fragment comprises the Fab.

12. The isolated polypeptide complex of claim 11, wherein the Fab comprises a light chain polypeptide having the amino acid sequence of SEQ ID NO:21 and a heavy chain polypeptide having the amino acid sequence of SEQ ID NO:24.

13. The isolated polypeptide complex of claim 11, wherein the Fab comprises a light chain polypeptide having the amino acid sequence of SEQ ID NO:21 and a heavy chain polypeptide having the amino acid sequence of SEQ ID NO:23.

14. The isolated polypeptide complex of claim 11, wherein the Fab comprises a light chain polypeptide having the amino acid sequence of SEQ ID NO:22 and a heavy chain polypeptide having the amino acid sequence of SEQ ID NO:23.

15. The isolated polypeptide complex of claim 11, wherein the Fab comprises a light chain polypeptide having the amino acid sequence of SEQ ID NO:22 and a heavy chain polypeptide having the amino acid sequence of SEQ ID NO:24.

16. The isolated polypeptide complex of claim 1, wherein the anti-EGFR binding domain is linked to the peptide through a linking moiety.

17. The isolated polypeptide complex of claim 16, wherein the linking moiety is a substrate for a tumor specific protease.

18. The isolated polypeptide complex of claim 17, wherein the tumor specific protease is selected from the group consisting of a matrix metalloprotease (MMP), a serine protease, a cysteine protease, a threonine protease, and an aspartic protease.

19. The isolated polypeptide complex of claim 16, wherein the linking moiety is bound to an N-terminus of the anti-EGFR binding domain.

20. The isolated polypeptide complex of claim 16, wherein the linking moiety is bound to a C-terminus of the anti-EGFR binding domain.

21. The isolated polypeptide complex of claim 16, wherein the linking moiety is a peptide sequence having at least 5 to no more than 50 amino acids.

* * * * *